(12) United States Patent
Weiner et al.

(10) Patent No.: US 11,192,939 B2
(45) Date of Patent: *Dec. 7, 2021

(54) METHODS AND COMPOSITIONS FOR PRODUCING A CHIMERIC POLYPEPTIDE

(71) Applicant: AxioMx, Inc., Branford, CT (US)

(72) Inventors: Michael Weiner, Guilford, CT (US); Margaret Kiss, Westbrook, CT (US); Melissa Batonick, Old Saybrook, CT (US)

(73) Assignee: AxioMx, Inc., Branford, CT (US)

( * ) Notice: Subject to any disclaimer, the term of this patent is extended or adjusted under 35 U.S.C. 154(b) by 241 days.

This patent is subject to a terminal disclaimer.

(21) Appl. No.: 15/950,782

(22) Filed: Apr. 11, 2018

(65) Prior Publication Data

US 2018/0230198 A1 Aug. 16, 2018

Related U.S. Application Data

(63) Continuation of application No. 15/175,739, filed on Jun. 7, 2016, now Pat. No. 9,969,792.

(60) Provisional application No. 62/220,060, filed on Sep. 17, 2015, provisional application No. 62/174,994, filed on Jun. 12, 2015.

(51) Int. Cl.
*C07K 16/00* (2006.01)
*C12N 15/10* (2006.01)
*C12N 15/63* (2006.01)

(52) U.S. Cl.
CPC .............. *C07K 16/00* (2013.01); *C12N 15/10* (2013.01); *C12N 15/1037* (2013.01); *C12N 15/63* (2013.01); *C07K 2317/35* (2013.01); *C07K 2317/51* (2013.01); *C07K 2317/515* (2013.01); *C07K 2317/62* (2013.01); *C07K 2317/622* (2013.01); *C07K 2317/64* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,140,471 A | 10/2000 | Johnson et al. | |
| 6,165,793 A | 12/2000 | Stemmer | |
| 6,746,870 B1 | 6/2004 | Ow et al. | |
| 9,969,792 B2 * | 5/2018 | Weiner | C07K 16/00 |
| 2014/0011981 A1 | 1/2014 | Tesar et al. | |

FOREIGN PATENT DOCUMENTS

| | | |
|---|---|---|
| WO | WO-93/19172 A1 | 9/1993 |
| WO | WO-95/21914 A1 | 8/1995 |
| WO | WO-01/05961 A1 | 1/2001 |
| WO | WO-2014/134166 A9 | 9/2014 |
| WO | WO-2015/085079 A2 | 6/2015 |
| WO | WO-2016/090130 A1 | 6/2016 |

OTHER PUBLICATIONS

Brian K. Kay, Affidavit filed Dec. 22, 2017 in U.S. Appl. No. 15/175,739.*
Fisher et al., "Efficient isolation of soluble intracellular single-chain antibodies using the twin-arginine translocation machinery," available in PMC Jan. 9, 2010, published in final edited form as: J Mol Biol. 385(1):299-311 (2009) (23 pages).
Gebauer et al., "Engineered protein scaffolds as next-generation antibody therapeutics," Curr Opin Chem Biol. 13(3):245-55 (2009).
Groth et al., "A phage integrase directs efficient site-specific integration in human cells," Proc Natl Acad Sci U.S.A. 97(11):5995-6000 (2000).
Hartley et al., "DNA cloning using in vitro site-specific recombination," Genome Res. 10(11):1788-95 (2000).
International Search Report and Written Opinion for International Application No. PCT/US2016/036233, dated Nov. 18, 2016 (20 pages).
Jackson, "A reappraisal of non-consensus mRNA splice sites," Nucleic Acids Res. 19(14):3795-8 (1991).
Lah et al., "Phage surface presentation and secretion of antibody fragments using an adaptable phagemid vector," Hum Antibodies Hybridomas. 5(1-2):48-56 (1994).
Lang et al., "Massive programmed translational jumping in mitochondria," Proc Natl Sci U.S.A. 111(16):5926-31 (2014).
Maus et al., "Antibody-modified T cells: CARs take the front seat for hematologic malignancies," Blood. 123(17):2625-35 (2014).
Mergulhao et al., "Recombinant protein secretion in *Escherichia coli*," Biotechnol Adv. 23(3):177-202 (2005).
Nishikura, "Functions and regulation of RNA editing by ADAR deaminases," available in PMC Oct. 12, 2010, published in final edited form as: Annu Rev Biochem. 79:321-49 (2010) (33 pages).
Pihkala et al., "An antigen-mediated selection system for mammalian cells that produce glycosylated single-chain Fv," Biochem Biophys Res Commun. 324(4):1165-72 (2004).
Portnoff et al., "Ubiquibodies, synthetic E3 ubiquitin ligases endowed with unnatural substrate specificity for targeted protein silencing," J Biol Chem. 289(11):7844-55 (2014).

(Continued)

*Primary Examiner* — Nancy J Leith
(74) *Attorney, Agent, or Firm* — Clark & Elbing LLP

(57) ABSTRACT

The present invention provides methods and compositions for converting a first polypeptide into a chimeric polypeptide. The invention includes two vectors: a first vector including the sequence of the first polypeptide and a second vector including a second polypeptide. The vectors include complementary site-specific recombination motifs such that site-specific recombination between the two vectors results in the generation of a chimeric polypeptide including at least a portion of the first polypeptide and at least a portion of the second polypeptide. A site-specific recombination motif may be positioned within an intron or within a coding sequence on the first or second vector.

17 Claims, 38 Drawing Sheets

Specification includes a Sequence Listing.

(56) References Cited

OTHER PUBLICATIONS

Quinlan et al., "Direct expression and validation of phage-selected peptide variants in mammalian cells," J Biol Chem. 288(26):18803-10 (2013).
Richards et al., The Admid System: Generation of Recombinant Adenoviruses by Tn7-Mediated Transposition in *E. coli*. Cloning and Expression Vectors for Gene Function Analysis. Lu, Quinn and Weiner, Michael p. 231-240 (2001).
Robinson et al., "Rapid inactivation of proteins by knocksideways," Curr Protoc Cell Biol. 61:15.20.1-7 (2013).
Robinson et al., "Rapid inactivation of proteins by rapamycin-induced rerouting to mitochondria," Dev Cell. 18(2):324-31 (2010).
Sadelain et al., "The basic principles of chimeric antigen receptor design," Cancer Discov. 3(4):388-98 (2013).
Savva et al., "The ADAR protein family," Genome Biol. 13(12):252 (2012) (10 pages).
Schoft et al., "Regulation of glutamate receptor B pre-mRNA splicing by RNA editing," Nucleic Acids Res. 35(11):3723-32 (2007).
Smith et al., "Site-specific recombination by phiC31 integrase and other large serine recombinases," Biochem Soc Trans. 38(2):388-94 (2010).
Stern et al., "Improving mammalian cell factories: The selection of signal peptide has a major impact on recombinant protein synthesis and secretion in mammalian cells," Trends Cell Mol Biol. (17 pages). (2007).
Tan et al., "*E. coli* selection of human genes encoding secreted and membrane proteins based on cDNA fusions to a leaderless beta-lactamase reporter," Genome Res. 13(8):1938-43 (2003).
Tesar et al., "A dual host vector for Fab phage display and expression of native IgG in mammalian cells," Protein Eng Des Sel. 26(10):655-62 (2013).
Zhou et al., "Genetically encoded short peptide tags for orthogonal protein labeling by Sfp and AcpS phosphopantetheinyl transferases," ACS Chem Biol. 2(5):337-46 (2007).
Batonick et al., "pMINERVA: A donor-acceptor system for the in vivo recombineering of scFv into IgG molecules," J Immunol Methods 431:22-30 (2016).
Buhr et al., "Use of micro-emulsion technology for the directed evolution of antibodies," Methods. 58(1):28-33 (2012) (6 pages).
Extended European Search Report for European Application No. 16808130.5, dated Dec. 13, 2018 (6 pages).
Holland et al., "AXM mutagenesis: an efficient means for the production of libraries for directed evolution of proteins," J Immunol Methods. 394(1-2):55-61 (2013).
Kiss et al., "Phage ESCape: an emulsion-based approach for the selection of recombinant phage display antibodies," J Immunol Methods. 367(1-2):17-26 (2011).
Communication Pursuant to Article 94(3) for European Application No. 16808130.5, dated Jul. 31, 2019 (7 pages).

\* cited by examiner

FIG. 2A-2C phiC31 Integrase (Int)

FIG. 23

Types of pMinerva constant framework libraries

| Antibody Type | Natural host | Possible Advantage(s) in producing as a pMinerva library |
|---|---|---|
| IgY | Avian | The cross-reactivity of IgY with proteins from mammals is markedly less than that of IgG |
| CameId | Camel, Llama | Thermal stability, single-chain, enhanced tissue penetration, can cross blood-brain-barrier and long CDR H3 |
| IgNAR | Shark | Stable in high concentrations of urea |
| IgG* | Bovine | Ultralong CDR3 H3 regions (35-60 AAs) that can form mini-domains |
| IgG | Rabbit | Thermal stability, more diverse antigen recognition; many of the smaller peptides and small molecules that elicit a poor response in mice generate a favorable one in rabbit |
| IgM | Mammalian | Pentameric, increased avidity |
| IgG | Mammalian | Dimeric, preferred therapeutic format. Different subclasses (IgG1, IgG2, IgG3 and IgG4) and light chains (lambda and kappa) are potentially available as constant frameworks for library construction |
| Fab | Various | Thermal stability and increased utility in converting to an IgG |
| Yeast display | Human (Fab) | Yeast secretion and glycosylation |

FIG. 24B-24E
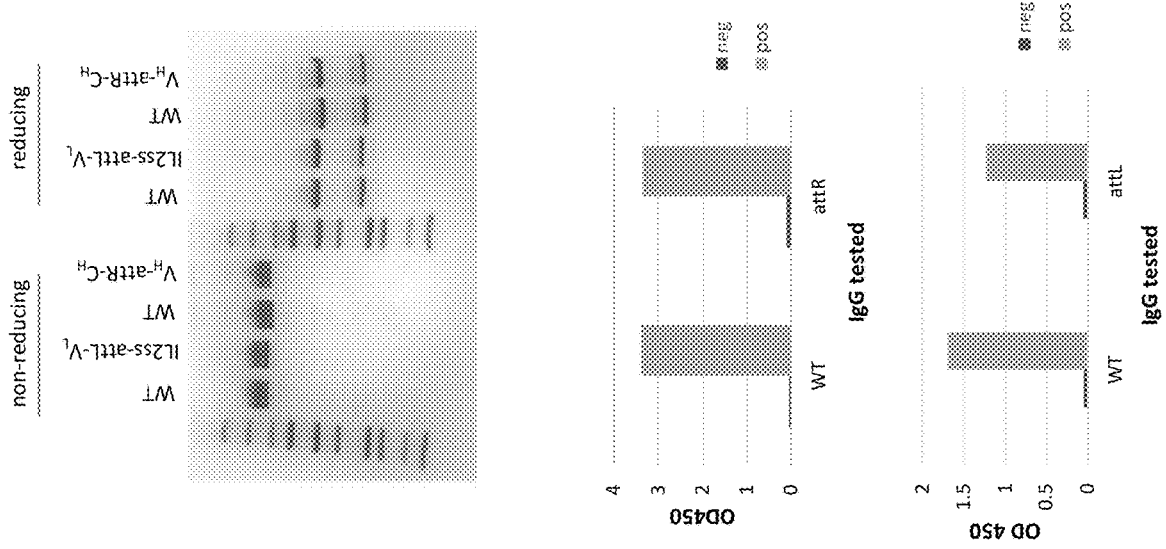
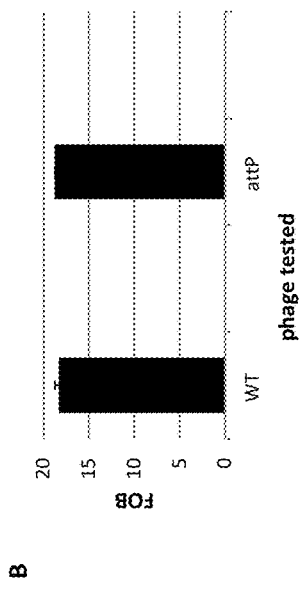
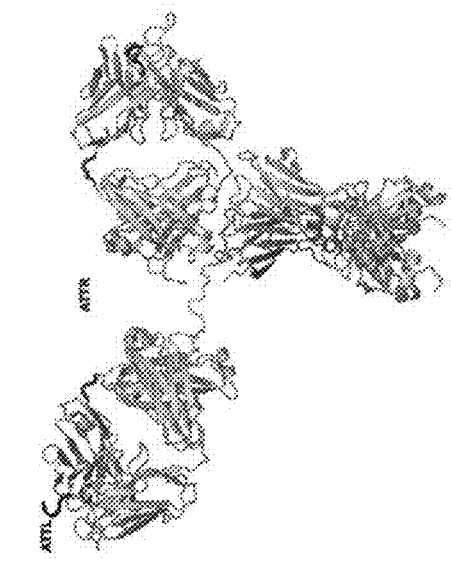

| Feature | Origin | Construct | Reference |
|---|---|---|---|
| pAPIII₆ | NA | Parental phage display vector | Haidaris et al., 2001 |
| phoA | pAPIII6 | Synthetic | Haidaris et al., 2001 |
| C_L | pFUSE2ss-CLIg-hk | Synthetic | Saito et al., 2015 |
| gpIII | pIT2 | synthetic | Holt and Tomlinson, 2000 |
| V_L | Herceptin | synthetic | DrugBank Acc#DB00072 |
| attP | NA | synthetic | Groth et al., 2000 |
| V_H | Herceptin | synthetic | DrugBank Acc#DB00072 |
| pCDF-1b | NA | Parental acceptor vector | EMD Millipore |
| C_H | pFUSEss-CHIg-hG1 | synthetic | Yamashita et al., 2015 |
| attB | NA | synthetic | Groth et al., 2004 |
| CAM | pACYC184 | Synthetic | GenBank: X06403.1 |
| phiC31 | NA | Synthetic | GenBank: CAC93948.1 |
| EF1a | pEF1a-acGFP-C1 | Synthetic | Matz et al., 2013 |
| IL2 ss | pFUSEss-CLIg-hk | Synthetic | Saito et al., 2015 |
| Splice sites | NA | Synthetic | Lodish et al., 1999, Molecular Cell Biology 4th edition | pDonor / pAcceptor / universal

| Antibody name | Yield (mg/L) |
|---|---|
| IgG A | 14.2 |
| IgG B | 4.4 |
| IgG C | 3.7 |
| IgG D | 3.4 |
| IgG E | 3.5 |
| IgG F | 4.7 |
| IgG G | 2.9 |
| IgG H | 4.4 |
| IgG I | 3.1 |
| IgG J | 4.1 |
| IgG K | 5.3 |

FIG. 28A

| Tag type | Examples of 3' fusion constructs |
|---|---|
| Enzyme | βGal, Alk Phos, HRP |
| Purification | His6, FLAG, protein A/G |
| Labeling | GFP, Halotag, sfp, SNAPtag |
| Endosomal | Ubiquitin ligase, FKB12 |
| Fc | Rabbit, cow, mouse, goat, human (IgG1, IgG2, IgG3, IgG4, IgM) |
| Other | Avitag, sfp synthase, ACP-tag, TCR T-cell receptors with different membrane spanning sequences |

H-H: human-human; H-R: human-rabbit chimera

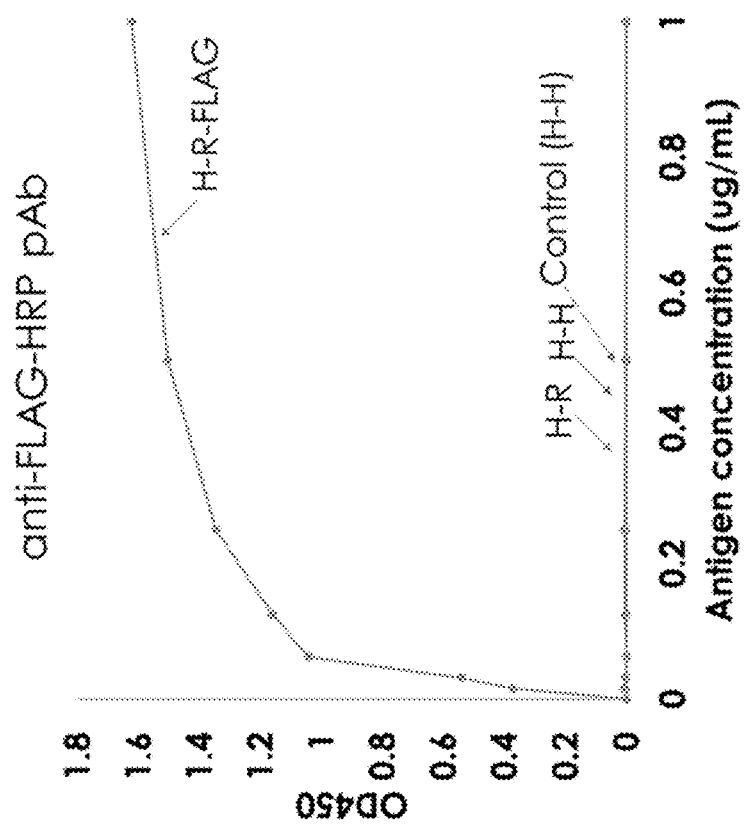

METHODS AND COMPOSITIONS FOR PRODUCING A CHIMERIC POLYPEPTIDE

The instant application contains a Sequence Listing which has been submitted electronically in ASCII format and is hereby incorporated by reference in its entirety. Said ASCII copy, created on Apr. 10, 2018, is named 50881-008004_Sequence_Listing_4.10.18_ST25 and is 29,395 bytes in size.

BACKGROUND OF THE INVENTION

Various methods have been utilized for the identification of binding moieties capable of binding particular antigens. Prior art methods have been used to generate antibodies or antibody fragments, such as IgG, IgM, IgA, IgD, IgE, Fab, Fab', F(ab')2, Fd, Fv, Feb, scFv, or SMIP. Because these types of binding moieties have distinct properties, it is sometimes advantageous to convert a binding moiety of a first type into a binding moiety of a second type. Certain existing methods for the conversion of a polypeptide of a first type to a polypeptide of a second type can be inefficient. Thus, there exists a need in the art for compositions and methods for the efficient conversion of a polypeptide of a first type into a polypeptide of a second type (e.g., a chimeric polypeptide).

SUMMARY OF THE INVENTION

The present invention provides methods and compositions for converting a polypeptide of a first type into a chimeric polypeptide (e.g., a polypeptide of a different type) including at least a portion of the polypeptide of the first type and, preferably, an additional polypeptide or a fragment thereof. In one embodiment, the invention includes two vectors: a first vector including the sequence of a first polypeptide (e.g., a binding moiety) and a second vector including the sequence of a second polypeptide (e.g., a framework). It is appreciated that the terms "first vector" and "second vector," and the terms "first polypeptide" and "second polypeptide," may be interchangeable. The vectors may further include complementary site-specific recombination motifs, such that site-specific recombination between the two vectors results in the generation of a chimeric polypeptide including at least a portion of the first polypeptide and at least a portion of the second polypeptide of the second vector.

In a first aspect, the invention features a method of converting a single-chain variable fragment (scFv) into a chimeric polypeptide. The method involves:

(a) providing a first vector including, in order from 5' to 3',
a first mammalian expression control motif,
a first *E. coli* expression control motif,
a sequence encoding a heavy chain variable region (VH) of the scFv,
a first site-specific recombination motif,
a sequence encoding a light chain variable region (VL) of the scFv,
a 5' mammalian splice site ($Mam_{5'ss}$),
a fusion display protein sequence,
a 3' mammalian splice site ($Mam_{3'ss}$), and
a sequence encoding a light chain constant region (CL), and (b) providing a second vector including, in order from 5' to 3',
a second mammalian expression control motif,
a second site-specific recombination motif, and
a sequence encoding a polypeptide; and (c) contacting the first vector and the second vector in the presence of a recombinase enzyme,
in which the recombinase enzyme combines the first vector and the second vector in a site-specific manner to form an integrant vector,
in which the integrant vector expresses the VL fused to the CL and a separate VH fused to the polypeptide,
thereby upon expression converting an scFv into a chimeric polypeptide.

In some embodiments of the first aspect, the first vector is a phagemid vector. In certain embodiments, the second vector is a phagemid vector. In one embodiment, the first vector is a phagemid vector and the second vector is not a phagemid vector.

In some embodiments of the first aspect, the first vector further includes: a 5' mammalian splice site ($Mam_{5'ss}$) positioned between the first mammalian expression control motif and the first *E. coli* expression control motif, and a 3' mammalian splice site ($Mam_{3'ss}$) positioned between the first *E. coli* expression control motif and the sequence encoding the VH of the scFv. In certain embodiments, the first vector further includes a leader sequence positioned between the second 3' mammalian splice site and the sequence encoding the VH of the scFv.

In some embodiments of the first aspect, the first vector further includes a leader sequence positioned between the first *E. coli* expression control motif and the sequence encoding the VH of the scFv.

In some embodiments of the first aspect, the first vector further includes: an additional 5' mammalian splice site ($Mam_{5'ss}$) positioned between the sequence encoding the VH of the scFv and the first site-specific recombination motif, and an additional 3' mammalian splice site ($Mam_{3'ss}$) positioned between the first site-specific recombination motif and the sequence encoding the VL of the scFv.

In some embodiments of the first aspect, the second vector further includes: a further 5' mammalian splice site ($Mam_{5'ss}$) positioned between the second mammalian expression control motif and the second site-specific recombination motif, and a further 3' mammalian splice site ($Mam_{3'ss}$) positioned between the second site-specific recombination motif and the sequence encoding the polypeptide.

In some embodiments of the first aspect, the polypeptide includes a heavy chain constant region.

In some embodiments of the first aspect, the integrant vector expresses an IgG antibody.

In some embodiments of the first aspect, the polypeptide includes a fusion protein. In certain embodiments, the fusion protein includes a tag (e.g., a FLAG, HA, Myc, V5, His, GST, MBP, AviTag, streptavidin tag, or any other tag known in the art). In various embodiments, the fusion protein includes a fluorescent protein (e.g., GFP, YFP, CFP, RFP, dsRed, mCherry, or any other fluorescent protein known in the art).

In some embodiments of the first aspect, the providing step further includes providing an additional vector including a polynucleotide encoding the recombinase enzyme. In certain embodiments, the recombinase enzyme is expressed by the additional vector.

In a second aspect, the invention features a method of converting a first polypeptide into a chimeric polypeptide. The method involves:

(a) providing:
i. a first vector including a first polynucleotide encoding a first polypeptide, the first polynucleotide including a first site-specific recombination motif;
ii. a second vector including a second site-specific recombination motif and a second polynucleotide encoding a second polypeptide; and
iii. a recombinase enzyme capable of recombining the first site-specific recombination motif with the second site-specific recombination motif; and (b) recombining the first vector and the second vector with the recombinase enzyme, thereby forming a recombinant vector encoding a chimeric polypeptide including:
i. the first polypeptide, or a portion thereof, and
ii. the second polypeptide, or a portion thereof.

In some embodiments of the second aspect, the first polypeptide-encoding region of the first polynucleotide includes the first site-specific recombination motif. In some embodiments, the first polypeptide includes a linker, and the portion of the polynucleotide encoding the linker includes the first site-specific recombination motif. In certain embodiments, the first vector or the second vector includes a polynucleotide encoding the recombinase enzyme. In particular embodiments, the providing step further includes providing an additional vector including a polynucleotide encoding the recombinase enzyme.

In a third aspect, the invention features a method of converting a first polypeptide into a chimeric polypeptide. The method involves:

(a) providing:
i. a first vector including a first polynucleotide encoding a first polypeptide, the first polynucleotide including an intron including a first site-specific recombination motif;
ii. a second vector including a second site-specific recombination motif and a second polynucleotide encoding a second polypeptide; and
iii. a recombinase enzyme capable of recombining the first site-specific recombination motif with the second site-specific recombination motif; and (b) recombining the first vector and the second vector with the recombinase enzyme, thereby forming a recombinant vector encoding a chimeric polypeptide including:
i. the first polypeptide, or a portion thereof, and
ii. the second polypeptide, or a portion thereof.

In some embodiments of the third aspect, the portion of the first polynucleotide encoding the first polypeptide includes the intron. In certain embodiments, the portion of the first polynucleotide encoding the first polypeptide does not include the intron. In particular embodiments, the first vector or the second vector includes a polynucleotide encoding the recombinase enzyme.

In some embodiments of the third aspect, the providing step further includes providing an additional vector including a polynucleotide encoding the recombinase enzyme.

In a fourth aspect, the invention features a method of converting a first polypeptide into one of at least two chimeric polypeptides. The method involves:

(a) providing a first vector including a first polynucleotide encoding a first polypeptide including a first site-specific recombination motif and an alternate site-specific recombination motif, and
i. a second vector including a second site-specific recombination motif and a second polynucleotide encoding a second polypeptide; and a recombinase enzyme capable of recombining the first site-specific recombination motif with the second site-specific recombination motif; or
ii. a third vector including a third site-specific recombination motif distinct from the first site-specific recombination motif and an alternate polynucleotide encoding an alternate polypeptide; and an alternate recombinase enzyme capable of recombining the alternate site-specific recombination motif with the third site-specific recombination motif; and (b) recombining the first vector and:
i. the second vector with the recombinase enzyme, thereby forming a recombinant vector encoding a chimeric polypeptide including the first polypeptide, or a portion thereof, and the second polypeptide, or a portion thereof; and/or
ii. the third vector with the alternate recombinase enzyme, thereby forming a recombinant vector encoding a chimeric polypeptide including the first polypeptide, or a portion thereof, and the alternate polypeptide, or a portion thereof.

In some embodiments of the fourth aspect, the first polynucleotide includes the first site-specific recombination motif. In certain embodiments, the first polynucleotide includes an intron including the first site-specific recombination motif. In various embodiments, the second polynucleotide includes an intron including the second site-specific recombination motif. In particular embodiments, the first vector or the second vector includes a polynucleotide encoding the recombinase enzyme, and/or the first vector or the third vector includes a polynucleotide encoding the alternate recombinase enzyme.

In a fifth aspect, the invention features a method of converting an scFv into a chimeric polypeptide. The method involves:

(a) providing:
i. a first vector including a first polynucleotide encoding a first polypeptide including an scFv including a light chain variable domain, a linker region, and a heavy chain variable domain, the portion of the first polynucleotide encoding the linker region including a first site-specific recombination motif (e.g., an attP site);
ii. a second vector including a second site-specific recombination motif and a second polynucleotide encoding a second polypeptide; and
iii. a recombinase enzyme capable of recombining the first site-specific recombination motif with the second site-specific recombination motif; and (b) recombining the first vector and the second vector with the recombinase enzyme, thereby forming a recombinant vector encoding a chimeric polypeptide including:
i. the light chain variable domain and/or the heavy chain variable domain, and
ii. the second polypeptide, or a portion thereof;
in which the chimeric polypeptide is not an scFv.

In some embodiments of any of the first through fifth aspects, the first polypeptide includes an antibody or antibody fragment. In certain embodiments, the antibody or antibody fragment is a human, mouse, goat, sheep, rabbit, chicken, guinea pig, hamster, horse, or rat antibody or antibody fragment. In various embodiments, the antibody is an IgG, IgA, IgD, IgE, IgM, or intrabody. In one embodiment, the antibody is an IgG.

In certain embodiments, the antibody fragment includes an scFv, single-domain antibody (sdAb), dAb, Fab, Fab', Fab'2, F(ab')2, Fd, Fv, Feb, or SMIP. In particular embodiments, the antibody fragment is an scFv. In one embodiment, the scFv is a cytosol-stable scFv. In certain embodiments, the scFv is a bovine scFv. In one embodiment, the sdAb is a camelid VHH. In various embodiments, the scFv includes a linker positioned between the light chain variable domain and the heavy chain variable domain of the scFv, the linker including the first site-specific recombination motif. In specific embodiments, the chimeric polypeptide includes the light chain variable domain of the scFv and/or the heavy chain variable domain of the scFv.

In some embodiments of any of the first through fifth aspects, the first polypeptide includes a chimeric antigen receptor (CAR). In certain embodiments, the first polypeptide includes a CD8 transmembrane domain, CD3-zeta cytoplasmic domain, 4-1 BB cytoplasmic domain, and/or CD28 cytoplasmic domain. In certain embodiments, the chimeric polypeptide includes the CD8 transmembrane domain, CD3-zeta cytoplasmic domain, 4-1 BB cytoplasmic domain, and/or CD28 cytoplasmic domain of the first polypeptide. In various embodiments, the chimeric polypeptide further includes a peptide linker domain positioned between: (i) the CD8 transmembrane domain, CD3-zeta cytoplasmic domain, 4-1 BB cytoplasmic domain, and/or CD28 cytoplasmic domain of the first polypeptide, and (ii) the first polypeptide, or the portion thereof. In particular embodiments, the peptide linker domain has a length of about 0-250 amino acids or about 1-250 amino acids (e.g., about 1-50, 1-10, 10-20, 20-50, or 50-100 amino acids). In a preferred embodiment, the peptide linker domain has a length of about 1-50 amino acids. In certain embodiments, the CAR includes an extracellular binding moiety (e.g., an scFv) capable of binding to an antigen associated with a disease. In particular embodiments, the disease is a cell proliferation disorder, such as cancer. In specific embodiments, the antigen is a tumor-associated antigen. In one embodiment, the antigen is CD19 and the disease is acute lymphoblastic leukemia (ALL).

In various embodiments, the chimeric polypeptide includes an antibody or antibody fragment. In particular embodiments, the antibody or antibody fragment is a human, mouse, goat, sheep, rabbit, chicken, guinea pig, hamster, horse, or rat antibody or antibody fragment. In specific embodiments, the antibody is an IgG, IgA, IgD, IgE, IgM, or intrabody. In various embodiments, the antibody is an IgG. In particular embodiments, the first polypeptide includes the variable light chain and/or variable heavy chains of the IgG. In specific embodiments, the first vector includes a polynucleotide encoding a constant domain of the IgG. In a particular embodiment, the constant domain includes a CL domain or an Fc domain. In one embodiment, the constant domain includes a CH domain including the Fc domain.

In certain embodiments, the antibody fragment includes an scFv, sdAb, dAb, Fab, Fab', Fab'2, F(ab')2, Fd, Fv, Feb, or SMIP. In particular embodiments, the antibody fragment is an scFv. In specific embodiments, the scFv is a cytosol-stable scFv. In an embodiment, the scFv is a bovine scFv. In one embodiment, the sdAb is a camelid VHH.

In some embodiments of any of the first through fifth aspects, the chimeric polypeptide includes a chimeric antigen receptor (CAR). In certain embodiments, the second polypeptide includes a CD8 transmembrane domain, CD3-zeta cytoplasmic domain, 4-1 BB cytoplasmic domain, and/or CD28 cytoplasmic domain. In particular embodiments, the first polypeptide is an scFv and the chimeric polypeptide includes the light chain variable domain of the scFv and the CD8 transmembrane domain, CD3-zeta cytoplasmic domain, 4-1 BB cytoplasmic domain, and/or CD28 cytoplasmic domain. In various embodiments, the chimeric polypeptide further includes a peptide linker domain positioned between: (i) the light chain variable domain of the scFv, and (ii) the CD8 transmembrane domain, CD3-zeta cytoplasmic domain, 4-1 BB cytoplasmic domain, and/or CD28 cytoplasmic domain. In particular embodiments, the peptide linker domain has a length of about 0-250 amino acids or about 1-250 amino acids (e.g., about 1-50, 1-10, 10-20, 20-50, or 50-100 amino acids). In a preferred embodiment, the peptide linker domain has a length of about 1-50 amino acids. In specific embodiments, the first polypeptide is an scFv and the chimeric polypeptide includes the heavy chain variable domain of the scFv and the CD8 transmembrane domain, CD3-zeta cytoplasmic domain, 4-1 BB cytoplasmic domain, and/or CD28 cytoplasmic domain. In various embodiments, the chimeric polypeptide further includes a peptide linker domain positioned between: (i) the heavy chain variable domain of the scFv, and (ii) the CD8 transmembrane domain, CD3-zeta cytoplasmic domain, 4-1 BB cytoplasmic domain, and/or CD28 cytoplasmic domain. In particular embodiments, the peptide linker domain has a length of about 0-250 amino acids or about 1-250 amino acids (e.g., about 1-50, 1-10, 10-20, 20-50, or 50-100 amino acids). In a preferred embodiment, the peptide linker domain has a length of about 1-50 amino acids. In other embodiments, the first polypeptide is an scFv and the chimeric polypeptide includes the heavy chain variable domain and the light chain variable domain of the scFv and the CD8 transmembrane domain, CD3-zeta cytoplasmic domain, 4-1 BB cytoplasmic domain, and/or CD28 cytoplasmic domain. In various embodiments, the chimeric polypeptide further includes a peptide linker domain positioned between: (i) the heavy chain variable domain and the light chain variable domain of the scFv, and (ii) the CD8 transmembrane domain, CD3-zeta cytoplasmic domain, 4-1 BB cytoplasmic domain, and/or CD28 cytoplasmic domain. In particular embodiments, the peptide linker domain has a length of about 0-250 amino acids or about 1-250 amino acids (e.g., about 1-50, 1-10, 10-20, 20-50, or 50-100 amino acids). In a preferred embodiment, the peptide linker domain has a length of about 1-50 amino acids. In certain embodiments, the CAR includes an extracellular binding moiety (e.g., an scFv) capable of binding to an antigen associated with a disease. In particular embodiments, the disease is a cell proliferation disorder, such as cancer. In specific embodiments, the antigen is a tumor-associated antigen. In one embodiment, the antigen is CD19 and the disease is acute lymphoblastic leukemia (ALL).

In some embodiments of any of the first through fifth aspects, the chimeric polypeptide includes an ubiquitin ligase domain. In certain embodiments, the second polypeptide includes the ubiquitin ligase domain. In particular embodiments, the ubiquitin ligase domain includes a CHIPΔTPR domain.

In some embodiments of any of the first through fifth aspects, the chimeric polypeptide includes a knocksideways prey domain. In certain embodiments, the second polypeptide includes the knocksideways prey domain. In specific embodiments, the knocksideways prey domain includes an FKBP domain. In certain embodiments, the providing step further includes providing a knocksideways bait protein. In particular embodiments, the knocksideways bait protein includes an FRB domain. In specific embodiments, the knocksideways bait protein includes a mitochondrial outer membrane targeting signal. In one embodiment, the knocksideways bait protein is a Mitotrap protein.

In certain embodiments, the chimeric polypeptide further includes a ubiquitin ligase domain. In particular embodiments, the second polypeptide includes the ubiquitin ligase domain. In one embodiment, the ubiquitin ligase domain includes a CHIPΔTPR domain.

In some embodiments of any of the first through fifth aspects, the recombinase enzyme is a serine family recombinase or a tyrosine family recombinase. In certain embodiments, the serine family recombinase is phiC31, BxB1, HIN invertase, or TN3 resolvase. In one embodiment, the serine family recombinase is phiC31. In certain embodiments, the providing step further includes providing an accessory factor. In one embodiment, the accessory factor includes Xis. In certain embodiments, the tyrosine family recombinase is bacteriophage lambda integrase, Cre, or Flp. In particular embodiments, the recombinase is selected from the integrases shown in Table 2.

In some embodiments of any of the first through fifth aspects, the first polypeptide, the second polypeptide, and/or the chimeric polypeptide includes a marker. In certain embodiments, the marker is an epitope tag and/or a fluorescent protein. In particular embodiments, the epitope tag is a FLAG, HA, Myc, V5, His, GST, MBP, AviTag, or streptavidin tag, or any other epitope tag known in the art. In particular embodiments, the fluorescent protein is EGFP, GFP, YFP, CFP, mCherry, dsRed, or any other fluorescent protein known in the art.

In some embodiments of any of the first through fifth aspects, the recombining step takes place in a cell. In particular embodiments, the cell is included in an emulsion droplet. In certain embodiments, the providing step further includes providing the cell, and the cell includes the vectors and the recombinase enzyme. In certain embodiments, the first vector is a plasmid or a phagemid. In particular embodiments, the first vector includes a polynucleotide encoding a display protein. In specific embodiments, the display protein is capable of displaying the first polypeptide, or a portion thereof, on the extracellular surface of a cell (e.g., the cell in which the recombining step takes place). In one embodiment, the display protein includes ompA. In another embodiment, the display protein includes bclA. In various embodiments, the cell is a bacterial cell. In particular embodiments, the bacterial cell is $E.\ coli$. In various embodiments, the cell is a eukaryotic cell. In particular embodiments, the eukaryotic cell is a mammalian cell or an insect cell.

In certain embodiments, the cell further includes a vector including a polynucleotide encoding the recombinase enzyme. In one embodiment, the cell further includes a chromosome including a polynucleotide encoding the recombinase enzyme.

In some embodiments of any of the first through fifth aspects, the recombining step takes place in a cell-free system. In certain embodiments, the cell-free system is a solution including the vectors and the recombinase enzyme. In one embodiment, the recombinase enzyme is bacteriophage lambda integrase. In various embodiments, the cell free system is included in an emulsion droplet. In particular embodiments, a plurality of such recombining steps can occur in a plurality of emulsion droplets in parallel. Massively multiplex recombination reactions in parallel, e.g., in such emulsion droplets, is contemplated. Such multiplex systems may include, for example, any liquid handling or emulsion droplet-based system known in the art.

In some embodiments of any of the first through fifth aspects, the first vector includes a plurality of distinct regulatory elements positioned adjacent to each other. In certain embodiments, one of the regulatory elements controls the expression of the first polypeptide, or a portion thereof, in a first cell type, and another of the regulatory elements controls the expression of the first polypeptide, or a portion thereof, in a second cell type. In particular embodiments, the first polypeptide, or portion thereof is fused to a protein fragment when expressed in the first cell type. In specific embodiments, the protein fragment includes a viral coat protein. In one embodiment, the viral coat protein is M13gpIII. In certain embodiments, the protein fragment further includes a bacterial signal peptide. In certain embodiments, the first cell type is a bacterial cell, and the second cell type is a eukaryotic cell. In one embodiment, the bacterial cell is an $E.\ coli$ cell. In particular embodiments, the eukaryotic cell is a mammalian cell, insect cell, or fungal cell. In one embodiment, the mammalian cell is a human cell. In another embodiment, the fungal cell is a yeast cell.

In some embodiments of any of the first through fifth aspects, the second vector includes a plurality of distinct regulatory elements positioned adjacent to each other. In certain embodiments, one of the regulatory elements controls the expression of the second polypeptide, or a portion thereof, in a first cell type, and another of the regulatory elements controls the expression of the second polypeptide, or a portion thereof, in a second cell type. In particular embodiments, the second polypeptide, or portion thereof is fused to a protein fragment when expressed in the first cell type. In specific embodiments, the protein fragment includes a viral coat protein. In one embodiment, the viral coat protein is M13gpIII. In certain embodiments, the protein fragment further includes a bacterial signal peptide. In certain embodiments, the first cell type is a bacterial cell, and the second cell type is a eukaryotic cell. In one embodiment, the bacterial cell is an $E.\ coli$ cell. In particular embodiments, the eukaryotic cell is a mammalian cell, insect cell, or fungal cell. In one embodiment, the mammalian cell is a human cell. In another embodiment, the fungal cell is a yeast cell.

In some embodiments of any of the first through fifth aspects, the recombinant vector includes a plurality of distinct regulatory elements positioned adjacent to each other. In various embodiments, one of the regulatory elements controls the expression of the chimeric polypeptide in a first cell type, and another of the regulatory elements controls the expression of the chimeric polypeptide in a second cell type. In certain embodiments, the first cell type is a bacterial cell, and the second cell type is a eukaryotic cell. In one embodiment, the bacterial cell is an $E.\ coli$ cell. In particular embodiments, the eukaryotic cell is a mammalian cell, insect cell, or fungal cell. In one embodiment, the mammalian cell is a human cell. In another embodiment, the fungal cell is a yeast cell.

In certain embodiments of any of the above, one or more of the distinct regulatory elements is a promoter. In particular embodiments, the promoter is a bacterial promoter (e.g., a lac promoter, T7 promoter, or T3 promoter). In one embodiment, the bacterial promoter is a lac promoter. In other embodiments, the promoter is a eukaryotic promoter (e.g., a promoter capable of controlling expression in a mammalian cell, an insect cell, or a fungal cell). In one embodiment, the promoter capable of controlling expression in a mammalian cell is a CMV promoter or an EF1a promoter. In another embodiment, the promoter capable of controlling expression in an insect cell is a polyhedron promoter.

In some embodiments of any of the first through fifth aspects, the first polynucleotide includes an intron including an intronic regulatory element. In certain embodiments, the intronic regulatory element controls the expression of the first polypeptide, or a portion thereof, in a prokaryotic cell. In particular embodiments, the prokaryotic cell is a bacterial cell. In one embodiment, the bacterial cell is *E. coli*. In various embodiments, the first polypeptide, or portion thereof, is fused to a protein fragment when expressed in the prokaryotic cell. In certain embodiments, the protein fragment includes a viral coat protein. In one embodiment, the viral coat protein is M13gpIII. In various embodiments, the protein fragment further includes a bacterial signal peptide. In certain embodiments, the intron further includes a polynucleotide encoding the protein fragment. In particular embodiments, the intronic regulatory element controls the expression of the protein fragment. In one embodiment, the intronic regulatory element is removed from the transcript of the first polynucleotide in a eukaryotic cell by RNA splicing. In certain embodiments, the eukaryotic cell is a mammalian cell, insect cell, or fungal cell.

In certain embodiments, the intronic regulatory element is a promoter. In particular embodiments, the promoter is a bacterial promoter (e.g., a lac promoter, T7 promoter, or T3 promoter). In one embodiment, the bacterial promoter is a lac promoter. In other embodiments, the promoter is a eukaryotic promoter (e.g., a promoter capable of controlling expression in a mammalian cell, an insect cell, or a fungal cell). In one embodiment, the promoter capable of controlling expression in a mammalian cell is a CMV promoter or an EF1a promoter. In another embodiment, the promoter capable of controlling expression in an insect cell is a polyhedron promoter.

In some embodiments of any of the first through fifth aspects, the first vector further includes a pair of complementary site-specific recombination motifs (e.g., two loxP sites, two FRT sites, or an attB site and an attP site). In certain embodiments, the first polynucleotide, a fragment thereof, and/or the first site-specific recombination motif are located between the pair of complementary site-specific recombination motifs. In some embodiments of any of the first through fifth aspects, the second vector further includes a pair of complementary site-specific recombination motifs. In certain embodiments, the second polynucleotide, a fragment thereof, and/or the second site-specific recombination motif are located between the pair of complementary site-specific recombination motifs.

In certain embodiments, the pair of complementary site-specific recombination motifs are oriented such that recombination of the pair of complementary site-specific recombination motifs results in the inversion of the intervening sequences. In other embodiments, the pair of complementary site-specific recombination motifs are oriented such that recombination of the pair of complementary site-specific recombination motifs results in the deletion of the intervening sequences.

In certain embodiments, the providing step further includes providing a recombinase enzyme capable of recombining the pair of complementary site-specific recombination motifs (e.g., Cre, FRT, phiC31, or bacteriophage lambda integrase). In particular embodiments, the method further includes the step of recombining the pair of complementary site-specific recombination motifs. In specific embodiments, the pair of complementary site-specific recombination motifs includes a pair of loxP sites. In one embodiment, the providing step further includes providing a Cre recombinase enzyme. In specific embodiments, the pair of complementary site-specific recombination motifs includes a pair of FRT sites. In one embodiment, the providing step further includes providing a Flp recombinase enzyme. In specific embodiments, the pair of complementary site-specific recombination motifs includes an attB site and an attP site. In certain embodiments, the providing step further includes providing a recombinase enzyme (e.g., phiC31 or BxB1) capable of recombining said first site-specific recombination motif and/or said second site-specific recombination motif, and a distinct recombinase enzyme (e.g., BxB1, phiC31, Cre, or Flp) capable of recombining the pair of complementary site-specific recombination motifs. In one embodiment, the providing step further includes providing a phiC31 or BxB1 recombinase enzyme suitable for recombining the attB site and the attP site of the pair of complementary site-specific recombination motifs.

In some embodiments of any of the first through fifth aspects, the first vector is a viral vector. In certain embodiments, the first vector is an adenoviral, lentiviral, or baculoviral vector. In some embodiments of any of the first through fifth aspects, the second vector is a viral vector. In certain embodiments, the second vector is an adenoviral, lentiviral, or baculoviral vector. In certain embodiments, one or more viral elements are located within an intron.

In some embodiments of any of the first through fifth aspects, the first vector is a phagemid vector. In some embodiments of any of the first through fifth aspects, the second vector is a phagemid vector.

In some embodiments of any of the first through fifth aspects, the first vector further includes a first recombination motif fragment and the second vector includes a second recombination motif fragment, and the recombinant vector includes a cryptic site-specific recombination motif including the first recombination motif fragment and the second recombination motif fragment, and the method further includes:

(c) recombining the recombinant vector and a further vector including
  (i) a further site-specific recombination motif, and
  (ii) a polynucleotide encoding a further polypeptide;
with a further recombinase enzyme capable of recombining the cryptic site-specific recombination motif with the further site-specific recombination motif,
thereby forming a second recombinant vector encoding a second chimeric polypeptide including:
  (i) the chimeric polypeptide, or a portion thereof, and
  (ii) the further polypeptide, or a portion thereof.

In certain embodiments, the first site-specific recombination motif and the cryptic site-specific recombination motif are the same. In other embodiments, the first site-specific recombination motif and the cryptic site-specific recombination motif are different. In various embodiments, the further recombinase enzyme is a serine family recombinase or a tyrosine family recombinase. In particular embodiments, the serine family recombinase is phiC31, BxB1, HIN invertase, or TN3 resolvase. In one embodiment, the serine family recombinase is BxB1. In particular embodiments, the tyrosine family recombinase is bacteriophage lambda integrase, Cre, or Flp. In certain embodiments, the further recombinase enzyme is selected from the integrases shown in Table 2.

In certain embodiments, the second chimeric polypeptide includes an antibody or antibody fragment. In one embodiment, the antibody is an IgG. In certain embodiments, the second chimeric polypeptide includes a CAR. In particular embodiments, the further polypeptide includes a CD3-zeta transmembrane domain, CD28 transmembrane domain, CD3-zeta cytoplasmic domain, CD28 cytoplasmic domain, 41 BB cytoplasmic domain, ICOS cytoplasmic domain, FcεRIγ cytoplasmic domain, influenza MP-1 cytoplasmic domain, VZV cytoplasmic domain, and/or OX40 cytoplasmic domain, or any combination or derivative thereof. In certain embodiments, the CAR includes an extracellular binding moiety (e.g., an scFv) capable of binding to an antigen associated with a disease. In particular embodiments, the disease is a cell proliferation disorder, such as cancer. In specific embodiments, the antigen is a tumor-associated antigen. In one embodiment, the antigen is CD19 and the disease is acute lymphoblastic leukemia (ALL). In another embodiment, the antigen is Tyro3. In certain embodiments, the further polypeptide includes a ubiquitin ligase domain. In certain embodiments, the further polypeptide includes a knocksideways prey domain. In one embodiment, the further polypeptide includes a ubiquitin ligase domain and a knocksideways prey domain.

In some embodiments of any of the first through fifth aspects, an mRNA transcript encoding the first polypeptide, the second polypeptide, and/or the chimeric polypeptide is capable of being edited by an ADAR enzyme. In certain embodiments, the editing includes activation of a cryptic splice site in the mRNA transcript to remove an exon from the transcript. In various embodiments, the editing includes removal of a splice site in the mRNA transcript. In certain embodiments, the mRNA transcript includes a first region and a second region capable of hybridizing to the first region to form a duplex. In one embodiment, the first region is complementary to the second region, and the duplex is at least 100 bp in length. In another embodiment, the duplex is no more than 30 bp in length and includes an editing-site complementary sequence. In a further embodiment, the duplex is greater than 30 bp in length and includes one or more mismatched bases, bulges, or loops. In certain embodiments, the first vector or the second vector further includes a polynucleotide encoding an ADAR enzyme.

In some embodiments of any of the first through fifth aspects, an mRNA transcript encoding the first polypeptide, the second polypeptide, and/or the chimeric polypeptide includes one or more translational bypassing elements (byps).

In a sixth aspect, the invention features a composition including:
(a) a first vector including a first polynucleotide encoding a first polypeptide, the first polynucleotide including a first site-specific recombination motif;
(b) a second vector including a second site-specific recombination motif and a second polynucleotide encoding a second polypeptide; and
(c) a recombinase enzyme capable of recombining the first site-specific recombination motif with the second site-specific recombination motif;
in which the recombining results in formation of a recombinant vector encoding a chimeric polypeptide including:
i. the first polypeptide, or a portion thereof, and
ii. the second polypeptide, or a portion thereof.

In some embodiments of the sixth aspect, the first polypeptide-encoding region of the first polynucleotide includes the first site-specific recombination motif. In some embodiments, the first polypeptide includes a linker, and the portion of the polynucleotide encoding the linker includes the first site-specific recombination motif. In certain embodiments, the first vector or the second vector includes a polynucleotide encoding the recombinase enzyme. In various embodiments, the composition further includes an additional vector including a polynucleotide encoding the recombinase enzyme.

In a seventh aspect, the invention features a composition including:
(a) a first vector including a first polynucleotide encoding a first polypeptide, the first polynucleotide including an intron including a first site-specific recombination motif;
(b) a second vector including a second site-specific recombination motif and a second polynucleotide encoding a second polypeptide; and
(c) a recombinase enzyme capable of recombining the first site-specific recombination motif with the second site-specific recombination motif;
in which the recombining results in formation of a recombinant vector encoding a chimeric polypeptide including:
i. the first polypeptide, or a portion thereof, and
ii. the second polypeptide, or a portion thereof.

In some embodiments of the seventh aspect, the portion of the first polynucleotide encoding the first polypeptide includes the intron. In other embodiments of the seventh aspect, the portion of the first polynucleotide encoding the first polypeptide does not include the intron.

In certain embodiments, the first vector or the second vector includes a polynucleotide encoding the recombinase enzyme. In further embodiments, the composition includes an additional vector including a polynucleotide encoding the recombinase enzyme.

In an eighth aspect, the invention features a composition including:
(a) a first vector including a first polynucleotide encoding a first polypeptide including a first site-specific recombination motif and an alternate site-specific recombination motif, and
(b) (i) a second vector including a second site-specific recombination motif and a second polynucleotide encoding a second polypeptide; and a recombinase enzyme capable of recombining the first site-specific recombination motif with the second site-specific recombination motif, or
(ii) a third vector including a third site-specific recombination motif distinct from the first site-specific recombination motif and an alternate polynucleotide encoding an alternate polypeptide; and an alternate recombinase enzyme capable of recombining the alternate site-specific recombination motif with the third site-specific recombination motif;
in which the recombining of the first vector and the second vector by the recombinase enzyme results in formation of a recombinant vector encoding a chimeric polypeptide including the first polypeptide, or a portion thereof, and the second polypeptide; and
in which the recombining of the first vector and the third vector by the alternate recombinase enzyme results in formation a recombinant vector encoding a chimeric polypeptide including the first polypeptide, or a portion thereof, and the alternate polypeptide.

In some embodiments of the eighth aspect, the first polynucleotide includes the first site-specific recombination motif. In certain embodiments, the first polynucleotide includes an intron including the first site-specific recombination motif. In particular embodiments, the first vector or the second vector includes a polynucleotide encoding the recombinase enzyme, and/or the first vector or the third vector includes a polynucleotide encoding the alternate recombinase enzyme.

In an ninth aspect, the invention features a composition including:
  (a) a first vector including a first polynucleotide encoding an scFv including a light chain variable domain, a linker region, and a heavy chain variable domain, the portion of the first polynucleotide encoding the linker region including a first site-specific recombination motif (e.g., an attP site);
  (b) a second vector including a second site-specific recombination motif and a second polynucleotide encoding a second polypeptide; and
  (c) a recombinase enzyme capable of recombining the first site-specific recombination motif with the second site-specific recombination motif;
in which recombination of the first vector with the second vector by the recombinase enzyme forms a recombinant vector encoding a chimeric binding moiety including:
  i. the light chain variable domain and/or the heavy chain variable domain, and
  ii. the second polypeptide, or a portion thereof.

In some embodiments of any of the sixth through ninth aspects, the first polypeptide is an antibody or antibody fragment. In certain embodiments, the antibody or antibody fragment is a human, mouse, goat, sheep, rabbit, chicken, guinea pig, hamster, horse, or rat antibody or antibody fragment. In particular embodiments, the antibody is an IgG, IgA, IgD, IgE, IgM, or intrabody. In one embodiment, the antibody is an IgG.

In certain embodiments, the antibody fragment is an scFv, sdAb, dAb, Fab, Fab', Fab'2, F(ab')2, Fd, Fv, Feb, or SMIP. In particular embodiments, the antibody fragment is an scFv. In specific embodiments, the scFv is a cytosol-stable scFv. In one embodiment, the scFv is a bovine or camelid scFv. In one embodiment, the sdAb is a camelid VHH. In particular embodiments, the scFv includes a linker positioned between the light chain variable domain and the heavy chain variable domain of the scFv, the linker including the first site-specific recombination motif. In various embodiments, the chimeric polypeptide includes the light chain variable domain of the scFv and/or the heavy chain variable domain of the scFv.

In some embodiments of any of the sixth through ninth aspects, the first polypeptide is a chimeric antigen receptor (CAR). In certain embodiments, the first polypeptide includes a CD8 transmembrane domain, CD3-zeta cytoplasmic domain, 4-1 BB cytoplasmic domain, and/or CD28 cytoplasmic domain. In particular embodiments, the chimeric polypeptide includes the CD8 transmembrane domain, CD3-zeta cytoplasmic domain, 4-1 BB cytoplasmic domain, and/or CD28 cytoplasmic domain of the first polypeptide. In certain embodiments, the chimeric polypeptide further includes a peptide linker domain positioned between: (i) the CD8 transmembrane domain, CD3-zeta cytoplasmic domain, 4-1 BB cytoplasmic domain, and/or CD28 cytoplasmic domain of the first polypeptide, and (ii) the first polypeptide, or the portion thereof. In particular embodiments, the peptide linker domain has a length of about 0-250 amino acids or about 1-250 amino acids (e.g., about 1-50, 1-10, 10-20, 20-50, or 50-100 amino acids). In a preferred embodiment, the peptide linker domain has a length of about 1-50 amino acids. In certain embodiments, the CAR includes an extracellular binding moiety (e.g., an scFv) capable of binding to an antigen associated with a disease. In particular embodiments, the disease is a cell proliferation disorder, such as cancer. In specific embodiments, the antigen is a tumor-associated antigen. In one embodiment, the antigen is CD19 and the disease is acute lymphoblastic leukemia (ALL).

In some embodiments of any of the sixth through ninth aspects, the chimeric polypeptide is an antibody or antibody fragment. In certain embodiments, the antibody or antibody fragment is a human, mouse, goat, sheep, rabbit, chicken, guinea pig, hamster, horse, or rat antibody or antibody fragment. In particular embodiments, the antibody is an IgG, IgA, IgD, IgE, IgM, or intrabody. In a specific embodiment, the antibody is an IgG. In one embodiment, the first polypeptide includes the variable light chain and/or variable heavy chains of the IgG. In particular embodiments, the first vector includes a polynucleotide encoding a constant domain of the IgG. In specific embodiments, the constant domain includes a CL domain or an Fc domain. In on embodiment, the constant domain includes a CH domain including the Fc domain.

In certain embodiments, the antibody fragment is an scFv, dAb, Fab, Fab', Fab'2, F(ab')2, Fd, Fv, Feb, or SMIP. In a particular embodiment, the antibody fragment is an scFv. In a specific embodiment, the scFv is a cytosol-stable scFv. In one embodiment, the scFv is a bovine or camelid scFv.

In some embodiments of any of the sixth through ninth aspects, the chimeric polypeptide is a chimeric antigen receptor (CAR). In certain embodiments, the second polypeptide includes a CD8 transmembrane domain, CD3-zeta cytoplasmic domain, 4-1 BB cytoplasmic domain, and/or CD28 cytoplasmic domain. In particular embodiments, the first polypeptide is an scFv and the chimeric polypeptide includes the light chain variable domain of the scFv and the CD8 transmembrane domain, CD3-zeta cytoplasmic domain, 4-1 BB cytoplasmic domain, and/or CD28 cytoplasmic domain. In certain embodiments, the chimeric polypeptide further includes a peptide linker domain positioned between: (i) the light chain variable domain of the scFv, and (ii) the CD8 transmembrane domain, CD3-zeta cytoplasmic domain, 4-1 BB cytoplasmic domain, and/or CD28 cytoplasmic domain. In particular embodiments, the peptide linker domain has a length of about 0-250 amino acids or about 1-250 amino acids (e.g., about 1-50, 1-10, 10-20, 20-50, or 50-100 amino acids). In a preferred embodiment, the peptide linker domain has a length of about 1-50 amino acids. In other embodiments, the first polypeptide is an scFv and the chimeric polypeptide includes the heavy chain variable domain of the scFv and the CD8 transmembrane domain, CD3-zeta cytoplasmic domain, 4-1 BB cytoplasmic domain, and/or CD28 cytoplasmic domain. In certain embodiments, the chimeric polypeptide further includes a peptide linker domain positioned between: (i) the heavy chain variable domain of the scFv, and (ii) the CD8 transmembrane domain, CD3-zeta cytoplasmic domain, 4-1 BB cytoplasmic domain, and/or CD28 cytoplasmic domain. In particular embodiments, the peptide linker domain has a length of about 0-250 amino acids or about 1-250 amino acids (e.g., about 1-50, 1-10, 10-20, 20-50, or 50-100 amino acids). In a preferred embodiment, the peptide linker domain has a length of about 1-50 amino acids. In further embodiments, the first polypeptide is an scFv and the chimeric polypeptide includes the heavy chain variable domain and the light chain variable domain of the scFv and the CD8 transmembrane domain, CD3-zeta cytoplasmic domain, 4-1 BB cytoplasmic domain, and/or CD28 cytoplasmic domain. In certain embodiments, the chimeric polypeptide further includes a peptide linker domain positioned between: (i) the heavy chain variable domain and the light chain variable domain of the scFv, and (ii) the CD8 transmembrane domain, CD3-zeta cytoplasmic domain, 4-1 BB cytoplasmic domain, and/or CD28 cytoplasmic domain. In particular embodiments, the peptide linker domain has a length of about 0-250 amino acids or about 1-250 amino acids (e.g., about 1-50, 1-10, 10-20, 20-50, or 50-100 amino acids). In a preferred embodiment, the peptide linker domain has a length of about 1-50 amino acids. In certain embodiments, the CAR includes an extracellular binding moiety (e.g., an scFv) capable of binding to an antigen associated with a disease. In particular embodiments, the disease is a cell proliferation disorder, such as cancer. In specific embodiments, the antigen is a tumor-associated antigen. In one embodiment, the antigen is CD19 and the disease is acute lymphoblastic leukemia (ALL).

In some embodiments of any of the sixth through ninth aspects, the chimeric polypeptide includes an ubiquitin ligase domain. In certain embodiments, the second polypeptide includes the ubiquitin ligase domain. In particular embodiments, the ubiquitin ligase domain includes a CHIPΔTPR domain.

In some embodiments of any of the sixth through ninth aspects, the chimeric polypeptide includes a knocksideways prey domain. In certain embodiments, the second polypeptide includes the knocksideways prey domain. In one embodiment, the knocksideways prey domain includes an FKBP domain.

In certain embodiments, the composition further includes a knocksideways bait protein. In a particular embodiment, the knocksideways bait protein includes an FRB domain. In specific embodiments, the knocksideways bait protein includes a mitochondrial outer membrane targeting signal. In one embodiment, the knocksideways bait protein is a Mitotrap protein.

In certain embodiments, the chimeric polypeptide further includes a ubiquitin ligase domain (e.g., a chimeric polypeptide including a knocksideways prey domain and a ubiquitin ligase domain). In a particular embodiment, the second polypeptide includes the ubiquitin ligase domain. In one embodiment, the ubiquitin ligase domain includes a CHIPΔTPR domain.

In some embodiments of any of the sixth through ninth aspects, the recombinase enzyme is a serine family recombinase or a tyrosine family recombinase. In certain embodiments, the serine family recombinase is phiC31, BxB1, HIN invertase, or TN3 resolvase. In one embodiment, the serine family recombinase is phiC31. In certain embodiments, the composition further includes an accessory factor. In one embodiment, the accessory factor includes Xis. In further embodiments, the tyrosine family recombinase is bacteriophage lambda integrase, Cre, or Flp. In particular embodiments, the recombinase enzyme is selected from the integrases shown in Table 2.

In some embodiments of any of the sixth through ninth aspects, the first polypeptide, the second polypeptide, and/or the chimeric polypeptide includes a marker. In certain embodiments, the marker is an epitope tag and/or a fluorescent protein. In particular embodiments, the epitope tag is a FLAG, HA, Myc, V5, His, GST, MBP, AviTag, or streptavidin tag, or any other epitope tag known in the art. In particular embodiments, the fluorescent protein is EGFP, GFP, YFP, CFP, mCherry, dsRed, or any other fluorescent protein known in the art.

In some embodiments of any of the sixth through ninth aspects, the composition further includes a cell including the vectors and the recombinase enzyme. In particular embodiments, the cell is included in an emulsion droplet. In certain embodiments, the first vector is a plasmid or a phagemid. In particular embodiments, the first vector includes a polynucleotide encoding a display protein. In specific embodiments, the display protein is capable of displaying the first polypeptide, or a portion thereof, on the extracellular surface of a cell (e.g., the cell in which the recombining step takes place). In one embodiment, the display protein includes ompA. In another embodiment, the display protein includes bclA. In certain embodiments, the cell is a bacterial cell. In one embodiment, the bacterial cell is E. coli. In other embodiments, the cell is a eukaryotic cell. In particular embodiments, the eukaryotic cell is a mammalian cell or an insect cell. In certain embodiments, the cell further includes a vector including a polynucleotide encoding the recombinase enzyme. In further embodiments, the cell further includes a chromosome including a polynucleotide encoding the recombinase enzyme.

In some embodiments of any of the sixth through ninth aspects, the vectors and the recombinase enzyme (e.g., phiC31 or bacteriophage lambda integrase) are located within a cell-free system. In one embodiment, the recombinase enzyme is bacteriophage lambda integrase. In certain embodiments, the cell free system is included in an emulsion droplet.

In some embodiments of any of the sixth through ninth aspects, the first vector includes a plurality of distinct regulatory elements positioned adjacent to each other. In certain embodiments, one of the regulatory elements controls the expression of the first polypeptide, or a portion thereof, in a first cell type, and another of the regulatory elements controls the expression of the first polypeptide, or a portion thereof, in a second cell type. In particular embodiments, the first polypeptide, or portion thereof is fused to a protein fragment when expressed in the first cell type. In specific embodiments, the protein fragment includes a viral coat protein. In one embodiment, the viral coat protein is M13gpIII. In certain embodiments, the protein fragment further includes a bacterial signal peptide.

In some embodiments of any of the sixth through ninth aspects, the second vector includes a plurality of distinct regulatory elements positioned adjacent to each other. In certain embodiments, one of the regulatory elements controls the expression of the second polypeptide, or a portion thereof, in a first cell type, and another of the regulatory elements controls the expression of the second polypeptide, or a portion thereof, in a second cell type. In particular embodiments, the second polypeptide, or portion thereof is fused to a protein fragment when expressed in the first cell type. In specific embodiments, the protein fragment includes a viral coat protein. In one embodiment, the viral coat protein is M13gpIII. In certain embodiments, the protein fragment further includes a bacterial signal peptide.

In some embodiments of any of the sixth through ninth aspects, the recombinant vector includes a plurality of distinct regulatory elements positioned adjacent to each other. In certain embodiments one of the regulatory elements controls the expression of the chimeric polypeptide in a first cell type, and another of the regulatory elements controls the expression of the chimeric polypeptide in a second cell type. In particular embodiments, the first cell type is a bacterial cell, and the second cell type is a eukaryotic cell. In one embodiment, the bacterial cell is an E. coli cell. In specific embodiments, the eukaryotic cell is a mammalian cell, insect cell, or fungal cell. In one embodiment, the mammalian cell is a human cell. In a further embodiment, the fungal cell is a yeast cell.

In certain embodiments of any of the above, one or more of the distinct regulatory elements is a promoter. In particular embodiments, the promoter is a bacterial promoter (e.g., a lac promoter, T7 promoter, or T3 promoter). In one embodiment, the bacterial promoter is a lac promoter. In other embodiments, the promoter is a eukaryotic promoter (e.g., a promoter capable of controlling expression in a mammalian cell, an insect cell, or a fungal cell). In one embodiment, the promoter capable of controlling expression in a mammalian cell is a CMV promoter or an EF1a promoter. In another embodiment, the promoter capable of controlling expression in an insect cell is a polyhedron promoter.

In some embodiments of any of the sixth through ninth aspects, the first polynucleotide includes an intron including an intronic regulatory element. In certain embodiments, the intronic regulatory element controls the expression of the first polypeptide, or a portion thereof, in a prokaryotic cell. In a particular embodiment, the prokaryotic cell is a bacterial cell. In one embodiment, the bacterial cell is E. coli. In certain embodiments, the first polypeptide, or portion thereof, is fused to a protein fragment when expressed in the prokaryotic cell. In a particular embodiment, the protein fragment includes a viral coat protein. In one embodiment, the viral coat protein is M13gpIII. In certain embodiments, the protein fragment further includes a bacterial signal peptide. In particular embodiments, the intron further includes a polynucleotide encoding the protein fragment. In various embodiments, the intronic regulatory element controls the expression of the protein fragment. In certain embodiments, the intronic regulatory element is removed from the transcript of the first polynucleotide in a eukaryotic cell by RNA splicing. In particular embodiments, the eukaryotic cell is a mammalian cell (e.g., a human cell), insect cell, or fungal cell.

In certain embodiments, the intronic regulatory element is a promoter. In particular embodiments, the promoter is a bacterial promoter (e.g., a lac promoter, T7 promoter, or T3 promoter). In one embodiment, the bacterial promoter is a lac promoter. In other embodiments, the promoter is a eukaryotic promoter (e.g., a promoter capable of controlling expression in a mammalian cell, an insect cell, or a fungal cell). In one embodiment, the promoter capable of controlling expression in a mammalian cell is a CMV promoter or an EF1a promoter. In another embodiment, the promoter capable of controlling expression in an insect cell is a polyhedron promoter.

In some embodiments of any of the sixth through ninth aspects, the first vector further includes a pair of complementary site-specific recombination motifs (e.g., two loxP sites, two FRT sites, or an attB site and an attP site). In certain embodiments, the first polynucleotide, a fragment thereof, and/or the first site-specific recombination motif are located between the pair of complementary site-specific recombination motifs. In some embodiments of any of the sixth through ninth aspects, the second vector further includes a pair of complementary site-specific recombination motifs (e.g., two loxP sites, two FRT sites, or an attB site and an attP site). In certain embodiments, the second polynucleotide, a fragment thereof, and/or the second site-specific recombination motif are located between the pair of complementary site-specific recombination motifs.

In certain embodiments, the pair of complementary site-specific recombination motifs are oriented such that recombination of the pair of complementary site-specific recombination motifs results in the inversion of the intervening sequences. In other embodiments, the pair of complementary site-specific recombination motifs are oriented such that recombination of the pair of complementary site-specific recombination motifs results in the deletion of the intervening sequences. In certain embodiments, the composition further includes a recombinase enzyme (e.g., Cre, FRT, phiC31, or bacteriophage lambda integrase) capable of recombining the pair of complementary site-specific recombination motifs.

In particular embodiments, the pair of complementary site-specific recombination motifs includes a pair of loxP sites. In one embodiment, the composition further includes a Cre recombinase enzyme.

In other embodiments, the pair of complementary site-specific recombination motifs includes a pair of FRT sites. In one embodiment, the composition further includes a Flp recombinase enzyme.

In yet further embodiments, the pair of complementary site-specific recombination motifs includes an attB site and an attP site. In specific embodiments, the composition further includes a phiC31 or BxB1 recombinase enzyme suitable for recombining the attB site and the attP site of the pair of complementary site-specific recombination motifs. In certain embodiments, the composition further includes a recombinase enzyme (e.g., phiC31 or BxB1) capable of recombining said first site-specific recombination motif and/or said second site-specific recombination motif, and a distinct recombinase enzyme (e.g., BxB1, phiC31, Cre, or Flp) capable of recombining the pair of complementary site-specific recombination motifs. In one embodiment, the composition further includes a phiC31 or BxB1 recombinase enzyme suitable for recombining the attB site and the attP site of the pair of complementary site-specific recombination motifs.

In some embodiments of any of the sixth through ninth aspects, the first vector is a viral vector. In certain embodiments, the first vector is an adenoviral, lentiviral, or baculoviral vector. In further embodiments, the second vector is a viral vector. In certain embodiments, the second vector is an adenoviral, lentiviral, or baculoviral vector. In particular embodiments, one or more viral elements are located within an intron.

In some embodiments of any of the sixth through ninth aspects, the first vector is a phagemid vector. In other embodiments of any of the sixth through ninth aspects, the second vector is a phagemid vector.

In some embodiments of any of the sixth through ninth aspects,
the first vector further includes a first recombination motif fragment and the second vector includes a second recombination motif fragment, and
the recombinant vector includes a cryptic site-specific recombination motif including the first recombination motif fragment and the second recombination motif fragment,
in which recombining the recombinant vector and a further vector including
(i) a further site-specific recombination motif, and
(ii) a polynucleotide encoding a further polypeptide;
with a further recombinase enzyme capable of recombining the cryptic site-specific recombination motif with the further site-specific recombination motif results in formation of a second recombinant vector encoding a second chimeric polypeptide including:
(i) the chimeric polypeptide, or a portion thereof, and
(ii) the further polypeptide, or a portion thereof.

In certain embodiments, the first site-specific recombination motif and the cryptic site-specific recombination motif are the same. In other embodiments, the first site-specific recombination motif and the cryptic site-specific recombination motif are different.

In certain embodiments, the further recombinase enzyme is a serine family recombinase or a tyrosine family recombinase. In particular embodiments, the serine family recombinase is phiC31, BxB1, HIN invertase, or TN3 resolvase. In one embodiment, the serine family recombinase is BxB1. In further embodiments, the tyrosine family recombinase is bacteriophage lambda integrase, Cre, or Flp. In certain embodiments, the further recombinase enzyme is selected from the integrases shown in Table 2.

In certain embodiments, the second chimeric polypeptide includes an antibody or antibody fragment. In one embodiment, the antibody is an IgG. In further embodiments, the second chimeric polypeptide includes a CAR. In particular embodiments, the further polypeptide includes a CD3-zeta transmembrane domain, CD28 transmembrane domain, CD3-zeta cytoplasmic domain, CD28 cytoplasmic domain, 41 BB cytoplasmic domain, ICOS cytoplasmic domain, FcεRIy cytoplasmic domain, influenza MP-1 cytoplasmic domain, VZV cytoplasmic domain, and/or OX40 cytoplasmic domain, or any combination or derivative thereof. In certain embodiments, the CAR includes an extracellular binding moiety (e.g., an scFv) capable of binding to an antigen associated with a disease. In particular embodiments, the disease is a cell proliferation disorder, such as cancer. In specific embodiments, the antigen is a tumor-associated antigen. In one embodiment, the antigen is CD19 and the disease is acute lymphoblastic leukemia (ALL). In another embodiment, the antigen is Tyro3. In yet further embodiments, the further polypeptide includes a ubiquitin ligase domain. In additional embodiments, the further polypeptide includes a knocksideways prey domain. In a specific embodiment, the further polypeptide includes a ubiquitin ligase domain and a knocksideways prey domain.

In some embodiments of any of the sixth through ninth aspects, the composition further includes an mRNA transcript encoding the first polypeptide, the second polypeptide, and/or the chimeric polypeptide, in which the mRNA transcript is capable of being edited by an ADAR enzyme. In certain embodiments, the editing includes activation of a cryptic splice site in the mRNA transcript to remove an exon from the transcript. In various embodiments, the editing includes removal of a splice site in the mRNA transcript. In particular embodiments, the mRNA transcript includes a first region and a second region capable of hybridizing to the first region to form a duplex. In one embodiment, the first region is complementary to the second region, and the duplex is at least 100 bp in length. In another embodiment, the duplex is no more than 30 bp in length and includes an editing-site complementary sequence. In an alternate embodiment, the duplex is greater than 30 bp in length and includes one or more mismatched bases, bulges, or loops. In certain embodiments, the first vector or the second vector further includes a polynucleotide encoding an ADAR enzyme.

In some embodiments of any of the sixth through ninth aspects, the composition further includes an mRNA transcript encoding the first polypeptide, the second polypeptide, and/or the chimeric polypeptide, in which the mRNA transcript includes one or more translational bypassing elements (byps).

In some embodiments of any of the sixth through ninth aspects, the first vector includes a promoter capable of controlling expression of the first polypeptide in a bacterial cell (e.g., E. coli). In some embodiments of any of the sixth through ninth aspects, the first vector includes a promoter capable of controlling expression of the first polypeptide in a eukaryotic cell (e.g., a mammalian cell, such as a human cell; an insect cell; or a fungal cell, such as a yeast cell). In certain embodiments, the first vector includes a promoter capable of controlling expression of the first polypeptide in a bacterial cell (e.g., E. coli) and a promoter capable of controlling expression of the first polypeptide in a eukaryotic cell (e.g., a mammalian cell, such as a human cell; an insect cell; or a fungal cell, such as a yeast cell).

In some embodiments of any of the sixth through ninth aspects, the second vector includes a promoter capable of controlling expression of the second polypeptide in a bacterial cell (e.g., E. coli). In some embodiments of any of the sixth through ninth aspects, the second vector includes a promoter capable of controlling expression of the second polypeptide in a eukaryotic cell (e.g., a mammalian cell, such as a human cell; an insect cell; or a fungal cell, such as a yeast cell). In certain embodiments, the second vector includes a promoter capable of controlling expression of the second polypeptide in a bacterial cell (e.g., E. coli) and a promoter capable of controlling expression of the second polypeptide in a eukaryotic cell (e.g., a mammalian cell, such as a human cell; an insect cell; or a fungal cell, such as a yeast cell). In certain embodiments of any of the above, the promoter capable of controlling expression of the first or second polypeptide in a bacterial cell is a lac promoter, T7 promoter, or T3 promoter. In certain embodiments of any of the above, the promoter capable of controlling expression of the first or second polypeptide in a mammalian cell is a CMV promoter or an EF1a promoter. In certain embodiments of any of the above, the promoter capable of controlling expression of the first or second polypeptide in an insect cell is a polyhedron promoter.

In some embodiments of any of the sixth through ninth aspects, the portion of the first vector encoding the first polypeptide, or a portion thereof, further encodes a fusion to a protein fragment. In specific embodiments, the protein fragment includes a viral coat protein. In one embodiment, the viral coat protein is M13gpIII. In certain embodiments, the protein fragment further includes a bacterial or mammalian signal peptide.

In some embodiments of any of the sixth through ninth aspects, the portion of the second vector encoding the second polypeptide, or a portion thereof, further encodes a fusion to a protein fragment. In specific embodiments, the protein fragment includes a viral coat protein. In one embodiment, the viral coat protein is M13gpIII. In certain embodiments, the protein fragment further includes a bacterial or mammalian signal peptide.

In some embodiments of any of the sixth through ninth aspects, the first site-specific recombination motif is positioned upstream of (e.g., 5' to) the first polynucleotide. In certain embodiments, the first site-specific recombination motif is positioned upstream of (e.g., 5' to) a polynucleotide encoding a marker (e.g., a resistance marker, such as a chloramphenicol (CAM) gene, ampR gene, or any other marker described herein). In certain embodiments, the second site-specific recombination motif is positioned between a regulatory element (e.g., a promoter) and the second polynucleotide. In one embodiment, the regulatory element controls expression of the second polynucleotide. In particular embodiments, the second site-specific recombination motif is positioned between a regulatory element (e.g., a promoter, such as a bacterial promoter, e.g., a CAM resistance gene promoter) and a polynucleotide encoding a recombinase enzyme (e.g., phiC31, bacteriophage lambda integrase, BxB1, Cre, or Flp). In a specific embodiment, the regulatory element does not control expression of the recombinase enzyme. In one embodiment, the regulatory element controls expression of the marker. In a preferred embodiment, the recombinant vector includes, in order, the promoter and the polynucleotide encoding the marker, such that the promoter controls expression of the marker from the recombinant vector.

In some embodiments of any of the sixth through ninth aspects, the second site-specific recombination motif is positioned upstream of (e.g., 5' to) the second polynucleotide. In certain embodiments, the second site-specific recombination motif is positioned upstream of (e.g., 5' to) a polynucleotide encoding a marker (e.g., a resistance marker, such as a CAM gene, ampR gene, or any other marker described herein). In certain embodiments, the first site-specific recombination motif is positioned between a regulatory element (e.g., a promoter) and the first polynucleotide. In one embodiment, the regulatory element controls expression of the first polynucleotide. In particular embodiments, the first site-specific recombination motif is positioned between a regulatory element (e.g., a promoter, such as a CAM promoter) and a polynucleotide encoding a recombinase enzyme (e.g., phiC31, bacteriophage lambda integrase, BxB1, Cre, or Flp). In a specific embodiment, the regulatory element does not control expression of the recombinase enzyme. In one embodiment, the regulatory element controls expression of the marker. In a preferred embodiment, the recombinant vector includes, in order, the promoter and the polynucleotide encoding the marker, such that the promoter controls expression of the marker from the recombinant vector.

In a tenth aspect, the invention features a kit including any of the compositions described herein (e.g., a composition of the sixth through tenth aspects) and instructions for producing a chimeric polypeptide according to any of the methods described herein (e.g., a method of the first through fifth aspects).

In an eleventh aspect, the invention features a method of converting a single-chain variable fragment (scFv) into an immunoglobulin G (IgG) antibody, comprising
  (a) providing a first phagemid vector comprising, in order from 5' to 3',
    a first Mammalian expression control motif,
    optionally, a first 5' mammalian splice site (Mam5'SS),
    a first *E. coli* expression control motif,
    optionally, a first 3' mammalian splice site (Mam3'SS),
    a sequence encoding a heavy chain variable region (VH) of the scFv,
    optionally, a second 5' mammalian splice site ($Mam_{5'ss}$),
    a first site-specific recombination motif,
    optionally, a second 3' mammalian splice site ($Mam_{3'ss}$),
    a sequence encoding a light chain variable region (VL) of the scFv,
    a third 5' mammalian splice site ($Mam_{5'ss}$),
    a fusion display protein sequence
    a third 3' mammalian splice site ($Mam_{3'ss}$),
    a sequence encoding a light chain constant region (CL),
  (b) providing a second phagemid vector comprising, in order from 5' to 3',
    a second Mammalian expression control motif
    optionally, a fourth 5' mammalian splice site (Mam5'SS),
    a second site-specific recombination motif,
    optionally, a fourth 3' mammalian splice site (Mam3'SS);
    a sequence encoding a fragment crystallizable (Fc) region (e.g., a region encoding a CH region); and
  c) contacting the first phagemid vector and the second phagemid vector in the presence of a recombinase,
    wherein the recombinase combines the first phagemid vector and the second phagemid vector in a site-specific manner to form an integrant vector,
    wherein the integrant vector expresses the VL fused to the CL and a separate VH fused to a polypeptide domain including the Fc (e.g., the CH region) to form an IgG,
    thereby upon expression converting a scFv into an IgG antibody.

In a twelfth aspect, the invention features a method of converting a single-chain variable fragment (scFv) into a CAR, comprising
  (a) providing a first phagemid vector comprising, in order from 5' to 3',
    a first Mammalian expression control motif,
    optionally, a first 5' mammalian splice site (Mam5'SS),
    a first *E. coli* expression control motif,
    optionally, a first 3' mammalian splice site (Mam3'SS),
    a sequence encoding a heavy chain variable region (VH) of the scFv,
    optionally, a second 5' mammalian splice site ($Mam_{5'ss}$),
    a first site-specific recombination motif,
    optionally, a second 3' mammalian splice site ($Mam_{3'ss}$),
    a sequence encoding a light chain variable region (VL) of the scFv,
    a third 5' mammalian splice site ($Mam_{5'ss}$),
    a fusion display protein sequence
    a third 3' mammalian splice site ($Mam_{3'ss}$),
    a sequence encoding a light chain constant region (CL),
  (b) providing a second phagemid vector comprising, in order from 5' to 3',
    a second site-specific recombination motif, and
    a sequence encoding a TCRζ region; and
  c) contacting the first phagemid vector and the second phagemid vector in the presence of a recombinase,
    wherein the recombinase combines the first phagemid vector and the second phagemid vector in a site-specific manner to form an integrant vector,
    wherein the integrant vector expresses the VL fused to the CL and a separate VH fused to the TCRζ region to form a CAR,
    thereby upon expression converting a scFv into an IgG antibody.

In some embodiments of the eleventh and twelfth aspects, the first phagemid vector includes a first termination codon between the third 5' mammalian splice site and the fusion display protein sequence and/or a second termination codon between the fusion display protein sequence and the third 3' mammalian splice site. In certain embodiments, the integrant vector is capable of expressing a selectable marker. In particular embodiments, the integrant vector is only capable of expressing the selectable marker after integration occurs.

Definitions

By "chimeric polypeptide" is meant a polypeptide including a fusion of at least two polypeptides and/or polypeptide fragments thereof. A chimeric polypeptide may include two or more distinct domains, each including at least one of the polypeptides (or a portion thereof) or polypeptide fragments. In some instances, a chimeric polypeptide includes an antigen-determining region of a binding moiety (e.g., an antibody variable domain) fused to a polypeptide domain with a desired functionality (e.g., an antibody constant domain, a CD3-zeta domain, a ubiquitin ligase domain, or a knocksideways prey domain). A polynucleotide (e.g., a vector) encoding a chimeric polypeptide can be generated according to the recombination methods described herein. For example, a chimeric polypeptide can be encoded by a polynucleotide in which the coding sequence of a first polypeptide, or a portion thereof, is attached to the coding sequence of a second polypeptide (or a fragment thereof), e.g., by recombination according to the methods of the present invention. Exemplary chimeric polypeptides include IgGs generated by fusing a variable domain (e.g., one or more VH or VL domains) from an antibody or antibody fragment (e.g., an scFv) to a constant domain (e.g., one or more CH or CL domains), chimeric antigen receptors (CARs) generated by fusing a variable domain from an antibody (e.g., one or more VH or VL domains) to a heterologous transmembrane domain and cytoplasmic domain (e.g., a CD3-zeta domain), and fusions between a binding moiety (or a portion thereof) and a ubiquitin ligase domain or knocksideways prey domain.

"Polypeptide fragment," as used herein, means any amino acid sequence that is less than a full-length wild-type polypeptide. A polypeptide fragment of the invention can include one or more of, for example, an antigen-determining region (e.g., an antibody variable domain), a structural domain (e.g., an antibody constant domain), a framework (e.g., as described herein), a transmembrane domain (e.g., a CD3-zeta transmembrane domain), a domain capable of signal transduction (e.g., a CD3-zeta cytoplasmic domain), a domain having a desired function (e.g., a ubiquitin ligase domain or knocksideways prey domain), or any other polypeptide portion known in the art. In some instances, a polynucleotide encoding a polypeptide fragment can be present on a vector (e.g., a first vector or a second vector). In certain instances, the polynucleotide encoding the polypeptide fragment can be conjugated to another polynucleotide encoding a polypeptide (e.g., a first polypeptide, a second polypeptide, or a fragment thereof) by recombination of the vector with a vector including the other polynucleotide according to the methods of the invention.

"Recombinant vector" or "integrant vector" means a polynucleotide vector formed by recombination of two parent vectors (e.g., a first vector and a second vector of the invention). The parent vectors to be recombined may each include a site-specific recombination motif, such that the two site-specific recombination motifs can be recombined by a recombinase enzyme to attach at least a portion of one vector to at least a portion of the other, thereby forming the new recombinant vector. A recombinant vector may include one or more polynucleotides encoding the same or different polypeptides from those of the parent vectors. In some instances, a polynucleotide encoding a first polypeptide, or a fragment thereof (e.g., an antigen-determining region, such as a variable domain from an antibody or an antibody fragment), from one parent vector (e.g., a first vector of the invention) can be attached to a polynucleotide encoding a second polypeptide (e.g., a framework, such as a constant region from an antibody or antibody fragment; a CAR transmembrane and/or cytoplasmic domain; a ubiquitin ligase domain; and/or a knocksideways prey domain), or a fragment thereof, from the other vector to form a polynucleotide in the recombinant vector that encodes a chimeric polypeptide, which includes both the polypeptide, or a fragment thereof, from the first parent vector and the second polypeptide, or a fragment thereof, from the second parent vector.

"Binding moiety" means an agent capable of binding a target molecule, for example, a target protein, such as an antigen. In some instances, a binding moiety is a protein, polypeptide, polypeptide fragment, nucleic acid, polysaccharide, small molecule, aptamer, or any combination thereof. A particular binding moiety is a "cognate" to a target if it is capable of binding that target. A binding moiety can, in some instances, include one or more subunits (e.g., one or more of the same subunit, or one or more distinct subunits), e.g., such that the subunits must be in close physical proximity for the binding moiety to function. In certain instances in which a binding moiety is composed of multiple subunits, the subunits may be brought into close proximity by the interaction of two or more of the subunits. Exemplary binding moieties include, without limitation, antibodies, antibody fragments, and binding proteins, or fragments thereof.

"Antibody" means any form of immunoglobulin, heavy chain antibody, light chain antibody, LRR-based antibody, or other protein scaffold with antibody-like properties, as well as any other immunological binding moiety known in the art, including antibody fragments (e.g., a Fab, Fab', Fab'2, F(ab')$_2$, Fd, Fv, Feb, scFv, or SMIP). The subunit structures and three-dimensional configurations of different classes of antibodies are known in the art.

"Antibody fragment" means a binding moiety that includes a portion derived from or having significant homology to an antibody, such as the antigen-determining region of an antibody. Exemplary antibody fragments include Fab, Fab', Fab'2, F(ab')$_2$, Fd, Fv, Feb, scFv, and SMIP.

By "chimeric antigen receptor" (CAR) is meant a polypeptide binding moiety including a binding moiety portion, a transmembrane domain, and a cytoplasmic domain, in which binding of a ligand to the binding moiety portion results in activation of a downstream signaling pathway by the cytoplasmic domain. In some instances, the binding moiety portion is an antibody or antibody fragment (e.g., an scFv). In certain instances, the transmembrane domain and/or cytoplasmic domain are derived from membrane-bound receptors expressed by an immune cell (e.g., a T cell). For example, the transmembrane domain and/or cytoplasmic domain may be derived from CD8 (e.g., the hinge and/or transmembrane domain of CD8), CD3-zeta and/or CD28. The cytoplasmic domain may include one or more polypeptide domains capable of transmitting activation signals to the immune cell (e.g., the T cell). For example, the polypeptide domains can include a CD3-zeta cytoplasmic domain, a CD28 cytoplasmic domain, a 4-1 BB cytoplasmic domain, an OX40 domain, an ICOS domain, and/or any combination or derivative thereof. A CAR, or portions thereof, can be fused to another polypeptide (e.g., a binding moiety) according to the recombination methods of the invention.

"Ubiquitin ligase domain," as used herein, means a polypeptide domain capable of catalyzing the transfer of ubiquitin to a polypeptide substrate. A ubiquitin ligase domain can be fused to another polypeptide (e.g., a binding moiety) according to the recombination methods of the invention. In some instances, ubiquitin ligase domains useful in the methods and compositions of the invention include E3 ligase domains (e.g., C-terminus of Hsc70 Interacting Protein (CHIP) E3 ligase). Ubiquitin ligases and uses thereof, e.g., for targeted protein silencing, are described, for example, in Portnoff et al. (*J. Biol. Chem.* 289: 7844-7855, 2014), incorporated by reference herein in its entirety.

"Knocksideways prey domain" means a polypeptide domain that can be used for rapid inactivation of a target protein by sequestering the target protein to an intracellular region, for example, as described in Robinson and Hirst (*Curr. Protoc. Cell Biol.* 61:15.20.1-15.20.7, 2013) and Robinson et al. (*Dev. Cell* 18: 324-331, 2010), each of which is incorporated by reference herein in its entirety. In some instances, a knocksideways prey domain can bind to a knocksideways bait protein in the presence of a particular small molecule (e.g., rapamycin or a rapamycin analogue). In certain instances, a knocksideways prey domain includes a binding domain that recognizes a target protein to be sequestered (e.g., a binding moiety of the invention) and a second binding domain that recognizes the small molecule, such that the presence of the small molecule results in the formation of a complex including the knocksideways prey domain, the target protein, the small molecule, and the knocksideways bait protein. The knocksideways bait protein may, in some instances, be attached to an intracellular organelle (e.g., a mitochondrion), such that the formation of the complex results in sequestration of the target protein to the intracellular organelle. In certain embodiments, the knocksideways bait protein includes an FRB domain, the knocksideways prey domain includes an FKBP domain, and the small molecule is rapamycin or a derivative thereof. In one embodiment, the knocksideways bait protein is a Mitotrap protein, as described in Robinson and Hirst, supra.

"Fusion protein" means a single protein or polypeptide that includes two protein or polypeptide segments joined together. Generally, the two protein or polypeptide segments are not naturally joined together.

"Linker," as used herein, means a peptide that connects two polypeptide regions. A linker may be, for example, 0-100 amino acids in length (e.g., about 0, 1, 2, 3, 4, 5, 6, 7, 8, 9, 10, 11, 12, 13, 14, 15, 20, 25, 30, 40, 50, 75, or 100 amino acids in length). A linker may include a stalk region (e.g., a stalk region including a site-specific recombination motif, such as an attB site or an attP site). The stalk may be of any length suitable for placing distance between the two linked polypeptide regions (e.g., about 1, 2, 3, 4, 5, 6, 7, 8, 9, 10, 11, 12, 13, 14, 15, 20, 21, 22, 23, 24, 25, 30, 40, 50, 75, or 100 amino acids in length, or more). In some instances, a linker connects two segments of a fusion protein. In some instances, a linker connects two antigen-determining regions of a binding moiety (e.g., variable domains of an antibody or antibody fragment). In one embodiment, a linker connects the heavy chain variable domain of an scFv to the light chain variable domain.

"Constant region" means a portion of a binding moiety (e.g., an antibody or antibody fragment) that is substantially conserved across binding moieties of a particular type or group. The identification of binding moiety constant regions, in some instances referred to as constant domains, is well known in the art.

"Framework," as used herein, means a set of one or more constant regions of a particular type or group of polypeptides (e.g., binding moieties), or a portion thereof, optionally in an arrangement characteristic of that type or group of binding moiety. In some instances, a framework includes an antibody framework region (e.g., a region in the variable domain of an antibody outside of and having less variability than the complementarity determining regions). In other instances, a framework includes a constant region of an antibody (e.g., an immunoglobulin light chain constant region or an immunoglobulin heavy chain constant region). In certain instances, the framework includes a fragment crystallizable (Fc) region.

"Antigen-determining region" means a portion of a binding moiety that substantially varies within a particular type or group of binding moieties. The identification of antigen-determining regions, in some instances referred to as variable domains, is well known in the art. Exemplary antigen-determining regions include, for example, a heavy chain variable domain (VH), a light chain variable domain (VL), and a complementarity determining region (CDR; e.g., a CDR located within a VH or VL domain).

As used herein, the "type" of a polypeptide (e.g., a binding moiety) means a group of polypeptides (e.g., binding moieties) characterized by the particular configuration of constituent regions, optionally including one or more functional domains, constant regions, one or more antigen-determining regions, one or more linkers, and/or other optional binding moiety cassettes known in the art. Types of polypeptides, such as binding moieties, are known to those of skill in the art and include, without limitation, IgG (e.g., IgG1, IgG2, IgG3, and IgG4), IgM, IgA (e.g., IgA1, IgA2, and IgAsec), IgD, IgE, Fab, Fab', Fab'2, F(ab')$_2$, Fd, Fv, Feb, scFv, or SMIP binding moieties. In some embodiments, a polypeptide is an scFv.

"Conversion" of a first polypeptide to a chimeric polypeptide means that the first polypeptide, or one or more portions thereof, is fused to a second polypeptide, or one or more portions thereof, thereby forming a chimeric polypeptide including at least a portion of the first polypeptide and at least a portion of the second polypeptide. In some instances, polynucleotide segments encoding an antigen-determining region of a binding moiety, or fragments thereof, are combined with a polynucleotide segment encoding at least a portion of the framework of a distinct binding moiety to form a polynucleotide segment encoding a chimeric binding moiety (e.g., a binding moiety of a different type). For example, the methods of the invention can be used to convert an scFv binding moiety to, e.g., an IgG binding moiety.

"Recombination motif" means a nucleic acid sequence or domain having a first pattern of nucleic acids that is capable of participating in a recombination event with a second nucleic acid sequence or domain having a second pattern of nucleic acids. Two recombination motifs recombination motifs capable of participating in a recombination reaction with each other may be referred to as, e.g., complementary. Two recombination motifs recombination motifs incapable of participating in a recombination reaction with each other may be referred to as, e.g., orthogonal. The recombination reaction may involve additional reagents or specific conditions. "Recombination enzyme" or "recombinase enzyme" means an enzyme or plurality of enzymes capable of facilitating recombination between complementary recombination motifs.

"Site-specific recombination motif" means a recombination motif capable of participating in a recombination event with a second recombination motif in a sequence-dependent manner. The site-specific recombination event may involve additional reagents or specific conditions. A "cryptic site-specific recombination motif" is a site-specific recombination motif that is hidden until a particular event (e.g., recombination according the methods described herein or digestion by a restriction enzyme) occurs. For example, a cryptic site-specific recombination motif may be made up of two or more separate nucleic acid elements that are brought together after recombination of two vectors according to the methods of the invention, such that upon recombination, a complete and unbroken site-specific recombination motif capable of being recognized by a recombinase enzyme is formed. In some instances, a cryptic site-specific recombination motif can be converted into a functional site-specific recombination motif by a restriction digestion, such as well known in the art.

An "ADAR enzyme" is a double-stranded RNA-specific adenosine deaminase enzyme capable of modifying a polynucleotide at specific nucleic acids (e.g., mRNA). In some instances, an ADAR enzyme performs post-transcriptional modification, or "editing," of an mRNA sequence, for example, by converting an adenosine to inosine. As inosine mimics the activity of a guanosine (e.g., pairing with cytosine), this can effectively result in the formation of a single-nucleotide polymorphism in the transcribed mRNA sequence. In some instances, editing can result in the formation a "cryptic" splice site, recombination motif, or other nucleic acid element. ADAR enzymes and RNA editing are described in Savva et al. (*Genome Biol.* 13: 252, 2012), Nishikura (*Annu. Rev. Biochem.* 79: 2.1-2.29, 2010), and Schoft et al. (*Nuc. Acids Res.* 35(11): 3723-3732, 2007), each of which is incorporated herein in its entirety.

"Express" or "expression" means the transcription, or transcription and translation, of a polynucleotide segment. A polynucleotide segment that is expressed is a polynucleotide segment from which a transcript has been generated and, optionally, that a protein has been generated from the transcript. Accordingly, a transcript or protein that has been expressed is a transcript or protein generated by the transcription, or transcription and translation, respectively, of a polynucleotide segment. Two proteins, polypeptides, or polynucleotide segments that may be expressed as a single transcript and/or protein or polypeptide may be referred to as "fused."

"Regulatory element" means a polynucleotide segment that contributes to the control of the expression of a polynucleotide segment present in the same nucleic acid, such as an adjacent and/or 3' polynucleotide segment, or the sequence thereof. A regulatory element may, for example, increase or decrease the expression of the polynucleotide segment. A regulatory element may be activated or inhibited by the binding of one or more transcription factors. Exemplary regulatory elements include, without limitation, promoters, enhancers, and silencers.

The term "vector," as used herein, refers to any polynucleotide molecule that can be used to carry genetic material, for example, into a cell, as known in the art. In some instances, a vector is an expression vector including one or more polynucleotides (e.g., polynucleotides encoding polypeptides) to be expressed. Exemplary vectors include, without limitation, plasmids, phagemids, cosmids, viral vectors, and artificial chromosomes (e.g., bacterial artificial chromosomes or yeast artificial chromosomes). Viral vectors may include, for example, retroviral vectors, lentiviral vectors, and adenoviral vectors. Methods for producing such vectors are well known in the art.

By "Mitotrap protein" is meant a knocksideways bait protein including a mitochondrial outer membrane targeting signal derived from the yeast protein Tom70, a YFP reporter, an HA tag, and an FRB domain, as described, for example, by Robinson and Hirst, supra. The Mitotrap protein and other knocksideways bait proteins as contemplated herein and as known in the art, or portions thereof, may be useable first polypeptides, second polypeptides, or chimeric polypeptides of the invention.

A "cryptic splice site" is an mRNA splice site that is hidden until a particular event (e.g., recombination between a first vector and a second vector according the methods described herein) occurs. For example, a cryptic splice site may be made up of two or more separate nucleic acid elements that are brought together after recombination of two vectors according to the methods of the invention, such that upon recombination, a complete and unbroken mRNA splice site is present in a polynucleotide in the resultant integrant vector. As a result, when the polynucleotide is transcribed, e.g., in a eukaryotic cell capable of performing mRNA splicing, the polynucleotide will be spliced at the splice site generated by the recombination event.

BRIEF DESCRIPTION OF THE DRAWINGS

FIGS. 2A-2C are a series of schematics showing a multifunctional intron including a promoter and signal peptide designed for multiple expression hosts. (A) An artificially-constructed DNA sequence is shown, which includes, e.g., a CMV promoter (nucleic acid sequence shown), mammalian and bacterial signal peptides (amino acid sequence and nucleic acid sequence shown), the first portion of a VH sequence, and sequences for miscellaneous elements. (B) In this panel, the elements of the bacterial expression cassette, which includes an *E. coli* lac promoter, the bacterial signal peptide, and the VH gene, are highlighted. (C) In this panel, the elements of the mammalian expression cassette, which includes the CMV promoter, mammalian signal peptide, the intron containing the bacterial elements (which may be excised during mRNA processing), and the VH gene, are highlighted.

FIGS. 21A-21O are a series of diagrams showing an scFv to IgG reformatting approach based on dual expression promoter systems: (A, C) promoter splicing (Pro$^{splice}$) or (B, D) catenated polyfunctional promoter (Pro$^{cat}$). (A) In the Pro$^{splice}$ spliced promoter system, a bacterial promoter (e.g., LacPO) is positioned within a mammalian intron, such that the bacterial promoter will be used to drive transcription in a bacterial cell, but will be spliced out in a cell capable of splicing, such as a mammalian cell. (B) In the Pro$^{cat}$ catenated promoter system, multiple promoters (e.g., a CMV promoter, polyhedron promoter, and LacPO promoter) are concatenated to each other upstream of the gene to be expressed. ATG start codons are removed from the promoters downstream of the 5'-most promoter, such that the start site is identical for all cell types (e.g., mammalian, insect, and bacterial cells, respectively). (C) In one embodiment of a Pro$^{splice}$ dual function promoter system, the LacPO and bacterial signal peptide (SigPep$^{E.c.}$) sequence may be contained within the mammalian intron. The bacterial signal peptide sequence may, for example, overlap the 3' splice site (3'ss). In E. coli, transcription from the bacterial promoter within the mammalian intron results in the expression of the scFv in the bacterial periplasm fused to the M13gp3 protein in an amber-suppressing strain of E. coli (e.g., TG1). In mammalian cells, intron splicing of the mRNA at the 5' (5'ss) and 3'ss removes the bacterial LacPO regulatory sequences located within the intron. Intron splicing may desirably generate the mammalian signal sequence. This intron nucleotide sequence may include promoter consensus sequences, signal sequence consensus sequences, and splice site consensus sequences such as those known in the art. (D) In another example of a catenated promoter system, the ATG start sites downstream of a mammalian promoter (e.g., $P^{CMV}$) may be removed from a lac promoter/operator (LacPO) controlling element. A downstream polyhedron promoter may be included as described herein. The Kozak sequence and E. coli ribosomal binding site (RBS) may be designed such that the first ATG fMet start site for bacterial, insect, and/or mammalian expression is identical. In one example, the same signal sequence (Sig Pep) may be used for all three organisms.

FIGS. 22A-22B are a series of images showing the results of splicing of a gp3 gene in the expression of a light chain in mammalian cell culture and expression of dual expression promoters. (A) Comparison of a wild-type light chain with a light chain incorporating a gp3-splice gene. The arrow indicates the band corresponding to the light chain gene product. (B) Expression comparison of an IgG grown in HEK293 cells under the expression control of either an E1A promoter, Pro$^{splice}$ or Pro$^{cat}$.

FIG. 23 is a table showing different types of potential pMINERVA constant framework libraries. Exemplary framework regions useful in the vector systems of the invention include, without limitation, IgY (avian), camelid, IgNAR (shark), mammalian IgG (e.g., bovine, rabbit), other IgGs, mammalian IgM, and Fab (e.g., yeast display Fab). Potential advantages for such frameworks, in the context of a pMINERVA library, are also provided.

FIGS. 24A-24E are a series a diagrams showing the pMINERVA transformer system and the expression and function of scFvs and IgGs including phiC31 integrase sites. (A) The pMINERVA system features three vectors: a pDonor phagemid vector encoding an scFv, a pAcceptor vector, and an IgG expression vector. scFv antibodies encoded on the pDonor vector as M13gpIII-fusions can be screened in a phage display biopanning procedure to identify a phagemid encoding a scFv with the desired biophysical properties. This phagemid is transduced into an E. coli strain expressing phiC31 integrase and harboring an IgG acceptor vector. The recombination event fuses the VH region to the CH region. Furthermore, the recombination event introduces both a mammalian promoter and functional protein initiation site 5' to the $V_L$ gene. Of special note, the linker between the $V_H$ and $V_L$ domains of the scFv is composed of a phiC31 36-bp attP site that is able to function as both: (i) a peptide linker between the heavy and light variable domains, and (ii) a 36-bp functional substrate for phiC31 integrase. $P_{mam}$, mammalian promoter; 5'ss and 3'ss, splice signals; $V_L$, variable section of the light chain; $V_H$, variable section of the heavy chain; gp3, phage M13 gene3 product; $P_{E.\ coli}$, E. coli promoter; $C_H$ or Fc, constant region of the heavy chain; attB, attP, substrates for an integrase gene; attR and attL, products of an integrase gene; polyA, polyadenylation sequence; Cam$^S$, CamR, chloramphenicol resistance gene without and with a promoter, respectively; Pro$^{splice}$, Pro$^{cat}$, dual-function promoter-types; RBS, ribosome binding site. (B) The same scFv with two different linker sequences, WT (Gly$_4$Ser)$_3$ or the phiC31 attP site in reading frame 2, was produced. Both phage-scFvs were tested in an ELISA against the purified target protein or a non-relevant antigen control. Anti-M13 antibody that is conjugated to Horseradish peroxidase (HRP) was used for phage detection and the enzyme linked immunosorbent assay (ELISA) was developed with Ultra Tetramethylbenzidine (TMB) reagent. The fold over background (FOB), which is the signal against target over the signal against non-relevant control, is shown for each phage tested. Error bars represent the standard deviation of phage binding tested in triplicate. (C) IgG molecule modeled with attL and attR. The attL (thick blue loop) and attR (thick red loop) peptides are inserted schematically in a typical human IgG1 molecule (PDB ID: 1 hzh) shown as ribbons (heavy chain: white, light chain: cyan). (D) The same IgG, with either no linker or the recombined phiC31 integrase attL site between the IL2 signal sequence (ss) and V$_L$, was produced. In parallel, expression of the wild-type IgG was compared to expression of the same IgG with the recombined phiC31 integrase site attR site between V$_H$ and C$_H$. A coommassie stained SDS-PAGE gel is shown. (E) An IgG with attL between the IL2ss and the V$_L$ (top graph) and an IgG with attR between V$_H$ and C$_H$ (bottom graph) were tested for binding to both a specific and a non-relevant target antigen in a cell ELISA. The binding of both molecules was compared to the binding of a wildtype IgG. Both ELISAs used anti-human-HRP to detect the IgGs and the ELISA was developed with Ultra TMB reagent. The ODs at 450 nm are shown.

FIGS. 25A-25J are a series of diagrams and tables showing use and validation of the pMINERVA system and permutations thereof. (A) Positive selection of phiC31 integrase activity. The two plasmids of the pMINERVA system, pDonor and pAcceptor, each having a needed component in trans for a functional camR gene, were constructed. The attP site (underlined) in pDonor was flanked upstream by the *E. coli* 5' controlling elements and. The attB site (lower case DNA sequence) in pAcceptor was placed 5' of the promoter-less camR gene. Successful recombination between the attP and attB sites on the two plasmids in the presence of the phiC31 integrase (blue dashed line) generates the co-integrant (pMINERVA; bottom sequence) and fuses an *E. coli* promoter in front of the bi-cistronic heavy chain-Cam$^R$ message. (B) Expression and function of scFvs and IgG containing splice sites flanking the M13 gpIII gene. Competent TG1 cells containing pAcceptor were transformed with pDonor or a control mock-recombined vector and grown on plates containing ampicillin or chloramphenicol. The ratio of colonies on the ampicillin plates to the chloramphenicol plates was calculated. (C) Phage-scFv fusions with and without splice sites flanking the M13gpIII gene in pDonor were produced from *E. coli* and tested for functionality in a phage ELISA. The phage-scFv were tested for binding to purified target antigen and a non-relevant control protein. The fold over background (FOB) is shown for both. Error bars represent the standard deviation of phage binding, tested in triplicate. (D) The same IgG, with either no linker or the intron containing the M13gpIII gene between the V$_H$ and C$_H$ was produced. An ochre stop codon placed 3' of the M13gpIII gene prevents full length light chain protein expression from non-spliced mRNAs. The upper arrow indicates the band corresponding to the heavy chain and the lower arrow corresponds to the light chain gene product in the SDS-PAGE. IgG molecules were tested for functionality in an ELISA using purified antigen. FOB (fold-over-background) signal is shown for both. (E) In the catenated dual promoter system (Pro$^{cat}$), the ATGs downstream of the mammalian EF1a promoter (P$^{EF1a}$) are removed from the downstream polyhedron (not shown) and PhoA bacterial promoter. The Kozak sequence and *E. coli* ribosomal binding site (RBS) are designed such that the first ATG fMet start site for either bacterial, insect (not shown) or mammalian expression is identical. In this case, the same signal sequence (Sig Pep) is used for all three organisms. (F) In the spliced dual function promoter system (Pro$^{splice}$), the LacPO and bacterial signal peptide (SigPep$^{E.c.}$) sequence are contained within the mammalian intron. The bacterial signal peptide sequence overlaps the 3' splice site (3'ss). In *E. coli*, transcription from the bacterial promoter within the mammalian intron results in the expression of the scFv in the bacterial periplasm fused to the M13gpIII protein in an amber-suppressing strain of *E. coli* (for example, TG1). In mammalian cells, intron splicing of the mRNA at the 5' (5'ss) and 3'ss removes the bacterial LacPO regulatory sequences located within the intron. Intron splicing generates the mammalian signal sequence. (G) Phage-scFv production from the Pro$^{cat}$ and Pro$^{splice}$ promoters. Phage were tested for binding to purified target antigen and to a non-relevant control antigen in a phage ELISA. FOB (fold-over-background) signal is shown and error bars represent the standard deviation of phage binding tested in triplicate. (H) Expression of the wild type (wt), Pro$^{splice}$ and Pro$^{cat}$ promoters in HEK293 mammalian cells. IgG purification from HEK293 cells where the IgG heavy chain gene was under the expression control of either an EF1A promoter alone, Pro$^{splice}$ or Pro$^{cat}$. (I) Genetic elements used in the pDonor and pAcceptor system. The source of each element used in the pMINERVA system is indicated. Also indicated is whether the genetic element was synthesized or cloned from an existing plasmid. (J) Yield analysis of IgG expression test vector. Eleven scFv V$_H$ and V$_L$ sequences were cloned into a single IgG expression test vector using the Pro$^{cat}$ promoter to drive the heavy chain. The IgG vectors were transfected into HEK293 cells and the secreted IgG proteins were purified from the supernatant six days post-transfection. The amount of final purified IgG was determined and yields were calculated based on transfecting 100 mL cell culture volumes.

FIGS. 28A-28B are a series of diagrams showing examples of 3' fusion constructs that may be used, for example, in pAcceptor plasmids of the invention (FIG. 28A), and an exemplary pAcceptor vector expressing an scFv that may be converted to a pMINERVA integrant vector expressing an IgG (FIG. 28B).

FIG. 32 is a graph showing functional validation of a hybrid chimera. The FLGA tag in the hybrid chimera was confirmed to be functional.

DETAILED DESCRIPTION

Figure 1:
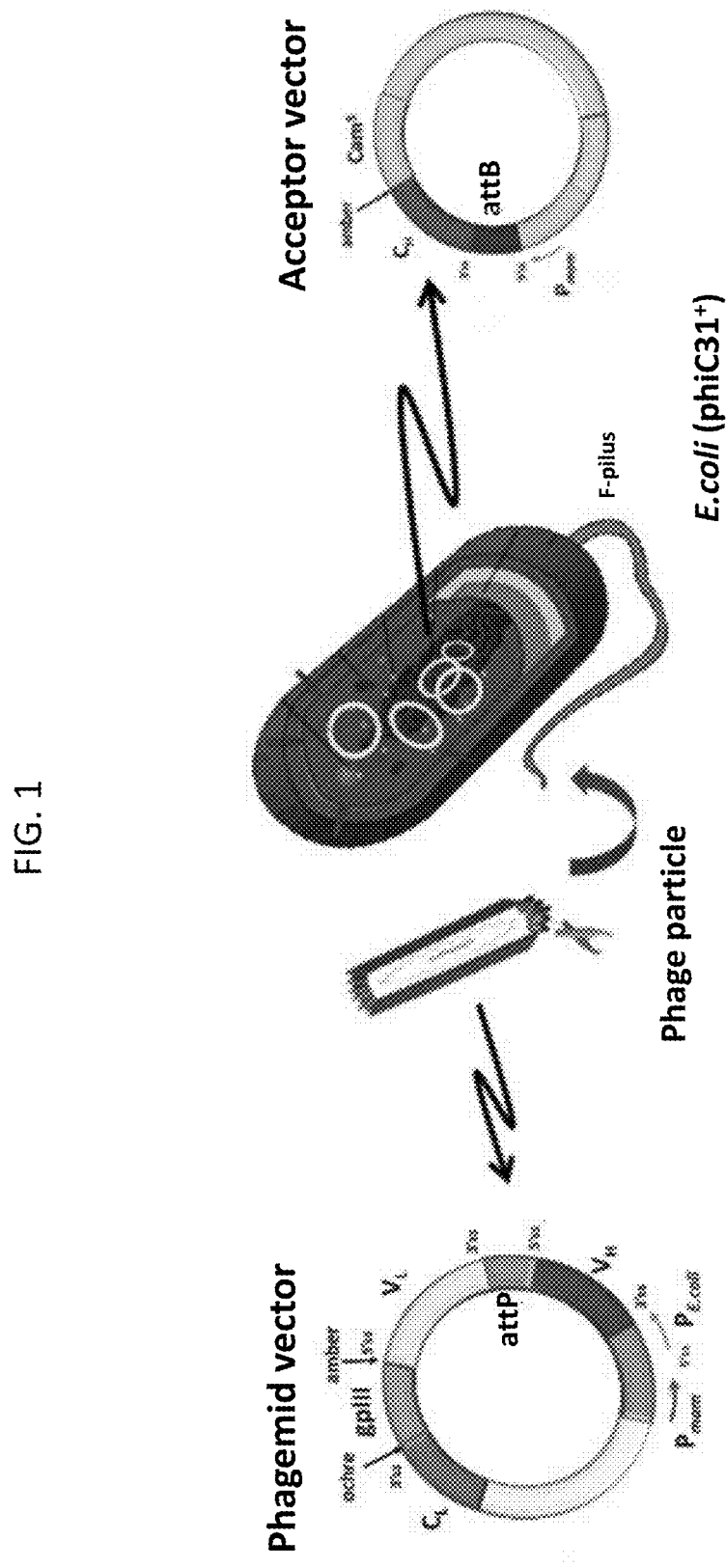
FIG. 1 is a schematic showing transduction of an *E. coli* cell with a phagemid vector. The *E. coli* cell includes an acceptor vector that can be recombined with the phagemid vector, for example, by a recombinase enzyme (e.g., phiC31). In this example, the phagemid vector encodes an scFv, in which the linker is encoded by a site-specific recombination motif (e.g., an attP or attB site; preferably an attP site), and the acceptor vector includes a heavy chain constant region and a chloramphenicol resistance cassette.

In general, the present invention provides methods and compositions for converting a first polypeptide into a chimeric polypeptide. In some embodiments, the invention includes at least two vectors: a first vector including the sequence of the first polypeptide and a second vector including the sequence of a second polypeptide. The vectors include complementary site-specific recombination motifs such that site-specific recombination between the two vectors results in the generation of a chimeric polypeptide including at least a portion of the first polypeptide and at least a portion of the second polypeptide. A site-specific recombination motif may be positioned within an intron or within a coding sequence on the first or second vector.

Methods of Converting a First Polypeptide into a Chimeric Polypeptide

The present invention provides methods for converting a first polypeptide into a chimeric polypeptide using, for example, a pair of vectors that can be recombined. For example, one of the vectors includes a polynucleotide segment encoding the first polypeptide, or a fragment thereof, while the second vector includes a polynucleotide segment encoding the second polypeptide, or a fragment thereof. Each of the vectors further includes a recombination motif (e.g., a site-specific recombination motif), such that the two vectors can be integrated by a recombinase enzyme, such as an integrase (e.g., phiC31 integrase). Thus, the methods of the invention involve providing the pair of vectors and inducing recombination, thereby integrating the two vectors into an integrant vector in which the first polypeptide, or a fragment thereof, and the second polypeptide, or a fragment thereof, are fused to form the chimeric polypeptide. Vectors, recombinase enzymes, and recombination motifs that may be used in the methods of the invention are described in detail below.

In some instances, the recombination event occurs in a cell. For example, a cell may contain both vectors and the recombinase enzyme, thereby initiating integration of the vectors. In certain embodiments, the cell initially contains one vector (e.g., the second vector) and is transfected or transformed with the other vector. A gene encoding the recombinase enzyme may be present in one of the first or second vectors, a third vector within the cell, or in the genome of the cell. A variation of this method is contemplated in which the polynucleotide encoding a first polypeptide or a second polypeptide can be present in the genome of the cell, rather than in a vector. The genomic sequence may be positioned near to or contain a recombination motif that can be recombined with the recombination motif of a first vector or a second vector of the invention. As such, recombination between the recombination motif of the vector and the genomic recombination motif results in integration of elements of the vector (e.g., a polynucleotide sequence encoding a first polypeptide or a second polypeptide, or a fragment thereof) into the genome of the cell.

In some instances, the recombination event occurs in vitro. For example, the first and second vector may be present in a solution together with a recombinase enzyme (e.g., bacteriophage lambda integrase). In certain instances, the first vector, second vector, and a recombinase enzyme may be present in a container, such as an emulsion droplet. Distinct combinations of first vectors, second vectors, and/or recombinase enzymes can be present in each of a plurality of emulsion droplets. As such, a plurality of distinct integrant vectors can be generated in a series of parallel reactions, each occurring in a separate emulsion droplet. Emulsion droplets may thus be used for, e.g., immunorepertoire cloning.

For example, a plurality of polypeptides (e.g., polypeptides each including a distinct antigen-determining region, such as variable domains or CDRs) may each be encoded on separate first vectors. In some instances, each first vector is contained in a separate emulsion droplet. Each emulsion droplet may further include a second vector and a recombinase enzyme. In one embodiment, each of the second vectors encodes the same framework. Thus, in this example, a plurality of integrant vectors, each including, e.g., a distinct antigen-determining region, but all containing the same second polypeptide, or a fragment thereof, are produced as a result of recombination between the first vector and the second vector present within each emulsion droplet.

Compositions

The invention features compositions including a vector encoding a first polypeptide that can be converted to a chimeric polypeptide (e.g., a polypeptide of a different type) according to the methods described herein. The composition may further include a second vector encoding a second polypeptide. The second polypeptide, or a fragment thereof, can be combined with the first polypeptide, or a fragment thereof, to form the chimeric polypeptide. Each of the vectors may include a recombination motif (e.g., a site-specific recombination motif). In some instances, the site-specific recombination motif of the two vectors are complementary, such that a recombinase enzyme (e.g., as described herein) can recombine the two vectors to form an integrant vector including components of both of the original vectors (e.g., the polynucleotide encoding the first polypeptide, the polynucleotide encoding the second polypeptide, or portions thereof). The composition may also include the recombinase enzyme. Exemplary vectors and recombinase enzymes suitable for inclusion in compositions of the invention are described in detail herein.

Vectors

The present invention features nucleic acid vectors (e.g., a first vector or a second vector) that may be used to convert a first polypeptide into a chimeric polypeptide (e.g., a polypeptide of a different type). Two such nucleic acid vectors may include site-specific recombination motifs that permit recombination between the two vectors to produce a recombination product (e.g., an integrant vector) including elements from the two original vectors (e.g., in the form of a polynucleotide segment encoding a chimeric polypeptide). Preferably, a first vector includes a first polypeptide to be converted, and a second vector includes a second polypeptide (e.g., a polypeptide including a binding moiety framework and/or a functional domain of interest). The second polypeptide, or a fragment thereof, may be fused to the first polypeptide, or a fragment thereof, to form a chimeric polypeptide. As such, site-specific recombination between the first vector and the second vector results in the formation of an integrant vector encoding the chimeric polypeptide.

An integrant vector of the invention may include any component of a first vector and/or a second vector. In some instances, an integrant vector may be used as a first vector or a second vector in a further recombination reaction with a further vector (e.g., a further vector including a further first polypeptide or a further second polypeptide), thereby forming another integrant vector including portions of the original integrant vector and the further vector. This may be used, for example, to convert the chimeric polypeptide back into the first polypeptide, or to, e.g., convert the chimeric polypeptide into a further chimeric polypeptide including at least a portion of the chimeric polypeptide and the further first polypeptide or further second polypeptide.

A vector of the invention (e.g., a first vector, a second vector, or an integrant vector) may include multiple distinct site-specific recombination motifs (e.g., orthogonal site-specific recombination motifs or complementary site-specific recombination motifs). For example, a vector may include 1, 2, 3, 4, 5, 6, 7, 8, 9, 10, or more site-specific recombination motifs. In some instances, a vector may include a mix of complementary and orthogonal site-specific recombination motifs, such that the vector can be recombined internally via the complementary site-specific recombination motifs, or recombined with another vector containing a site-specific recombination motif complementary to one of the site-specification recombination motifs of the vector.

In some instances, a vector of the invention may be capable of expressing one gene (e.g., a gene encoding a first polypeptide) in one cell type, and a second gene in a second cell type. In certain instances, a vector may be capable of expressing one variant of a gene (e.g., a gene encoding a first polypeptide) in one cell type (e.g., expressing an scFv in bacterial cells), and a second variant of the same gene in a second cell type (e.g., an scFv-Fc fusion or an IgG in mammalian or insect cells). For example, one or more portions of one variant of the gene may be positioned within an intron, such that these portion(s) are expressed in cells that do not perform intron splicing, such as bacteria, but are removed from the transcript by intron splicing in eukaryotic cells (e.g., mammalian cells and insect cells). In one example, an antibody fragment (e.g., a Fab fragment or scFv) fused to a phage coat protein, suitable for use in phage display, can be expressed in bacteria (e.g., E. coli) while a full-length IgG variant of the antibody fragment can be expressed in mammalian cells from a single vector by embedding the phage coat protein in an intron within the immunoglobulin heavy chain gene (see, e.g., Tesar and Hotzel, Prot. Eng. Des. Selection 26(10): 655-662, 2013; incorporated herein by reference).

A vector may include regulatory elements (e.g., promoters, enhancers, and silencers) that control the expression of particular variants in particular cell types. In some instances, a vector of the invention may be able to express a gene (or variants and/or portions thereof) in multiple cell types. For example, the vector may include a plurality of regulatory elements, each capable of controlling (e.g., activating or inhibiting) expression of the gene in a distinct cell type. In certain instances, one or more of these regulatory elements may be positioned in an intron, as described herein.

In some instances, a vector includes one or more site-specific recombination motifs. Such site-specific recombination motifs may, for example, permit excision of elements from the vector and/or site-specific recombination with a second vector to generate a hybrid vector. Site-specific recombination between two vectors may result in the generation of an integrant vector encoding a chimeric polypeptide, as described herein. A vector of the invention (e.g., a first vector or a second vector) can be produced, for example, according to methods well known in the art. For example, existing expression vectors can be modified by standard techniques, including, for example, restriction enzyme digestion, ligation, polymerase chain reaction (PCR), site-directed mutagenesis, and random mutagenesis. Vectors can also be synthesized, for example, as described in U.S. Provisional Application No. 62/087,440, incorporated herein by reference. A library of vectors (e.g., a phage display library) can be generated according to methods known in the art. For example, a library can be produced by directed evolution, e.g., as described in PCT Application No. PCT/US2014/018672, incorporated herein by reference. A library of vectors (e.g., first vectors or second vectors) may be generated, for example, as variants of an initial clone (e.g., by mutagenesis methods well known in the art). A vector library may also be generated, for example, by the methods described in PCT Publication No. WO 2014/134166, incorporated herein by reference in its entirety.

The vectors of a vector library can be screened for antigen binding, for example, by delayed infectivity methods (e.g., delayed emulsion infectivity screening), such as described in PCT Application No. PCT/US2014/068595, incorporated herein by reference in its entirety, or by other screening methods known in the art (e.g., biopanning methods such as phage display screens). In some instances, a vector library is screened in multiplex. scFvs identified as binding to target molecules (e.g., proteins) of interest according to such methods can then be converted to chimeric polypeptides (e.g., IgGs and chimeric antigen receptors) according to the methods of the present invention. In some instances, the nucleic acid sequence of a vector of the invention (e.g., a first vector or a second vector), or a portion thereof, can be determined according to sequencing methods well known in the art (e.g., Sanger sequencing or next-generation sequencing techniques).

Particular vectors useful in the methods of the present invention are described in detail below. It is appreciated that a first vector, as described herein, may be used as a second vector, and a second vector, as described herein, may be used as a first vector.

The First Vector

The present invention involves, in some instances, two vectors: a first vector encoding a first polypeptide (e.g., a binding moiety) and a second vector encoding a second polypeptide (e.g., a binding moiety framework, or portions thereof). In some instances, the first vector is a phagemid vector (FIG. 1). In certain instances, the first polypeptide is fused to a viral protein, such as a viral coat protein (e.g., GpIII). Preferably, a phage particle expressing the first polypeptide is capable of infecting a cell, such as a bacterial cell (e.g., an *E. coli* cell), thereby transducing the phagemid DNA into the cell. In particular instances, the bacterial cell contains the second vector (shown in FIG. 1 as the acceptor vector) and a recombinase enzyme (e.g., phiC31), such that the first and second vector undergo recombination in the bacterial cell to form a vector containing a polynucleotide encoding a chimeric polypeptide (e.g., a chimeric polypeptide including at least a portion of the first polypeptide and at least a portion of the second polypeptide). The first polypeptide encoded by the first vector may be a binding moiety having been selected, cloned, isolated, sequenced, or otherwise generated or identified by a method of screening for, e.g., antibodies capable of binding one or more particular antigens. For instance, the first polypeptide can be a binding moiety identified by a biopanning technique such as phage display, ribosome display, or Phage Emulsion, Secretion, and Capture (Phage ESCape). In some embodiments, the first polypeptide is a binding moiety generated by rational design. In various embodiments of the present invention, because biopanning often includes expression of candidate binding moieties from a vector, the first polypeptide of the present invention is encoded by a vector used to express the first polypeptide in a method of biopanning, examples of which include phage display, ribosome display, or Phage ESCape.

The first vector encoding the first polypeptide may further encode one or more functional cassettes (e.g., as described herein). A functional cassette of the first vector may be any polynucleotide segment capable of contributing to the generation, expression, or isolation of a chimeric polypeptide, other than the polynucleotide encoding the first polypeptide itself. The polynucleotide segment encoding the first polypeptide, or a portion thereof, may be fused to a functional cassette encoding a second polypeptide, or a fragment thereof, such that the first polypeptide is expressed as a fusion protein including the first polypeptide and one or more additional amino acids encoded by one or more functional cassettes. A functional cassette may encode a protein or polypeptide expressed independently of the first polypeptide, such that, when expressed, it is transcribed as a separate transcript from any transcript encoding the first polypeptide.

The expression of one or more polypeptides and/or functional cassettes can be driven by various regulatory cassettes, as described herein. Multiple promoter cassettes may be arranged such that the first polypeptide, or variants thereof, may be expressed in a plurality of distinct cell types, or such that cell type can determine the expression of protein variants, each variant including at least a segment encoded by the same polynucleotide segment.

The first vector can further encode one or more signal peptide functional cassettes (e.g., a cassette encoding a bacterial signal peptide or a mammalian signal peptide). In some instances, the first vector encodes one or more signal peptides 3' of the first polypeptide. In certain instances, the first vector encodes one or more signal peptides 5' of the first polypeptide. A signal peptide functional cassette may be fused to the first polypeptide or to another functional cassette. In particular instances, the first polypeptide encoded by the first vector is expressed in a fusion protein that includes one or more signal peptides, e.g., an N terminal signal peptide.

In some embodiments of the present invention, the expression of one or more signal peptides depends upon the cell in which the first vector is present. For instance, the first vector may encode each of a mammalian signal peptide and a bacterial signal peptide 5' of the first polypeptide. In some instances, the mammalian signal peptide is encoded 5' of the bacterial signal peptide, although the opposite order, e.g., is also contemplated. The mammalian signal peptide may be expressed from a mammalian promoter, while the bacterial signal peptide may be expressed from a bacterial promoter. In particular embodiments, the bacterial promoter and bacterial signal peptide functional cassette are proximal to the first polypeptide-encoding sequence, such that expression in bacteria results in a fusion protein including the bacterial signal peptide and the first polypeptide. Further, the bacterial promoter and signal peptide cassette are flanked by splice sites, such that, in mammalian cells, expression of the mammalian promoter results in a fusion protein including the mammalian signal peptide and the first polypeptide, but not the bacterial signal peptide or promoter. In one example of such an embodiment, the first vector encodes, from 5' to 3', a mammalian promoter, a mammalian signal peptide, a splice site, a bacterial promoter, a bacterial signal peptide, a second splice site, and the first polypeptide. In some instances, a polynucleotide encoding a signal peptide (e.g., a bacterial or mammalian signal peptide) is positioned within an intron, such that it is only expressed by a prokaryotic cell (e.g., a bacterial cell), as it would be removed during intron splicing in a eukaryotic cell. In a particular instance, a polynucleotide encoding a bacterial signal peptide is positioned in an intron, such that it is expressed as a fusion with the first polypeptide in a bacterial cell, but is spliced out in a mammalian cell.

The first polypeptide may be present in a fusion protein that includes a segment that enables display. This may be the case, e.g., if the first vector encodes a binding moiety identified by a biopanning technique in which the binding moiety was displayed. In some instances, a first polypeptide is present in a fusion protein that further includes a segment that enables viral display. A segment that enables viral display may be, e.g., a polypeptide including a sequence of a known viral transmembrane domain or a sequence derived therefrom. In particular examples, a polypeptide (e.g., a first polypeptide) of the present invention is present in a fusion protein that includes GpIII (e.g., M13 GpIII). The functional cassette encoding GpIII may be, e.g., 3' of the polynucleotide segment encoding the binding moiety. Many other constructs for display or other use in particular methods of biopanning are known in the art. The first vector may further encode one or more marker proteins that, upon expression, manifest a detectable phenotype. In particular instances, the first vector encodes two or more marker proteins, e.g., two or more marker proteins expressed from distinct promoters. In such instances, it may be that one marker protein is expressed, e.g., from a bacterial or mammalian promoter and another marker protein is expressed, e.g., from a second bacterial or mammalian promoter. In certain instances, one marker protein is expressed from bacterial promoter, and another is expressed from a mammalian promoter. In some instances, a polynucleotide encoding a marker protein is positioned within an intron, such that it is only expressed by a prokaryotic cell (e.g., a bacterial cell), as it would be removed during intron splicing in a eukaryotic cell.

The first vector may include one or more site-specific recombination motifs (e.g., complementary and/or orthogonal site-specific recombination motifs). Recombination between two complementary site-specific recombination motifs present on two separate vectors can result in the production of a recombinant product that includes, for example, nucleic acids of the first vector and nucleic acids of the second vector (e.g., a recombinant product encoding a chimeric polypeptide, in which the chimeric polypeptide includes at least a portion of a first polypeptide encoded by a first vector and at least a portion of a second polypeptide encoded by a second vector). Methods and compositions for conversion of a first polypeptide into a chimeric polypeptide using such a first vector and a second vector are described herein.

In other instances, a first vector may include two complementary site-specific recombination motifs, such that recombination may occur within the vector between these two complementary site-specific recombination motifs. In certain instances, recombining these two site-specific recombination motifs within the first vector results in excision or inversion of the nucleic acids positioned between the two complementary site-specific recombination motifs. Alternatively, recombination between these two site-specific recombination motifs may result in conversion of a first polypeptide into a chimeric polypeptide (e.g., without utilizing a second vector). In either case, the point or points of recombination may be marked by hybrid recombination sites, generated as the combination of a portion of the first site-specific recombination motif and portion of the second site-specific recombination motif. As an example, attL and attR are hybrid recombination motifs produced by recombination between a first vector having an attB site-specific recombination motif and a second vector having an attP site-specific recombination motif.

The first vector may include a pair of complementary site-specific recombination motifs positioned such that, in the presence of a recombinase enzyme capable of mediating recombination between the site specific recombination motifs, a portion of the first vector is excised. A pair of complementary site-specific recombination motifs present in the same vector may be referred to as an excision motif pair. In particular embodiments, the excision removes from the first vector one or more functional units, such as a functional cassette encoding a marker protein. In some embodiments, the excision removes a portion of a polypeptide (e.g., a first polypeptide), such as a binding moiety constant region. In some instances, the excision could remove a GpIII (e.g., M13 GpIII)-encoding functional cassette of a binding moiety fusion protein. The excision of a portion of the first vector may be a desirable step in achieving conversion of a first polypeptide into a chimeric polypeptide according to the methods described herein.

The first vector can encode a binding moiety framework functional cassette. In some instances, the binding moiety framework functional cassette is separated from the polynucleotide segment encoding the first polypeptide by one or more other functional cassettes. In particular instances, all or a substantial portion of the intervening polynucleotides between the polynucleotide segment encoding the first polypeptide and the binding moiety framework functional cassette are flanked by the site-specific recombination sites of an excision motif pair. In such embodiments, excision results in the generation of a polynucleotide segment capable of expressing a fusion protein that includes all or a portion of the first polypeptide and the framework encoded by the binding moiety framework cassette. In some instances, a binding moiety framework cassette of the first binding moiety may encode a framework corresponding to a different polypeptide type from the type of the first polypeptide. In other instances, the binding moiety framework cassette and/or second polypeptide is of the same type but its arrangement contributes to the conversion of the first polypeptide to a polypeptide of a different type.

The first vector may include a polynucleotide segment encoding a transcriptional stop signal, such as a polyA cassette. For example, if the first vector includes a binding moiety framework cassette, the polyA cassette may be 3' of the framework cassette. Eukaryotic transcriptional stop signals include, e.g., a polyA addition sequence (AAAUAA) and/or a plurality of downstream nucleotides. Numerous transcriptional stop sequences are known in the art and a variety of these have been used in the expression of genes from vectors. Certain arrangements involve the inclusion of a fragment including an intron and a transcriptional stop sequence following the end of a coding sequence. Examples of introns known in the art include the rabbit β-globin intron and the SV40 intron. Examples of transcriptional stop sequences include those from SV40 or human growth hormone. Examples of combined sequences include an SV40 intron/stop, the last exon of human growth hormone plus stop sequences, or the entire human growth hormone gene.

In some embodiments, the first vector includes a recombination motif (e.g., a site-specific recombination motif) capable of participating in a site-specific recombination event with the second vector of the present invention. Preferably, the second vector, but not the first vector, has a site-specific recombination motif complementary to such a site-specific recombination motif of the first vector (i.e., the first vector does not include the complement of the motif capable of recombining with the second vector). It is contemplated that the first vector may include multiple, distinct, site-specific recombination motifs capable of recombination with the second vector, and further contemplated that the presence of various recombinase enzymes may mediate which, if any, of these motifs may recombine. The first vector may further include one or more cryptic recombination motifs, each including a plurality of polynucleotide segments that can be joined to form a functional recombination motif. The cryptic recombination motif may be non-functional prior to joining of the polynucleotide segments. For example, the first vector may undergo a first recombination event that results in the formation of a functional recombination motif from the polynucleotide segments of the cryptic recombination motif.

The presence of complementary site-specific recombination motifs can be evaluated in view of the available recombinase enzymes. In certain embodiments, the first vector includes only one of each site-specific recombination motif capable of participating in a site-specific recombination event with the second vector. Various sets of complementary recombination motifs suitable for use in the first vector are known in the art. For example, a pair of complementary recombination motifs may include an attP motif and an attB motif. In a second example, a pair of complementary recombination motifs may include a hixL motif and hixR motif. Other examples of site-specific recombination motifs include the Tn7 site-specific attTn7 motif. Other examples are known in the art.

In addition to the above-mentioned cassettes and other sequence elements, the first vector of the present invention can include as an additional functional cassette one or more stop codons. Because the vectors of the present invention, or polynucleotide segments thereof, can be expressed in multiple cell types, it is relevant that codon usage of stop codons varies across some species. For instance, the amber stop codon (UAG) can be suppressed by certain strains of bacteria. Accordingly, it is possible to include stop codons that function in certain cell types while being read through in others, e.g., certain bacterial cell types. Exemplary stop codons that can be used selectively in this fashion include amber stop codons, ochre stop codons (UAA), and opal stop codons (UGA). The first vector of the present invention can include, e.g., an amber stop codon between the last nucleotide encoding the first polypeptide and the first nucleotide encoding a subsequent cassette. In still more particular examples, the first vector includes an scFv binding moiety in a fusion protein including GpIII (e.g., M13 GpIII), and the amber stop codon is positioned between the last nucleotide encoding the $V_H$ or $V_L$ of the scFv and the first nucleotide encoding GpIII (e.g., M13 GpIII).

The Second Vector

The second vector of the present invention recombines with the first vector to generate a recombination product encoding a chimeric polypeptide. In some instances, the second vector encodes a second polypeptide, for example, a framework (i.e., at least one constant region) of a binding moiety, or a portion thereof. The second polypeptide encoded by the second vector may be a framework corresponding to a type of polypeptide different from the type of the first polypeptide (e.g., a distinct binding moiety type). Alternatively, the framework encoded by the second polypeptide may be consistent with the type of the first polypeptide, but positioned in a manner such that the rearrangement of antigen-determining and constant regions in the chimeric polypeptide nevertheless constitutes conversion. The second polypeptide of the second vector may be encoded by one or more framework cassettes. The chimeric polypeptide may be a single protein or two or more independently expressed proteins capable of forming, for example, a single binding moiety, such as a pair of antibody chains. Distinct second vectors can be used in the methods of the invention (e.g., to recombine with a particular first vector) to construct distinct recombination products including polynucleotide segments encoding distinct chimeric polypeptides (e.g., distinct IgG fusions, chimeric antigen receptors, ubiquitin ligase fusions, and/or knocksideways proteins). For example, distinct second vectors each including a framework from a different species can be used to swap one or more antigen-determining regions between binding moiety frameworks from each species. In one example, a light chain and/or heavy chain variable domain from a first vector is fused to a human framework in the second vector to form a humanized binding moiety (e.g., a humanized IgG).

In some instances, a framework encoded by the second vector includes at least one constant region of a binding moiety. For instance, the framework may be, be derived from, or include, e.g., an immunoglobulin constant region, such as a CL, CH1, CH2, or CH3. In certain instances, the framework may include an entire CH domain (e.g., including CH1, CH2, and CH3). An immunoglobulin constant region may be, be derived from, or include a constant region associated with or derived from, e.g., a human Ig κ, Ig λ, IgA α1, IgA α2, IgD δ, IgE ε, IgG γ1, IgG γ2, IgG γ3, IgG γ4, or IgM μ chain. A framework may also be, be derived from, or include a combination of these, such as an Fc region. A framework may be, be derived from, or include one or more human T cell constant regions, such as a TcR Cγ1 or TcR Cγ2. A framework of the present invention may be derived from a chicken, human, rabbit, goat, mouse, camel, shark, or other organism capable of producing antibodies or other binding moieties that include constant regions. A framework of the present invention may also be the framework of an artificially designed binding moiety. A framework may be modified from any form known to be present in nature, provided that the framework is capable of functioning within a binding moiety construct. Many binding moiety constructs are known in the art and any of these may be utilized in whole or in part within the constructs of the present invention. All or a portion of any of these frameworks, or a framework derived therefrom, may be included in a first vector or second vector framework cassette.

The second vector may further encode one or more functional cassettes in addition to the one or more framework cassettes. A functional cassette of the second vector may be any polynucleotide segment capable of contributing to the generation, expression, or isolation of a chimeric polypeptide. A functional cassette may encode a protein or polypeptide, e.g., a protein or polypeptide that is not fused to a binding moiety framework of the second vector. A functional cassette may alternatively be a regulatory polynucleotide segment, such as a promoter, polyA sequence, Kozak sequence, or other polynucleotide segment that regulates expression. A functional cassette may be a polynucleotide segment that mediates transcription or transcript stability, translation, or recombination. A regulatory cassette can be, e.g., a promoter capable of driving expression of a chimeric polypeptide or a component thereof. Numerous polynucleotide sequences capable of regulating gene expression are known in the art, as are methods for their application in directing expression. In some instances, two or more functional cassettes may be expressed as a fusion protein.

The expression of one or more cassettes encoding protein or polypeptide may be driven by various regulatory cassettes. As is known in the art, various promoters are optimized for expression in a particular cell type. For instance, some promoters are only, or substantially only, capable of driving expression when present in a bacterial cell. Other promoters are only, or substantially only, capable of driving expression when present in a mammalian cell, or in an insect cell. Some promoters are only, or substantially only, capable of driving expression in still more particular subsets of cell types, while others may functional broadly, e.g., in both a bacterial cell and a mammalian cell. These differences may result, in part, from the availability and function of distinct cellular proteins endogenous to the relevant cell types. As described in greater detail herein, multiple promoter cassettes may be arranged such that a single polynucleotide segment encoding a protein or polypeptide may be expressed in a plurality of distinct cell types, or such that cell type can determine the expression of protein variants, each variant including at least a portion encoded by the same polynucleotide segment.

In some instances, the second vector encodes one or more signal peptide functional cassettes. In some instances, the second vector encodes one or more signal peptides 5' of a second polypeptide cassette (e.g., a framework cassette). In certain instances, the second vector encodes one or more signal peptides 5' of a framework cassette. A signal peptide cassette may be optionally fused to a framework cassette or to another cassette. In particular instances, the chimeric polypeptide or a component thereof is expressed in a fusion protein that includes one or more signal peptides originating from the second vector.

The second vector may further encode one or more marker proteins that, upon expression, manifest a detectable phenotype. In particular instances, the second vector encodes two or more marker proteins, e.g., two or more marker proteins expressed from distinct promoters. In such instances, it may be that one marker protein is expressed, e.g., from a bacterial or mammalian promoter and another marker protein is expressed, e.g., from a second bacterial or mammalian promoter. In certain instances, one marker protein is expressed from bacterial promoter, and another is expressed from a mammalian promoter.

The second vector may include one or more site-specific recombination motifs (e.g., complementary and/or orthogonal site-specific recombination motifs). In some instances, the second vector includes a site-specific recombination motif capable of participating in a site-specific recombination event with the first vector of the present invention. In certain instances, the first vector, but not the second vector, has a site-specific recombination motif complementary to such a site-specific recombination motif of the second vector (i.e., the second vector does not include the complement of the motif capable of recombining with the first vector). It is contemplated that the second vector may include multiple, distinct, site-specific recombination motifs capable of recombination with the first vector, and further contemplated that the presence of various recombinase enzymes may mediate which, if any, of these motifs may recombine. It is also contemplated that the second vector may include one or more pairs of complementary site-specific recombination motifs, e.g., capable of recombining with each other.

The second vector may further include one or more cryptic recombination motifs, each including a plurality of polynucleotide segments that can be joined to form a functional recombination motif. The cryptic recombination motif may be non-functional prior to joining of the polynucleotide segments. For example, the second vector may undergo a first recombination event that results in the formation of a functional recombination motif from the polynucleotide segments of the cryptic recombination motif. In some instances, a first and second vector can each include one or more polynucleotide segments making up a cryptic recombination motif, such that recombination between the first and second vector results in joining of the polynucleotide segments to form a functional recombination motif.

The presence of complementary site-specific recombination motifs is evaluated in view of the available recombinase enzymes. In certain embodiments, the second vector includes only one of each site-specific recombination motif capable of participating in a site-specific recombination event with the first vector.

The second vector may include a polynucleotide segment encoding a transcriptional stop signal, such as a polyA cassette. For example, a polyA cassette may be 3' to and fused to a framework cassette. Eukaryotic transcriptional stop signals include, e.g., a polyA addition sequence (AAAUAA) and/or a plurality of downstream nucleotides. Numerous transcriptional stop sequences are known in the art and a variety of these have been used in the expression of genes from vectors. Certain arrangements involve the inclusion of a fragment including an intron and a transcriptional stop sequence following the end of a coding sequence. Examples of introns known in the art include the rabbit β-globin intron and the SV40 intron. Examples of transcriptional stop sequences include those from SV40 or human growth hormone. Examples of combined sequences include an SV40 intron/stop, the last exon of human growth hormone plus stop sequences, or the entire human growth hormone gene.

Various sets of complementary recombination motifs suitable for use in the second vector are known in the art. For example, a pair of complementary recombination motifs may include an attP motif and an attB motif. In a second example, a pair of complementary recombination motifs may include a hixL motif and hixR motif. Other examples of site-specific recombination motifs include the Tn7 site-specific attTn7 motif. Other examples are known in the art.

In addition to the above-mentioned cassettes and other sequence elements, the second vector of the present invention can include as an additional functional cassette one or more stop codons. Because the vectors of the present invention, or polynucleotide segments thereof, can be expressed in multiple cell types, it is relevant that codon usage of stop codons varies across some species. For instance, the amber stop codon (UAG) can be suppressed by certain strains of bacteria. Accordingly, it is possible to include stop codons that function in certain cell types while being read through in others, e.g., certain bacterial cell types. Exemplary stop codons that can be used selectively in this fashion include amber stop codons, ochre stop codons (UAA), and opal stop codons (UGA). The second vector of the present invention can include, e.g., an amber stop codon between the last nucleotide of a gene (e.g., a gene encoding a polypeptide as described herein) and a polyA cassette, which may, in some instances, be upstream of a cassette capable of expressing a marker protein.

It will be appreciated by those of skill in the art that the critical aspects of the present invention may not be limited to the presence or absence of any one component of either of the first or second vector, but include at least the combination and the particular arrangement of their components such that conversion of a binding moiety occurs through recombination of the first vector and the second vector of the present invention. Further, it will be appreciated that the first vectors and the second vectors of the invention may be interchangeable.

Multiple Vectors and Vector Libraries

In some instances, a plurality of distinct first polypeptides can be converted to polypeptides of another type according to the methods of the invention simultaneously. For example, each of the first polypeptides may be a particular variant of a binding moiety (e.g., an antibody). A library can be constructed including a plurality of first vectors, each encoding one of the variants, according to methods well known in the art. In certain instances, a library in which each vector encodes an antibody can be constructed in which the light chain of each of the antibodies is identical and the heavy chain of each antibody is distinct. For example, each of the antibodies may include one or more distinct heavy chain antigen-determining regions (e.g., CDRs). In other instances, a library in which each vector encodes an antibody can be constructed in which the heavy chain of each of the antibodies is identical and the light chain of each antibody is distinct. For example, each of the antibodies may include one or more distinct light chain antigen-determining regions (e.g., CDRs). Such libraries may, e.g., be screened against antigens of interest (e.g., an antigen recognized by the portion of the antibodies held constant), e.g., using methods known in the art to identify strong-binding clones or clones showing improved binding affinity.

In some instances, the invention features first vectors (e.g., phagemid vectors) that may be capable of integrating with multiple distinct second vectors (e.g., acceptor vectors). In some instances, a first vector includes a plurality of distinct recombination motifs (e.g., 2, 3, 4, 5, 6, 7, 8, 9, 10, or more distinct recombination motifs). The recombination motifs may be, e.g., site-specific recombination motifs. For example, the first vector may include a first site-specific recombination motif and a second site-specific recombination motif that is orthogonal to the first site-specific recombination motif. The first and second site-specific recombination motifs may permit integration of the first vector with two distinct second vectors. Each of the integrant vectors produced by recombination of the first vector with one of the distinct second vectors may, for example, produce a distinct chimeric polypeptide (e.g., a binding moiety of a different type from the first polypeptide). In one example, a second vector includes both attP and attP2 site-specific recombination motifs. In some instances, a first vector may include an attP2 site positioned downstream of an scFv-encoding sequence but upstream of a gpIII sequence. This second integrase site can be used to produce fusions of the scFv to other polypeptides and/or polypeptide fragments (e.g., as described herein).

In some instances, the first site-specific recombination motif permits integration of the first vector with a second vector (e.g., an acceptor vector including a binding moiety framework) such that the resultant integrant vector is capable of expressing an IgG including the polypeptide (or a portion thereof) from the first vector; and the second site-specific recombination motif permits integration of the first vector with a different second vector (e.g., a vector including any functional domain described herein, such as a CAR), such that, for example, the resultant integrant vector is capable of expressing an scFv fused to the functional domain. For example, the scFv may be fused to a ubiquitin ligase domain, knocksideways domain, or CAR domain. The CAR domain may, for example, include a CD3-zeta or CD28 transmembrane domain, and/or a CD3-zeta, CD28, 41BB, ICOS, FcεRIy, influenza MP-1, VZV, and/or OX40 cytoplasmic domain, or any combination or derivative thereof. In one embodiment, the scFv is fused to a CD3-zeta domain, thereby forming an scFv-CD3-zeta fusion protein, e.g., an scFv-CD3-zeta fusion protein including a transmembrane domain between the scFv and the CD3-zeta (e.g., a CD3-zeta transmembrane domain). Such an scFv-CD3-zeta fusion protein may, for example, involve the scFv being presented extracellularly by a host cell (e.g., a T cell) including the integrant vector, such that binding of the scFv to a cognate binding partner results in transmission of an intracellular zeta signal by the CD3-zeta domain. This may in turn, e.g., result in activation of the T cell.

Adenoviral Vectors

In some instances, a vector of the invention (e.g., a first vector or second vector) may be an adenoviral vector. Recombinant adenoviruses can be generated using any means known in the art. For example, Tn7-mediated transposition in *E. coli* can be used to produce adenoviruses suitable for use as vectors of the invention. In one example, a low copy number *E. coli* plasmid containing a full-length adenoviral genome with lacZattTn7 replacing E1 is constructed. The adenovirus plasmid, or "admid," as well as high copy number progenitors, can be stably maintained in cells, such as *E. coli* (e.g., *E. coli* strain DH10B). An exemplary admid system is described in Richards et al. (*Cloning and Expression Vectors for Gene Function Analysis*, Chapter 39: 231-240, 2001), incorporated herein by reference. Transfer vectors containing a mammalian expression cassette flanked by Tn7R and Tn7L can be used as donors to transpose the mini-Tn7 into the E1 region of the adenoviral genome. Thus, transposed recombinant admids can be readily identified by their β-galactosidase phenotype. Transfection of admid DNA into producer cells results in the efficient production of infectious adenovirus. This system may reduce the time involved in generating pure, clonal stocks of recombinant adenovirus without successive rounds of plaque purification from 4-6 weeks to just 2-3 days.

Marker Proteins

Vectors of the present invention can include one or more marker proteins, which upon expression may permit the selection of cells containing the vector. Expression of a marker protein may result in the manifestation of a detectable phenotype. Examples of detectable phenotypes that may result from expression of a marker protein include, without limitation, luminescence, fluorescence, antibiotic resistance, antibiotic sensitivity, toxin resistance, toxin sensitivity, altered growth rate, altered response to an analyte, altered cell structure, altered colony formation, or altered auxotrophy. Additional detectable phenotypes are known in the art. Furthermore, genes capable of manifesting these detectable phenotypes are also known in the art. For example, a detectable phenotype may result from expression of green fluorescent protein (e.g., gfp), a red fluorescent protein (e.g., rfp), a yellow fluorescent protein (e.g., yfp), an ampicillin resistance gene (amp), a tetracycline resistance gene (tet), a kanamycin resistance gene (kan), beta galactosidase (β-gal), an alanine synthesis gene (e.g., argA), a cystein synthesis gene (e.g., cysE), a leucine synthesis gene (e.g., lysA), a threonine synthesis gene (e.g., thrC), or any of a plurality of other natural or synthetic genes known in the art. Alternatively, the marker protein may be a functional cassette that directs or contributes to the expression of a gene that manifests a detectable phenotype, e.g., by expression of a transcription factor. In such instances, the gene that manifests the detectable phenotype may be endogenous to a cell, present on a first vector, present on a second vector, or present on another vector. In some instances, a marker protein (e.g., zeocin or chloramphenicol) can be used to select integrants by including expression elements (e.g., a promoter) on a first vector and a marker gene on second vector, such that recombination joins the promoter element(s) upstream of the marker gene.

Methods for selecting or isolating cells having a detectable phenotype are known in the art. Selecting or isolating one or more cells having a phenotype resulting from expression of a marker protein may include, depending upon the detectable phenotype, flow cytometry, culturing a population of cells in the presence of the relevant antibiotic or toxin, culturing a population of cells in the presence or absence of a particular organic compound, or microscopy techniques. Additional methods of selecting and isolating cells having particular detectable phenotypes are known in the art.

Functional Cassettes

A vector of the invention may be suitable for expressing one or more genes in multiple distinct cell types (e.g, bacteria, mammalian cells, and insect cells). For instance, the vector may encode one or more functional cassettes. A functional cassette may be, for example, any polynucleotide segment capable of contributing to the generation, expression, or isolation of a gene (e.g., a gene encoding a binding moiety). A functional cassette may encode a protein or polypeptide. The polynucleotide segment encoding such a protein or polypeptide (e.g., a binding moiety) may be fused to a functional cassette encoding a protein or polypeptide, such that the protein or polypeptide (e.g., binding moiety) is expressed as a fusion protein including the protein or polypeptide and one or more additional amino acids encoded by one or more functional cassettes. A functional cassette may encode a further protein or polypeptide expressed independently of the protein or polypeptide (e.g., binding moiety), meaning that, when expressed, it is transcribed as a separate transcript from any transcript encoding the first protein or polypeptide.

A. Regulatory Cassettes

A functional cassette may include one or more regulatory cassettes. A regulatory cassette may be a polynucleotide segment that mediates transcription or transcript stability, translation, or recombination. Exemplary regulatory cassettes include a regulatory sequence, such as a promoter, polyA sequence, Kozak sequence, or any other polynucleotide sequence that regulates expression (e.g., of a binding moiety). A regulatory cassette can be a cassette that regulates expression of a polypeptide or a cassette that regulates the expression of one or more other functional cassettes. Numerous polynucleotide segments capable of regulating gene expression are known in the art, as are methods for their application in directing expression. In some instances, two or more functional cassettes may be expressed as a fusion protein.

The expression of one or more polypeptides or functional cassettes can be driven by various regulatory cassettes. As is known in the art, various promoters are optimized for expression in a particular cell type. For instance, some promoters are only, or substantially only, capable of driving expression when present in a bacterial cell (e.g., an E. coli lac promoter). Other promoters are only, or substantially only, capable of driving expression when present in a mammalian cell (e.g., a CMV promoter), or in an insect cell (e.g., a polyhedron promoter). Some promoters are only, or substantially only, capable of driving expression in still more particular subsets of cell types, while others may functional broadly, e.g., in both a bacterial cell and a mammalian cell. These differences may result, in part, from the availability and function of distinct cellular proteins endogenous to the relevant cell types. Furthermore, multiple promoter cassettes may be arranged such that a single polynucleotide segment encoding a protein or polypeptide may be expressed in a plurality of distinct cell types, or such that cell type can determine the expression of protein variants, each variant including at least a segment encoded by the same polynucleotide segment.

In some instances, a vector may include a plurality of promoters placed in series to control expression of a single gene located 3' to the promoters. For example, a vector may include a dual promoter element, such as catenated promoters and/or intronic promoters, as described below.

(1) Catenated Promoters

Multiple promoter cassettes may be arranged in series to form a set of catenated promoters capable of controlling (e.g., increasing or decreasing) the expression of a downstream gene (e.g., a gene encoding a first polypeptide, second polypeptide, chimeric polypeptide, or any combination or fragment thereof, of the invention), in which each of the catenated promoters controls the expression of the downstream gene in a particular organism. In one embodiment, two or more promoters are catenated 5' relative to a gene to be expressed, such that the first ATG present downstream of either promoter is the start codon of the gene to be expressed. In some instances, a catenated promoter may drive expression of a protein to be secreted. In certain instances, the protein to be secreted includes a signal peptide that operates in both bacterial and mammalian cells (e.g., an IL2 signal sequence). Examples of catenated promoters are described, e.g., in Kadwell et al. ("Update to: The Admid System: Generation of recombinant adenoviruses by Tn7-mediated transposition in *E. coli*," Chapter 39, *Cloning and Expression Vectors for Gene Function Analysis*, 2001) and Tan et al. (*Genome Res.* 13: 1938-1943, 2003), each of which is incorporated herein by reference.

(2) Intronic Promoters

In another embodiment, a vector may include a promoter (e.g., a prokaryotic promoter, such as a bacterial promoter) positioned within an intron (an "intronic promoter"), such that if expressed in a eukaryotic cell (e.g., a mammalian cell or an insect cell), the promoter sequence is spliced out of the resultant transcript. This may be desirable, for example, if the exon located 3' to the intronic promoter is to be expressed under the control of the intronic promoter, but the exon located 5' to the intronic promoter is not. The intron may, in certain instances, further include additional regulatory elements or coding regions (e.g., signal peptides). For example, the intronic promoter may be a bacterial promoter and both the 5' exon and the 3' exon may be located downstream of a mammalian promoter. Thus, if the vector is in a mammalian cell (e.g., a HEK-293 cell), both exons are transcribed and the intron including the bacterial promoter is removed during RNA splicing. If the vector is in a bacterial cell, only the 3' exon is transcribed. As such, this dual promoter system permits the expression of distinct variants of a particular protein in distinct cell types.

Figures 2A, 2B, 2C:
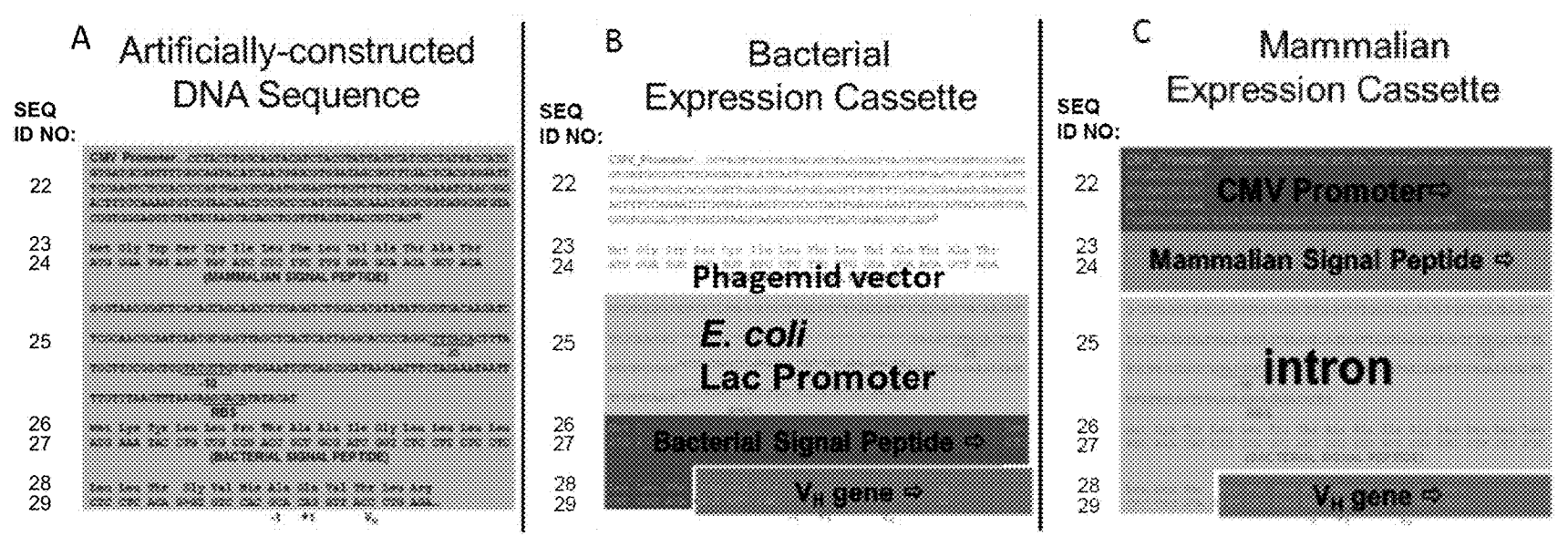

In one example of such a dual promoter system, a phagemid vector is designed in which an *E. coli* lac promoter and a bacterial signal peptide are placed within an intron of a mammalian expression cassette (FIG. 2). A promoter (e.g., a CMV promoter or an EF1a promoter) and a mammalian signal peptide are located 5' to this intron, and a gene encoding a VH gene is positioned in the exon located 3' to this intron. Thus, in a mammalian cell, the promoter drives the production of a VH gene fused to a mammalian signal peptide, whereas in a bacterial cell, the lac promoter drives expression of a VH gene fused to a bacterial signal peptide. Further vectors including such dual promoters are described, for example, in U.S. Pat. No. 7,112,439, incorporated herein by reference.

B. Signal Peptide Cassettes

The first vector can encode one or more signal peptide functional cassettes. In some instances, the first vector encodes one or more signal peptides 3' of the first polypeptide. In certain instances, the first vector encodes one or more signal peptides 5' of the first polypeptide. A signal peptide functional cassette may be fused to the first polypeptide or to another functional cassette. In particular instances, the first polypeptide encoded by the first vector is expressed in a fusion protein that includes one or more signal peptides, e.g., an N-terminal signal peptide. In some instances, a signal peptide functional cassette encodes a signal peptide that operates in both bacterial and mammalian cells (e.g., an IL2 signal sequence).

In some embodiments of the present invention, the expression of one or more signal peptides depends upon the cell in which the first vector is present. For instance, the first vector may encode each of a mammalian signal peptide and a bacterial signal peptide 5' of the first polypeptide. In some instances, the mammalian signal peptide is encoded 5' of the bacterial signal peptide, although the opposite order, e.g., is also contemplated. The mammalian signal peptide may be expressed from a mammalian promoter, while the bacterial signal peptide may be expressed from a bacterial promoter. In particular embodiments, the bacterial promoter and bacterial signal peptide functional cassette are proximal to the first polypeptide, such that expression in bacteria results in a fusion protein including the bacterial signal peptide and the first polypeptide. Further, the bacterial promoter and signal peptide cassette are flanked by splice sites, such that, in mammalian cells, expression of the mammalian promoter results in a fusion protein including the mammalian signal peptide and the first polypeptide, but not the bacterial signal peptide or promoter. In one example of such an embodiment, the first vector encodes, from 5' to 3', a mammalian promoter, a mammalian signal peptide, a splice site, a bacterial promoter, a bacterial signal peptide, a second splice site, and the first polypeptide.

Recombination Motifs

A segment of a nucleic acid with which a recombination motif may participate in a recombination event may be referred to as a complementary recombination motif. Site-specific recombination motifs selectively participate in recombination with complementary recombination motifs having a particular sequence or particular sequence characteristics. For example, the complementary recombination motifs attB and attP can be recombined with each other in a reaction catalyzed by, e.g., phiC31 integrase or bacteriophage lambda integrase. In some instances, a recombination motif may be divided, having two or more regions with particular sequence requirements separated by one or more sequences that are not substantially constrained and/or do not directly participate in recombination. In some instances, complementary recombination motifs are identical (e.g., paired loxP sites or paired FRT sites). In other instances, complementary recombination motifs are non-identical. In some instances, all of the nucleotides comprising a site-specific recombination motif may be defined. In other instances, only a subset of the nucleotides comprising a site-specific recombination motif may be defined, such as 5%, 10%, 15%, 20%, 25%, 50%, 60%, 70%, 80%, 90%, 95%, 99%, or 99.5% of nucleotides present in the site-specific recombination motif. Complementary recombination motifs may include, e.g., a phage motif, a bacterial motif, or a direct repeat motif. In some instances, a segment of a nucleic acid may serve as both a recombination motif and, when translated into its corresponding amino acid sequence, a linker between two polypeptide moieties (e.g., VH and VL protein, as shown in FIG. 1).

Figure 3:
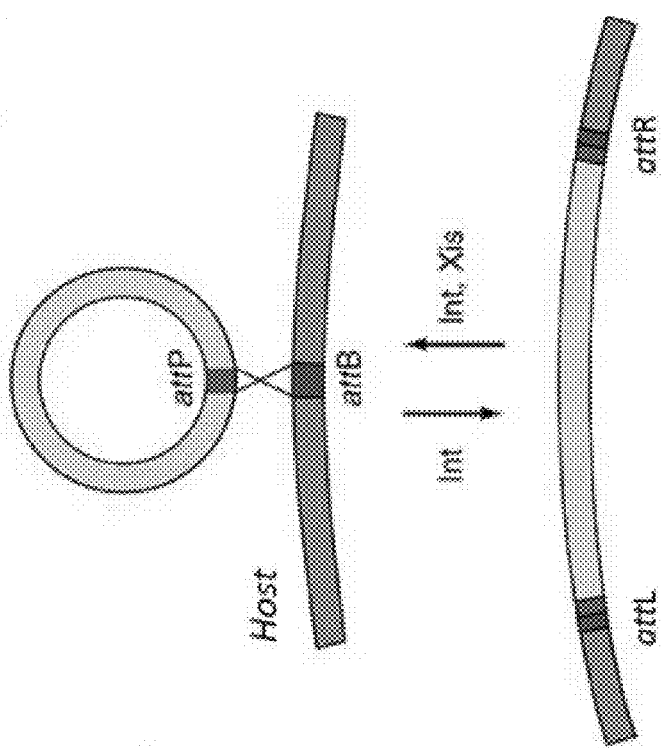
FIG. 3 is a schematic showing phiC31-mediated integration of a small vector containing an attP site into a larger host vector containing an attB site. The positions at which the two vectors recombine form attL and attR sites upon integration.

Exemplary recombination motifs that may be used as recombination motifs in vectors of the invention include, without limitation: attB, attP, loxP, FRT, hixL, hixR and variants thereof. Variants of recombination motifs are known in the art (e.g., JT15, a loxP variant showing comparable recombination efficiency to wild-type loxP), and may be substituted and tested, e.g., in the methods and compositions described herein. Examples of attB and attP variants with suitable recombination efficiencies can be found, for example, in FIG. 3 of Groth et al. (PNAS 97(11): 5995-6000, 2000), incorporated herein by reference. Certain recombination motifs may be preferable for use in in vitro recombination reactions, such as the bacteriophage lambda integrase, e.g., as described in Hartley et al. (*Genome Res.* 10: 1788-1795, 2000), which is incorporated herein by reference. In further examples, the complementary site-specific recombination motif pairs attB1/attP1 and attB1/attP1 can be used in vectors of the present invention. In some instances, variants of recombination motifs may be capable of replacing the original recombination motif from which the variant was derived. In other instances, variants of recombination motifs may not be capable of replacing the original recombination motif. In particular instances, the variant recombination motifs may form distinct groups of complementary recombination motifs. For example, attB1 can recombine with attP1, but not with attP2.

Recombinase Enzymes

Recombination of certain site-specific recombination motifs may be facilitated by one or more recombinase enzymes. A recombinase enzyme may be a recombinase or integrase. A recombinase enzyme may be, e.g., a serine family recombinase or tyrosine family recombinase. As is known in the art, the serine and tyrosine recombinase families are named according to the conserved nucleophilic amino acid that interacts with DNA during recombination. Serine family recombinases include, for example, phiC31, which recognizes attB and attP sites, HIN invertase, which recognizes hix sites, Bxb1 integrase, phiRv1 integrase, phiBT1 integrase, phiFC1 integrase, and Tn3 resolvase. Bxb1 integrase, phiRv1 integrase, phiBT1 integrase, and phiFC1 integrase, like phiC31 integrase, may recognize attB and attP sites, and may further catalyze the reverse reaction, e.g., in the presence of an accessory factor such as Xis. Serine recombinases are reviewed in detail in Smith et al. (*Biochem. Soc. Trans.* 38: 388-394, 2010), incorporated by reference herein. Tyrosine family recombinases include, for example, bacteriophage lambda integrase, which, like phiC31, recognizes att sites, Cre, which recognizes lox sites, and Flp, which recognizes frt sites. For example, bacteriophage lambda integrase, together with an integration host factor (IHF) protein, mediates recombination between an attB site and an attP site, forming an attL and attR site (see, e.g., Hartley et al., supra). The reverse reaction (attL+attR to attB+attP) is mediated by bacteriophage lambda integrase, IHF, and excisionase (Xis). Bacteriophage lambda integrase may be particularly well-suited for recombination performed in vitro (e.g., not within a cell). In various embodiments of the present invention, Cre recombinase induces recombination between two loxP sites. In other embodiments, Flp recombinase induces recombination between two FRT sites. In some instances, a recombinase enzyme may excise a portion of a polynucleotide (e.g., a vector). Such a recombinase enzyme may be referred to herein as an "excision enzyme." In certain instances, an excision enzyme may be Cre or Flp.

In some embodiments, phiC31 integrase is used to drive integration between two vectors of the invention (FIG. 3). phiC31 integrase is a site-specific serine recombinase that recognizes 36-bp site-specific recombination motifs (e.g., attP, attB, attL, and attR). For example, recombination of two nucleic acids, one containing an attP motif and the other containing an attB motif, by phiC31 integrase results in the integration of the two nucleic acids at the motif sites and replacement of the attP and attB motifs with attL and attR motifs. phiC31 integrase can also induce the reverse reaction (in which attL and attR are converted to attP and attB, e.g., to excise an integrated nucleic acid segment), although this may require the presence of the accessory protein Xis. Other recombinase enzymes that may be suitable for use in the binding moiety conversion methods of the present invention are known in the art.

Polypeptides

The invention provides methods and compositions for converting a first polypeptide into a chimeric polypeptide (e.g., a polypeptide of a different type). In some instances, a polypeptide (e.g., a first polypeptide, second polypeptide, or chimeric polypeptide) is or includes a binding moiety, such as an antibody, antibody fragment, a chimeric antigen receptor, and/or a portion thereof. A polypeptide of the invention may include or be fused to one or more functional domains (e.g., a binding moiety may be fused to the one or more functional domains). Exemplary functional domains to which a polypeptide of the invention can be fused include, without limitation, a binding moiety, ubiquitin ligase domain, a knocksideways prey domain, and a marker protein (e.g., alkaline phosphatase, lacZ, or a fluorescent protein, such as GFP, RFP, YFP, CFP, dsRed, mCherry, or any other marker protein known in the art). Such functional domains can be combined to impart useful functionality to the polypeptide, e.g., as described herein.

It is appreciated that a first polypeptide, as described herein, may be used as a second polypeptide, and a second polypeptide, as described herein, may be used as a first polypeptide.

Chimeric Polypeptides

A chimeric polypeptide of the present invention may be encoded, for example, by an integrant vector formed upon recombination of at least a first vector with a second vector according to the methods of the invention. The integrant vector produced by this recombination event includes a polynucleotide encoding the chimeric polypeptide. The integrant vector may encode a single chimeric polypeptide or a set of two or more chimeric polypeptides, such as, for example, a heavy chain and a light chain. In some instances, the chimeric polypeptide includes at least a portion (e.g., an antigen-determining region) of a first polypeptide encoded by the first vector and at least a portion of a second polypeptide (e.g., a binding moiety framework cassette) encoded by the second vector. A polynucleotide encoding a chimeric polypeptide may also be present in a non-integrant vector. For example, the polynucleotide encoding the chimeric polypeptide may be transferred to a different vector by subcloning methods known in the art.

A chimeric polypeptide of the present invention may be expressed within a cell at levels greater than, equal to, or less than the expression of a polypeptide of the same type expressed from a vector known in the art. For example, a chimeric polypeptide encoded by a recombinant product of the present invention may be an IgG antibody that is expressed at a level greater than, equal to, or less than the level at which an IgG isolated from a human and expressed from a known vector is expressed. Alternatively, a chimeric polypeptide may be expressed in vitro, for example, using a cell-free expression system as well known in the art.

Binding Moieties

The present invention features vectors (e.g., a first vector or a second vector) including nucleic acid sequences encoding one or more polypeptides, or fragments thereof. The polypeptides encoded by the vectors may include, for example, binding moieties or fragments thereof. A binding moiety of the present invention may be any protein or polypeptide capable of binding an antigen, e.g., as described herein. Certain binding moieties of the invention may include an antigen-determining region and/or a framework (e.g., a constant region or a framework region of a variable domain).

In some instances, a binding moiety is an antibody, such as a whole antibody, or an antibody fragment, such as an antigen-binding antibody fragment. Alternatively, a binding moiety of the present invention may be a protein or polypeptide that is not an antibody. A binding moiety may be, e.g., avidin, streptavidin, beta galactosidase, an affinity tag (e.g., HA, His, FLAG, SNAP, avitag, or any other peptide tag known in the art), a short peptide tag capable of being labeled by, e.g., SFP or AcpS phosphopantetheinyl transferase (e.g., an S6 or A1 tag; see, e.g., Zhou et al., *ACS Chem. Biol.* 2(5):337-346, 2007, incorporated by reference herein), a fluorescent protein (e.g., GFP, YFP, CFP, RFP, dsRed, mCherry, or any other fluorescent protein known in the art), alkaline phosphatase, a kinase, a phosphatase, a proteasomal protein, a protein chaperone, a receptor (e.g., an innate immune receptor or signaling peptide receptor), a chimeric antigen receptor, a synbody, an artificial antibody, a protein having a thioredoxin fold (e.g., a disulfide isomerase, DsbA, glutaredoxin, glutathione S-transferase, calsequestrin, glutathione peroxidase, or glutathione peroxiredoxin), a protein having a fold derived from a thioredoxin fold, a repeat protein, a protein known to participate in a protein complex, a protein known in the art as a protein capable of participating in a protein-protein interaction, or any variant thereof (e.g., a variant that modifies the structure or binding properties thereof). A binding moiety of the present invention may be any protein or polypeptide having a protein binding domain known in the art, including any natural or synthetic protein that includes a protein binding domain. A binding moiety of the present invention may also be any protein or polypeptide having a polynucleotide binding domain known in the art, including any natural or synthetic protein that includes a polynucleotide binding domain. A binding moiety may include, for example, a signal peptide (e.g., a bacterial signal peptide or a mammalian signal peptide) that targets it for secretion or expression as a transmembrane protein, e.g., on the cell surface.

A binding moiety of the invention may include one or more functional domains (e.g., a binding moiety may be fused to the one or more functional domains). Exemplary functional domains to which a binding moiety can be fused include, without limitation, a ubiquitin ligase domain, a knocksideways prey domain, and a marker protein (e.g., alkaline phosphatase, lacZ, or a fluorescent protein, such as GFP, RFP, YFP, CFP, dsRed, mCherry, or any other marker protein known in the art). Such functional domains can be combined to impart useful functionality to the binding moiety. For example, fusion of a ubiquitin ligase domain to a binding moiety may be used to ubiquinate and drive proteasomal degradation of a target molecule to which the binding moiety is capable of binding. In a second example, a knocksideways prey domain can be fused to a binding moiety such that a target molecule to which the binding moiety is capable of binding is sequestered to a particular intracellular region (e.g., the mitochondria). In some instances, a binding moiety is an antigen receptor, such as, for example, a T-cell receptor. In certain instances, a binding moiety is an engineered antigen receptor or antibody. In particular embodiments, a binding moiety is a chimeric antigen receptor (CAR), for example, as described in Sadelain et al. (*Cancer Discovery* 3: 388-398, 2013; incorporated herein by reference) and as well known in the art. In some instances, a CAR may be suitable for expression by a T cell for use in detecting tumor associated antigens (TAAs). In certain instances, the CAR is presented on the surface of the T cell (e.g., anchored to the T cell surface by a transmembrane domain positioned in the plasma membrane of the T cell). CARs expressed by T cells generally include an extracellular TAA-specific binding moiety (e.g., an scFv composed of antibody variable heavy and light chain genes joined by a short, flexible linker). The binding moiety of the CAR may be linked, e.g., via hinge and transmembrane domains, to an intracellular signaling domain (from, e.g., CD28, CD3ζ, or 4-1 BB). Interaction between the CAR and antigen may trigger effector functions and can, for example, mediate cytolysis of tumor cells. CAR-engineered T cells can mediate tumor regression in multiple cancers. For example, CARs directed to the CD19 antigen on lymphoid malignancies have shown positive results in the treatment of acute lymphoblastic leukemia (ALL).

In some instances, a binding moiety of the invention has been selected, cloned, isolated, sequenced, or otherwise generated or identified by a method of screening for antibodies capable of binding one or more particular antigens. For example, a moiety can be a binding moiety identified by a biopanning technique, such as phage display, ribosome display, or Phage Emulsion, Secretion, and Capture (Phage ESCape). In some embodiments, the first binding moiety is a binding moiety generated by rational design. In various embodiments of the present invention, because biopanning often includes expression of candidate binding moieties from a vector, the first binding moiety of the present invention is a vector used to express a the first binding moiety in a method of biopanning, examples of which include phage display, ribosome display, or Phage ESCape.

The methods and compositions of the invention can also be used to convert a binding moiety to a variant of the binding moiety having the same or similar type. For example, the binding moiety may include a framework sequence that can be switched with an alternate framework sequence. In some instances, the binding moiety is an antibody or antibody fragment, which is converted to an antibody or antibody fragment of the same or similar type having a different framework. In another example, an antibody from a hybridoma is converted into a thermal stable or cytosol-stable antibody.

Antibodies and Antibody Fragments

The vectors of the invention (e.g., first vectors, second vectors, and integrant vectors) may encode antibodies, or fragments thereof. In some instances, a first polypeptide encoded by a first vector is an antibody or antibody fragment. In certain instances, a second polypeptide encoded by a second vector includes an antibody, antibody fragment, or framework. In particular instances, a chimeric polypeptide encoded by an integrant vector encodes an antibody or antibody fragment (e.g., an antibody or antibody fragment of a different type than an antibody or antibody fragment encoded by the first vector). In some instances, an antibody or antibody fragment can be converted into another type of polypeptide (e.g., a CAR, ubiquitin ligase fusion, and/or knocksideways prey domain fusion), or vice versa, according to the methods of the invention.

An antibody of the present invention may be a whole antibody or immunoglobulin or an antibody fragment. An antibody may be multispecific, e.g., bispecific. An antibody of the present invention may be mammalian (e.g., human or mouse), humanized, chimeric, recombinant, synthetically produced, or naturally isolated. Exemplary antibodies of the present invention include, without limitation, IgG (e.g., IgG1, IgG2, IgG3, and IgG4), IgM, IgA (e.g., IgA1, IgA2, and IgAsec), IgD, IgE, Fab, Fab', Fab'2, F(ab')$_2$, Fd, Fv, Feb, scFv, scFv-Fc, and SMIP binding moieties. In certain embodiments, the antibody is an scFv. The scFv may include, for example, a flexible linker allowing the scFv to orient in different directions to enable antigen binding. In various embodiments, the antibody may be a cytosol-stable scFv or intrabody that retains its structure and function in the reducing environment inside a cell (see, e.g., Fisher and DeLisa, J. Mol. Biol. 385(1): 299-311, 2009; incorporated by reference herein). In particular embodiments, the scFv is converted to an IgG or a chimeric antigen receptor according to the methods described herein.

In most mammals, including humans, whole antibodies have at least two heavy (H) chains and two light (L) chains connected by disulfide bonds. Each heavy chain consists of a heavy chain variable region (VH) and a heavy chain constant region (CH). The heavy chain constant region consists of three domains (CH1, CH2, and CH3) and a hinge region between CH1 and CH2. Each light chain consists of a light chain variable region (VL) and a light chain constant region (CL). The light chain constant region consists of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

Antibodies of the present invention include all known forms of antibodies and other protein scaffolds with antibody-like properties. For example, the antibody can be a monoclonal antibody, a polyclonal antibody, human antibody, a humanized antibody, a bispecific antibody, a monovalent antibody, a chimeric antibody, or a protein scaffold with antibody-like properties, such as fibronectin or ankyrin repeats. The antibody can have any of the following isotypes: IgG (e.g., IgG1, IgG2, IgG3, and IgG4), IgM, IgA (e.g., IgA1, IgA2, and IgAsec), IgD, or IgE.

An antibody fragment of the present invention may include one or more segments derived from an antibody. A segment derived from an antibody may retain the ability to specifically bind to a particular antigen. An antibody fragment may be, e.g., a Fab, Fab', Fab'2, F(ab')2, Fd, Fv, Feb, scFv, or SMIP. An antibody fragment may be, e.g., a diabody, triabody, affibody, nanobody, aptamer, domain antibody, linear antibody, single-chain antibody, or any of a variety of multispecific antibodies that may be formed from antibody fragments.

Examples of antibody fragments include: (i) a Fab fragment: a monovalent fragment consisting of VL, VH, CL, and CH1 domains; (ii) a F(ab')2 fragment: a bivalent fragment comprising two Fab fragments linked by a disulfide bridge at the hinge region; (iii) a Fd fragment: a fragment consisting of VH and CH1 domains; (iv) an Fv fragment: a fragment consisting of the VL and VH domains of a single arm of an antibody; (v) a dAb fragment: a fragment including VH and VL domains; (vi) a dAb fragment: a fragment that is a VH domain; (vii) a dAb fragment: a fragment that is a VL domain; (viii) an isolated complementarity determining region (CDR); and (ix) a combination of two or more isolated CDRs which may optionally be joined by one or more synthetic linkers. Furthermore, although the two domains of the Fv fragment, VL and VH, are coded for by separate genes, they can be joined, using recombinant methods, e.g., by a synthetic linker that enables them to be expressed as a single protein, of which the VL and VH regions pair to form a monovalent binding moiety (known as a single chain Fv (scFv)). Antibody fragments may be obtained using conventional techniques known to those of skill in the art, and may, in some instances, be used in the same manner as intact antibodies. Antigen-binding fragments may be produced by recombinant DNA techniques or by enzymatic or chemical cleavage of intact immunoglobulins. An antibody fragment may further include any of the antibody fragments described above with the addition of additional C-terminal amino acids, N-terminal amino acids, or amino acids separating individual fragments.

An antibody may be referred to as chimeric if it includes one or more antigen-determining regions or constant regions derived from a first species and one or more antigen-determining regions or constant regions derived from a second species. Chimeric antibodies may be constructed, e.g., by genetic engineering. A chimeric antibody may include immunoglobulin gene segments belonging to different species (e.g., from a mouse and a human).

An antibody of the present invention may be a human antibody. A human antibody refers to a binding moiety having variable regions in which both the framework and CDR regions are derived from human immunoglobulin sequences. Furthermore, if the antibody contains a constant region, the constant region also is derived from a human immunoglobulin sequence. A human antibody may include amino acid residues not identified in a human immunoglobulin sequence, such as one or more sequence variations, e.g., mutations. A variation or additional amino acid may be introduced, e.g., by human manipulation. A human antibody of the present invention is not chimeric.

An antibody of the present invention may be humanized, meaning that an antibody that includes one or more antigen-determining regions (e.g., at least one CDR) substantially derived from a non-human immunoglobulin or antibody is manipulated to include at least one immunoglobulin domain substantially derived from a human immunoglobulin or antibody. An antibody may be humanized using the conversion methods described herein, for example, by inserting antigen-recognition sequences from a non-human antibody encoded by a first vector into a human framework encoded by a second vector. For example, the first vector may include a polynucleotide encoding the non-human antibody (or a fragment thereof) and a site-specific recombination motif, while the second vector may include a polynucleotide encoding a human framework and a site-specific recombination complementary to a site-specific recombination motif on the first vector. The site-specific recombination motifs may be positioned on each vector such that a recombination event results in the insertion of one or more antigen-determining regions from the non-human antibody into the human framework, thereby forming a polynucleotide encoding a humanized antibody.

In particular embodiments, one or more binding moieties of the present invention are antibodies derived from the sequence of an antibody expressed by a cell (e.g., a B-cell) of an inoculated subject. In particular embodiments, one or more binding moieties of the present invention are antibodies derived from the sequence of an antibody expressed by a naïve cell.

In certain embodiments of the present invention, a binding moiety is based on an alternative scaffold. Scaffolds based on different human or non-human proteins or protein domains are known in the art (see, e.g., Gebauer et al. 2009 *Curr. Opin. Chem. Biol.* 13:245-255). Different proteins have been investigated, including affibodies, lipocalins, ankyrin-repeat proteins, natural peptide binding domains, enzymes, GFP, small disulfide-bonded peptides, protease inhibitors, and others.

Linkers

In some embodiments, a first polypeptide, second polypeptide, or chimeric polypeptide includes a linker, i.e., one or more amino acids that are not defined as a binding moiety constant region or as an antigen-determining region, but rather form a link between two such regions (e.g., two constant regions, two antigen-determining regions, or one of each). The polynucleotide segment encoding the linker can be positioned, for example, between a polynucleotide segment encoding a first antigen-determining region and a polynucleotide segment encoding a second antigen-determining region. In certain embodiments including a linker, the first polypeptide, second polypeptide, or chimeric polypeptide is an scFv. The polynucleotide segment encoding the linker can include a site-specific recombination motif, e.g., a recombination motif of an excision motif pair or a recombination motif capable of mediating recombination with a second vector of the present invention. In certain embodiments, each nucleotide of the polynucleotide segment encoding the linker is translated into an amino acid of the first polypeptide, second polypeptide, or chimeric polypeptide. Accordingly, in certain instances, the linker is bifunctional; that is, it is or includes a site-specific recombination motif and each nucleotide of the linker, including the nucleotides of the site-specific recombination motif, are transcribed and translated such that each nucleotide corresponds to an amino acid of the binding moiety.

The present invention includes the identification, optimization, use, and/or design of bifunctional linkers. For instance, the attR site having the sequence 5'-ccc-caactggggtaacctttgggctccccgggcgcgtac-3' (SEQ ID NO: 1) can be translated in 5 reading frames that do not contain a stop codon (PNWGNLWAPRAR, SEQ ID NO: 2; PTGVTFGLPGRV, SEQ ID NO: 3; VRARGAQRLPQLG, SEQ ID NO: 4; YAPGEPKGYPSW, SEQ ID NO: 5; and TRPGSPKVTPVG, SEQ ID NO: 6) as well as a 6th reading frame that does contain a stop codon. The generation and optimization of linkers that both encode a segment of a first polypeptide, second polypeptide, or chimeric polypeptide and include a site-specific recombination motif is one of the aspects of the present invention.

Chimeric Antigen Receptors

One type of polypeptide included in the present invention, e.g., as a first polypeptide, a second polypeptide, or a chimeric polypeptide, is a chimeric antigen receptor (CAR). As known in the art, CARs are chimeric cell surface receptors (e.g., immunoreceptors) that include a binding moiety (e.g., an antibody or antibody fragment) fused to an effector domain capable of inducing a downsteam effect in the cell expressing the CAR. In some instances, the binding moiety is displayed on the exterior of the cell surface and the effector domain is a cytoplasmic domain facing the interior of the cell. The binding moiety and the effector domain are generally connected by a transmembrane domain, or stalk. The stalk may vary in length (e.g., the length of an scFv linker or the length of a T-cell receptor transmembrane domain). Binding between the binding moiety and a target molecule can, in some instances, result in induction of an intracellular signaling pathway. A CAR can be converted to a polypeptide of another type according to the methods of the present invention, for example, by placing the binding moiety of the CAR, or a portion thereof, into a framework from a polypeptide of another type (e.g., an antibody or antibody fragment). Conversely, a polypeptide of another type (e.g., an antibody or antibody fragment) can be converted to a CAR according to the methods of the present invention, for example, by fusing a binding moiety from the polypeptide of another type (e.g., one or more antigen-determining regions from an antibody or antibody fragment) to a CAR transmembrane domain and/or one or more CAR effector domains, e.g., as described herein.

In certain instances, a CAR is an engineered T cell receptor in which one or more T cell receptor domains is attached to a binding moiety (e.g., an antibody or antibody fragment), such that binding of the binding moiety to a target molecule results in activation of the T cell expressing the CAR. The T cell may then proceed to recognize and kill cells expressing the target molecule. The binding moiety of the CAR may, for example, include an antibody or antibody fragment (e.g., an scFv). The transmembrane domain may, for example, include a CD3-zeta or CD28 transmembrane domain. The effector domain may, for example, include a CD3-zeta, CD28, 41 BB, ICOS, FcεRIy, influenza MP-1, VZV, and/or OX40 cytoplasmic domain, or any combination or derivative thereof. Further binding moieties, transmembrane domains, and effector moieties that can be used in CARs are known in the art. For example, antibody-modified CARs are described in Maus et al. (*Blood* 123(17): 2625-2635, 2014), incorporated herein by reference in its entirety.

In some instances, a library of CAR variants including variants of a stalk region (e.g., such as a stalk described herein or as known in the art) may be generated, e.g., by the methods of the present invention. For example, a plurality of stalk variants may be generated according to methods known in the art, and then each of the stalk variants inserted into a CAR (e.g., between the T-cell receptor and the scFv domains of a CAR), thereby generating a library of CARs sharing identical TCR and scFv domains and variable stalks. The stalk variants may be inserted into the CARs, for example, by the conversion methods described herein. Such a CAR library may be, in some embodiments, screened for a desired property (e.g., enhanced activity in T cells). Candidate CAR variants showing improvement in the desired property may be selected using screening methods known in the art (e.g., fluorescence activated cell sorting or in vivo assays), and optionally identified by sequencing the vector expressing the selected CAR variants. This approach may be utilized to identify stalk regions that impart an improvement in such a desired property to the CAR.

Ubiquitin Ligases

A further polypeptide type that can be used in the methods and compositions of the present invention, for example, as a first polypeptide, a second polypeptide, or a chimeric polypeptide, are polypeptides including a ubiquitin ligase domain. Ubiquitin ligases (e.g., E3 ubiquitin ligases), as well known in the art, are ubiquitin-conjugating enzymes that attached ubiquitin, a small regulatory protein, to a polypeptide substrate at a lysine residue. Polyubiquitination of such a polypeptide substrate targets the substrate for degradation by the proteasome. As such, a ubiquitin ligase can be used to drive the degradation of polypeptides.

The ubiquitin conjugating domain, or ubiquitin ligase domain, of a ubiquitin ligase can be attached to a binding moiety to form a "ubiquibody" capable of targeting a particular polypeptide of interest for proteasomal degradation. For example, a binding moiety (e.g., an antibody or antibody fragment) can be fused to a ubiquitin ligase domain according to the methods of the present invention to form a ubiquitin that targets the binding moiety's binding partner for degradation. A ubiquibody may be produced, for example, by recombination of a first vector encoding a binding moiety (e.g., an antibody or antibody fragment) and a second vector encoding a ubiquitin ligase domain, thereby forming an integrant vector encoding a chimeric polypeptide in which the binding moiety is fused to the ubiquitin ligase domain. Alternatively, a ubiquibody can be used as a first polypeptide of the invention and converted to a polypeptide of another type according to the methods of the current invention. Ubiquitin ligase domains suitable for use in the methods and compositions of the invention include any E3 ubiquitin ligase domain known in the art (e.g., a CHIP or CHIPΔTPR ubiquitin ligase domain). Methods for producing ubiquibodies, and examples thereof, are described, for example, in Portnoff et al. (*J. Biol. Chem.* 289(11) 7844-7855, 2014), incorporated herein in its entirety.

Knocksideways Proteins

Polypeptides of the invention may include or be fused to a functional domain that promotes sequestration of the polypeptide to a particular intracellular region or compartment. For example, a polypeptide may include a localization signal (e.g., a signal peptide) that directs the polypeptide to a particular location within a cell (e.g., localization within an organelle, insertion into a membrane (e.g., a cell membrane, endoplasmic reticulum membrane, mitochondrial membrane, golgi membrane, endosomal membrane, or any other cellular membrane), or secretion from the cell). Alternatively, a polypeptide may include or be fused to a knocksideways prey or bait domain. The knocksideways system is described, e.g., in Robinson and Hirst (*Curr. Protoc. Cell Biol.* 15.20.1-15.20.7, 2013) and Robinson et al. (*Dev. Cell* 18: 324-331, 2010), each of which is incorporated herein in its entirety.

Briefly, the knocksideways system may be used to sequester a polypeptide of interest into a particular intracellular location (e.g., the mitochondrial surface), which may, for example, inactivate the polypeptide of interest. The polypeptide of interest may be any polypeptide for which modulation of its intracellular location is desired. In some instances, sequestration of the polypeptide of interest results in functional inactivation of the polypeptide of interest. The knocksideways system includes a bait protein and a prey protein. The bait protein may include a sequestration domain (e.g., a mitochondrial transmembrane domain) and a first binding moiety (e.g., an FRB domain or an FKBP domain) capable of recognizing a signal molecule (e.g., rapamycin or a rapamycin analog, such as AP21967). The prey protein may include the polypeptide of interest and a second binding moiety also capable of recognizing the signal molecule (e.g., an FRB domain or an FKBP domain). This second binding moiety, or portions thereof, is also referred to herein as a knocksideways prey domain. As such, when the signal molecule is present, the bait protein and the prey protein both bind and are thus brought together. Because the bait protein is sequestered to the region of the cell to which the sequestration domain is targeted, the prey protein is likewise sequestered to that region of the cell.

In one example, the bait protein includes an FRB domain and a transmembrane domain attached to a mitochondrial outer membrane, while the prey protein includes an FKBP domain and a protein to be inactivated (Robinson and Hirst, supra). In one embodiment, the bait protein is a Mitotrap protein. In the absence of rapamycin or a rapamycin analog, the prey protein is free-floating within the cytosol while the bait protein is restricted to the surface of the mitochondria. However, when rapamycin or a rapamycin analog is added, the FRB domain and the FKBP domain both bind to rapamycin molecules. A single rapamycin or rapamycin analog molecule can bind to both an FRB domain and an FKBP domain simultaneously. As a result, each rapamycin or rapamycin analog molecule can bring bait and prey proteins together. Because the bait protein is already restricted to the mitochondrial surface, this results in sequestration of the FKBP domain-containing prey protein to the mitochondrial surface as well. As such, if the protein to be inactivated must be localized elsewhere in the cell to function, then addition of rapamycin or a rapamycin analog results in inactivation of the protein to be inactivated.

The methods and compositions of the invention may be used to produce prey proteins or bait proteins suitable for use in the knocksideways system—in other words, the chimeric polypeptide may be a knocksideways prey or bait protein. For example, a binding moiety of another type (e.g., an antibody or antibody fragment) or a first polypeptide fused to another functional domain (e.g., a ubiquitin ligase domain or the extracellular, transmembrane, and/or intracellular domain(s) of a CAR) can be converted to a knocksideways bait or prey protein. The binding moiety or first polypeptide can be encoded on a first vector of the invention, which is recombined with a second vector including a knocksideways prey or bait protein (or a portion thereof, e.g., a knocksideways prey domain), thereby producing an integrant vector encoding a fusion protein including the binding moiety or first polypeptide, or a portion thereof, and the knocksideways prey or bait protein, or portion thereof. Knocksideways prey or bait proteins may also serve as the first polypeptide of the methods and compositions of the present invention, and may therefore be converted to polypeptides of other types according to the methods described herein.

RNA Editing

The vectors of the invention include polynucleotide segments encoding polypeptides (e.g., first polypeptides, second polypeptides, and chimeric polypeptides). These polynucleotide segments may include, for example, introns, exons, and various regulatory and non-coding elements. In some instances, the non-coding elements include one or more sites that, once transcribed to RNA, are capable of undergoing RNA editing. As known in the art, RNA editing is generally performed by an RNA editing enzyme, such as an adenosine deaminase acting on RNA (ADAR) enzyme. Briefly, ADAR enzymes catalyze the conversion of adenosines to inosines in double-stranded RNA substrates. Inosine mimics the properties of guanosine and therefore preferentially forms base pairs with cytosine. As such, the adenosine-to-inosine conversion catalyzed by an ADAR enzyme effectively results in an A-to-G single nucleotide polymorphism in the RNA, which can alter, for example, the amino acid sequence encoded by the RNA, RNA splicing, translational efficiency, RNA half-life, capacity of the RNA to hybridize to another polynucleotide (e.g., binding capacity or specificity of an siRNA, shRNA, miRNA, or other RNA for a target polynucleotide), and/or any other factors impacted by the nucleotide sequence of an RNA molecule as known in the art.

An ADAR enzyme may be present in a solution containing a vector of the invention, or the vector and the ADAR enzyme can both be present within a cell. In some instances, the vector of the invention includes a polynucleotide encoding an ADAR enzyme. In some instances, the ADAR enzyme is encoded in another vector or in the genome of the cell. ADAR enzymes may induce adenosine-to-inosine conversion in double-stranded RNAs (e.g., a self-hybridized RNA strand or two RNA strands hybridized to each other). In some instances, a vector of the invention includes a polynucleotide segment encoding a polypeptide (e.g., a first polypeptide, second polypeptide, or chimeric polypeptide), which is transcribed to produce an mRNA transcript. The mRNA transcript may, in certain instances, be capable of self-hybridization to form a double-stranded RNA molecule. For example, the mRNA transcript may include a first region and a second region capable of hybridizing to the first region to form a duplex. Such double-stranded RNA regions capable of being edited by ADAR enzymes are known in the art. In a first example, long double-stranded RNAs including at least about 100 base pairs (bp) (e.g., at least 100 bp, 110 bp, 120 bp, 130 bp, 140 bp, 150 bp, 175 bp, 200 bp, 250 bp, 300 bp, 400 bp, 500 bp, 600 bp, 700 bp, 800 bp, 900 bp, 1000 bp, 1250 bp, 1500 bp, 1750 bp, 2000 bp, 2500 bp, 3000 bp, 4000 bp, 5000 bp, 6000 bp, 7000 bp, 8000 bp, 9000 bp, 10,000 bp, or more) may be edited promiscuously (i.e., at adenosine residues throughout the sequence). In certain instances, about 50% of all adenosine residues in such a long double-stranded RNA may be converted to inosines. In a second example, short double-stranded RNAs (e.g., RNAs including about 1-100 bp; preferably RNAs including about 20-30 bp, e.g., about 20 bp, 21 bp, 22 bp, 23 bp, 24 bp, 25 bp, 26 bp, 27 bp, 28 bp, 29 bp, and 30 bp) include one or more specific editing-site complementary sequences (ECS), which form an imperfect fold-back double-stranded RNA structure between the exon sequence surrounding an adenosine-to-inosine editing site and a downstream (e.g., intronic) complementary sequence. Such ECSes can be, for example, used for site-specific RNA editing. In a third example, a double-stranded RNA region greater than about 30 bp in length (e.g., at least 30 bp, 40 bp, 50 bp, 60 bp, 70 bp, 80 bp, 90 bp, or 100 bp, or more) may include one or more mismatched bases, bulges or loops. In this example, adenosine residues in the sequence can be, e.g., selectively edited to inosines.

Exemplary RNA editing enzymes useful in the methods and compositions of the invention include, without limitation, mammalian ADAR1, ADAR2, and ADAR3; *Caenorhabditis elegans* CeADR1 and CeADR2, *Drosophila* ADAR, chicken ADAR, zebrafish ADAR, sea urchin ADAR, sea anemone ADAR, any other ADAR known in the art, adenosine deaminases acting on tRNAs (ADATs), and prokaryotic tRNA adenosine deaminase (TadA) enzymes. Exemplary RNA editing enzymes and mechanics through which such enzymes perform RNA editing are described, for example, in Nishikura (*Annu. Rev. Biochem.* 79:2.1-2.29, 2010), Savva et al. (*Genome Biol.* 13:252, 2012), and Schoft et al. (*Nuc. Acids Res.* 35(11): 3723-3732, 2007), each of which is incorporated by reference herein in its entirety. In some instances, an mRNA can be edited after transcription by programmed translational bypassing, by which a ribosome bypasses an interval of the mRNA sequence (see, e.g., Lang et al., PNAS 111(16): 5926-5931, 2014; incorporated herein by reference). For example, an mRNA encoded by a vector of the invention (e.g., an mRNA encoding a first polypeptide, second polypeptide, or chimeric polypeptide) may include one or more translational bypassing elements (byps), e.g., including a takeoff codon upstream of a stop codon followed by a sequence capable of forming a hairpin, as well as a matching landing triplet, e.g., about 50 nucleotides downstream.

Cells

The present invention provides methods and compositions for converting a first polypeptide, or fragment thereof, into a second polypeptide, or fragment thereof. The methods of the invention may be performed in a cell. For example, two vectors, one encoding a first polypeptide, and the other encoding a second polypeptide, can be recombined in a cell (e.g., a cell expressing a recombinase enzyme) to form an integrant vector encoding a chimeric polypeptide including the first polypeptide, or a fragment thereof, and the second polypeptide, or a fragment thereof. The compositions of the invention may include a cell (e.g., a cell including one or both of a first vector and a second vector of the invention). In some instances, the cell includes a recombinase enzyme capable of recombining the first vector and the second vector, e.g., according to the methods of the invention. A cell of the present invention may be any manipulable cell known in the art, such as a cell descending from a laboratory, commercial, or industrial cell line known in the art. A cell may be an archaeal cell, bacterial cell, fungal cell, or eukaryotic cell. A cell may be a yeast cell, plant cell, or animal cell. In some instances, the cell may be an E. coli cell, S. cerevisiae cell, or animal cell. The cell may be, e.g., a mammalian cell such as a human cell. Alternatively, the cell may be, for example, an insect cell (e.g., a Drosophila cell). A cell may be an immortalized cell. Alternatively, a cell may be a non-immortalized cell. Because the vectors of the present invention may include multiple promoters capable of driving each of one or more proteins or polypeptides encoded by the vectors in any of one, two, or more types of cells, the vectors of the present invention may be capable of expressing one or more proteins in each of one or more different cell types in accordance with the arrangement of promoters, splice sites, and other expression-determining sequences. It is understood that in various embodiments of the present invention, the first, second, and/or recombinant vectors of the present invention are intended to express one or more proteins or polypeptides in each of two or more cell types.

In order for site-specific recombination to occur within a cell of the present invention, the cell must include a recombinase enzyme. One or more recombinase enzymes of the present invention may be desired, in a particular recombination reaction, based upon the particular site-specific recombination sites present on the first vector and/or second vector. For instance, a first recombinase enzyme may be used for recombination between the first vector and second vector, while a different recombinase enzyme may be used to mediate an excision event. A recombinase enzyme may be endogenous to a cell (i.e., naturally encoded by the genome of that cell) or may be transgenic (i.e., introduced by a technique of molecular biology). A transgenic recombinase enzyme expressed in a cell may be expressed from a vector, such as a first or second vector of the present invention or another vector.

A recombinase enzyme may be any recombinase known in the art. In some instances, a recombinase enzyme may be an integrase. In certain instances, a recombinase enzyme may be a serine family recombinase or tyrosine family recombinase. The serine and tyrosine recombinase families are each named according to the conserved nucleophilic amino acid that interacts with DNA during recombination. Serine family recombinases include, for example, phiC31 integrase, which recognizes att sites, HIN invertase, which recognizes hix sites, and Tn3 resolvase. Tyrosine family recombinases include, for example, lambda integrase, which recognizes att sites, Cre, which recognizes lox sites, and FLP, which recognizes frt sites. Other recombinase enzymes are known in the art. For the purposes of the present invention, a recombinase enzyme capable of facilitating recombination of complementary recombination motifs present in one or more vectors of the present invention may be selected.

The invention includes various combinations of recombinase enzymes, e.g., recombinases and integrases. In some instances a plurality of recombinase enzymes are expressed in the same cell at the same time and function independently.

In Vitro Conversion

The present invention provides methods and compositions for converting a first polypeptide, or fragment thereof, into a chimeric polypeptide. The conversion methods of the invention may be performed in vitro (e.g., outside of a cell, such as in a cell-free system). In one example, two vectors, one encoding a first polypeptide and the other encoding a second polypeptide, can be recombined in a solution (e.g., a solution including a first vector, a second vector, and a recombinase enzyme of the invention) to form an integrant vector encoding a chimeric polypeptide including the first polypeptide, or a fragment thereof, and the second polypeptide, or a fragment thereof. The solution may include additional factors, reagents, and/or buffers that may enable the recombinase enzyme to successfully catalyze the recombination reaction (e.g., as known in the art). In some embodiments, multiple instances of the method can be performed in parallel using multiplexed systems as known in the art. For example, parallel reactions can be run in oil-in-water emulsion droplets, multiwell plates, multiple tubes, or other systems including multiple compartments.

The compositions of the invention may include one or both of a first vector and a second vector of the invention. In some instances, the composition includes a recombinase enzyme capable of recombining the first vector and the second vector, e.g., according to the methods of the invention. In certain instances, the composition may not include a cell, or may include a cell not containing the first vector, second vector, and/or recombinase enzyme. In some instances, the compositions of the invention may include multiple compartments, each containing a first vector, a second vector, and/or a recombinase enzyme, such that the first vector of each compartment may recombine with the second vector of that compartment according to the methods of the invention, thereby resulting in multiple conversion reactions occurring in parallel.

In one example, a solution is provided containing a first vector, a second vector, and a recombinase enzyme. The first vector includes a polynucleotide encoding a first polypeptide and a site-specific recombination site (e.g., an attP site). For example, the first polypeptide may be an scFv and the attP site may be located within the polynucleotide encoding the linker region of the scFv. The first vector may further include one or more additional polypeptide-encoding elements (e.g., a polynucleotide encoding a CH or CL domain). The second vector includes a polynucleotide encoding a second polypeptide and a site-specific recombination site (e.g., an attB site). For example, the second polypeptide may include portions of an IgG (e.g., a CL domain). The attB site may be positioned upstream of the CL domain. The recombinase enzyme (e.g., bacteriophage lambda integrase or phiC31 integrase) is capable of recombining the site-specific recombination sites of the first vector and the second vector. The solution may further include, e.g., accessory factors (e.g., Xis excisionase and integration host factor (IHF)), reagents (e.g., spermidine and BSA), buffers and solutes (e.g., Tris HCl, NaCl, and EDTA). For example, the solution may include 25 mM Tris Hcl pH 7.5, 22 mM NaCl, 5 mM EDTA, 5 mM spermidine HCl, and 1 mg/mL BSA (e.g., as described in Hartley et al., supra). Recombination between the first vector and the second vector by the recombinase enzyme results in the formation of an integrant vector encoding a chimeric polypeptide (e.g., an IgG including the variable domains of the scFv, the CH domain of the first vector, and the CL domain of the second vector) including at least a portion of the first polypeptide fused to at least a portion of the second polypeptide.

Arrangements of Polypeptide-Encoding Sequences and Functional Cassettes for Achieving Conversion An important aspect of the present invention is that the components of the first polypeptide and components of the second polypeptide are positioned such that recombination between the first and second vectors results in a functional chimeric polypeptide, e.g., of a type different from that of the first binding moiety. The description and examples provided herein provide sufficient information for the construction of a wide variety of first and second vectors capable of recombining in such a manner. Without limiting the scope of the present invention, a number of first and second vector pairs are described herein as illustrative examples.

In one embodiment, the first polypeptide encoded by the first vector is an scFv including, from 5' to 3', an immunoglobulin light chain (VL), a linker, and a variable region of an immunoglobulin heavy chain (VH). The first vector includes a promoter capable of directing expression of the scFv, such as a bifunctional promoter or trifunctional promoter. Importantly, the linker of the scFv of the first vector is bifunctional, capable of being translated into an amino acid linker positioned between the VL and VH and also encoding a site-specific recombination motif. The first vector additionally includes, 3' and separate from the polynucleotide segment encoding the scFv, an CH cassette and a polyA cassette. The polynucleotide segment encoding the CH and polyA is separated from the polynucleotide segment encoding the scFv by a plurality of nucleotides. These nucleotides are flanked an excision motif pair (e.g., loxP sites). The second vector of this embodiment includes a site-specific recombination site complementary to that of the linker. The second vector encodes, 5' of the site-specific recombination site, a promoter, such as a bifunctional or trifunctional promoter. It also encodes, 3' of the site-specific recombination site, a polyA cassette and an immunoglobulin light chain constant region cassette. Two recombination events in this embodiment mediate the conversion of the scFv to an immunoglobulin. In one event, recombination between the site-specific recombination motifs of the excision motif pair (e.g., by a Cre recombinase enzyme) excises the plurality of polynucleotides between the VH of the scFv of the first binding moiety and the CH of the first binding moiety. This event brings together the VH, CH, and PolyA to form a substantial portion of an immunoglobulin heavy chain. In another event, which may occur before, after or concurrently with the excision event, the site-specific recombination motif present in the linker of the first binding moiety recombines with the site-specific recombination motif of the second vector. This event separates the VH and VL of the scFv and instead associates the VH with the promoter of the second vector, completing an expressible immunoglobulin heavy chain construct. In addition, the VL of the scFv becomes associated with the light chain constant region and polyA of the second vector, completing an expressible immunoglobulin light chain construct.

Depending on the site-specific recombination motifs present in the described vectors, it is understood that the described recombination events may occur in the presence of any of one or more particular desired recombinase enzymes. It is appreciated that many if not all of a wide variety of known site-specific recombination motifs and associated enzymes are appropriate to the uses of the present invention. It is additionally appreciated that any or all of the recombination motifs or hybrid motifs left following recombination may be bifunctional (amino acid-encoding) in this or other methods of the present invention.

Kits

The vectors, libraries, cells (e.g., *E. coli* strains), recombinase enzymes, and/or other materials described herein may be assembled into a kit. The kit may include instructions for producing chimeric polypeptides according to the methods of the invention.

EXAMPLES

The below exemplary methods shall not limit the scope of the invention as otherwise described above. The below exemplary methods illustrate a subset of the presently invented methods.

Example 1: Conversion of an scFv Binding Moiety into an IgG Binding Moiety

Binding moieties capable of binding one or more particular antigens may be identified by biopanning techniques such as phage display. Many binding moieties identified by such techniques are single-chain binding moieties, such as an scFv. However, IgG molecules may be desirable for certain applications, e.g., for reasons related to stability, commercial preferences, research preferences, potential for integration or combination with existing or developing technologies, and increased binding of antigens, due, e.g., due to the avidity effect. Single-chain antibodies can be converted to IgG type antibodies by methods involving sub-cloning. This can involve substantial time and expense. This Example describes the conversion of an scFv, e.g., an scFv identified by display biopanning as having high affinity for a particular antigen, into an IgG molecule. The method utilizes recombination between a first vector and a second vector within *E. coli*. More specifically, the scFv is encoded by a first vector and is converted to an IgG by recombination between this first vector and a second vector that includes an IgG framework. The recombinant product of this recombination is capable of expressing an IgG light chain and an IgG heavy chain (together, an IgG molecule), each including an antigen-determining region originating from the scFv. Importantly, this IgG molecule was not encoded by the first vector, the second vector, or the first and second vector when taken as a pair. The recombinant product is capable of expressing the IgG molecule in a mammalian cell, e.g., for production purposes.

Figures 4A, 4B, 4C:
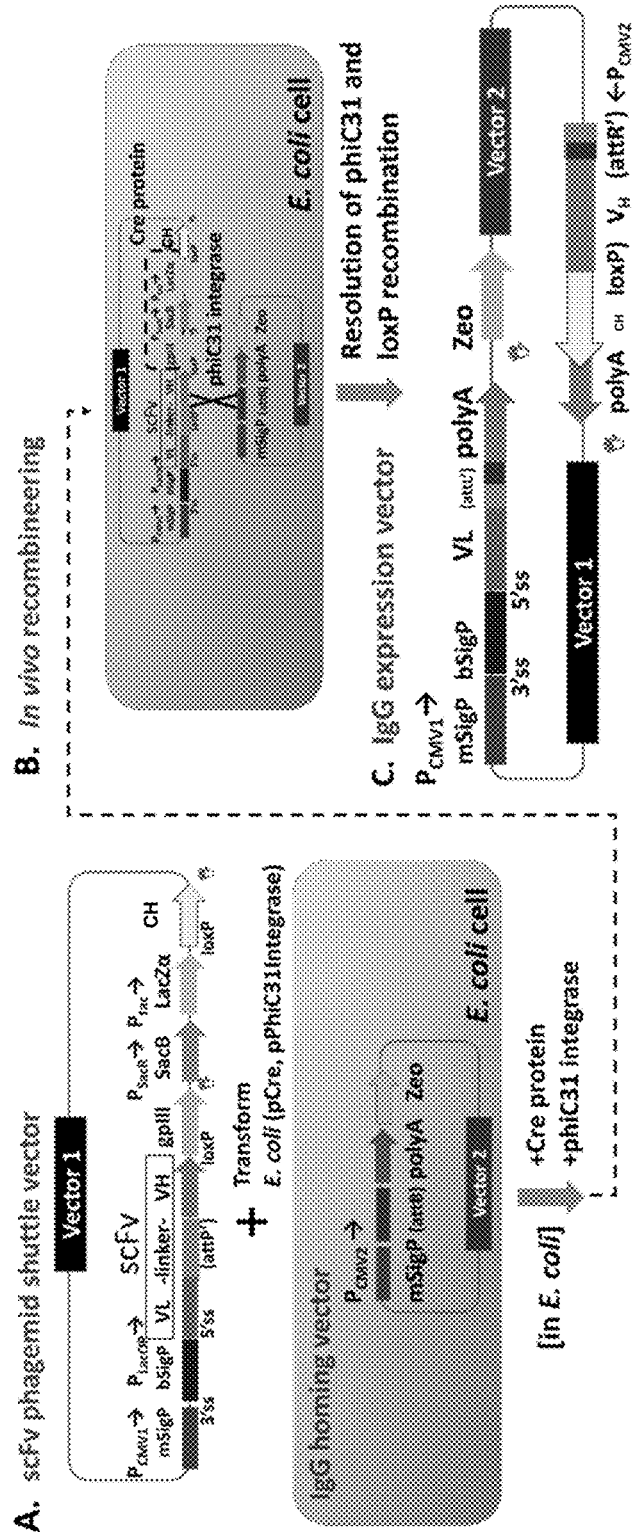
FIGS. 4A-4C are a series of schematics showing (A) a first vector and a second vector, (B) recombination between the first vector and the second vector, and (C) the recombinant product of recombination between the first vector and the second vector, which encodes an immunoglobulin chimeric polypeptide.

As summarized in FIG. 4, the first vector (Vector 1 of FIG. 4A) is a phagemid donor vector including an scFv binding moiety that is fused to GpIII (together, an scFv fusion protein). This first vector is a vector having been identified in a phage display biopanning procedure for phagemids encoding an scFv capable of binding a particular antigen. The components of the scFv binding moiety, shown within a box, include a variable region of an immunoglobulin light chain (VL), a linker, and a variable region of an immunoglobulin heavy chain (VH). Importantly, the linker of the scFv of vector 1 is bifunctional. It encodes the scFv linker of 12 or more amino acids and additionally encodes a site-specific recombination site that is a substrate of phiC31 (attP'). The phiC31 integrase is from *Streptomyces* phiC31 and is an enzyme that mediates unidirectional, site-specific recombination between complementary site-specific recombination sites, namely the 36 bp phage attachment site, attP, and the 36 bp bacterial attachment site, attB. The attP' of the scFv linker is optimized from a known attP site for bifunctional use.

Positioned 5' of the scFv fusion protein, the first vector encodes, from 5' to 3', a first CMV promoter ($P_{cmv1}$), a mammalian signal peptide (mSigP), a first splice site (5' ss), a lac operon promoter ($P_{LacOP}$), a bacterial signal peptide (bSigP), and a second splice site (3' ss). As a result of this arrangement, expression from $P_{cmv1}$, e.g., in a mammalian cell, results in an scFv protein that includes a mammalian signal peptide but not a bacterial signal peptide, while expression from $P_{LacOP}$ results in an scFv fusion protein that includes a bacterial signal peptide but not a mammalian signal peptide. It is to be understood that modification of polynucleotides 3' of these promoter and signal peptide functional cassettes may modify the translated protein without altering the basic effect of this arrangement, namely the cell-specific translation of a protein having one or the other of the two signal peptides.

Positioned 3' of the scFv, the first vector encodes, from 5' to 3', a site-specific recombination site that is a substrate of Cre recombinase (loxP, e.g., JT15), an amber stop codon (not shown), a cassette encoding the phage M13 gene 3 product (GpIII), a *B. subtilis* SacR promoter ($P_{SacR}$), a selectable marker (SacB), a chimeric trp and lac promoter ($P_{tac}$), a selectable marker (LacZα), a second substrate of cre recombinase (loxP), a polynucleotide segment encoding the second and third constant domains of an IgG heavy chain (CH; it is noted that while CH can mean a binding moiety including two each of the second and third constant domains of an immunoglobulin, it is here used within this example to mean an immunoglobulin antibody chain fragment that includes one of each), an amber stop codon, and a polyadenylation sequence (polyA; not shown). In some instances, a zeocine gene is present between the amber stop codon and the polyA. The amber stop codon positioned between the scFv and the GpIII gene allows expression of the scFv in non-suppressing *E. coli* hosts.

The loxP sites of the first vector are an excision motif pair. Excision occurs in the presence of the loxP site recombinase enzyme Cre recombinase. Cre recombinase is a tyrosine recombinase enzyme derived from the P1 bacteriophage. Cre recombinase catalyzes the site-specific recombination of loxP sites, which are 34 bp sites that include two 13 bp palindromic sequences that flank and 8 bp spacer region. The product of the recombination of loxP sites depends upon the location and relative orientation of the loxP sites. DNA between two loxP sites that are oriented in the same direction is excised as a circular loop of DNA, as occurs in the present example. As a result of the present arrangement of loxP sites, incubating the first vector with cre recombinase results in excision of the nucleotides flanked by the loxP sites (FIGS. 4B and 4C). Also, as shown in FIG. 4C, the excision event leaves a hybrid loxP site in the excision product.

The first vector is transferred into *E. coli*. In some embodiments represented by the present example, the first vector is transformed into the *E. coli* cell. In other embodiments represented by the present example, the first vector is transduced into the *E. coli* cell, in which instances the *E. coli* cell is an F⁺ *E. coli* cell. The *E. coli* cell into which the first vector is transduced includes a second vector (FIG. 4B). The second vector encodes, from 5' to 3', a CMV promoter ($P_{cmv2}$), a mammalian signal peptide (mSigP), a 36 bp site-specific recombination site that is a substrate of phiC31 integrase and that is complementary to attP' (attB), an immunoglobulin light chain constant region, an amber stop codon, a polyadenylation sequence (polyA), and a zeocin resistance protein (Zeo). The zeocin resistance cassette confers selection in both mammalian cells and in *E. coli*. In some instances, the zeocin resistance cassette is used to replace an ampicillin resistance cassette that may be present in the first vector prior to the steps described in the present example. In other instances, the zeocin resistance cassette may be replaced by an alternate resistance cassette (e.g., a CamR cassette). In certain instances, a polyadenylation signal site (polyA) is present 3' of the attB site. In particular instances, a variable chain constant region is present between the attB site and the polyA.

In addition to the second vector, the *E. coli* cell into which the first vector is transformed includes, for example, cre recombinase and phiC31 integrase. As described, and as is known in the art, cre recombinase is capable of mediating site-specific recombination between loxP sites and phiC31 integrase is capable of mediating site-specific recombination between attP' and attB. Accordingly, if the first and second vectors of this example are present together in the cell, at least two recombination events occur within the cell. It is not specified in the present example whether one or both of the phiC31 integrase and the cre recombinase are endogenous to the *E. coli* cell or introduced to the *E. coli* cell by techniques of molecular biology, e.g., by integration or expression from the first vector, the second vector, or one or more other vectors. It is further not specified whether these elements are constitutively or inducibly expressed. Accordingly, in some embodiments the Cre recombinase mediated and phiC31 integrase mediated recombination events may occur in any order or simultaneously. In some embodiments of the present invention, the order may be wholly or partially regulated or controlled. However, such regulation or control may not be necessary.

In one example, Cre recombinase is expressed in a vector (e.g., a pAX889 vector). The Cre gene may be placed under the control of an inducible promoter such as, for example, the arabinose-inducible araC promoter in a vector carrying a different replication origin and antibiotic resistance gene (e.g., p15A origin and spectinomycin resistance) than the phagemid, so both plasmids can be maintained in the same *E. coli* cell. The pAX889 vector was tested using TG1 cells transformed with pAX889, which were infected with phage carrying a phagemid with two loxP sites as direct repeats flanking a 300 bp locus. In the presence of 2% arabinose (which induces Cre expression), the phagemid underwent intramolecular recombination to yield products with the intervening region deleted.

Cre recombinase mediates recombination between the loxP sites of the first vector, resulting in excision of the polynucleotide segments encoding GpIII, $P_{SacR}$, SacB, $P_{tac}$, and LacZα. In FIG. 4B, dashed lines form a bracket that indicates the excised segment. Furthermore, following excision, the number of nucleotides separating the polynucleotide segment encoding the scFv binding moiety and the CH cassette is greatly reduced. As shown in FIG. 4C, the VH and CH are yet separated by at least the hybrid loxP site remaining at the point of recombination following the excision event. More specifically, the CH is fused to the VH of the scFv such that the VH and CH could be expressed as a single protein (together, a VH-CH fusion protein). For instance, the nucleotides separating the VH and CH after excision could encode amino acids when transcribed and translated in frame with the VH and CH.

Alternatively, the nucleotides intervening between polynucleotide segments encoding the VH and CH could include splice sites, such that transcription of the polynucleotide segments encoding the VH and CH in a single transcript could result in a mature mRNA capable of expressing a single protein including the VH and CH. In a VH-CH fusion protein so expressed, the terminal amino acids of the VH and CH may be directly adjacent or separated by one or more amino acids encoded by intervening nucleotides. Excision can be monitored for occurrence or efficiency by screening for phenotypes connected with the SacB and a LacZα cassettes. In particular, cells in which one or all first vectors have undergone excision survive on sucrose due to loss of SacB and will thus appear white, rather than blue, when cultured in the presence of the LacZ substrate X-gal.

In the phiC31 integrase-mediated recombination event, the attP' site-specific recombination motif of the first vector and the attB site-specific recombination motif of the second vector recombine to generate a recombinant product (e.g., a recombinant product in which one or more regulatory elements are introduced to control expression of a gene expressing, for example, an VH-CH fusion protein). In some instances, regulatory elements (e.g., a mammalian and/or bacterial promoter, and a functional protein initiation site) are added 5' to the VH-CH fusion protein-encoding gene. As shown in FIG. 4B, this recombination event results in crossover between the first vector (within the linker) and second vector (between the mammalian signal peptide and the polyA). When this recombination event occurs, in combination with the above-described excision event of the present example, a polynucleotide segment encoding a chimeric polypeptide is generated. As shown in FIG. 4C, this encoded chimeric polypeptide includes two separately expressed proteins: a protein including the VL of the scFv and an (not shown) immunoglobulin light chain constant region (an immunoglobulin light chain) and protein that includes the VH of the scFv and an immunoglobulin heavy chain CH (an IgG heavy chain). Accordingly, the first binding moiety, an scFv, has been converted to an immunoglobulin having two chains, each chain including a portion of the scFv.

To generalize some of the major events entailed by the conversion of the present example, one can look to the general results of each of the two recombination events. The Cre recombinase-mediated excision event results in an scFv fusion protein that includes the CH. This fusion protein includes all of the constant and antigen-determining regions of an immunoglobulin heavy chain (VH and CH). However, it further includes the light chain antigen-determining region, VL. The linker separating the VL from the VH includes an attP' recombination motif. When recombination with the second vector attB motif occurs, the VL is separated from the VH and CH, and is fused with a light chain constant region (LC) encoded by the second vector. As a result of these recombination events together, the recombinant product includes an immunoglobulin light chain and an immunoglobulin heavy chain that are separately expressed. Accordingly, the scFv has been converted to an immunoglobulin. While this brief description does not capture every advantage of the present invention, it provides a basic overview of the general mechanism of one embodiment.

With reference to the other functional cassettes of the first and second vector, the following occur in the present example. The segment of the first vector encoding $P_{CMV1}$, mSigP, 5' ss, $P_{LacOP}$, bSigP, and 3' ss remains associated with $V_L$. After recombination with the second vector, the $V_L$ is followed by an attL' hybrid recombination motif, amber stop codon, polyA derived from the second vector, and zeocin resistance cassette derived from the second vector. Separately, the CH and polyA of the first vector remain associated with the VH. After recombination with the second vector, the VH is preceded by the $P_{cmv2}$ promoter derived from the second vector, a mammalian signal peptide derived from the second vector (not shown), and an attR hybrid recombination motif. Thus, both the immunoglobulin light chain and the immunoglobulin heavy chain of the chimeric polypeptide may be expressed in mammalian cells. While not explicitly noted in FIG. 4, the recombinant product includes functional protein initiation sequences 5' of the polynucleotide segment encoding each immunoglobulin chain of the chimeric polypeptide. It is contemplated that in various embodiments of the present invention the chimeric polypeptide protein or proteins may include promoters and other sequence elements for expression in any of one or more of bacterial cells, insect cells, or mammalian cells.

Example 2: Bifunctional Expression Constructs

The present example relates the use of a particular bifunctional expression construct for use within the technique of Example 1. As used in the present examples, an expression construct means a combination of regulatory elements directed to the expression of a particular protein or a set of variants of that protein.

It is known that the requirements for the expression of proteins in, e.g., bacteria, mammalian cells, and insect cells can differ. Furthermore, it is known that the requirements for expression can vary among bacteria, among mammalian cells, and among insect cells. An expression construct may be a bifunctional expression construct such that the particular protein or set of variants of that protein can be expressed in both mammalian cells and bacterial cells. The present example includes a human IgG1 framework as the first vector Fc and second vector LC because human IgG is one of a variety of frameworks of therapeutic value, e.g., for use against pathogens and cancer cells.

With respect to the bifunctional expression construct of the present example, the construct includes a cassette based on the strong cytomegalovirus (CMV) promoter. This CMV promoter is sub-cloned 5' of the scFv of a phagemid similar to that of Example 1. The construct further includes a cassette based on the mammalian promoter shown in FIG. 2. The CMV promoter is positioned 5' of a mammalian IgG heavy chain secretion signal that includes an intron, which can then be expressed from the CMV promoter. The mammalian intron contains the lac promoter/operator. Positioned 3' of the lac promoter/operator, and still within the mammalian intron, is a polynucleotide segment encoding a bacterial signal peptide. The bacterial signal peptide sequence overlaps with a splice acceptor site (see Quinlan et al., J. Biol. Chem. 288: 18803-10, 2013; incorporated herein by reference). The bacterial promoter, signal peptide, and splice sites can be or include previously characterized consensus sequences that are well known in the art. The bacterial signal peptide is a pelB signal peptide having a consensus splice acceptor site known to support Fab production in the E. coli periplasm and to be spliced efficiently in mammalian cells (see U.S. Pat. No. 7,112,439, incorporated herein by reference). The intron nucleotide sequence may be designed using, for example, promoter consensus sequences, signal sequence consensus sequences, and splice site consensus sequences well-known in the art (see, e.g., Mergulhao et al., *Biotechnology Advances* 23: 177-202, 2005; Stern et al., *Trends Cell Mol. Biol.* 2: 1-17, 2007; and Jackson, *Nucleic Acids Res.* 19: 3795-3798, 1991; each of which is incorporated herein by reference).

Within *E. coli*, this expression construct may express, from the bacterial promoter within the mammalian intron, an scFv protein including a bacterial signal peptide. This protein may be present,f for example, in the bacterial periplasm. This protein may be displayed on the surface of a virus (e.g., M13 bacteriophage), for example, as a fusion to a coat protein (e.g., GpIII). The same expression construct in a mammalian cell may splice out the bacterial promoter/operator and signal peptide sequence, resulting in the expression of an scFv protein including the mammalian signal peptide.

Proper expression of proteins in particular cell types may further involve a polyadenylation signal. In the present example, each of the first and second vector includes a polyadenylation signal that is the SV40 polyadenylation signal. This signal is isolated or synthesized and cloned, e.g., 3' of the Fc cassette, which is a human IgG1 Fc.

Example 3: Trifunctional Expression Constructs

Binding moieties, e.g., first polypeptides, second polypeptides, and chimeric polypeptides, of the present invention can be expressed from trifunctional expression constructs. In particular, it is known that the requirements for the expression of proteins in, e.g., bacteria, mammalian cells, and insect cells can differ. Furthermore, it is known that the requirements for expression can vary among bacteria, among mammalian cells, and among insect cells. An expression construct may be a trifunctional expression construct such that it is capable of promoting the expression of a particular protein or set of variants of that protein in mammalian cells, bacterial cells, and insect cells.

Figure 5:
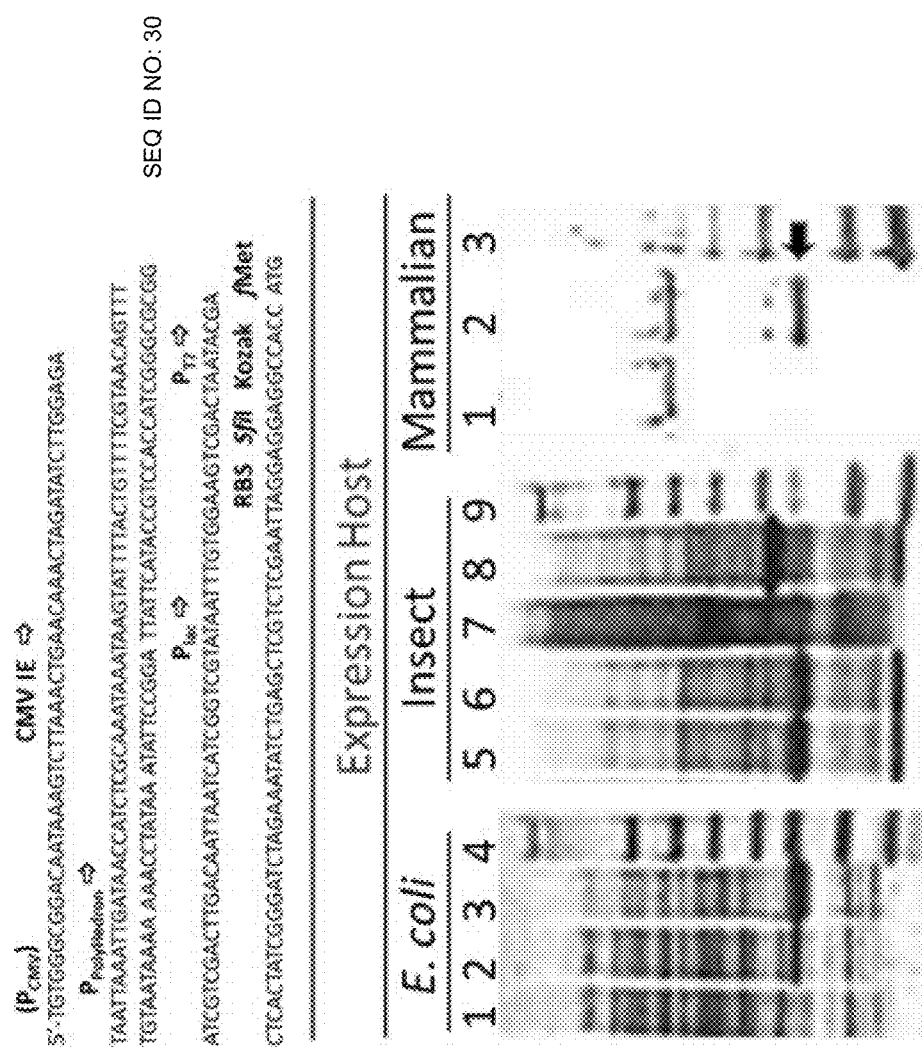
FIG. 5 is a schematic showing the sequence of a multifunctional promoter (top) and protein blots showing expression of a CAM resistance protein, from the multifunctional promoter (bottom) in a number of vectors and cell types. Lanes 1-9 are Coomassie stained. *E. coli* lane 1 shows expression of a protein from the multifunctional promoter in pSK215 vector in *E. coli*. *E. coli* lane 2 shows expression of a protein from the multifunctional promoter in pSK215cat vector in *E. coli*. *E. coli* lane 3 shows expression of a protein from the multifunctional promoter in pRSETcat vector in *E. coli*. *E. coli* lane 4 contains a molecular weight marker. Insect lane 5 shows expression of a protein from the multifunctional promoter in pSK215cat (bacmid) in insect *T. ni* cells. Insect lane 6 shows expression of a protein from the multifunctional promoter in pFastBacCat (bacmid) in insect *T. ni* cells. Insect lane 7 shows uninfected *T. ni* cells. Insect lane 8 shows *T. ni* cells infected with wild type baculovirus. Insect lane 9 contains a molecular weight marker. Mammalian lanes 1 to 3 show Western analysis of mammalian cell line expression of cat using an anti-Cat antibody. Mammalian late 1 shows Western analysis of untreated CV-1 cells. Mammalian lane 2 shows Western analysis of CV-1 cells transfected with pSK215cat. Lane 3 contains a molecular weight marker. Arrow indicates the cat gene product. The upper band is an artifact that is also observed in Western analysis of untreated cells.

A variety of functional cassettes may be utilized in a multifunctional expression construct. These cassettes include the CMV intron/enhancer region (CMV IE), polyhedron promoter ($P_{PH}$, from baculovirus), tac promoter ($P_{tac}$), bacteriophage T7 promoter ($P_{T7}$), $P_{CMV}$ promoter (complete sequence not shown in FIG. 5), *E. coli* ribosome binding site (RBS), and Kozak sequence. FIG. 5 shows an arrangement of these functional polynucleotide cassettes leading up to a protein translation ATG start site (fMet). The arrangement includes the removal of all ATG sequences from the cassettes, in order to eliminate the presence of potential fMet protein initiation sites from within the trifunctional expression construct. As shown these cassettes are assembled, from 5' to 3', in the order of $P_{CMV}$, CMV IE, $P_{polyhedron}$, $P_{tac}$, $P_{T7}$, RBS, SfiI restriction site, and Kozak, the last being immediately prior to fMet. This concatenation of CMV, polyhedron, and Lac promoters enables a single multifunctional expression construct capable of expressing a protein from a single coding sequence in any of three types of hosts: mammals, insects, and bacteria.

Example 4: Validation of Transformation or Transduction of *E. Coli* with the First Vector and Second Vector The first and second vectors of Examples 1 and 2 may include amber stop codons. These amber stop codons can be suppressed in TG1 *E. coli* cells. TG1 cells can be TG1 cells that express Cre and PhiC31. According to the present example, the techniques presented in Examples 1 and 2 are executed using TG1 *E. coli* cells. TG1 cells successfully transformed or transduced with the second vector can be positively selected by growth in the presence of zeocin.

TG1 cells successfully transformed or transduced with the first vector can be identified by response to growth on 6% sucrose. TG1 cells expressing SacB fail to grow on the sucrose media. Accordingly, transformed or transduced TG1 cells are grown in duplicate by patching or replica plating on plates with and without 6% sucrose to distinguish cells that do or do not express SacB. Transformed or transduced TG1 cells can also, or alternatively, be patched, replica plated, or grown onto plates containing X-gal and IPTG to confirm expression of the LacZα gene by blue white selection.

Example 5: Optimization of a Bifunctional att Site-Specific Recombination Sites

In various embodiments of the present invention, a first binding moiety includes a linker that is or includes a site-specific recombination motif. In particular embodiments, polynucleotide segments encoding two components of a binding moiety protein are separated by a number of nucleotides, each of which encodes an amino acid of a linker. Accordingly, the number of intervening nucleotides must be a multiple of three, each nucleotide part of a codon encoding an amino acid of the binding moiety. Various known site-specific recombination motifs are not amenable to this bifunctional use. That is, they do not include a reading frame that can be transcribed or translated. In some instances, this may be because all reading frames include at least one stop codon or because the motif does not normally include a number of nucleotides that is a multiple of three. The present example describes the optimization of site-specific recombination motifs in order to identify bifunctional variants thereof.

Libraries of variant attP and/or attB sequences may be produced by random mutagenesis starting from known, functional site-specific recombination sites. The libraries may be cloned into test vectors. In particular, a set of vectors including attP variants may be produced and a set of vectors including attB variants may be produced. Optionally, these sites could be flanked with hydrophilic flexible amino acids (e.g., $(Gly_4Ser)_N$) of various lengths. It is noted that 9 of the 12 reading frames cumulatively present in the attB and attP sites are open reading frames.

An assay has been designed that allows the identification of two vectors that, when present in a single cell that includes a phiC31 integrase, are able to recombine. Each vector includes a site-specific recombination site. In a first test vector, a portion of a chloramphenicol resistance (CamR) gene (a construct including a polynucleotide encoding a protein that, when expressed, results in chloramphenicol resistance) is 5' of and adjacent to a variant recombination motif, here a variant or known attP motif. In a second test vector, the remainder of the CamR gene is 3' of and adjacent to a potentially complementary recombination motif, here a variant or known attB motif. Thus, the assay may be carried out using variants of an attP motif on the first test vector and a known attB motif on second test vector, a known attP motif on the first test vector and variants of an attB motif on second test vector, or variants in both vectors. Recombination between a first test vector and a second test vector in a cell including a phiC31 integrase results in the manifestation of a CamR phenotype.

Figure 6:
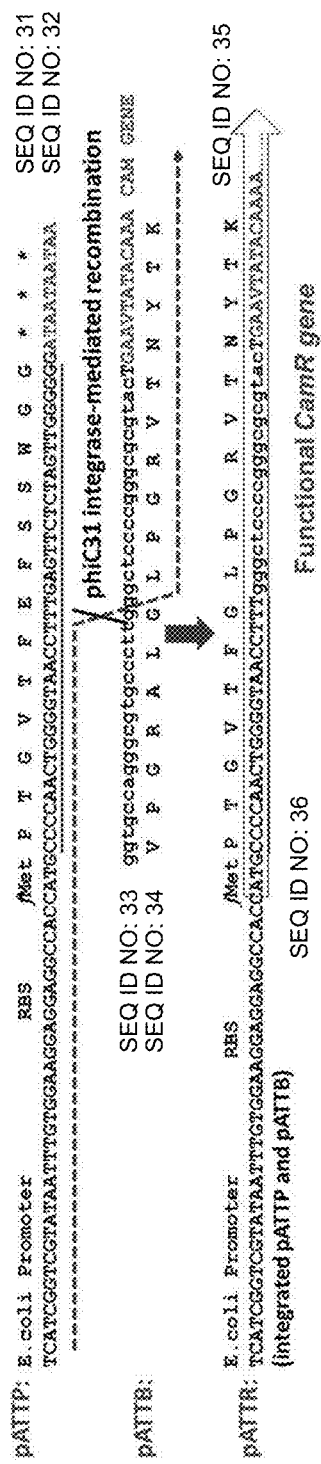
FIG. 6 is a schematic showing a first polynucleotide including a site-specific recombination motif, a second polynucleotide (pATTB) including a site-specific recombination motif complementary to that of the pATTP construct, and a recombinant product resulting from recombination between pATTP and pATTB.

In one particular example, the CamR gene includes an *E. coli* promoter and a CamR protein encoding region that includes an ATG protein initiation site. The portion 5' of the attP motif includes the promoter and ATG protein initiation site (FIG. 6, pATTP). The portion 3' of the attB motif includes the remainder of the CamR gene (FIG. 6, pATTB). The nucleotides of the attP motif are illustrated as underlined letters (FIG. 6, pATTP) and the nucleotides of the attB motif are illustrated as lower case letters (FIG. 6, pATTB). As shown in FIG. 6, recombination between two such test vectors results in a product that includes an attR hybrid motif within a functional CamR gene (FIG. 6, pATTR). If the attR is not capable of expression such that each nucleotide of the attR contributes to a codon that contributes an amino acid to the protein product of the CamR gene, a CamR phenotype is not manifested. Accordingly, growth on LB media including Cam may be used to identify cells having a recombinant product with an attR that can be translated. Recombinant products present in these cells may be cloned, sequenced, or otherwise identified by any of a variety of means known in the art.

Utility of identified pairs of motifs may be tested. Pools of motifs may be subcloned into a phagemid in the linker position of a polynucleotide encoding an scFv identified as being capable of binding a target protein (e.g., the MS2 coat protein). Phage may be produced from the VL-(subclone)-VH scFv vectors. These phage may be biopanned against an antigen using standard phage display methodology or another method of biopanning known in the art. Clones expressing functional scFv binding moieties may be isolated and the sequence of the linker may be amplified by PCR with subsequent confirmation by DNA sequencing or other methods known in the art. Clones may be retested to eliminate false positives. Clones may also be tested in HEK-293 cells.

While the example describes in particular the optimization of bifunctional attP and attB motifs, it may be of value to further optimize other motifs for use in conjunction with or instead of attP and attB. Accordingly, the methodology of the present example may be used to optimize bifunctional variants of other site-specific recombination motifs. These may include FLP/FRT site-specific recombination motifs and other alternative recombinases such as those shown in Table I.

TABLE 1

Examples of site-specific recombinases

|  | Phage/ name | Host | Amino acid length | Overlap region | SEQ ID NO: | Works in mammalian cells? |
|---|---|---|---|---|---|---|
| Tyrosine integrases | λ | *Escherichia coli* | 356 | TTTATAC | 7 | yes |
|  | HK022 | *Escherichia coli* | 357 | AGGTGAA | 8 | yes |
|  | P22 | *Salmonella typhimurium* | 387 | TTCGTAA | 9 | unknown |
|  | HP1 | *Haemophilus influenzae* | 337 | TTTTAAA | 10 | unknown |
|  | L5 | *Mycobacterium smegmatis* | 371 | CTTCCAA | 11 | unknown |
| Other tyrosine recombinases | Cre (P1) | *Escherichia coli* | 343 | ATGTATGC | 12 | yes |
|  | FLP | *Saccharomyces cerevisiae* | 423 | TCTAGAAA | 13 | yes |
|  | XerC | *Escherichia coli* | 298 | TGTACA | 14 | unknown |
| Serine Integrases | phiC31 | *Streptomyces lividans* | 613 | TTG | 15 | yes |
|  | R4 | *Streptomyces parvulus* | 469 | GAAGCAGTGGTA | 16 | yes |
|  | TP901 | *Lactococcus lactis* | 485 | TCAAT | 17 | yes |
| Other serine recombinases | γδ | *Escherichia coli* | 183 | TATTATAAAT | 18 | yes |
|  | Tn3 | *Klebsiella pneumoniae* | 185 | TATTATAAAT | 19 | unknown |
|  | gin (phage Mu) | *Escherichia coli* | 193 | GA | 20 | unknown |

Example 6: Further Optimization of Bifunctional Site-Specific Recombination Motifs It may be beneficial, in some instances, to include in a bifunctional linker more codons than would be necessary to encode only a bifunctional recombination motif. For instance, it may be beneficial to develop a longer linker or the addition may improve the efficiency of transcription, translation, or recombination. The present example includes the identification of additional sequence material of inclusion in a bifunctional linker that does not disrupt the recombination function of the linker. For instance, vectors as described in the previous example could further include additional nucleotide positions 5' or 3' of the site-specific recombination motif. These additional sequences could be one or more flexible hydrophobic cassettes, such as $(Gly_4Ser)_N$. Such cassettes are commonly used as scFv linker sequences. These and other known linker sequences may be candidates for inclusion in bifunctional linkers in addition to a recombination motif. Selected bifunctional recombination motifs may be optimized by these means in order to further increase efficiency of expression, binding moiety activity, or the like. In some instances, a polynucleotide encoding a bifunctional linker, or a portion thereof, may be flanked by mammalian splice sites, such that the portion of the bifunctional linker encoded by the region flanked by the mammalian splice sites is only expressed in non-mammalian cells.

Another mechanism for the optimization of bifunctional linkers may be to insert restriction sites within the linker such that when a transcript is generated that includes the linker, restriction enzymes remove a portion of the transcript, the removal resulting in the extension of the open reading frame of the transcript. This technique may desirably involve intracellular ligation of the cleaved ends of the transcript subsequent to restriction and prior to translation.

These techniques may be applied to optimization of one or more recombinase enzymes or binding moieties. Efficiency may be by comparison to standard laboratory constructs or wild type constructs.

Example 7: Optimization of Bifunctional LoxP Site-Specific Recombination Sites

A library of variant LoxP sequences may be produced by random mutagenesis starting from known, functional LoxP sites. M13 phagemid vectors may be produced such that each vector includes, 3' of the GpIII cassette, a first portion of a polynucleotide encoding LacZα, a known or variant loxP, B. subtilis SacB, a second known or variant loxP element, and the remainder of the LacZα polynucleotide. SacB is lethal in E. coli when expressed in cells in the presence of sucrose. By contrast, loss of SacB confers growth on sucrose-containing media. Accordingly, the vectors are transferred into TG1 E. coli cells including Cre recombinase and incubated for a period sufficient to allow recombination. These cells are cultured on sucrose. Accordingly, only cells having excised the loxP-flanked SacB gene survive. Further, only cells in which the newly formed hybrid loxP site, now positioned between the first and second portions of the LacZα gene, is bifunctional (i.e., each nucleotide of the hybrid loxP site encodes an amino acid) will appear blue when cultured in the presence of X-gal. In various embodiments of this assay, the first loxP motif can be a variant loxP motif while the second loxP motif is a known loxP motif, the first loxP motif can be a known loxP motif while the second loxP motif is a variant loxP motif, both loxP motifs can be distinct variant loxP motifs, or both loxP motifs can be the same variant loxP motifs.

Example 8: Optimization of Various Aspects of the Techniques of the Present Invention Various aspects of the present invention may, if desired, be optimized. Optimization may occur be identifying from a plurality of variants those that are best capable of one or more particular functions.

One such function that may be optimized is the efficiency of secretion of the scFv into the periplasm. In various embodiments of the present invention, secretion of the scFv into the periplasm is directed by the pelB leader/signal peptide. In order to improve the efficiency of secretion of the scFv into the periplasm, pelB can be modified for use in conjunction with a mammalian splice acceptor site consensus sequence. Additionally, or alternatively, variation in the pelB sequence and be generated and variants can be screened for improved secretion using phage display. Alternative signal peptides (e.g., ompA, phoA) can be similarly tested and/or modified as desired. In some instances, a signal peptide may be used that operates in both bacterial and mammalian cells (e.g., an IL2 signal sequence).

A second function that may be optimized is the efficacy of SacB. If SacB does not effectively distinguish cells having been transformed with the first vector, and/or cells having been transformed with the first vector but having had the SacB cassette excised from the first vector, other selectable markers may be employed. Other selectable markers such as galK and thyA can be tested and/or modified as desired.

A third function that may be optimized is the expression of the chimeric polypeptide. In some instances, the chimeric polypeptide is an scFv-Fc. If an scFv-Fc is not well expressed, promoters other than the CMV promoter can be tested and/or modified to improve expression. Other regulatory sequences that may be tested include the hEF1-HTLV promoter, previously shown to support mammalian expression of scFv-Fc fusion binding moieties, the EF1a promoter, or known IgG heavy chain and light chain regulatory regions.

In addition, any binding moiety or framework of the present invention, including a chimeric polypeptide or any component before or after recombination of the first vector and the second vector, can be optimized for codon usage in one or more particular cell types. For instance, some embodiments of the present invention include an scFv first binding moiety. In such instances, first binding moiety scFvs of the present invention may be optimized for codon usage in E. coli prior to the generation of a chimeric polypeptide. In any embodiment, codon usage can be changed, e.g., from a bacterial codon usage to a mammalian codon usage.

It may be desirable to optimize the mammalian cell type for chimeric polypeptide expression. In some embodiments, the mammalian cell type is HEK-293. Optimization may involve assessment of chimeric polypeptide expression in a variety of cell types. For instance, CHO cells may be used in place of HEK-293 cells.

In some instances, it may be that chimeric polypeptides of the present invention do not bind target antigen(s) with sufficient affinity for certain applications. Techniques of affinity maturation are known in the art. Some may be performed in as little as one week. Other steps may also be taken. For instance, addition of the IgG dimerization domain is expected to increase the affinity of a binding moiety for an antigen by four to ten fold over scFvs due to avidity.

Efficiency of recombination may be optimized by modification of the recombinase gene. Various constitutive or inducible expression systems may be tested. For instance, the efficiency of inducible recombinase enzymes, e.g., recombinase enzymes the expression of which can be induced by the presence of arabinose, can be assayed. A wide variety of promoters, including, e.g., the tet promoter, are known in the art and could be tested for optimization of recombinase expression to increase recombination efficiency. Recombination efficiency can be monitored, e.g., by quantification of PCR amplification across an integration site.

Example 9: A Screen for Binding Moieties Targeting a Plurality of Antigens with Subsequent Conversion A library of vectors (e.g., a phage display library) encoding scFv binding moieties for display is constructed. The library includes greater than $10^{10}$ vectors, each encoding a variant scFv molecules and otherwise having essentially the same sequence as the other vectors in the library. The vectors are constructed essentially according to the first vector of Example 1. Such a library has been generated by Kunkel mutagenesis. However, such libraries may also be generated by other means. The phage display scFv library may be screened for scFv binding moieties capable of binding various proteins (for example, about 10 distinct proteins, e.g., USP11, SARI A, CTBP2, PLAA, MAP2K5, CTBP1, CDK2, MAPK8, HSP90B1, and COPS5). The variant scFv molecules may, in some instances, be screened in an automated screening pipeline, e.g., a pipeline utilizing approximately one milligram of each antigen. scFv molecules with the highest affinity and/or avidity for each antigen may be selected by methods known in the art. scFv molecules selected in this manner (e.g., the top 1-2 candidate scFv molecules) may be converted to IgG molecules, e.g., according to the methods described herein. In some instances, a total of 10 to 20 scFv molecules may be selected for conversion to IgG molecules. Thus, this example describes the conversion of 10 to 20 scFv binding moieties.

Selected vectors may be transformed into HB2151 E. coli cells that include a second vector constructed substantially according to Example 1 and that further express Cre recombinase and phiC31 integrase. This results in conversion of the scFv molecules to IgG molecules. HB2151 E. coli cells do not suppress amber stop codons.

Separately, the selected vectors may be transformed into HB2151 E. coli cells that Cre recombinase but do not include a second vector of the present invention or a phiC31 integrase. These vectors undergo an excision event resulting in the conversion of the scFv to an scFv-Fc.

The converted products may be transfected into and expressed in HEK-293 cells. Binding moieties are purified from culture supernatants after 5-7 days. The yield of the binding moieties (mg/L) and the affinity or avidity of the binding moieties for the relevant target antigen may be determined, for example, by Western blot and ELISA. As controls, the selected binding moieties may also be expressed in standard IgG and Fc fusion plasmids (e.g., pFuse-Fc, Invivogen) in HEK-293 cells. In addition, the selected scFv molecules may be expressed as soluble proteins in HB2151 E. coli cells.

Example 10: scFv to IgG Conversion Using the pAX688 Library Vector System

Figure 7:
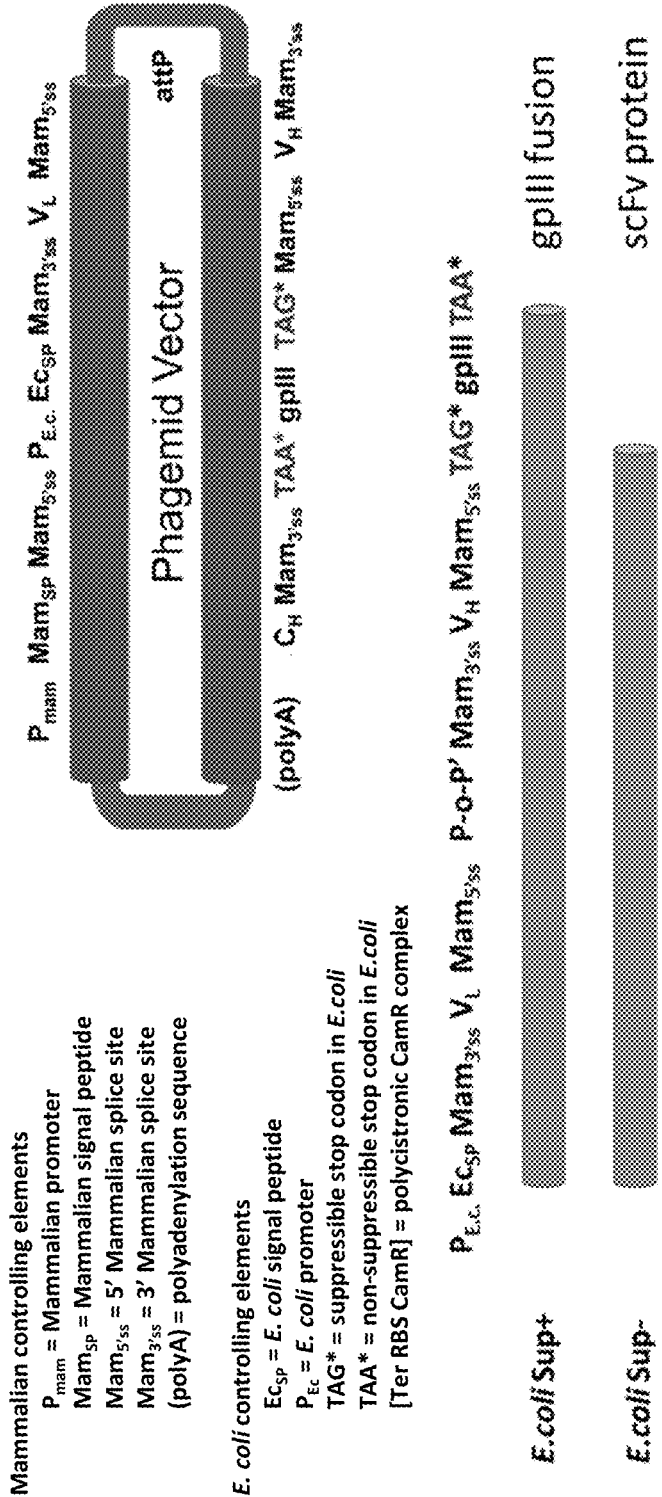
FIG. 7 is a schematic showing the structure of a phagemid vector (pAXM688), which contains VL, VH, CH (including an Fc region), and gpIII genes, as well as mammalian and bacterial controlling elements. The phagemid vector also includes suppressible and non-suppressible stop codons, which permit the expression of an scFv-gpIII fusion protein in suppressing E. coli strains (E. coli Sup+) and the expression of just the scFv in non-suppressing E. coli strains (E. coli Sup–).

In one example, phagemid vectors, each encoding an scFv, are converted by phiC31-mediated recombination into integrant vectors that may each express, in mammalian cells, an IgG including the VL and VH regions of the scFv. This system utilizes intron splicing and integrase activity to perform subcloning. FIG. 7 shows the structure of the pAXM688 phagemid vector. In order from 5' to 3', the phagemid vector includes, e.g., a mammalian promoter ($P_{mam}$), a mammalian signal peptide ($Mam_{SP}$), a first 5' mammalian splice site ($Mam_{5'ss}$), an E. coli promoter ($P_{E.c.}$), an E. coli signal peptide ($Ec_{SP}$), a first 3' mammalian splice site ($Mam_{3'ss}$), the VL gene, a second 5' mammalian splice site ($Mam_{5'ss}$), an attP site-specific recombination motif, a second 3' mammalian splice site ($Mam_{3'ss}$), the $V_H$ gene, a third 5' mammalian splice site ($Mam_{5'ss}$), a suppressible stop codon (e.g., an amber stop codon; TAG*), a gpIII gene, a non-suppressible stop codon (e.g., an ochre stop codon; TAA*), a third 3' mammalian splice site ($Mam_{3'ss}$), a CH gene, and a polyadenylation sequence (polyA). Due to the presence of the amber and ochre stop codons located 5' to and 3' to the GpIII gene, respectively, scFv fusion to gpIII can be controlled by amber suppression. In other words, if this vector is present in an amber suppressing strain of E. coli, an scFv-gpIII fusion is produced. If this vector is instead present in a non-suppressing E. coli strain, then just the scFv is produced.

The phagemid vector may, for example, be used to produce phage that display binding moiety proteins (e.g., scFv proteins including VH and VL domains encoded by the VH and VL genes of the phagemid vector) on its surface. Such phages may be used, for example, for phage display-based biopanning of the binding moiety proteins (e.g., to identify binding moieties, or antigen-determining regions thereof, capable of binding to a target molecule). A library of such phagemid vectors, each vector expressing a distinct scFv, can be generated according to methods well known in the art and/or methods as described herein.

Figure 8:
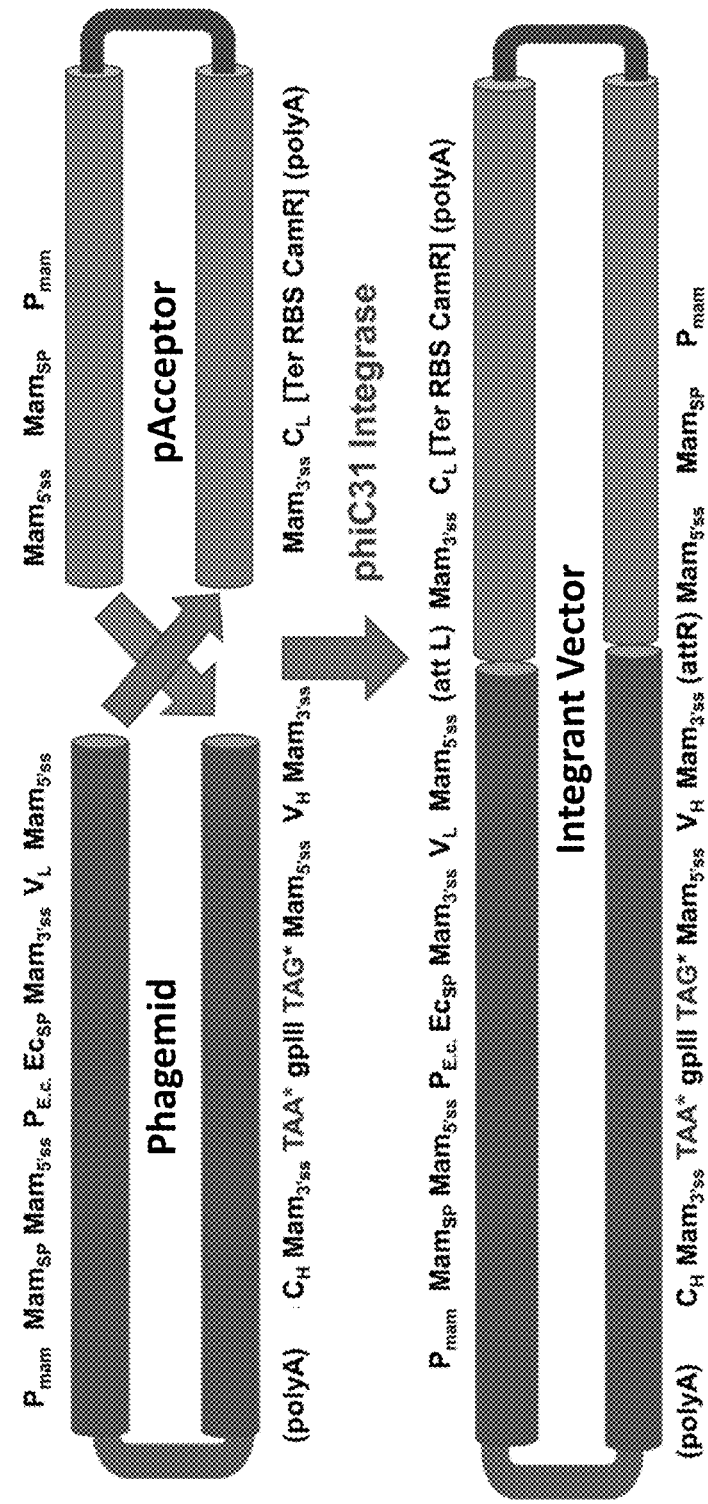
FIG. 8 is a schematic showing recombination between the phagemid vector pAXM688 and an acceptor vector (pAcceptor), mediated by a phiC31 integrase enzyme. Recombination results in the formation of an integrant vector including all elements of the phagemid and the acceptor vectors, except that the attB and attP sites are replaced by attL and attR sites.

As shown in FIG. 8, phiC31 integrase may be used to induce site-specific integration of the phagemid vector to an acceptor vector (pAcceptor). From 5' to 3', the pAcceptor vector includes, e.g., an attB site-specific recombination motif (not shown), a 5' mammalian splice site ($Mam_{5'ss}$), a mammalian signal peptide ($Mam_{SP}$), a mammalian promoter ($P_{mam}$), a polyadenylation sequence (polyA), a polycistronic CamR complex (Ter RBS CamR), a CL gene, and a 3' mammalian splice site ($Mam_{3'ss}$).

phiC31-mediated integration of the two vector yields an integrant vector that includes elements from both originating vectors. In this example, the integrant vector includes, from 5' to 3', e.g., a mammalian promoter ($P_{mam}$), a mammalian signal peptide ($Mam_{SP}$), a 5' mammalian splice site ($Mam_{5'ss}$), an E. coli promoter ($P_{E.c.}$), an E. coli signal peptide ($Ec_{SP}$), a 3' mammalian splice site ($Mam_{3'ss}$), the VL gene, a 5' mammalian splice site ($Mam_{5'ss}$), an attL site-specific recombination motif, a 3' mammalian splice site ($Mam_{5'ss}$), a CL gene, a polycistronic CamR complex (Ter RBS CamR), a polyadenylation sequence (polyA), a mammalian promoter ($P_{mam}$), a mammalian signal peptide ($Mam_{SP}$), a 5' mammalian splice site ($Mam_{3'ss}$), an attR site-specific recombination motif, a 3' mammalian splice site ($Mam_{3'ss}$), the VH gene, a 5' mammalian splice site ($Mam_{5'ss}$), a suppressible stop codon (e.g., an amber stop codon; TAG*), a gpIII gene, a non-suppressible stop codon (e.g., an ochre stop codon; TAA*), a 3' mammalian splice site ($Mam_{3'ss}$), a CH gene, and a polyadenylation sequence (polyA).

Figure 9A:
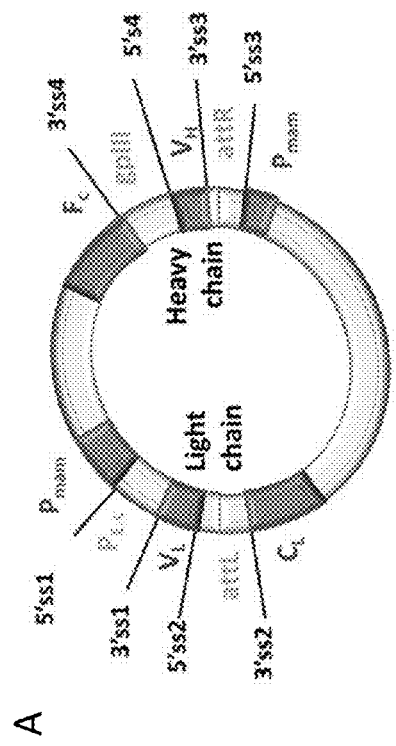
FIGS. 9A-9B are schematics showing mammalian expression of an IgG in an integrant vector produced, for example, by the integration scheme shown in FIG. 8. (A) The integrant vector includes a light chain gene and a heavy chain gene. The attL and attR site-specific recombination sites, the bacterial promoter ($P_{E.c.}$), and the gpIII gene are located between splice sites. (B) Thus, the pre-mRNA molecules produced by transcription of the light chain gene or heavy chain gene may have these elements spliced out, yielding mature mRNA molecules including only the respective mammalian signal peptides, variable and constant domains, and polyA tails.
Figure 9B:
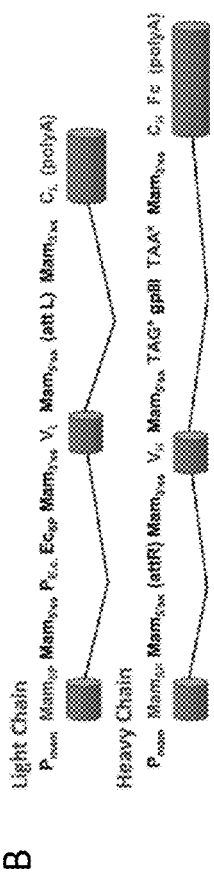

The integrant vector can express a light chain gene (including the VL fused to the CL) and a separate heavy chain gene (including the VH fused to the CH). As shown in FIG. 9A, the splice sites are located such that the bacterial regulatory elements and the attR site is spliced out of the light chain transcript, while the attL site and the gpIII gene is spliced out of the heavy chain transcript. The amber stop codon and ochre stop codon is spliced out of the heavy chain transcript as well. In addition, integration results in activation of the CamR cassette, such that successful integrants can be selected for by growth on media containing chloramphenicol. As shown in FIG. 9B, expression of the light chain and heavy chain genes from the integrant vector produces pre-mRNAs in which bacterial and viral elements are located in introns. The spliced, mature mRNA for the light chain includes the mammalian signal peptide, VL domain, CL domain, and poly A tail. The spliced, mature mRNA for the heavy chain includes the mammalian signal peptide, VH domain, CH domain, and polyA tail. Thus, in mammalian cells, splicing may be utilized to eliminate undesired elements for mammalian expression, resulting in an expression vector ready to be transfected into mammalian cells (e.g., CHO cells) for IgG production.

In an alternate example, the pAX688 phagemid vector includes an orthogonal site-specific recombination site (e.g., an integration site for a recombinase other than phiC31), located between the gpIII and CH-encoding genes. In some instances, the orthogonal site-specific recombination site is positioned upstream of a 3' mammalian splice site. The counterpart of this orthogonal site-specific recombination site is present on a second acceptor vector, which may encode a functional domain such as those described herein. For example, the functional domain can be a ubiquitin ligase domain, knocksideways domain, or CAR domain. The CAR domain may, for example, include a CD3-zeta or CD28 transmembrane domain, and/or a CD3-zeta, CD28, 41 BB, ICOS, FcεRIy, influenza MP-1, VZV, and/or OX40 cytoplasmic domain, or any combination or derivative thereof. In one instance, the acceptor vector includes a polynucleotide encoding, e.g., a CD3-zeta construct capable of expressing a CD3-zeta transmembrane domain and cytoplasmic domain (e.g., 14g2a-Zeta). Integration between the phagemid vector and the second acceptor vector results in a second integrant vector capable of expressing a fusion protein including the scFv of the phagemid vector (or a derivative thereof including at least one, and preferably both, of the variable domains of the scFv of the phagemid vector) and the CD3-zeta domains, oriented with the CD3-zeta transmembrane domain positioned between the scFv and the CD3-zeta endodomain. This can result in a functional transmembrane receptor in which binding of the scFv to a cognate antigen triggers a cytoplasmic zeta signal from the CD3-zeta endodomain. As such, if the second integrant vector is expressed in a T-cell, binding of the scFv to its cognate antigen results in activation of the T-cell. scFvs including antigen-determining regions capable of recognizing an antigen on a target cell type (e.g., malignant B-cells), can thus be integrated with CD3-zeta in this fashion and transfected into T-cells to produce T-cells to be tested rapidly, inexpensively, in multiplex, and/or at high throughput. In one example, this scheme can be used to convert an scFv to an scFv-CD3-zeta fusion ready for T-cell testing in one day or less.

Example 11: Rapid scFv to IgG Conversion Using the pMINERVA Vector System

Figure 10:
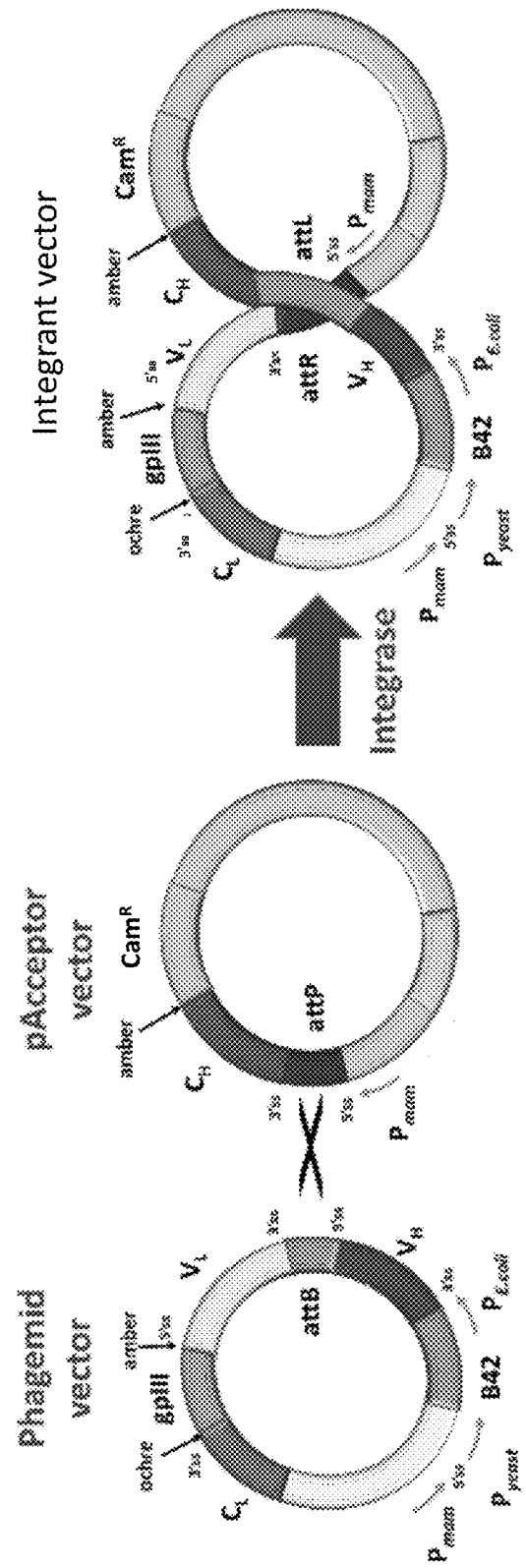
FIG. 10 is a schematic showing the pMINERVA system for scFv-to-IgG conversion. This system includes two vectors, a phagemid vector and an acceptor vector (pAcceptor), which can be recombined by phiC31 integrase to form an integrant vector, pMINERVA.
Figures 11A, 11B:
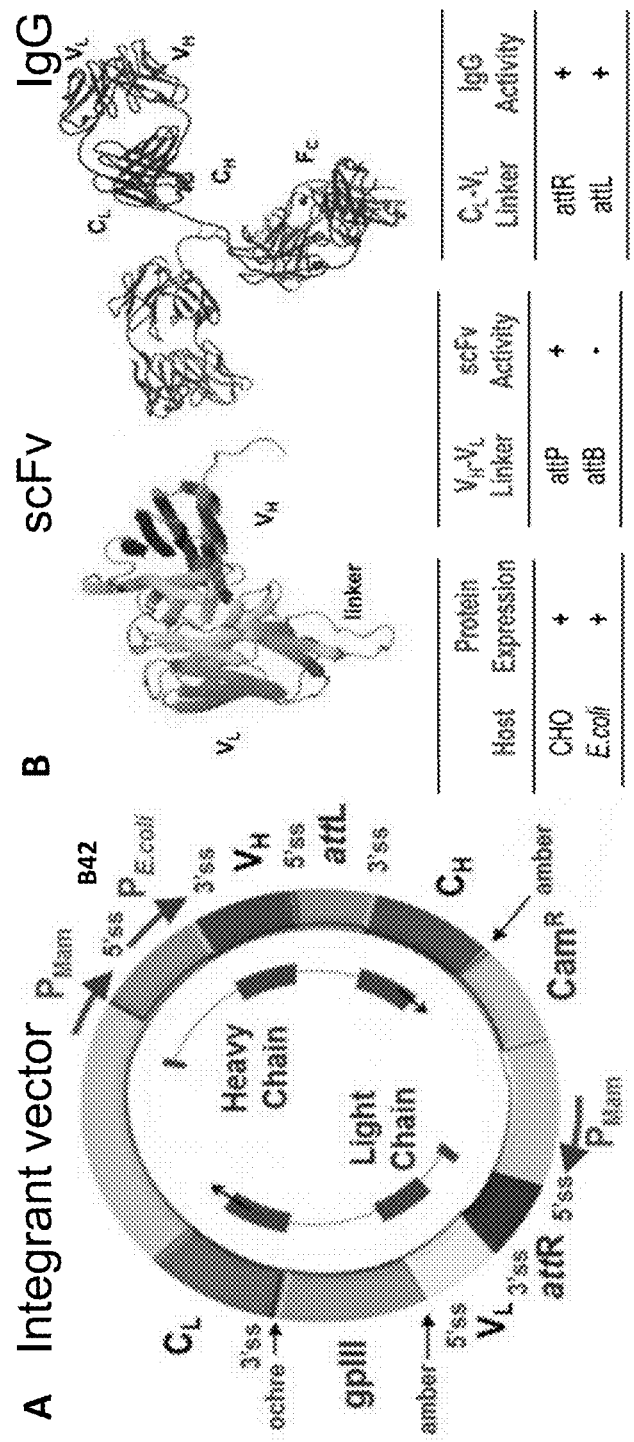
FIGS. 11A-11B are schematics and diagrams demonstrating that the pMINERVA system can be used to generate functional scFvs and IgGs. (A) The pMINERVA integrant vector includes a heavy chain expression cassette and a light chain expression cassette. (B) CHO cells transfected with the pMINERVA integrant vector can express IgG protein, while E. coli cells transfected with the phagemid vector express scFv protein. Of the phiC31 integrase site-specific recombination motifs, attP, but not attB, was successfully used as a VH-VL linker to produce a functional scFv. Both attL and attR motifs were shown to be suitable as CL-VL linkers to produce functional IgGs.

In one example, a phagemid vector (pMINERVA) encoding an scFv is converted by phiC31-mediated recombination with an acceptor vector (pAcceptor) into an integrant vector that may express, in a mammalian cell, an IgG binding moiety including the VL and VH genes of the scFv (FIG. 10). This system utilizes intron splicing and integrase activity to perform subcloning. In some instances, the system operates in a completely scarless fashion, e.g., in which all subcloning is performed by intron splicing and/or integrase activity, thereby obviating PCR, subcloning, and DNA sequencing steps. The phagemid vector includes from 5' to 3', for example, a mammalian promoter ($P_{mam}$), a first 5' mammalian splice site (5'ss), a yeast promoter ($P_{yeast}$), B42 transcription activation domain (B42), an E. coli promoter ($P_{E.\ coli}$), a first 3' mammalian splice site (3'ss), a VH gene, a second 5' mammalian splice site (5'ss), a site-specific recombination motif (e.g., an attB or attP site; preferably an attP site), a second 3' mammalian splice site (3'ss), a VL gene, a third 5' mammalian splice site (5'ss), a suppressible stop codon (e.g., an amber stop codon), a gpIII gene, a non-suppressible stop codon (e.g., an ochre stop codon), a third 3' mammalian splice site (3'ss), and a CL gene. In this example, the pAcceptor vector includes, for example, a mammalian expression cassette and, optionally, a bacterial expression cassette (e.g., oriented antiparallel relative to the mammalian expression cassette). The mammalian expression cassette includes, from 5' to 3', a mammalian promoter ($P_{mam}$), a first 5' mammalian splice site (5'ss), a site-specific recombination motif (e.g., an attB or attP site; preferably an attB site), a first 3' mammalian splice site (3'ss), a CH gene, a suppressible stop codon (e.g., an amber stop codon), and a chloramphenicol resistance marker gene ($Cam^R$). In one example the bacterial expression cassette includes an E. coli promoter ($P_{E.\ coli}$) and an Lpp-OmpA' fusion. In some instances, the attB and attP motifs may be swapped, such that the attB motif is present on the pAcceptor vector, and the attP motif is present on the phagemid vector.

phiC31 integrase may be used to induce site-specific integration of the phagemid vector and the pAcceptor vector. phiC31-mediated recombination between these vectors produces the integrant vector, which includes all of the elements of the phagemid vector and the pAcceptor vector, except that the attB and attP motifs are replaced by an attR motif and an attL motif. As shown in FIG. 11A, the resultant integrant vector includes a heavy chain expression cassette and a light chain expression cassette oriented parallel to each other. The physical linkage of the heavy and light chains in the form of the integrant vector may be useful for immunorepertoire screening. The heavy chain expression cassette includes, from 5' to 3', e.g., a mammalian promoter ($P_{mam}$), a 5' mammalian splice site (5'ss), a B42 transcription activation domain (B42), an E. coli promoter ($P_{E.\ coli}$), a 3' mammalian splice site (3'ss), a VH gene, a 5' mammalian splice site (5'ss), an attL site-specific recombination motif, a 3' mammalian splice site (3'ss), a CH gene, a suppressible stop codon (e.g., an amber stop codon), and a chloramphenicol resistance marker gene ($Cam^R$). The light chain expression cassette includes, from 5' to 3', e.g., a mammalian promoter ($P_{mam}$), a 5' mammalian splice site (5'ss), an attR site-specific recombination motif, a 3' mammalian splice site (3'ss), a VL gene, a 5' mammalian splice site (5'ss), a suppressible stop codon (e.g., an amber stop codon), a gpIII gene, a non-suppressible stop codon (e.g., an ochre stop codon), a 3' mammalian splice site (3'ss), and a CL gene. In one example, the antiparallel bacterial expression cassette for expressing the Lpp-OmpA' fusion from the pAcceptor vector is maintained. In some instances, RNA editing may be used to alter splicing on the integrant vector (or other vectors, such as the phagemid vector or the acceptor vector), thus permitting rapid construction of bifunctional antibodies.

We have generated the components of the pMINERVA system and have tested the phagemid vector and the integrant vector for their ability to produce functional binding moieties in mammalian or bacterial cells (FIG. 11B). This included determining whether the various site-specific recombination motifs can be used as linker regions connecting, for example, two antigen-determining regions (e.g., VH and VL domains, or CL and VL domains). We showed that protein expression from pMINERVA vector system could be detected in both HEK293 cells, which expressed IgGs, and in E. coli cells, which expressed scFvs. With respect to scFv expression from the phagemid vector, we showed that the attP motif is suitable as an scFv linker region between the VH and VL domains, as indicated by scFv activity, but that the attB motif was not. As such, it may be desirable to use the attP motif in the phagemid vector as the linker between the VL and VH domains of the scFv. In some instances, either the attP or attB motif may be suitable for use as a linker in phage display, in which high expression of the protein incorporating the recombination motif as the linker may be less important. With respect to IgG expression from the integrant vector, both the attR and attL motifs were found to be suitable CL-VL linkers, with the resultant IgGs showing detectable binding activity.

Figures 12A, 12B, 12C:
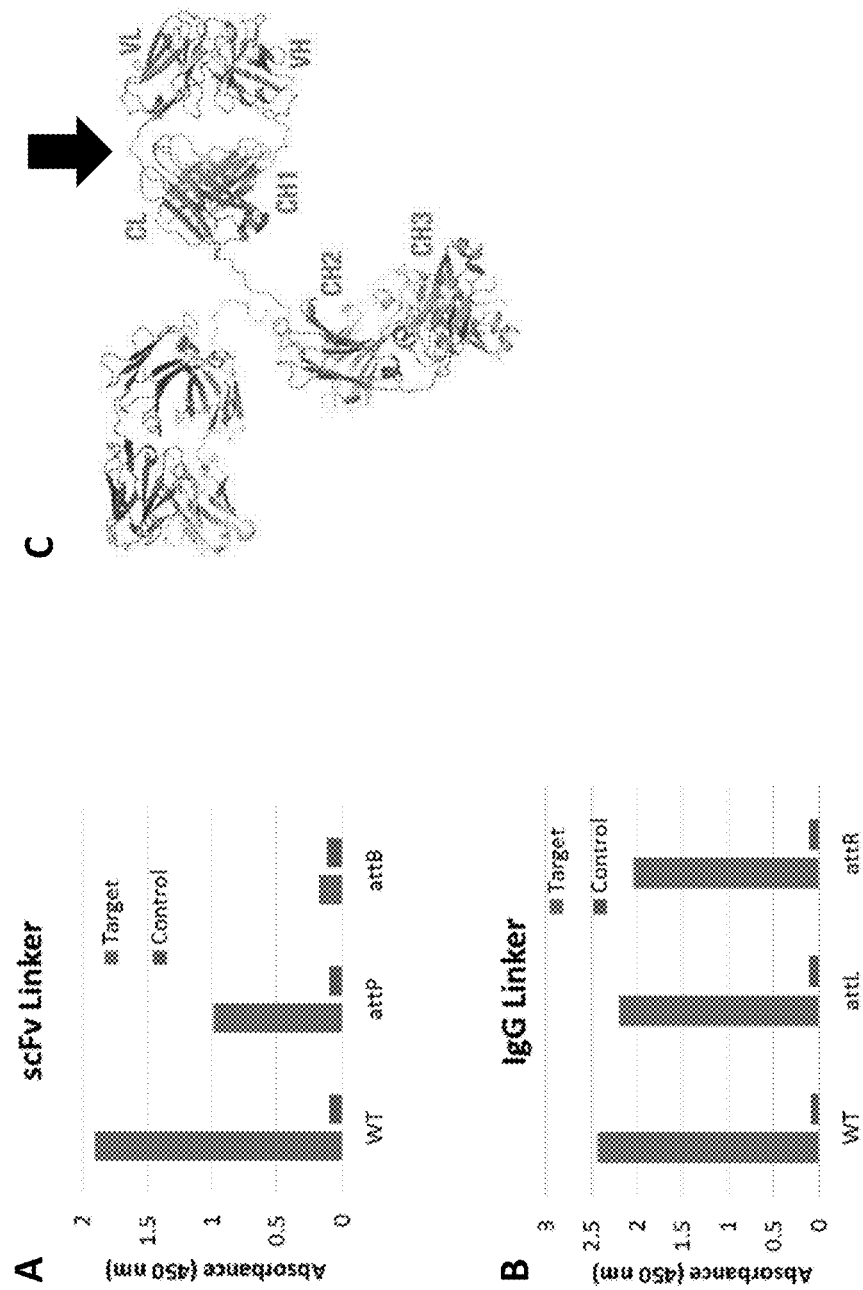
FIGS. 12A-12C are graphs and schematics showing that certain phiC31 integrase site-specific recombination motifs are suitable for use as linkers in scFvs or IgGs. (A) The same scFv with three different linker sequences (wild-type; WT (Gly4Ser)3, the phiC31 attB site, or the phiC31 attP site in reading frame 2) was produced. Each scFv was tested in an ELISA against the target protein or a non-relevant control. Anti-FLAG-HRP was used to detect a FLAG tag on the scFv and the ELISA was developed with Ultra TMB reagent. The scFv with the attP linker retained functionality relative to the standard linker. The attP motif was successfully used as a linker in a functional scFv showing binding activity, but use of the attB motif as a linker resulted in an scFv showing no binding activity. (B) The same IgG with no linker between VL and CL (WT), or the recombined phiC31 integrase sites (attL or attR) in reading frame 2, was produced. Each IgG was tested in an ELISA against the target protein or a non-specific control. Anti-mouse-HRP was used to detect the IgGs, and the ELISA was developed with Ultra TMB reagent. All three IgG constructs were expressed and functional. Each of the attL and attR motifs was successfully used as an IgG linker in a functional IgG molecule. (C) The attL and attR motifs were tested as CL-VL linkers in the light chain of the IgG.

We also performed a feasibility analysis of whether the phiC31 integrase site-specific recombination motifs can function as peptide linkers in scFvs or IgGs. The same scFv with three different linker sequences, WT (Gly4Ser)3, the phiC31 attB site, or the phiC31 attP site in reading frame 2, was produced. Each scFv was tested in an ELISA against the target protein or a non-relevant control. Anti-FLAG-HRP was used to detect a FLAG tag on the scFv and the ELISA was developed with Ultra TMB reagent. As can be seen in FIG. 12A, scFvs including the attP motif as the VH-VL linker domain showed binding activity, but that scFvs including the attB motif did not. The same IgG with no linker between VL and CL (WT), or the recombined phiC31 integrase sites, attL or attR, in reading frame 2, was produced. Each IgG was tested in an ELISA against the target protein or a non-specific control. Anti-mouse-HRP was used to detect the IgGs and the ELISA was developed with Ultra TMB reagent. As shown in FIG. 12B, IgGs including either an attL motif or an attR motif as the CL-VL linker (FIG. 12C) showed binding activity. All three IgG constructs were expressed and functional. The attP motif also worked as a 12-amino acid linker between the CL and VL domains in functional scFvs. These results confirm that the attP motif can function as a peptide linker in scFvs and IgGs, and that the attL and attR motifs can each function as peptide linkers in IgGs. In further embodiments, such recombination motifs (e.g., attB, attP, attL, or attR motifs) may be useful as CH-VH linkers on the heavy chain.

In an alternate example, the pMINERVA phagemid vector includes an orthogonal site-specific recombination site (e.g., an integration site for a recombinase other than phiC31), located between the gpIII and CL genes. The counterpart of this orthogonal site-specific recombination site is present on a second acceptor vector, which is a CD3-zeta construct capable of expressing a CD3-zeta transmembrane domain and cytoplasmic domain (e.g., 14g2a-Zeta). Integration between the phagemid vector and the second acceptor vector results in a second integrant vector capable of expressing a fusion protein including the scFv of the phagemid vector (or a derivative thereof including at least one, and preferably both, of the variable domains of the scFv of the phagemid vector) and the CD3-zeta domains, oriented with the CD3-zeta transmembrane domain positioned between the scFv and the CD3-zeta endodomain. This can result in a functional transmembrane receptor in which binding of the scFv to a cognate antigen triggers a cytoplasmic zeta signal from the CD3-zeta endodomain. As such, if the second integrant vector is expressed in a T-cell, binding of the scFv to its cognate antigen results in activation of the T-cell. scFvs including antigen-determining regions capable of recognizing an antigen on a target cell type (e.g., malignant B-cells), can thus be integrated with CD3-zeta in this fashion and transfected into T-cells to produce T-cells to be tested rapidly, inexpensively, in multiplex, and/or at high throughput. In one example, this scheme can be used to convert an scFv to an scFv-CD3-zeta fusion ready for T-cell testing in one day or less.

Example 12: Relative Positioning of Elements within Vectors

In some instances, the relative positioning of elements within a donor vector and an acceptor vector is important for dictating the positioning of elements within the integrant vector generated by recombination of the donor vector with the acceptor vector, For example, the placement of the *E. coli* promoter, attachment sites for phiC31 integrase, ribosome binding site, and antibiotic resistance gene can be important for the proper selection of phiC-mediated recombination events with the pMINERVA vector system described herein.

Figure 13:
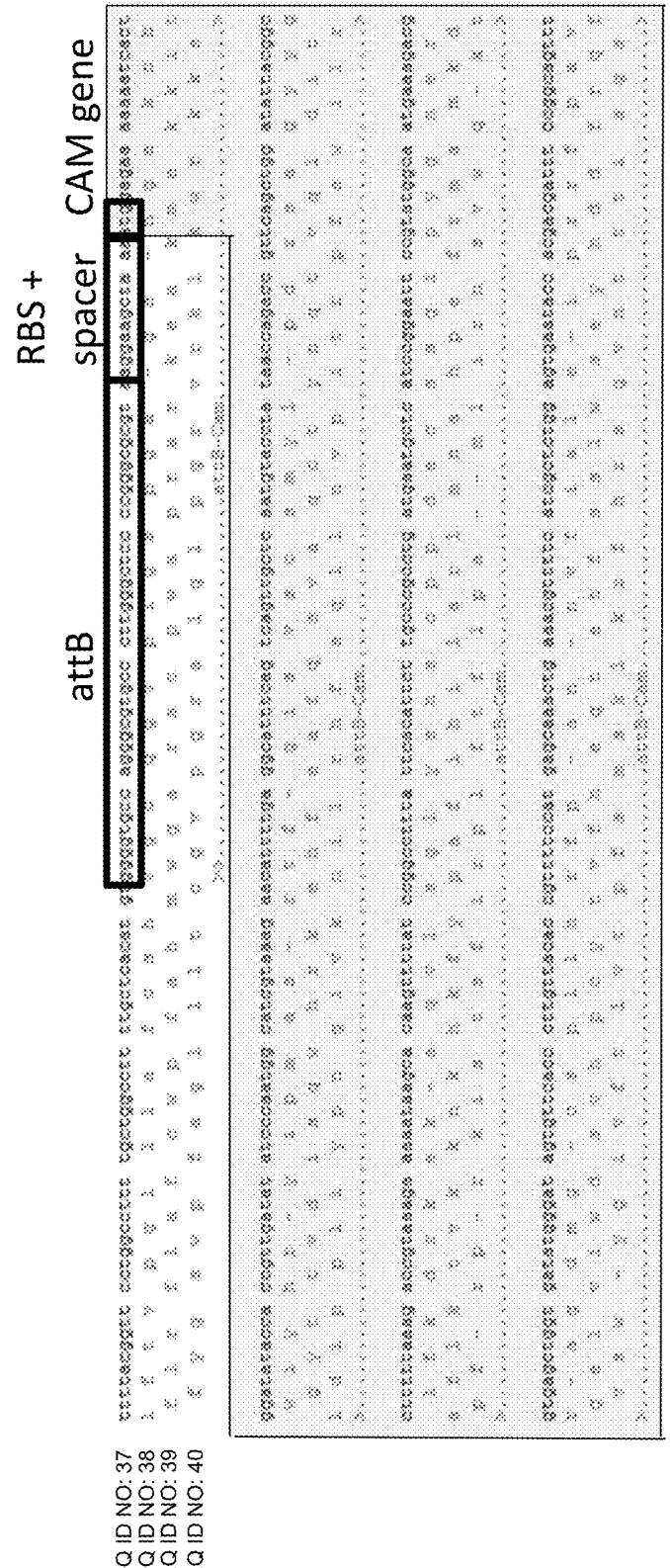
FIG. 13 is a diagram showing the relative positioning of an attB site, ribosome binding site (RBS) and spacer, and chloramphenicol-resistance gene (CAM) in an exemplary donor phagemid vector. In this donor vector, the attB site for phiC31 integrase precedes (e.g., is located 5' to) the RBS, fMet, and CAM gene. The initiating methionine (fMet) for the CAM gene is boxed. There is no promoter preceding this cassette, so cells containing the donor vector are CAM-sensitive.
Figure 14:
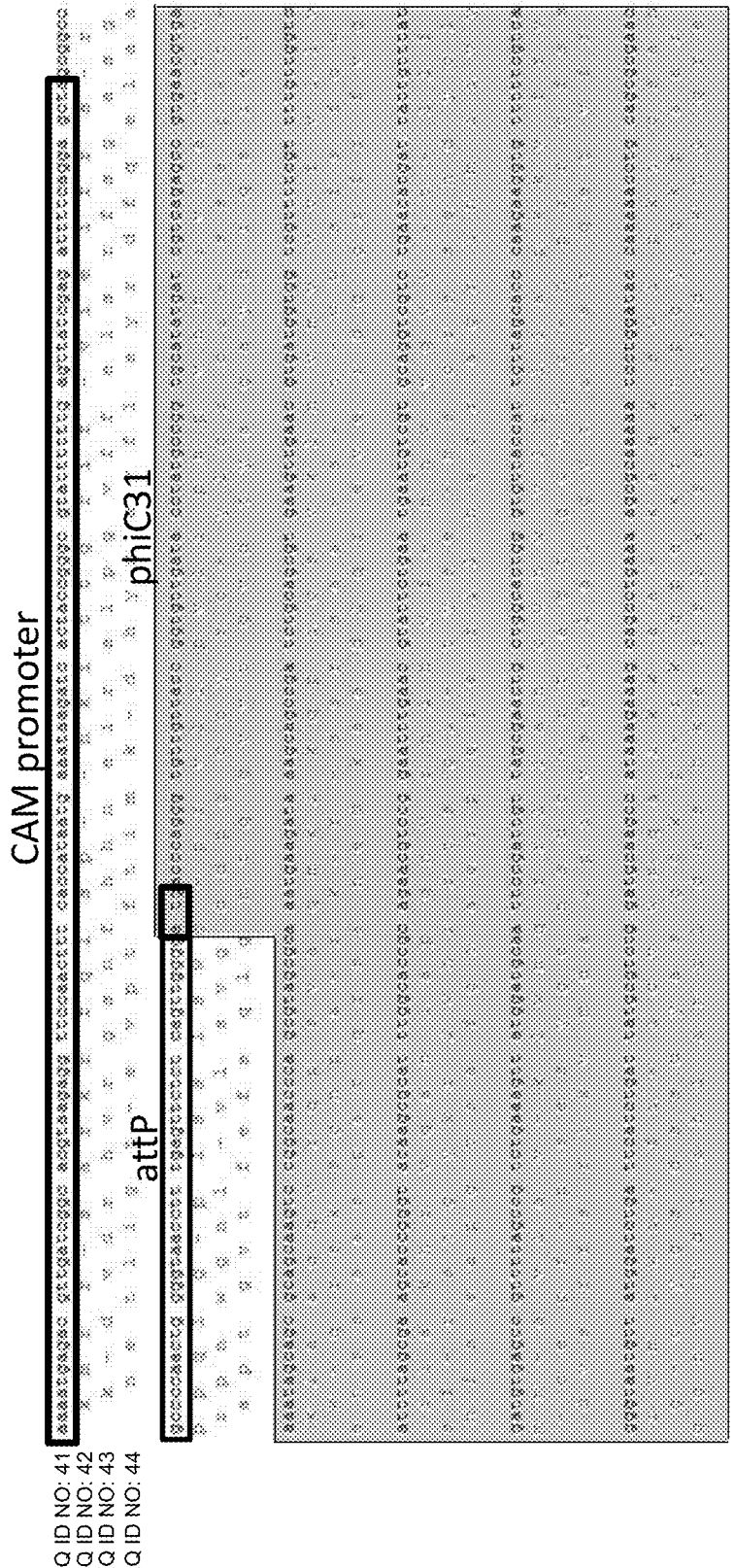
FIG. 14 is a diagram showing the relative position of a CAM promoter, attP site, and phiC31 gene in an exemplary acceptor vector. In this acceptor vector, the attP site is located downstream (e.g., 3' to) of the promoter and upstream (e.g., 5' to) of the phiC31 gene. The initiating methionine (fMet) for the phiC31 gene is boxed. This cassette lacks the CAM gene, so cells containing the acceptor vector are CAM-sensitive.

FIG. 13 shows the sequence for a donor phagemid vector used to validate phiC31 function. In this donor vector, the attB site-specific recombination site is located upstream of the ribosome binding site (RBS), spacer, and a chloramphenicol resistance gene (CAM). A portion of an acceptor vector sequence used to validate phiC31 function is shown in FIG. 14. In this acceptor vector, the attP site-specific recombination site is positioned between a CAM promoter and a phiC31 gene. Notably, neither the donor vector nor the acceptor vector includes both the CAM promoter and the CAM gene. As a result, a bacterial cell (e.g., an *E. coli* cell) containing either vector is sensitive to chloramphenicol.

Figure 15:
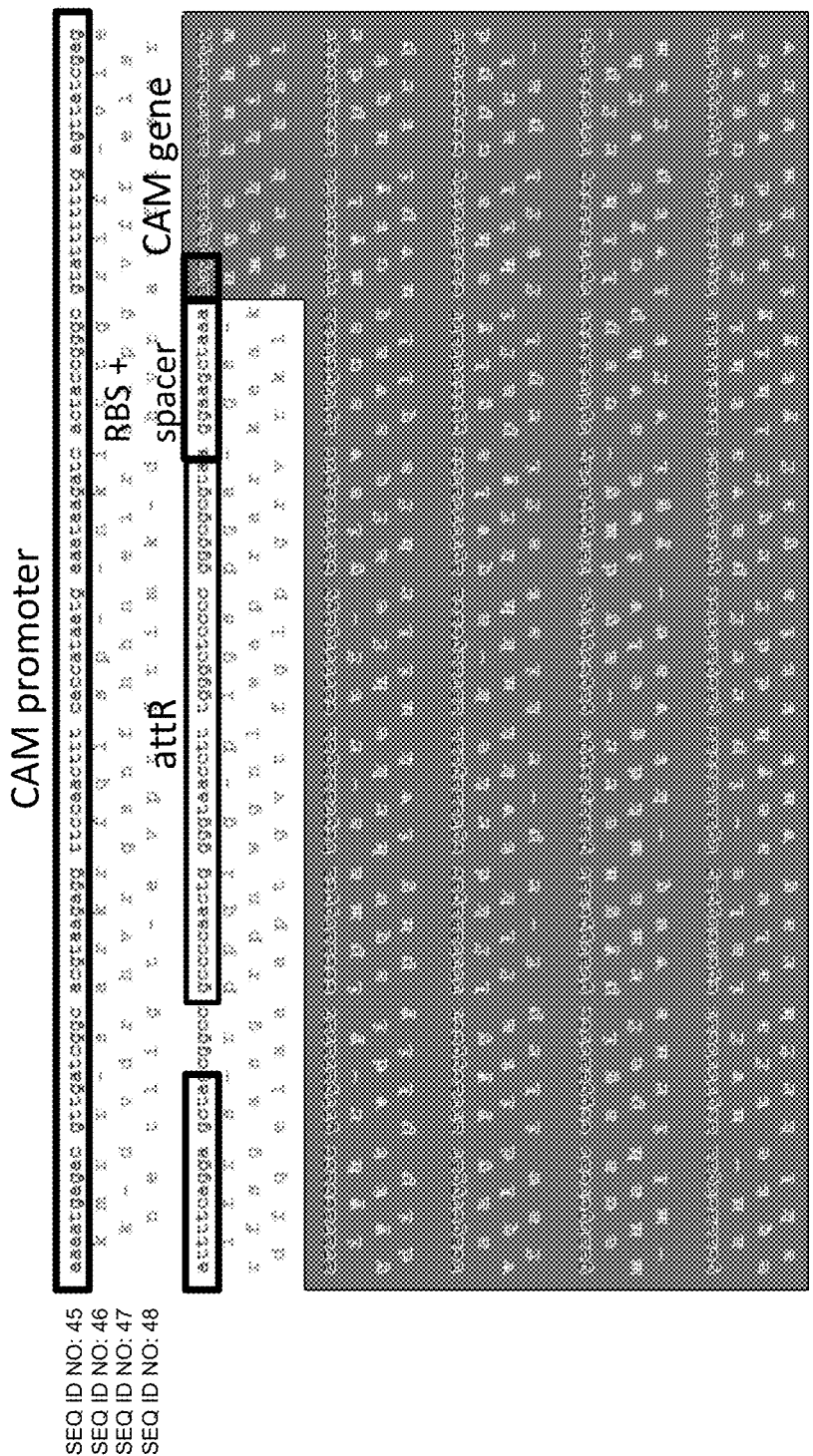
FIG. 15 is a diagram showing the integrant vector produced by recombination of the donor vector of FIG. 13 and the acceptor vector of FIG. 14, e.g., by a phiC31 recombinase. In this integrant vector, the recombined elements are arranged in the following order: CAM promoter, attR site, ribosome binding site (RBS), and CAM gene. In other words, the recombined phiC31 site (attR) is located downstream (e.g., 3' to) of the CAM promoter and upstream (e.g., 5' to) of the RBS, initiating methionine (fMet; indicated by a box) of the CAM gene, and the CAM gene. Furthermore, because the integrant vector includes a CAM promoter upstream of the CAM gene, cells containing this vector (e.g., cells that have undergone recombination of the donor vector and acceptor vector) are CAM-resistant.

Recombination between the donor vector and acceptor vector by a recombinase enzyme (e.g., phiC31) produces an integrant vector, of which a portion is shown in FIG. 15. Due to the positioning of the CAM promoter, RBS, spacer, and CAM gene relative to the corresponding site-specific recombination sites in the donor and acceptor vectors, the recombined integrant vector includes, in order from 5' to 3', a CAM promoter, an attR site-specific recombination site, a ribosome binding site, a spacer, and a CAM gene. As a result, a bacterial cell (e.g., an *E. coli* cell) containing the integrant vector (e.g., a cell in which the donor vector and the acceptor vector had undergone phiC31-mediated recombination) expresses the CAM gene and is thus resistant to chloramphenicol.

Example 13: Splicing of a Synthetic Intron

In some instances, an intron (e.g., a synthetic intron) can be added to a vector of the invention (e.g., a first vector or a second vector), such that a polynucleotide positioned within the intron (e.g., a polynucleotide encoding a polypeptide or polypeptide fragment) is expressed if the vector is in a prokaryotic cell (e.g., an bacterial cell, such as an *E. coli* cell), but not in a eukaryotic cell (e.g., a mammalian cell or an insect cell) capable of mRNA splicing.

Figure 16:
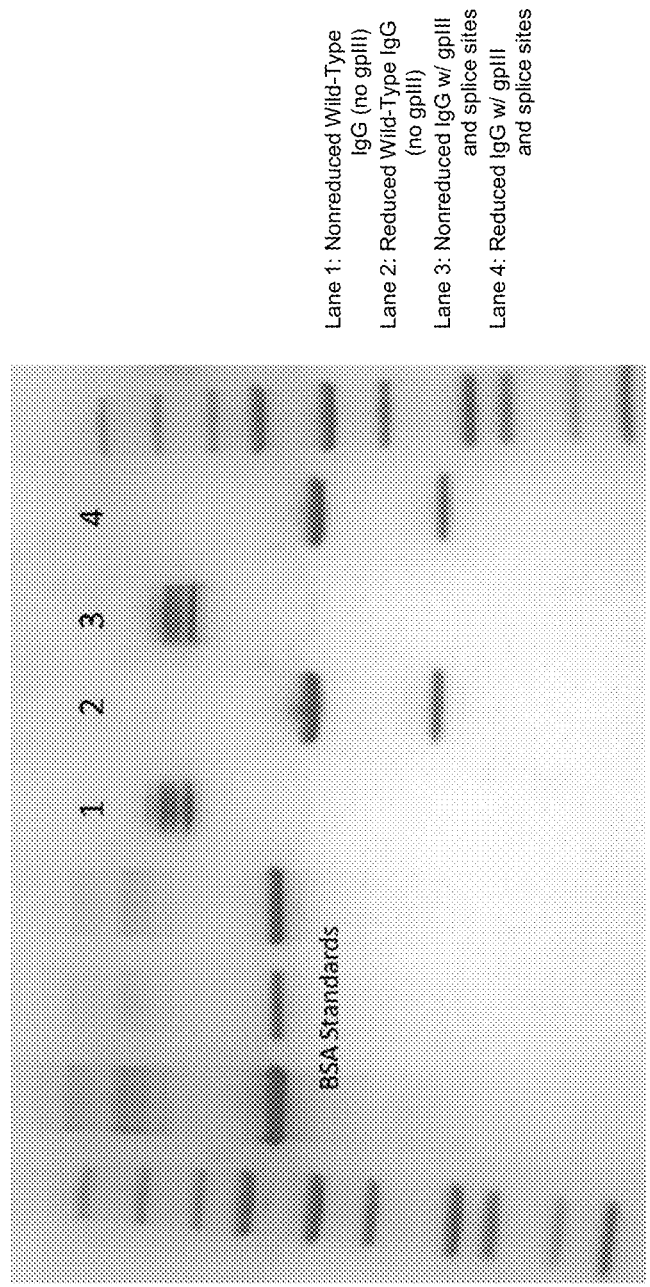
FIG. 16 is a diagram showing splicing of a synthetic intron containing gpIII introduced at the VH-CH junction of a polynucleotide encoding an IgG. The resultant vector, or a wild-type (WT) control, was transfected into HEK-293 cells and IgG was harvested and analyzed by SDS-PAGE. BSA standards are shown in the three lanes between the ladder and Lanes 1-4. Lanes 1 and 2 show protein expression from the wild-type vector, while lanes 3 and 4 show protein expression from the vector including the gpIII intron. Lanes 1 and 3 show non-reducing conditions and lanes 2 and 4 show reducing conditions.

In one example, a synthetic intron containing the M13gpIII fragment (e.g., as used for phage display) was introduced at the junction of the VH and CH region in the IgG expression vector (FIG. 16). The gpIII intron sequence is as follows (SEQ ID NO: 21):

```
GTCGACCGTACGCAGGTAAGTCACCATCACCATCACCATTAGACTGTT
GAAAGTTGTTTAGCAAAACCTCATACAGAAAATTCATTTACTAACGTC
TGGAAAGACGACAAAACTTTAGATCGTTACGCTAACTATGAGGGCTGT
CTGTGGAATGCTACAGGCGTTGTGGTTTGTACTGGTGACGAAACTCAG
TGTTACGGTACATGGGTTCCTATTGGGCTTGCTATCCCTGAAAATGAG
GGTGGTGGCTCTGAGGGTGGCGGTTCTGAGGGTGGCGGTTCTGAGGGT
GGCGGTACTAAACCTCCTGAGTACGGTGATACACCTATTCCGGGCTAT
ACTTATATCAACCCTCTCGACGGCACTTATCCGCCTGGTACTGAGCAA
AACCCCGCTAATCCTAATCCTTCTCTTGAGGAGTCTCAGCCTCTTAAT
```

-continued

```
ACTTTCATGTTTCAGAATAATAGGTTCCGAAATAGGCAGGGTGCATTA

ACTGTTTATACGGGCACTGTTACTCAAGGCACTGACCCCGTTAAAACT

TATTACCAGTACACTCCTGTATCATCAAAAGCCATGTATGACGCTTAC

TGGAACGGTAAATTCAGAGACTGCGCTTTCCATTCTGGCTTTAATGAG

GATCCATTCGTTTGTGAATATCAAGGCCAATCGTCTGACCTGCCTCAA

CCTCCTGTCAATGCTGGCGGCGGCTCTGGTGGTGGTTCTGGTGGCGGC

TCTGAGGGTGGCGGCTCTGAGGGTGGCGGCTCTGAGGGTGGCGGTTCT

GAGGGTGGCGGCTCTGAGGGTGGCGGTTCCGGTGGCGGCTCCGGTTCC

GGTGATTTTGATTATGAAAAAATGGCAAACGCTAATAAGGGGGCTATG

ACCGAAAATGCCGATGAAAACGCGCTACAGTCTGACGCTAAAGGCAAA

CTTGATTCTGTCGCTACTGATTACGGTGCTGCTATCGATGGTTTCATT

GGTGACGTTTCCGGCCTTGCTAATGGTAATGGTGCTACTGGTGATTTT

GCTGGCTCTAATTCCCAAATGGCTCAAGTCGGTGACGGTGATAATTCA

CCTTTAATGAATAATTTCCGTCAATATTTACCTTCTTTGCCTCAGTCG

GTTGAATGTCGCCCTTATGTCTTTGGCGCTGGTAAACCATATGAATTT

TCTATTGATTGTGACAAAATAAACTTATTCCGTGGTGTCTTTGCGTTT

CTTTTATATGTTGCCACCTTTATGTATGTATTTTCGACGTTTGCTAAC

ATACTGCGTAATAAGGAGTCTTAATAACTAATCTCCTTCTCCTCCTCC
```

C<u>AGGG</u>CCGTACGCTCGAG
Key:
<u>5' splice site</u>, His tag, <u>amber stop codon</u>, M13 gp3 gene fragment, <u>3' splice site</u>

HEK-293 cells were transiently transfected with the original wild-type (WT) vector or the variant containing the synthetic intron. Both versions of the IgG vector were from a single-vector, dual-promoter system. The modified WT IgG vector contained a truncated version of gpIII within an intron located between the VH and CH regions. Without splicing, there were multiple stop codons after the gpIII, which would result in no production of the CH. With splicing, the CH would remain in-frame and would thus be expressed.

IgG was harvested from the culture supernatants and analyzed by SDS-PAGE analysis under non-reducing (lanes 1 and 3) or reducing (lanes 2 and 4) conditions. The yield and purity of IgG was equivalent from the original (lanes 1 and 2) and intron-containing (lanes 3 and 4) constructs.

Example 14: Conversion of an scFv to Multiple IgGs and CARs Overnight

Figure 17:
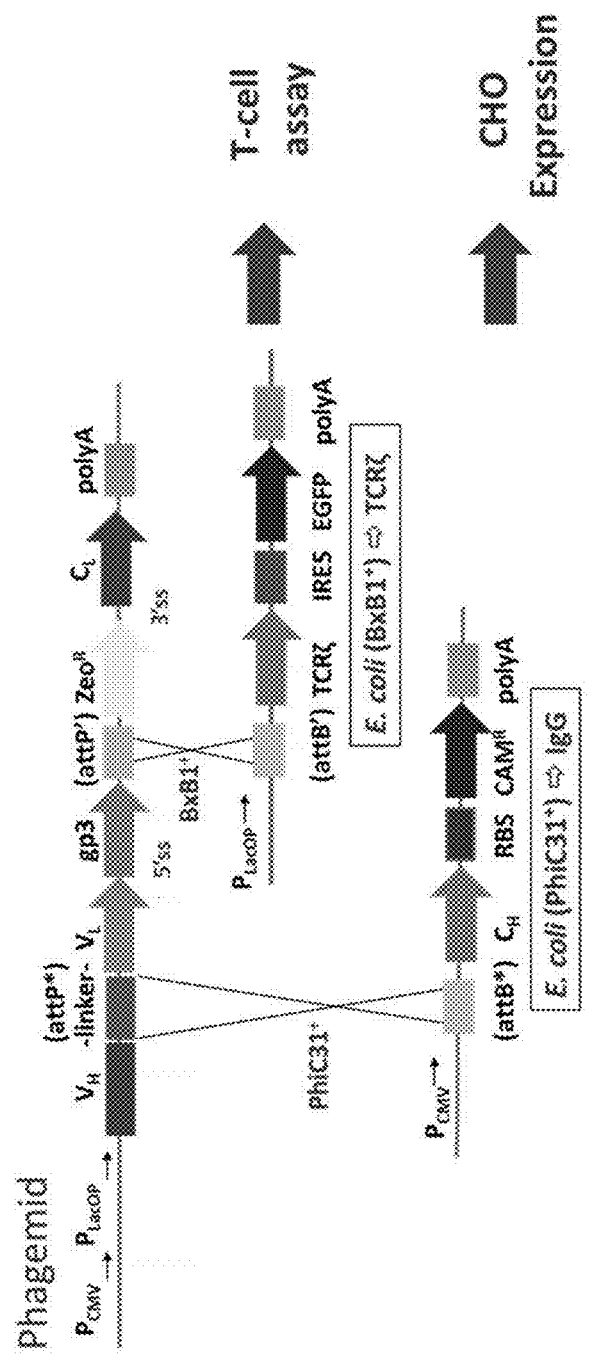
FIG. 17 is a diagram showing a means for converting an scFv to multiple IgGs and/or chimeric antigen receptors (CARs). In some instances, this conversion may occur in a short time frame (e.g., over about one night). This scheme may be used to produce both IgGs and CAR-Ts from the same vector system by use of orthologous integrases. In this scheme, a phagemid is recombined with two distinct acceptor vectors using two distinct integrases (phiC31 and BxB1). The phiC31 reaction results in formation of an integrant vector encoding an IgG (e.g., a vector suitable for expressing an IgG in a mammalian cell, such as a CHO cell), while the BxB1 reaction results in the formation of an integrant vector encoding a CAR (e.g., a CAR suitable for use in a T cell assay).

A vector system for antibody selection by phage display biopanning and in vivo conversion of the output pools of the selection to the chimeric antigen receptor (CAR) or IgG format, using in vivo recombineering, is shown in FIG. 17. This scheme makes use of multiple serine integrases that recognize different site-specific recombination motifs to selectively recombine distinct portions of a phagemid vector encoding an scFv with a particular acceptor vector. This method may be useful, for example, for rapid conversion to test Fc, enzyme fusions, CAR stalk sequences, or any of the other elements of the phagemid vector and/or the acceptor vector(s).

As shown in FIG. 17, phage containing a phagemid vector encoding an scFv are transduced into an E. coli strain expressing the BxB1 integrase and containing a lentiviral acceptor vector for creating the CAR fusion. BxB1-mediated recombination between the attP' site on the phagemid and the attB' site on the lentiviral vector fuses the scFv to the hinge and transmembrane and signaling domains of the TCRζ. In mammalian cells, an intron containing the M13 gp3 gene and attP site is removed by splicing. The recombination event also fuses an E. coli promoter to the zeocin gene, allowing integrants to be selected on zeocin media (Zeo$^R$). Virus can be produced from the final vector in a mammalian packaging cell line and used, for example, to transduce Jurkat cells for CAR-T assays.

Alternatively, the phage can be transduced into an E. coli strain expressing the phiC31 integrase and containing an IgG acceptor vector. Recombination between the attP and attB sites (shown as attP* and attB*) fuses the $V_H$ to the $C_H$ and the mammalian promoter to the $V_L$ gene. Splicing in CHO cells eliminates an intron flanking the M13 gp3 gene and fuses the $V_L$ in frame with the $C_L$. Integrants can be selected by chloramphenicol resistance (CAM$^R$). CHO cells can be transfected with the final vector to produce full-length IgGs.

Example 15: Vector System for In Vivo Conversion of scFvs to Chimeric Antigen Receptors (CARs) or IgGs The present invention features methods for converting polypeptides of a first type (e.g., scFvs) directly to polypeptides of a second type (e.g., IgGs and CARs) without requiring any sub-cloning and/or DNA sequence confirmation steps. In one example, a vector system is provided for conversion (e.g., in vivo conversion) of an scFv to the chimeric antigen receptor (CAR) format. This vector system may also be used to convert the scFv to a full-length immunoglobulin G (IgG). The initial scFvs may be used, if desired, in antibody selection by phage display biopanning, and the output pools of the selection can subsequently be converted to CARs or IgGs, e.g., as described herein. In some instances, the vector system makes use of bacteriophage integrases in E. coli and/or intron splicing in mammalian cells. Using this vector system, the output of phage selections can be screened directly on T-cells in the CAR format.

Vector System Incorporating Bacterial and Mammalian Control Elements Suitable for phiC31-Mediated Conversion A phagemid vector has been constructed that includes both bacterial and mammalian regulatory regions capable of supporting antibody expression in bacterial and mammalian cells, respectively. The bacterial control elements of the vector have been hidden within a mammalian intron (e.g., as shown in FIG. 2). The vector includes a polynucleotide encoding an scFv fused to the bacteriophage M13 gp3 gene in bacteria. The scFv may be converted to an IgG that can be expressed in mammalian cells by transducing the phagemid into a second E. coli F$^+$ strain. The phiC31 serine integrase can be used to recombine the $C_H$ gene from an acceptor plasmid to the $V_H$ gene and to introduce controlling elements upstream of the $V_L$ gene. The attP recognition site for phiC31 can be used as a linker in the scFv. The vector is designed such that the recombined phiC31 integrase sites (attL or attR) between the variable and constant domains do not interfere with IgG expression or function (see, e.g., FIG. 10). For the purpose of generating the light-chain $V_L$-$C_L$ fusion, mammalian splice sites flank the M13 gp3 gene, allowing the $V_L$ to be fused to the $C_L$ in mammalian cells. Thus, using this vector system, a single shuttle vector can be employed for phage library construction, phage display screening, and IgG antibody production in mammalian cells. Design and Testing of a Lentiviral Vector for Phage Display and CAR-T (A) Creation of a lentiviral vector for CAR expression. In this example, we generated an acceptor plasmid for producing CAR fusions based on a standard lentiviral vector. An scFv may be cloned into this vector in-frame with a hinge (e.g., a CD8 hinge domain) and a cytoplasmic domain (e.g., a transmembrane cytoplasmic signaling region derived from TCRζ). In some instances, the scFv has an N-terminal FLAG tag to facilitate detection. Downstream of the TCRζ region and stop codon, we may incorporate an internal ribosome entry site (IRES) and a marker, such as a gene encoding a fluorescent protein (e.g., an EGFP gene). The fluorescent protein may facilitate screening for transduced cells by immunofluorescence (IF) or fluorescence activated cell sorting (FACS). Virus may be produced in a packaging cell line and used to transduce cells (e.g., Jurkat cells). The percentage of EGFP$_+$ FLAG$_+$ cells may be evaluated, for example, by FACS. To assess function, the transduced Jurkat cells may be co-cultured with the antigen-expressing cells, and the expression of CD69 (an early marker of T cell activation) evaluated, e.g., by FACS.

(B) Incorporation of both mammalian and bacterial regulatory sequences. We have designed a regulatory cassette for both mammalian and bacterial expression in which the bacterial control elements are hidden within a mammalian intron (see, e.g., FIG. 2). To test its function in T cells, this regulatory cassette may be cloned in place of the CMV promoter in the lentiviral vector for CAR expression. CAR expression in Jurkat cells transduced with the virus may be evaluated and compared to expression in the lentiviral CAR expression vector, e.g., as described in section (A) above.

Figures 18A, 18B:
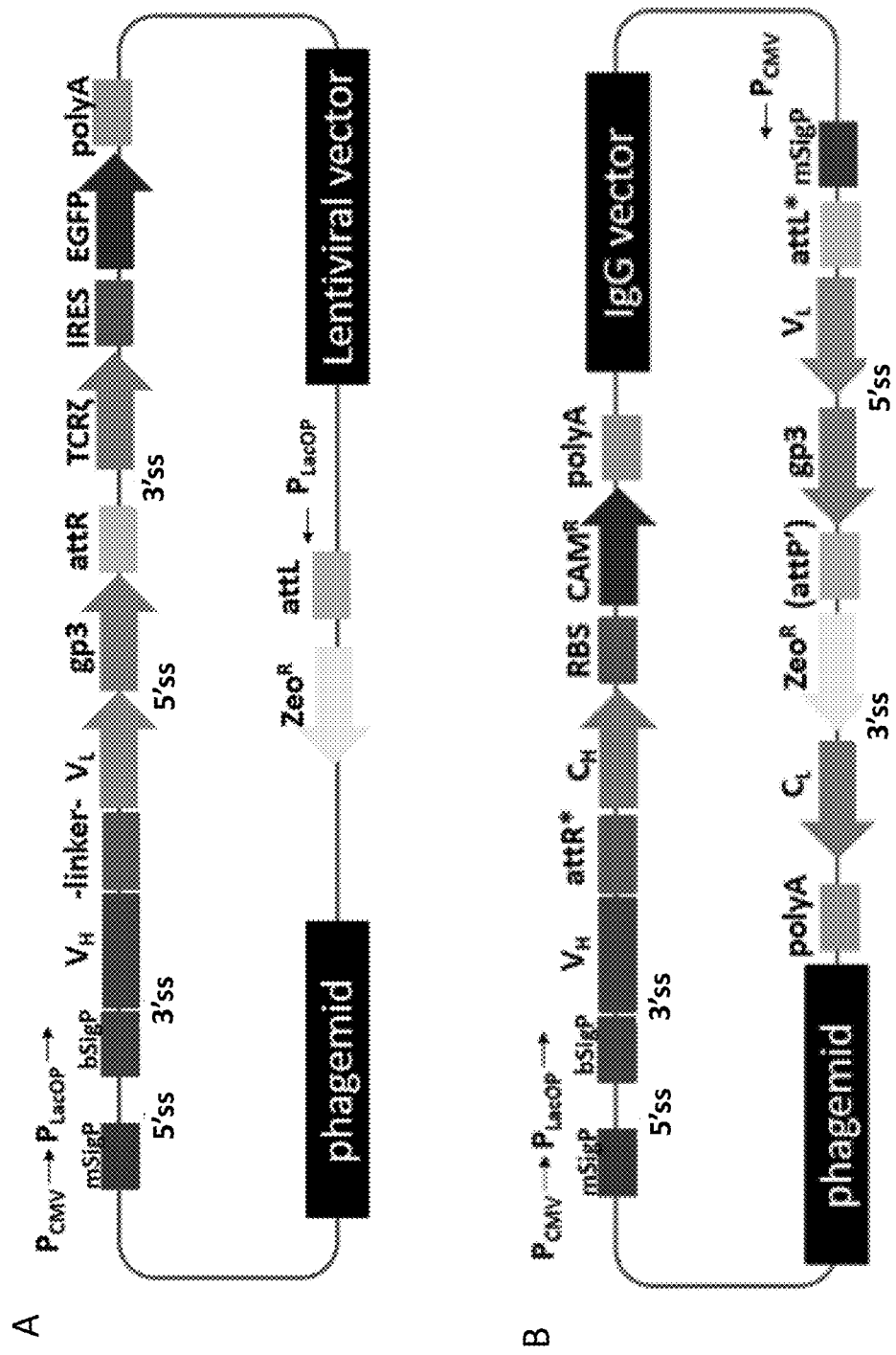
FIGS. 18A-18B are diagrams showing (A) a final vector for CAR expression, and (B) a final vector for IgG expression. (A) Mammalian splice sites (5' ss and 3' ss) flank the bacterial expression elements upstream of the scFv. Another intron contains the M13 gp3 gene and recombined BxB1 attachment site (attR). Proper splicing in mammalian cells removes the bacterial expression elements and fuses the scFv to the hinge, transmembrane, and signaling domains of the TCRζ. A HEK-293 packaging cell line can be used to produce lentivirus from this vector, and Jurkat cells can be subsequently transduced with the virus. Transduced cells express the CAR fusion and EGFP. (B) Mammalian splice sites (5' ss and 3' ss) flank the bacterial expression elements upstream of the heavy chain. Another intron contains the M13 gp3 gene, BxB1 attachment site (attP), and zeocin gene. Proper splicing in mammalian cells removes the bacterial expression elements upstream of the heavy chain and fuses the light chain variable domain ($V_L$) to the kappa light chain constant domain ($C_L$). CHO cells can be transfected with this vector to produce full length IgGs.

(C) Testing of mammalian splice sites flanking integrase attachment site and M13 gp3 in phage display. A synthetic intron flanked by natural splice donor and acceptor sequences may be generated, e.g., as described herein. The attachment site for a serine integrase may be encoded within this synthetic intron downstream of the gp3 gene on the phagemid (FIG. 18A). To test the splicing, this synthetic intron may be cloned between the scFv and TCRζ domain of the CAR. As such, the intron containing the gp3 gene and integrase attachment site may be spliced in mammalian cells. Proper splicing and expression of the CAR on the T-cells may be confirmed and, for example, compared to the constructs described in sections (A) and (B).

Figures 19A, 19B:
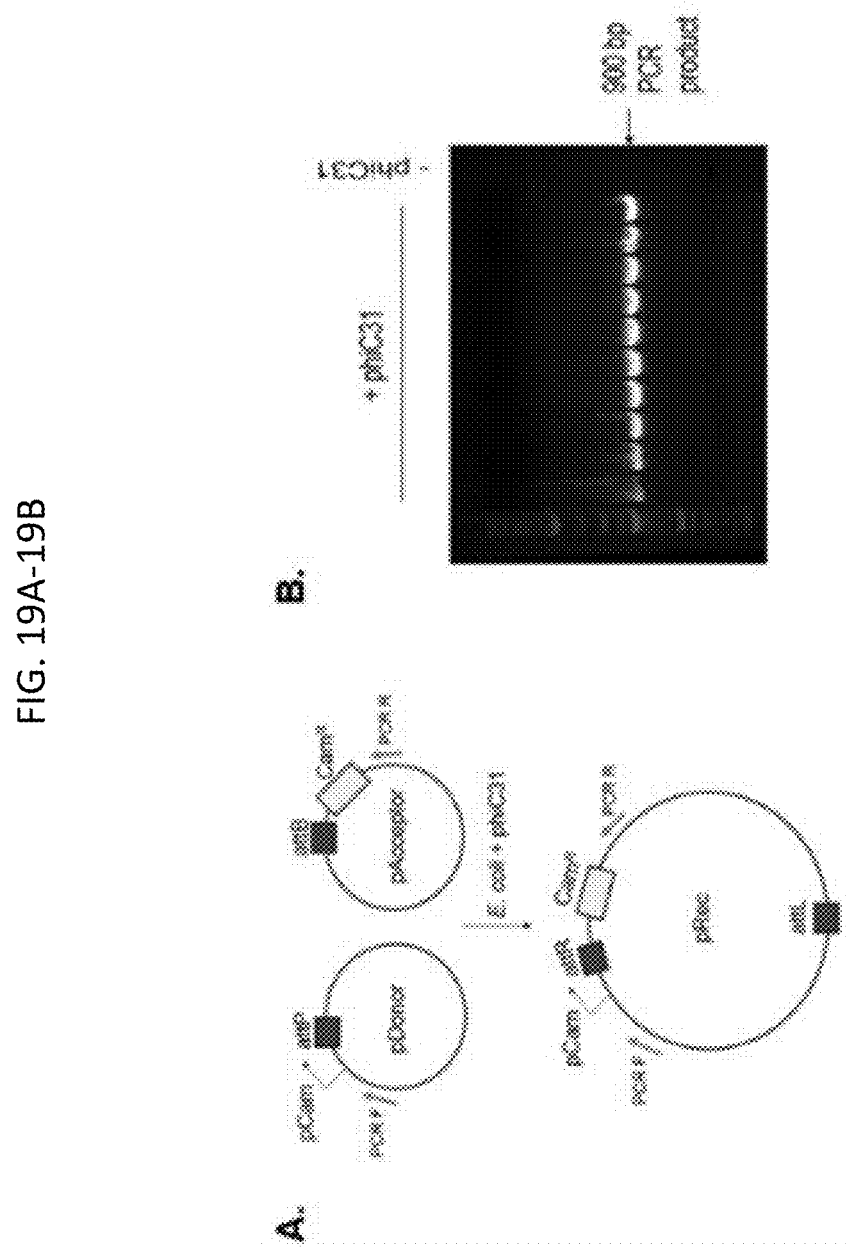
FIGS. 19A-19B are a series of diagrams showing phiC31-mediated recombination of a donor vector and an acceptor vector. (A) The pDonor and pAcceptor plasmids were co-transformed into E. coli expressing phiC31 integrase. phiC-mediated recombination between the attP and attB sites resulted in fusion of a promoter to the chloramphenicol resistance gene. Recombinants could be screened by PCR using a forward primer derived from the donor plasmid and a reverse primer derived from the acceptor plasmid. (B) A 900 bp PCR product was generated by phiC31-mediated recombination in E. coli. No product was detected when the two independent plasmids were mixed and used in the PCR reaction (-phiC31).

(D) Construction of vectors for testing integrase-mediated recombination. Serine integrases (e.g., a phage-encoded serine integrase) may mediate directionally regulated site-specific recombination between short attP and attB DNA sites without host factor requirements. Recombination between the attachment site on a donor phagemid (attP) and the corresponding attachment site on an acceptor plasmid (attB) in an *E. coli* strain expressing such an integrase (e.g., phiC31 integrase) may result in recombination of the scFv in the phagemid to the hinge (e.g., CD8) and transmembrane cytoplasmic signaling region (e.g., derived from TCRζ) on the lentiviral vector (see, e.g., FIG. 17). A strain for phiC31 integrase expression in *E. coli* has been created and its functionality demonstrated (FIGS. 19A and 19B). Alternate integrases (e.g., BxB1) may also be used to enhance flexibility of the system. For example, the promoter elements on the lentiviral vector may be replaced with an *E. coli* promoter such that recombination at the attachment site also fuses the *E. coli* promoter on the lentiviral vector to an antibiotic resistance marker (e.g., zeocin) on the phagemid (FIG. 18A), allowing selection for the integration event in *E. coli*. The efficiency of recombination may be determined by PCR screening colonies on non-selective media.

(E) Validation of vector function. In one example, a control anti-Tyro3 scFv was expressed from the phagemid vector described herein, and phage produced in *E. coli*. As described above, several exemplary anti-Tyro3 antibodies have been developed by whole cell panning against Tyro3-expressing human cells. Phage and soluble scFv binding to cells expressing a desired target molecule (e.g., Tyro3), and not to a control cell line not expressing the desired target molecule and/or expressing a different target molecule, may be confirmed, for example, by ELISA and/or FACS. *E. coli* containing the lentiviral acceptor vector and expressing the alternate serine integrase (e.g., BxB1) may be transduced with the phage and integrants may be selected by zeocin resistance. Virus may then be produced from the recombined vector and used to transduce Jurkat cells. Functional display of the CAR fusion can be confirmed as described herein. Development of a Tri-Functional Vector System for Phage Display, IgG Expression, and CAR-T.

(A) Testing of attP linker on scFv. As described above, a vector has been developed that utilizes an attachment site (attP) for the phiC31 integrase as a linker in an scFv. Functional expression of the scFv has been confirmed on phage and as soluble protein (FIG. 12A). It has also been confirmed that the attP sequence between the $V_L$ and $C_L$ domains of the IgG did not affect IgG expression or function (FIG. 12B). The same linker may optionally be used in the CAR fusion. If desired, expression and function of a CAR containing the attP linker may be evaluated and compared to the CAR with the wild-type scFv linker (e.g., as described herein).

(B) scFv conversion to both IgG and CAR. The phagemid described above may be modified to incorporate, for example, the human kappa light chain constant domain ($C_L$) downstream of the intron containing the M13 gp3 gene, the alternate integrase (e.g., BxB1) attachment site, and the zeocin resistance gene (FIG. 18B). The scFv may also be modified to contain the attP linker sequence validated in step (A). Phage derived from this vector may be used to transduce an acceptor strain for IgG conversion (e.g., as shown in FIGS. 10 and 17). In the acceptor strain, phiC31 integrase mediates recombination between the attP site on the phagemid and the attB site on the acceptor vector to fuse the $V_H$ on the phagemid to the human IgG1 constant domain ($C_H$) on the acceptor vector and to fuse the CMV promoter from the acceptor to the $V_L$ gene on the phagemid. The integration event can be selected for in *E. coli* by expression of the chloramphenicol (CAM) resistance gene (FIG. 18B). DNA from CAM-resistant clones may be isolated and, e.g., used to transiently transfect CHO cells. Splicing in mammalian cells results in removal of the intron and fusion of the $V_L$ to the $C_L$ domain. Expression of the IgG can be confirmed and compared to the expression level obtained with a standard vector. IgG function can be confirmed, for example, by ELISA and/or FACS against Tyro3-expressing cells. The IgG antibodies can be tested for the ability to compete with the Gas6 ligand for Tyro3.

Other phage integrase attachment sites may be used as alternatives to phiC31. attP variant libraries may be generated, for example, by random mutagenesis. phiC31-functional integrase substrate sites can be selected for growth in, e.g., LB$_+$ chloramphenicol media. Pools of these integrase-functional att sites can then be sub-cloned into the linker site of a linker-less scFv between the $V_H$ and $V_L$ domains. Phage can be produced from VL-att*-VH clones and biopanned against the target-expressing cells using, e.g., standard methodologies. Individual unique clones expressing functional scFvs and encoding functional att sequences can be re-tested. Those clones remaining positive can be further tested in the IgG and CAR formats.

Production and Screening of a Human Combinatorial Antibody Library Using the Tri-Functional Vector (A) Library construction. A functional phage display scFv library of, for example, at least $10^{10}$ different members may be constructed, e.g., in a constant framework using the vector system described herein. In some instances, such a library may be constructed by placing stop codons and restriction enzyme cleavage sites in the complementarity determining regions (CDRs) of the chosen scFv framework, and then using Kunkel-based site directed mutagenesis to replace these stop codons with oligonucleotides encoding NNK codons.

(B) Phage display screen. Stable cell lines have been generated that express cell surface targets of relevance to cancer (e.g., Tyro3, NRP2, ErbB2, xCT, and AGTR1). Alternatively, cells expressing CD19, which is a validated target for CAR therapy, may be utilized. A screen by phage display using whole cell panning may be performed to isolate de novo hits, for example, to Tyro3. The whole cell panning technology has been demonstrated to be used successfully to obtain binders to cell surface targets (e.g., Tyro3). A spiked library containing the model anti-Tyro3 scFv used to develop the vector system may be included as a positive control.

(C) Production of scFv, IgG, and CAR-T cells. In one example, a set of clones (e.g., about 2, 3, 4, 5, 10, 20, 30, 40, 50, 60, 70, 80, 90, 100, or more clones) from the selections are screened by phage ELISA against the Tyro3 expressing cells and a control cell line expressing a different cell surface receptor. The unique binders may be expressed as soluble protein from E. coli that cannot suppress the amber stop codon between the scFv and M13 gp3 (e.g., HB2151). The purified scFvs may be validated by ELISA against target-expressing cells and control cells. Phage derived from the positive hits may be used in parallel to transduce: (i) E. coli expressing the BxB1 integrase and containing the lentiviral acceptor vector, and/or (ii) E. coli expressing phiC31 integrase and containing the IgG acceptor vector. Lentiviral DNA may be extracted from zeocin-resistant recombined clones of E. coli expressing the BxB1 integrase and virus may be produced in the packaging cell line. Jurkat cells may then be transduced with the virus and the percentage of EGFP$_+$ FLAG$_+$ cells can be evaluated, for example, by FACS. Plasmid DNA may be extracted from CAM-resistant recombined clones of E. coli expressing phiC31 integrase and, e.g., used to transfect CHO cells. Soluble IgGs may then be purified from the culture supernatant and tested for binding to the target cells by, for example, ELISA and/or FACS.

(D) Functional validation of selected molecules. The transduced Jurkat cells may be co-cultured with the target expressing cells. The expression of CD69 can be evaluated, for example, by FACS, as described herein. The IgGs may be tested for competition with the receptor ligand, if available.

Example 16: pMINERVA Transformer System with Orthologous Integrase Site at the 5' End, Linker Region, or 3' End of the scFv In some instances, the invention features a vector system (e.g., the pMINERVA phagemid vector shown in FIG. 20) for converting a first polypeptide (e.g., an scFv, F(ab')2, Fab, Fab' or Fv fragment, or an immunoglobulin, such as an IgG) to various chimeric polypeptides (e.g., IgG, scFv, F(ab')2, Fab, Fab' Fv, CAR, or any other type of polypeptide as described herein), in which the recombination can occur at, for example, any of the 5' end, linker region, or 3' end of a first polypeptide (e.g, scFv)-encoding polynucleotide within the vector. For example, recombination at the 5' end of a first polypeptide may be used to exchange promoters, controlling elements, and/or leader peptides. Recombination at the linker of a first polypeptide may be used to fuse a portion of the first polypeptide to a portion of a second polypeptide. For example, an scFv variable domain (e.g., a VH domain) may be fused to a constant domain (e.g., a CH domain), for conversion to an IgG. Recombination at the 3' end of a first polypeptide may be used, for example, to exchange a 3' domain or to fuse the first polypeptide to various elements of interest. Such elements may include, for example, enzymes (e.g., βgal, alkaline phosphatase, and horseradish peroxidase), affinity tags (e.g., His6, FLAG, or proteinA), labels (e.g., GFP, Halotag, sfp, and SNAPtag), endosomal tags (e.g., ubiquitin ligase and FKB12), Avitags, sfp synthase, ACP-tag, TCRζ, and any other functional domains and/or binding moieties as described herein.

Figures 20A, 20B:
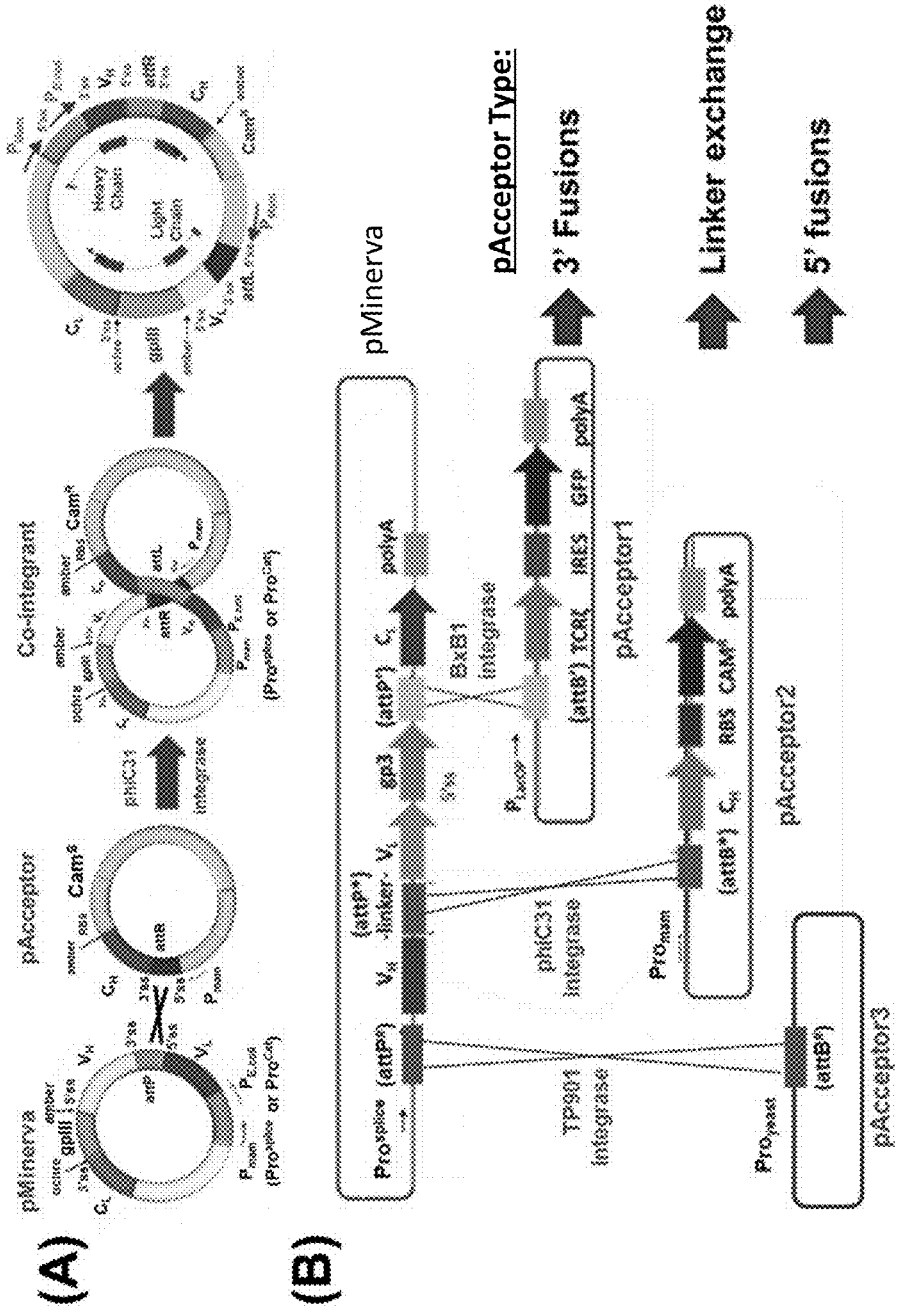
FIGS. 20A-20B are a series of diagrams showing a version of the pMINERVA vector system designed to recombine with any of at least three distinct acceptor vectors.

In one example, the pMINERVA vector includes an attP site positioned in the linker region of the scFv (i.e., between the VH and VL domains), as shown in FIG. 20A. This attP site may, for example, be recombined with a cognate attB site in an acceptor vector (e.g., pAcceptor) that includes a CH domain positioned such that the recombination results in formation of an integrant vector encoding the heavy chain and light chain of an IgG, which includes the VH and VL domains from the prior scFv of the pMINERVA vector. For example, the scFv Abs encoded on a pMINERVA phagemid donor vector as gp3-fusions may be screened in a phage display biopanning procedure to identify one or more phagemid clones encoding scFvs with certain desired biophysical properties (e.g., binding specificity and/or affinity for a target molecule). The identified phagemid clone may be transduced into an E. coli strain expressing phiC31 integrase and harboring, e.g., an IgG acceptor vector (pAcceptor). The recombination event may introduce a polyadenylation signal site adjacent at the 3' end of the $C_H$ gene. Furthermore, the recombination event may introduce a mammalian promoter and a functional protein initiation site 5' to the VL gene. Of special note, the linker between the VH and VL domains of the scFv is composed of a phiC31 36-bp attP site that is able to function as both: (i) a peptide linker between the heavy and light variable domains, and (ii) a 36-bp functional substrate for phiC31 integrase.

In a further example, the donor vector (e.g., pMINERVA) may be capable of integrating with multiple acceptor vectors (e.g., pAcceptor1, pAcceptor2, and pAcceptor3, as shown in FIG. 20B). In some instances, the donor vector may include a plurality of distinct orthologous site-specific recombination motifs, each capable of recombining with a particular cognate site-specific recombination motif. For example, the pMINERVA vector may include an attP #site 5' relative to the scFv gene, an attP* site within the linker region of the scFv gene, and an attP' site 3' relative to the scFv gene. Each of these recombination motifs may be capable of recombining a particular cognate recombination motif (e.g., attB #, attB*, and attB', respectively), which may be present on one or more distinct acceptor vectors. In certain instances, multiple orthologous cognate recombination motifs may be present on a single acceptor vector. In other instances, each distinct acceptor vector includes one of the orthologous cognate recombination motifs.

For example, FIG. 20B shows three acceptor vectors, each including one orthologous cognate recombination motif (shown as attB #, attB*, and attB'). pAcceptor1 includes an attB' site downstream of a LacOP promoter and upstream of a polynucleotide encoding the components of a CAR (e.g., a TCRζ domain and, optionally, a fluorescent marker protein, such as GFP). pAcceptor2 includes an attB* site positioned downstream of a mammalian promoter (e.g., a CMV promoter) and upstream of a heavy chain constant domain. pAcceptor3 includes an attB #site positioned downstream of a yeast promoter. When the pMINERVA phagemid vector and one of the acceptor vectors is present in an *E. coli* host, an integrase protein (e.g., phiC31 integrase) may recombine the attP and attB sequences of the two vectors, thereby producing a polynucleotide encoding a single chimeric molecule including both homing and donor vector sequences in a pre-defined orientation. The system may be extended through the use of orthologous integrases. In one example, a second integrase, such as those shown in Table 2 below, may be used to catalyze recombination at the attP #site downstream of the VL region (pAcceptor1).

TABLE 2

Exemplary Integrases

| Phage name | Host | Protein length | Function in mammalian host |
|---|---|---|---|
| Tyrosine integrases | | | |
| Lambda | *E. coli* | 356 | yes |
| HK022 | *E. coli* | 357 | yes |
| P22 | *S. typhimurium* | 387 | unknown |
| HP1 | *H. influenza* | 337 | unknown |
| L5 | *M. smegmatis* | 337 | unknown |
| Other tyrosine recombinases | | | |
| Cre (P1) | *E. coli* | 343 | yes |
| FLP | *S. cerevisiae* | 423 | yes |
| XerC | *E. coli* | 298 | unknown |
| Serine integrases | | | |
| phiC31 | *S. lividens* | 613 | yes |
| R4 | *S. parvulis* | 469 | yes |
| TP901 | *L. lactis* | 485 | yes |
| Other serine integrases | | | |
| gamma-delta | *E. coli* | 183 | yes |
| Tn3 | *K. pneumoniae* | 193 | unknown |
| gin | *E. coli* | 193 | unknown |

This recombination event could result in, for example, fusion of the scFv to a T-cell receptor to produce a CAR-T, and/or an exchange of the CL gene product downstream of the VL gene in a scFv or an IgG. Additional orthologous integrase sites (e.g., placed upstream of the VH gene, as in pAcceptor3) may be used to allow an exchange of promoters, leader peptides, or other elements of the donor and acceptor vectors.

Example 17: Spliced and Catenated Promoters

Vectors have been developed that are capable of expression in two or more distinct cell types, with expression in each cell type controlled by distinct regulatory elements. For example, such a vector may include a bacterial promoter and a mammalian promoter, which control the expression of a particular gene in bacteria or mammalian cells, respectively.

At least two different strategies for such multi-promoter vectors (e.g., vectors including dual expression promoters) can be used: (a) a spliced promoter (e.g., $\text{Pro}^{splice}$, as shown in FIG. 21A) and (b) a catenated promoter (e.g., $\text{Pro}^{cat}$, as shown in FIG. 21B).

Figures 21A, 21B, 21C, 21D:
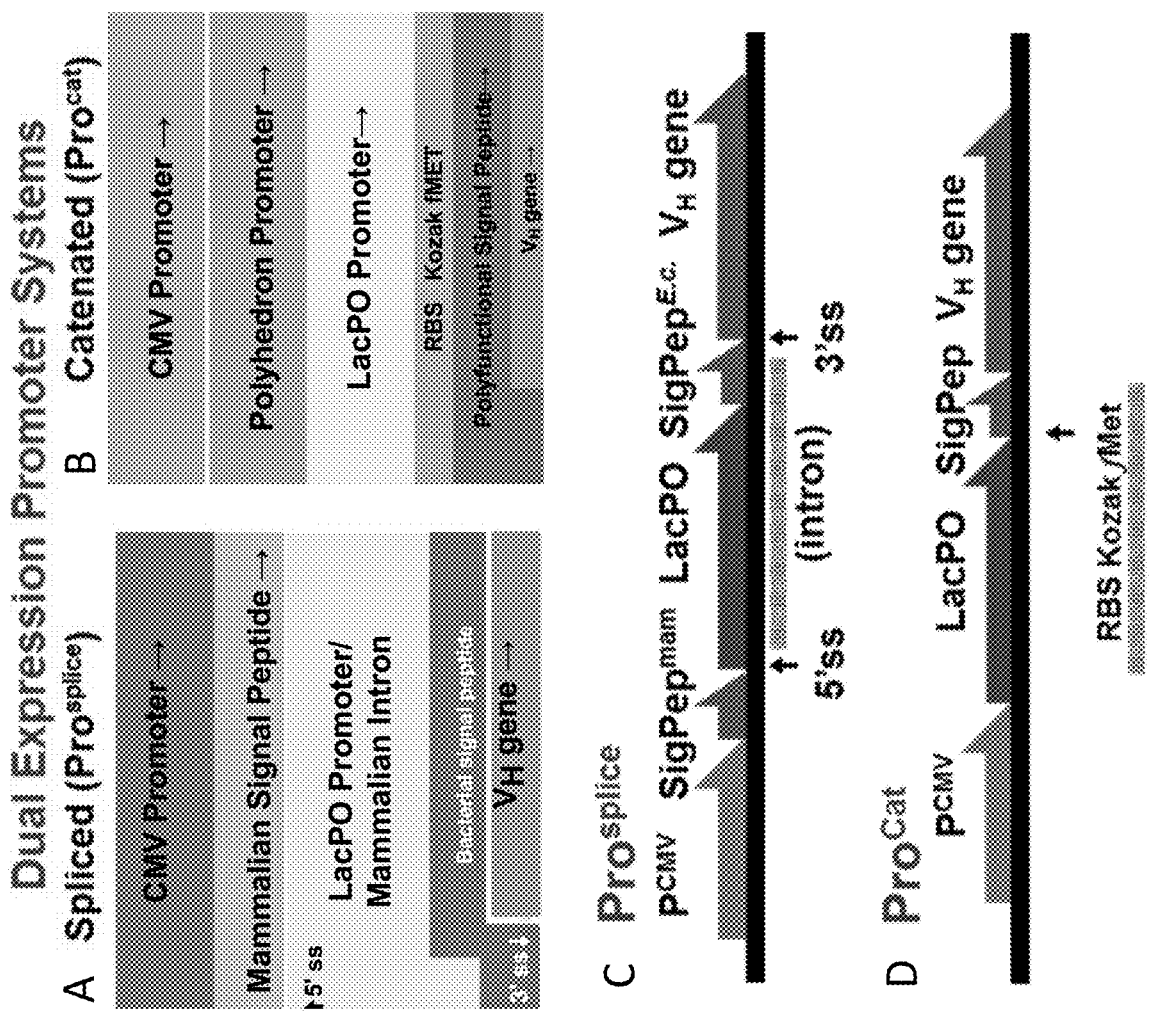

In an example of promoter splicing, an scFv can be expressed in *E. coli* from a lac promoter and in mammalian cells from a promoter (e.g., a CMV or EF1a promoter) using, e.g., a $\text{Pro}^{splice}$ vector having the layout shown in FIGS. 21A and 21C. In the $\text{Pro}^{splice}$ vector, a mammalian promoter (e.g., a CMV or EF1a promoter) controls the expression of a mammalian signal peptide (e.g., a mammalian IgG heavy chain secretion signal sequence) and a $V_H$ gene. The mammalian signal peptide of the $\text{Pro}^{splice}$ vector was designed to include an intron, which included a LacPO promoter/operator and a bacterial signal peptide. The bacterial signal sequence overlapped with the splice acceptor site. Thus, in a bacterial cell (e.g., *E. coli*), transcription from the bacterial promoter within the mammalian intron may result in expression of the scFv in the bacterial periplasm. By contrast, in a mammalian cell (or in another cell type capable of intron splicing), the bacterial regulatory sequences located in the intron may be removed by splicing, thereby generating a fusion of the mammalian signal sequence to the VH gene. The intron nucleotide sequence may include, in some instances, any promoter consensus sequences, signal sequence consensus sequences, and splice site consensus sequences known in the art.

Figures 22A, 22B:
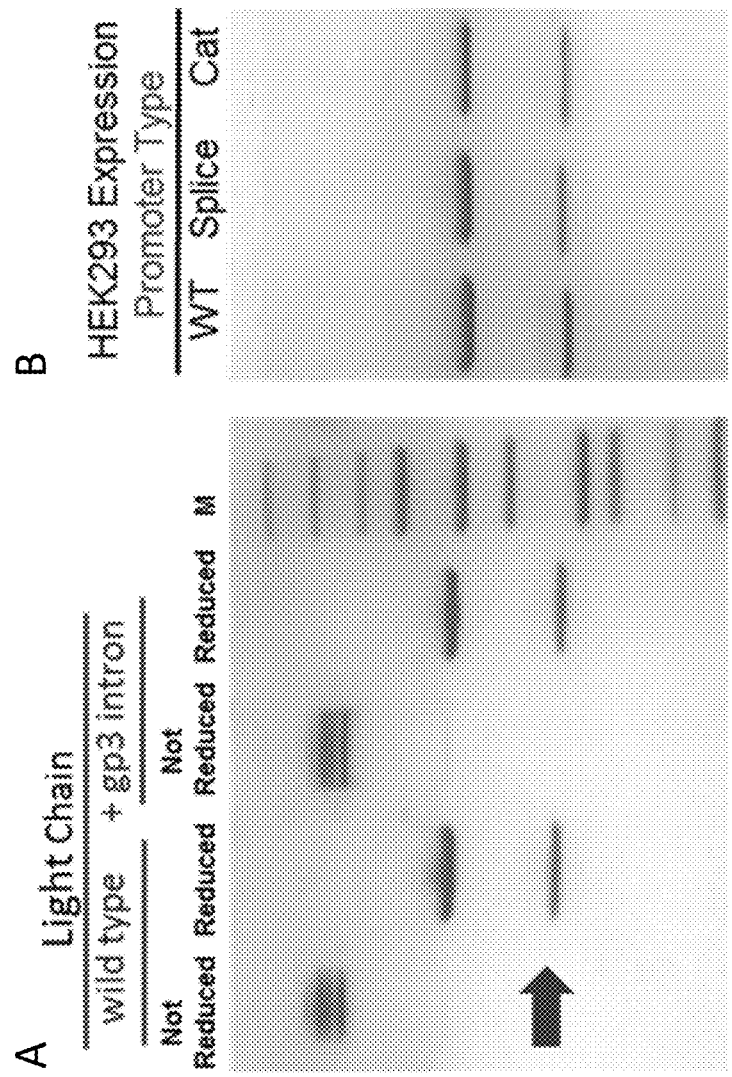
FIG. 22A shows integration between the pMINERVA phagemid vector and an exemplary acceptor vector, pAcceptor, after transduction of pMINERVA into a phiC31+ E. coli strain containing pAcceptor.
FIG. 22B shows possible integration reactions between pMINERVA and three exemplary acceptor vectors (pAcceptor1, pAcceptor2, and pAcceptor3). Recombination of pMINERVA with pAcceptor1 results in a 3' fusion of the scFv to CAR elements, thereby yielding an integrant vector capable of expressing a CAR including the scFv as an extracellular binding domain. Recombination of pMINERVA with pAcceptor2 results in linker exchange, in which the VH domain of the scFv is fused to a CH domain on pAcceptor2. Recombination of pMINERVA with pAcceptor3 results in a 5' fusion of the scFv, e.g., for switching to an alternate promoter. $P_{mam}$, mammalian promoter; $P_{yeast}$, yeast promoter; $P_{cmv}$, CMV promoter; 5'ss and 3'ss, splice signals; $V_L$, variable section of the light chain; $V_H$, variable section of the heavy chain; gp3, phage M13 gene3 product; $P_{E.\ coli}$, E. coli promoter; $C_H$ or Fc, constant region of the heavy chain; attB, attP, substrates for an integrase gene; attR and attL, products of an integrase gene; polyA, polyadenylation sequence; $Cam^S$, CamR, chloramphenicol resistance gene without and with a promoter, respectively; TCRzeta, T-cell receptor zeta; CAR-T, chimeric antigen receptor; Pro$^{splice}$, Pro$^{cat}$, dual-function promoter-types (see text for details); IRES, internal ribosome entry site; RBS, ribosome binding site.

In an example of the $\text{Pro}^{cat}$ catenated promoter system, a mammalian promoter (e.g., a CMV or EF1a promoter), polyhedron promoter (insect expression), and LacPO promoter (bacterial expression) were placed, in order, upstream of a ribosome binding site/Kozak fMet, polyfunctional signal peptide, and $V_H$ gene (FIG. 21B). In some instances, a catenated promoter may include at least a CMV promoter, LacPO promoter, signal peptide (e.g., an IL2 signal sequence), and gene to be expressed, as shown in FIG. 21D. In the example of the $\text{Pro}^{cat}$ system shown in FIG. 21B, the ATG start sites were removed from the polyhedron and lacPO promoters, such that the first ATG fMet start site for bacterial, insect and mammalian expression was identical. In this case, the same signal sequence was used for all three organisms. As a result, each of the three catenated promoters drove expression of the signal peptide-$V_H$ fusion in the appropriate cell type. The vectors of the invention were tested, in one example, by determining whether a desired protein product was generated by a cell type of interest. FIG. 22 shows the results of light chain or IgG expression in mammalian cell culture. In one example, expression of a light chain gene incorporating a gp3 splice gene was compared to that of a wild-type control light chain lacking the gp3 splice gene (FIG. 22A). The two dual expression promoters, $\text{Pro}^{splice}$ and $\text{Pro}^{cat}$, were also tested for their ability to drive expression of an IgG in HEK293 cells. An E1A promoter was used as a control. Both the $\text{Pro}^{splice}$ and $\text{Pro}^{cat}$ vectors were shown to successfully drive expression of the IgG at levels indistinguishable from that induced by the control promoter (FIG. 22B).

Example 18: Antibody Library Design

The present invention provides methods and compositions useful for converting a first polypeptide into a chimeric polypeptide. In some instances, it may be desirable to convert a library of antibodies or antibody fragments into a library of chimeric polypeptides of a different type (e.g., a different type of antibody or antibody fragment, a CAR, a ubiquitin ligase, a knocksideways domain, or any other polypeptide type as described herein). For such antibody libraries, any constant and variable domains as known in the art may be used. In some instances, the antibody or antibody fragment may be an immunoglobulin (e.g., an IgG, IgM, IgA, IgD, or IgE), scFv, F(ab')2, Fab, Fab' or Fv. In certain instances, the antibodies or antibody fragments of the library may differ in the amino acid sequences of the variable domains, but not the constant domains. In particular instances, each of the antibodies or antibody fragments in a library may include the same constant framework. Exemplary constant frameworks that may be used in such libraries are shown in FIG. 23.

Example 19: A Donor-Acceptor System for the In Vivo Recombineering of scFv into IgG Molecules Validation of recombinant antibodies selected by phage display often requires early production of the cognate full-length immunoglobulin G (IgG). The conversion of phage library outputs to a full immunoglobulin via standard sub-cloning can be time-consuming and/or limit the number of clones that can be evaluated. Described herein is a vector system for converting scFvs from a phage display vector directly into IgGs without any in vitro subcloning steps. This vector system, referred to herein as pMINERVA, makes use of site-specific bacteriophage integrases that are expressed in E. coli and intron splicing that occurs within mammalian cells. In the pMINERVA system, a phage display vector contains both bacterial and mammalian regulatory regions that support antibody expression in E. coli and mammalian cells. In one example, a single-chain variable fragment (scFv) antibody is expressed on the surface of bacteriophage M13 as a genetic fusion to the gpIII coat protein. The scFv is desirably converted to an IgG that can be expressed in mammalian cells by transducing a second E. coli strain. In the second E. coli strain, the phiC31 recombinase fuses the heavy chain constant domain from an acceptor plasmid to the heavy chain variable domain and introduces controlling elements upstream of the light chain variable domain. In mammalian cells, splicing removes a synthetic intron containing the M13 gpIII gene to produce the fusion of the light chain variable domain to the constant domain. Phage displaying scFv and recombinant IgGs generated using this system are expressed at wild-type levels and retain normal function. Use of pMINERVA may therefore eliminate the labor-intensive subcloning and DNA sequence confirmation steps previously required to convert a scFv into a functional IgG Ab.

Summary

Figure 24A:
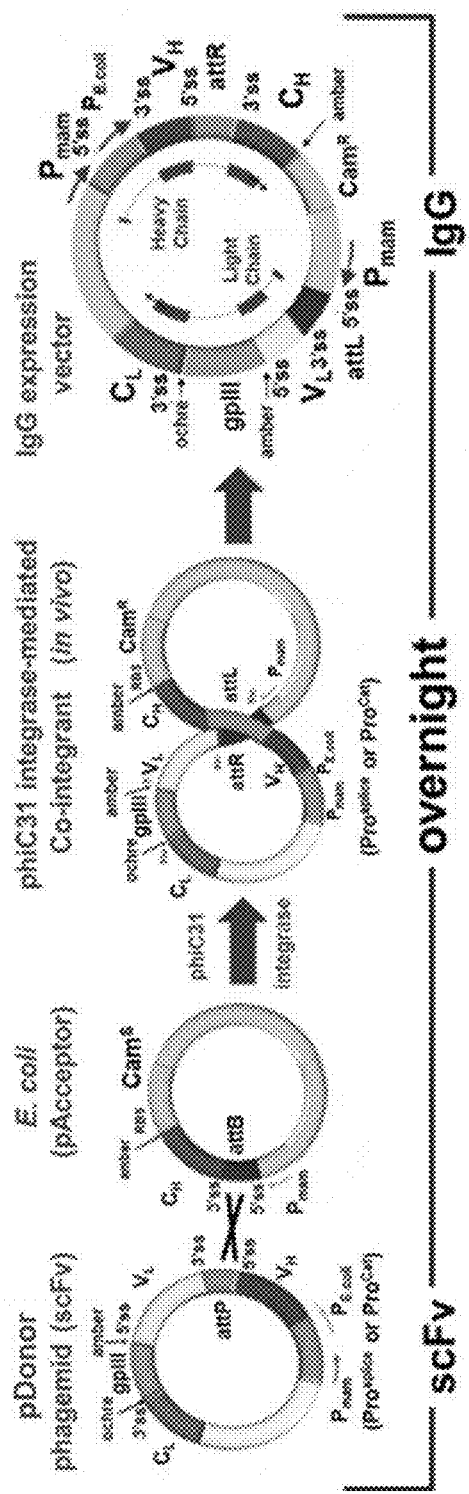

An exemplary low-cost system, pMINERVA, for the facile subcloning of phage display scFvs into IgG molecules in vivo is described herein. The system takes advantage of two genetic principles, recombination in E. coli and splicing in mammalian cells. As shown in FIG. 24A, the pMINERVA phage display vector contains both bacterial and mammalian regulatory regions that support antibody expression in bacteria and mammalian systems. The scFv is expressed as a fusion to the bacteriophage M13 gp3 gene in bacteria and converted to an IgG that can be expressed in mammalian cells by transducing the phagemid into a second E. coli F+ strain. In the second E. coli strain, the phiC31 serine integrase is used to fuse the heavy chain constant domain ($C_H$) from an acceptor plasmid to the heavy chain variable domain ($V_H$) and to introduce controlling elements upstream of the light chain variable domain ($V_L$). Positive selection for the recombination events is built into the system. To generate the light-chain $V_L$-$C_L$ fusion, mammalian splice sites flank the M13 gill gene, allowing the $V_L$ to be fused to the light chain constant domain ($C_L$) in mammalian cells. Thus, using the pMINERVA vector system, a single shuttle vector can be employed for phage library construction, phage display screening, and IgG antibody production in mammalian cells.

Materials and Methods

Bacterial strains and vectors. The TG1 E. coli strain (F' (traD36 proAB+ laclq lacZΔM15) supE thi-1 Δ(lac-proAB) Δ(mcrB-hsdSM)5, (rK-mK-) was purchased from Lucigen. The template phagemid, pAX1565, is a derivative of the phagemid, pAP-III$_6$ with a single-chain variable fragment antibody (scFv) fused to coat protein III of bacteriophage M13. The scFv in pAX1565 is based on the monoclonal antibody, HERCEPTIN® (DrugBank #DB00072), and contains a (Gly$_4$Ser)$_3$ linker between the $V_H$ and $V_L$ domains.

Molecular Biology. Standard cloning methods, as well understood in the art, were used for cloning, sub-cloning, DNA extraction, protein purification, protein and DNA quantitation. Required mutagenesis was done using site directed mutagenesis kits (Agilent). Synthetic genes were constructed at GENEART™ (Life Technologies, Carlsbad, Calif.). Plasmid pCDF-1b was purchased from Novagen (EMD Millipore, Billerica, Mass.). Restriction enzymes, ligases and polymerases were purchased from (New England Biolabs, Ipswich, Mass.) and used according to the manufacturer's recommendations. Electrocompetent cells were purchased from Lucigen (Middletown, Wis.). CHO FREESTYLE™ and HEK293 FREESTYLE™ cells were acquired from Life Technologies (Carlsbad, Calif.). Mammalian cell growth media was purchased from Life Technologies.

Construction of pDonor and pAcceptor plasmids. The phagemid pAPIII$_6$ was used as the template vector for the pDonor construct. The full-length M13gpIII gene flanked by splice sites was synthesized by GENEART™ (Life Technologies, Carlsbad, Calif.) and cloned into pAPIII$_6$ vector using Sal I and Xho I restriction sites. The constant region of the kappa light chain ($C_L$) and the SV40 late polyA sequence was synthesized by GENEART™ and cloned into the above vector using the Xho I restriction site. Recombinants were sequence confirmed for directionality. A synthetic scFv based on the anti-Her2 antibody, HERCEPTIN®, with the 36 bp attP sequence for phiC31 as a linker between the variable heavy ($V_H$) and variable light ($V_L$) genes was cloned between the Hind III and Sal I sites in the vector. A Mlu I site was introduced by site-directed mutagenesis (QUIKCHANGE®, Agilent Technologies, Santa Clara, Calif.) upstream of the phoA promoter in the vector. The synthetic promoters and leader peptides (e.g., Pro$^{cat}$ or Pro$^{splice}$) were cloned between the Mlu I site and Hind III sites, replacing the phoA promoter upstream of the scFv gene. The origin and references (each of which is incorporated herein in its entirety) for all genes and regions included in the pDonor vector are listed in the table shown in FIG. 25I.

To engineer the pAcceptor vector, the phiC31 gene was synthesized by GENEART™ (Life Technologies) and cloned into pCDF-1b (EMD Millipore, Billerica, Mass.) using Not I and Avr II restriction sites. The heavy chain acceptor construct consisting of the human EF1a promoter, IL-2 signal sequence, 36 bp attB sequence for phiC31 in frame with the signal sequence, human IgG1 constant domain, a ribosome binding site and spacer followed by the chloramphenicol gene (CAM), the BGH polyA sequence, and the T7 transcription terminator, was synthesized by GENEART™ (Life Technologies). This 3.3 Kb DNA region was cloned into the pCDF-1b/phiC31 vector using the Acc65 I restriction site to generate pAcceptor. Recombinants were sequence confirmed. The origin and references for all genes and regions included in the pAcceptor vector are listed in the table shown in FIG. 25I.

Construction of IgG expression test vector. A single vector system for IgG expression consisting of the EF1a promoter upstream of the light chain (variable light ($V_L$) and constant light ($C_L$) regions) and a second mammalian promoter upstream of the heavy chain (variable heavy ($V_H$) and constant heavy ($C_H$) regions) was used to test individual components of the pMINERVA system. For the addition of the attL sequence between the signal sequence and $V_L$, the attL duplex was cloned into the IgG expression vector using the Not I restriction enzyme (NEB) and sequenced to screen for directionality. For the addition of the attR sequence between $V_H$ and $C_H$, site-directed mutagenesis was performed to introduce the 36 base pair attR sequence following the manufacturer's protocol (QUIKCHANGE®, Agilent Technologies). To introduce the M13gpIII sequence flanked by splice sites between $V_H$ and $C_H$ of the IgG expression test vector, the gene was synthesized by GENEART™ (Life Technologies) and cloned into the IgG expression test vector using BsiW I restriction sites. Recombinants were screened for directionality by sequencing. To exchange the mammalian promoter driving the light chain of the IgG with $Pro^{cat}$ or $Pro^{splice}$, the promoter sequences were synthesized by GENEART™ (Life Technologies) and cloned into the IgG expression test vector using Mlu I and Not I restriction sites. To exchange the mammalian promoter driving the heavy chain of the IgG with $Pro^{cat}$, the $Pro^{cat}$ sequence was synthesized by GENEART™ (Life Technologies) and cloned into the IgG expression test vector using EcoR V and Nde I restriction sites. To exchange $V_H$ and $V_L$ regions in the IgG vector, the $V_H$ gene was PCR amplified from a commercially available human IgG heavy chain expression vector (Invivogen, San Diego, Calif.) and cloned into the IgG expression test vector using Nde I and BsiW I restriction enzymes (NEB) and T4 DNA ligase (NEB). The entire light chain ($V_L$ and $C_L$) and a piece of the SV40 late polyA sequence were PCR amplified from a commercially available human IgG light chain expression vector (Invivogen) and cloned into the IgG expression test vector containing the correct $V_H$ using Not I and Hpa I restriction sites. Recombinants were sequence confirmed.

DNA transformation. In this example, transformation reactions were set up as follows: 0.5 µl ligation product was mixed with 50 µl of TG1 electrocompetent cells (Lucigen) and added to a 0.1 cm gap cuvette. DNA was electroporated into bacterial cells using a Gene Pulser (Bio-Rad, at the following settings: 1.6 kV, 200 ohms, 25 µF). One ml of recovery media was added and the electroporated cells were transferred to 14 ml culture tubes and shaken at 37° C. After 1 hr, one hundred µl of each of the dilutions was plated onto LB plates containing ampicillin (100 µg/ml), and the plates were incubated overnight at 37° C. Chemically competent NEB5α cells (NEB) were transformed according to the manufacturer's protocol. Briefly, 50 µL of cells were incubated with 1 µL of DNA for 30 min on ice, heat shocked at 42° C. for 30 sec and 250 µL of recovery media was added. Cells were incubated while shaking for 1 hr at 37° C. and 100 µL was plated on LB plates with 100 µg/mL of ampicillin.

Monoclonal phage ELISA. For vectors containing the $Pro^{Splice}$ promoter, a single colony of transformed TG1 cells was picked off of a TYE/Amp/Glucose plate into a 2 ml starter culture of 2YT supplemented with ampicillin (100 µg/ml) and 1% glucose. Single colonies containing $Pro^{cat}$ vectors were picked off of LB plates containing ampicillin (100 µg/ml) into a 2 ml starter culture of LB supplemented with ampicillin (100 µg/ml). Cultures were incubated at 37° C. for 2-3 hours with shaking, diluted into 50 ml of their respective media, and further incubated at 37° C. with shaking until an absorbance at 600 nm of 0.4 was reached. Once the cultures reached mid-log phase, 10 ml were transferred into individual 15 ml conical tubes, and 5 µl of KM13 helper phage was added. After a 30 min incubation at 37° C. without shaking, tubes were centrifuged at 2000×g for 10 minutes and the supernatants were aspirated. Pellets were resuspended in 50 ml of appropriate media ($Pro^{Splice}$: 2YT supplemented with ampicillin (100 µg/ml), kanamycin (50 µg/ml) and 0.1% glucose; $Pro^{cat}$: LB supplemented with ampicillin (100 µg/ml) and kanamycin (50 µg/ml)) and incubated at 30° C. with shaking overnight. After overnight incubation, the cultures were centrifuged at 15,000×g for 10 minutes. Supernatants were transferred to an ELISA plate pre-coated with the specific target antigen.

For coating of the ELISA plates, 100 µl/well of antigen diluted to 2.5 µg/ml in 1×PBS was added to maxisorp ELISA plates (ThermoScientific, NUNC) and incubated overnight at 4° C. Wells were coated with either specific antigen or with non-relevant protein to test for non-specific binding. The wells were washed three times with PBS (250 µl/well) and blocked for 1 hr with 2% nonfat dry milk in PBS (MPBS). The wells were washed for a total of three times with PBS. 100 µl of undiluted supernatant containing phage was added to the ELISA plate and incubated for 1 hr at room temperature. Wells were washed three times with PBS containing 0.01% Tween (PBS-T) followed by a 1 hr room temperature incubation with anti-M13 monoclonal antibody conjugated to Horseradish Peroxidase (HRP; GE Healthcare, Piscataway, N.J.). The ELISA was developed by adding 100 µl TMB Ultra (Pierce, cat #34029) to each well, and the reactions were stopped with 50 µl 2M $H_2SO_4$. Plates were read at 450 nm in a standard plate reader and fold over background (FOB) was calculated by dividing the OD450 of a well containing phage on specific antigen by the signal of the same phage on non-relevant protein.

Production and purification of soluble IgG antibodies. IgG expression vectors were transiently transfected into mammalian HEK293 (Life Technologies; 293-F; cat #R790-07) suspension cells under sterile conditions in a cell culture ventilation hood. On the day prior to transfection, the HEK293 suspension cells were diluted back to $0.7×10^6$ cells/ml in 30 ml total volume using Freestyle 293 Expression Medium (Life Technologies). On the day of transfection, 24 µg of sterile IgG expression vector DNA was diluted in 3 ml Freestyle 293 Expression Medium and vortexed for 10 seconds. To the diluted DNA, 24 µl of FectoPRO transfection reagent (Polyplus-transfection, New York, N.Y.) was added and vortexed for 10 sec. The DNA-transfection reagent mixture was incubated at room temperature for 10 min. The DNA-transfection reagent mixture was added to the 30 ml culture of HEK293 suspension cells that were seeded the day prior. Post-transfection the HEK293 cells were incubated at 3° C. in 8% $CO_2$ with shaking at 130 rpm for 72 hours, at which point 15 ml of fresh Freestyle 293 Expression Medium was added. The cultures continued incubating at 3° C. and 8% $CO_2$, shaking at 130 rpm for an additional 48-72 hours. The transfected cells were centrifuged at 1,000×g for 10 min and the IgG-containing supernatants were transferred to new, sterile tubes. The IgG antibodies were purified from the clarified supernatants with 0.5 ml Protein A bead slurry. The Protein A beads were washed three times with PBS and incubated with 45 mL of IgG supernatant for one hour while rocking at 4° C. The Protein A bead+IgG mixture was poured into an empty 2 ml chromatography column and loaded via gravity flow. The columns were washed twice with 3 mL of PBS supplemented with 1 mM PMSF and eluted with 1.5 mL of 0.1 M glycine at pH 3.0 and neutralized with 60 µl of 1 M Tris buffer at pH 9.0. The eluate was analyzed by SDS-PAGE under reducing and non-reducing conditions. Final purified IgG was quantitated using the Coomassie Plus assay kit (Thermo Fisher, cat #23236).

Human IgG ELISA on protein. For biotinylated antigens, ELISA plates were coated with 100 µL per well of neutravidin at 10 µeµl/well) and blocked for 1 hr at room temperature with 3% bovine serum albumin (BSA) in PBS. The wells were incubated with 1 µg/mL of biotinylated peptide (either specific target or non-relevant protein) for 1 hr at room temperature after which they were washed three times with PBS (250 µL/well) and blocked again for 1 h with 3% BSA in PBS. After washing the wells with PBS 3×, the purified IgG antibodies were added at 1 µg/ml in 3% BSA/PBS and incubated for 1 hr at room temperature. The wells were washed four times with PBS+0.01% Tween (PBS-T) and incubated with anti-human-IgG-HRP (ThermoFisher, cat #AH10404) diluted 1:5,000 in block for 1 hr at room temperature. The wells were washed three times with PBS-T and the HRP-conjugated secondary antibody was detected with TMB reagent (100 µL/well) with a 2-3 minute incubation. The reaction was stopped with 2M $H_2SO_4$ (50 µL/well), absorbance was read at 450 nm and FOB was calculated by dividing the OD450 of a well containing IgG on specific antigen by the signal of the same IgG on non-relevant protein.

Human IgG ELISA on mammalian cells. HEK293 cells stably expressing a target antigen and HEK293 cells not expressing the antigen were added to V-bottom ELISA plates (Phenix, cat #MPG-651101) at a concentration of $2.3 \times 10^6$ cell/mL (0.15 mL per well). Cells were blocked with 3% BSA for 30 min at room temperature after which they were centrifuged at 500×g for 4 min and the supernatant was removed. Purified IgG was added to the cells at 1 µg/mL (100 µL per well) and incubated while shaking for 1 hr at room temperature. Cells were washed 2× with PBS, centrifuging the plate in between each wash at 500×g for 4 min. Cells were incubated while shaking with anti-human-HRP at 1:5,000 in block for 1 hr at room temperature, Cells were washed 2× with PBS and transferred to a pre-blocked V-bottom plate and washed once more. 100 µL of luminescence reagent (Piece, cat #37069) was added to the cells/well and transferred to a white bottom ELISA plate (NUNC, cat #436110). After a 2 min incubation the plates were read with a luminescence detector and FOB was calculated by dividing the relative luminescence unit (RLU) of a well containing IgG on HEK293 cells expressing the target antigen by the RLU of the same IgG on HEK293 cells not expressing the target antigen.

Testing phiC31 recombinase function. Competent TG1 cells containing the spectinomycin-resistant pAcceptor plasmid were prepared according to standard methods. The cells were transformed with the pDonor or a mock-recombined control plasmid following standard electroporation procedure (described above). Transformants were plated on LB media containing ampicillin (100 µg/ml) or chloramphenicol (10 µg/ml). The ratio of ampicillin to chloramphenicol-resistant transformants was determined.

Results

Cloning of phiC31 phage integrase and in vivo testing of functionality using a promotorless CamR gene polycistronic message. Phage-encoded serine integrases mediate directionally regulated site-specific recombination between short attP and attB DNA sites without host factor requirements. The phiC31 serine integrase can be used to induce recombination between two plasmids in E. coli. In this example, phiC31 is used to fuse the heavy chain variable domain ($V_H$) on a phagemid vector (pDonor) to the heavy chain constant domain ($C_H$) on a second plasmid (pAcceptor). These vectors are shown in FIG. 24A. For this approach to be feasible, the linker between the variable heavy ($V_H$) and variable light ($V_L$) domains of the scFv may contain a 36 bp phiC31 integrase recognition site (attP or attB) that is able to function as both a peptide linker in the scFv and a functional substrate for phiC31 integrase.

The wild-type $(Gly_4Ser)_3$ linker between the $V_H$ and $V_L$ of a model scFv (anti-Her2) in our phagemid vector was replaced with the phiC31 integrase site (i.e., attP or attB). The phage-scFv were produced in E. coli and tested for function in a phage ELISA against the target antigen, Her2, or a non-relevant control protein. As shown in FIGS. 24B-24E, phage containing the attP linker bound selectively to Her2 with comparable activity to phage containing the wild-type linker (FIG. 24B). Phage with the attB site as a linker in the scFv was unable to bind to its specific antigen.

Successful recombination between the attP site on the phagemid and the attB site on the acceptor plasmid generated a 36 base pair recombined phiC31 site (attR) at the hinge junction of the variable heavy domain and constant heavy domain of the immunoglobulin (FIG. 24A). In addition, a 36 base pair recombined phiC31 site (attL) was produced between the leader peptide and variable domain of the light chain ($V_L$) (FIG. 24C). Tested IgGs containing the attR or attL sequences at these junctions, respectively, expressed at wild-type levels and recognized their respective target antigens (FIGS. 24D and 24E).

Figures 25A, 25B:
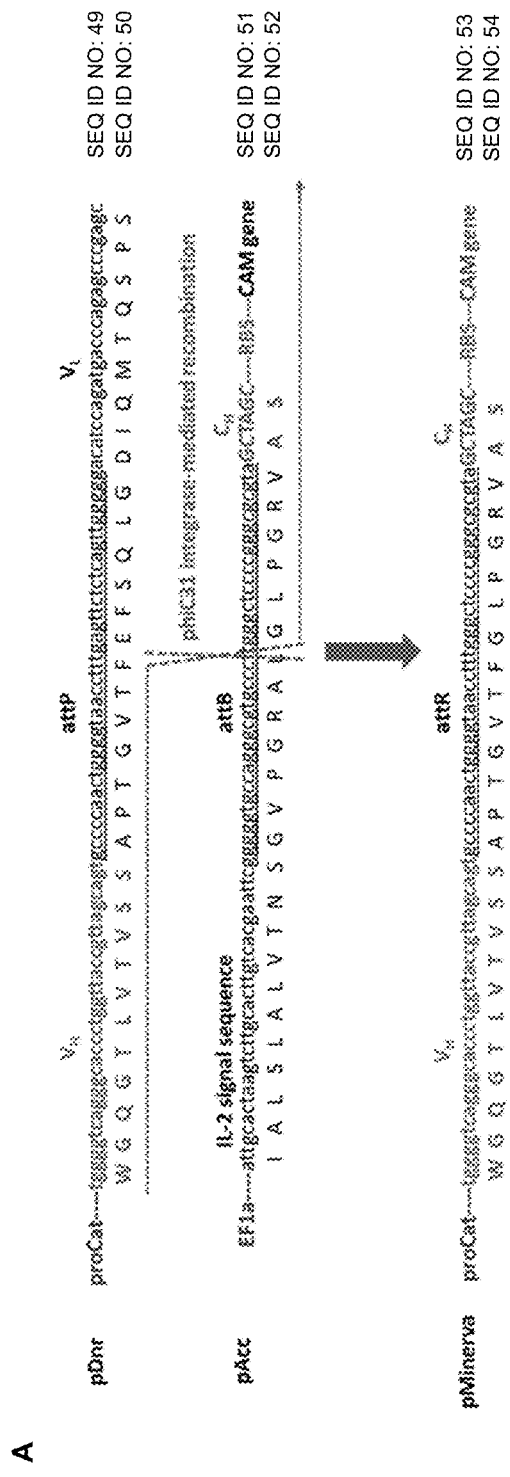

To test the function of phiC31 in our system, the gene was cloned into a plasmid (derived from pCDF-1b; Novagen) under the control of a constitutive E. coli promoter (pCam; pACYC184) and transformed into the E. coli strain, TG1. A promoterless chloramphenicol resistance (camR) gene was placed 3' of the phiC31 integrase attB site on the same plasmid (pAcceptor). Successful integration of the phagemid (pDonor) into the pAcceptor plasmid placed an E. coli promotor upstream of the pAcceptor camR gene and produced a bicistronic gene-pair composed of the immunoglobulin heavy chain and camR genes (FIG. 25A). The cells that were harboring this resulting co-integrated plasmid thereby became chloramphenicol resistant. The phiC31-mediated integration efficiency was tested in E. coli by transforming a pAcceptor TG1 strain with the pDonor plasmid and measuring the percent of ampicillin-resistant transformants converting to camR. Conversion would only occur as a result of successful co-integration. The ratio of chloramphenicol-resistant (camR) transformants to ampicillin-resistant (ampR) transformants was compared with the ratio of camR to ampR transformants using an already co-integrated plasmid in TG1 cells. The results demonstrated that the phiC31 integrase is able to site-specifically recombine the pDonor vector into a pAcceptor vector at >90% efficiency (FIG. 25B). No chloramphenicol-resistant colonies were obtained when the pDonor lacked the attP site.

Figures 25C, 25D:
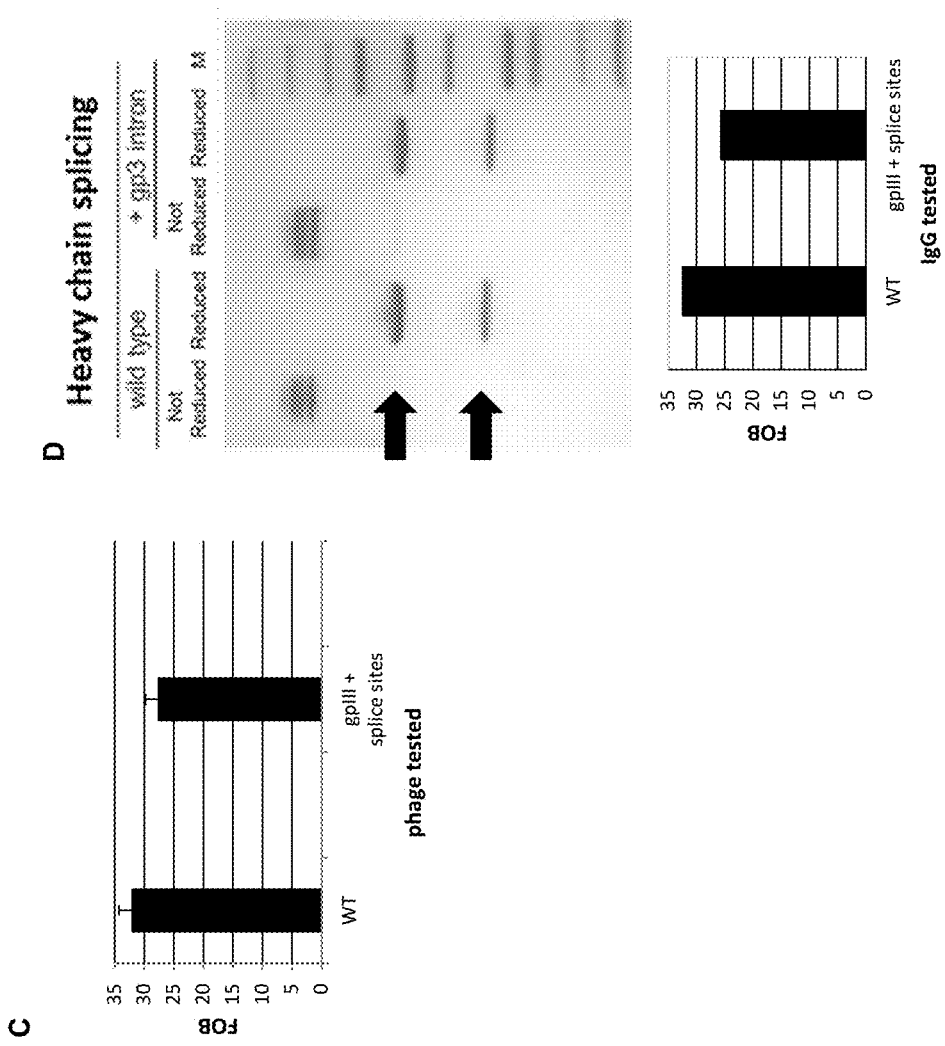

Design and testing of synthetic intron containing M13gpIII. While phiC31-mediated recombination was used to join the $V_H$ to the $C_H$ domain in the pMINERVA system, the light chain variable domain ($V_L$) domain in the scFv may also be fused to the light chain constant domain ($C_L$) (FIG. 24A). In eukaryotic cells, large sequences can be efficiently removed from mRNA by the RNA splicing machinery. A synthetic intron was designed, which contained the M13gpIII gene flanked by consensus 5' and 3' splice site sequences. Thus, in E. coli, the scFv is expressed on the surface of bacteriophage M13 as a genetic fusion to the gpIII gene, whereas in mammalian cells, the intron containing the gpIII gene is excised, creating a fusion of the $V_L$ to the $C_L$ (FIG. 24A). In the absence of proper splicing, the $C_L$ will be out of frame with the $V_L$, and functional IgG cannot be produced. As shown in FIG. 25C, introduction of splice sites between the scFv and gpIII gene did not interfere with phage production or function. In HEK-293 cells, IgG expression from the intron-containing vector was comparable to expression from the original construct containing no intron, indicating that splicing was efficient (FIG. 25D; top panel). Both IgGs tested were functional and showed comparable activity in an ELISA against the target antigen (FIG. 25D, bottom panel).

Design and testing of dual-functional promoters: $Pro^{splice}$ and $Pro^{cat}$ expression in mammalian cells and E. coli. A dual-functional promoter that supports both E. coli and mammalian expression was used to enable scFv production in bacteria and IgG production in mammalian cells. Two different promoter systems were tested: a promoter intron-splicing system ($Pro^{splice}$) and a catenated polyfunctional promoter system ($Pro^{cat}$) (FIGS. 25E-25H). In the $Pro^{splice}$ system, the EF1a promoter was followed by the mammalian IgG heavy chain secretion signal sequence that contains an intron. The lac promoter/operator and bacterial signal peptide was contained within the mammalian intron, and the bacterial signal sequence overlapped the splice acceptor site. Thus, in E. coli, transcription from the bacterial lac promoter/operator within the mammalian intron resulted in expression of the scFv in the bacterial periplasm, whereas in mammalian cells, splicing removed the bacterial regulatory sequences located in the intron, generating the mammalian signal sequence.

Figures 25E, 25F, 25G, 25H:
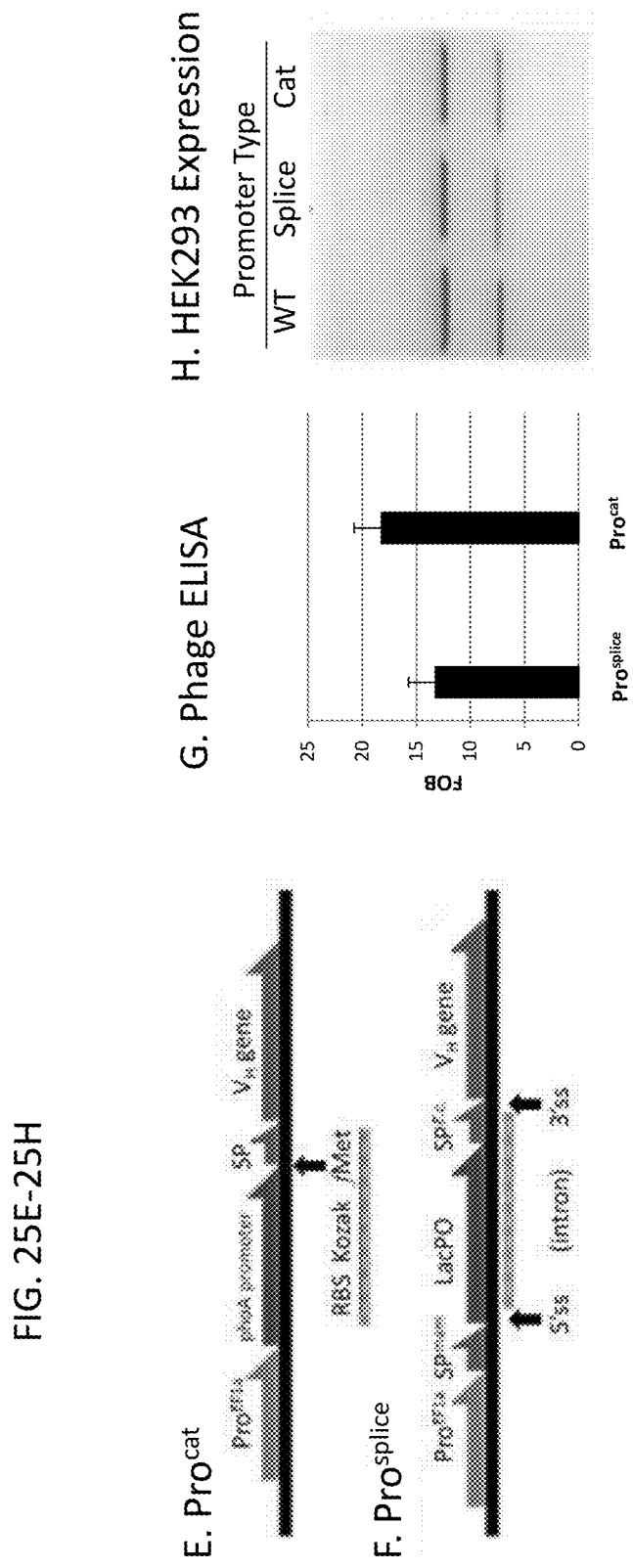

In the catenated promoter system ($Pro^{cat}$), the mammalian promoter is followed by a polyhedron promoter (for expression in insect cells) and a bacterial promoter. The ATGs were removed from the downstream polyhedron and bacterial promoter such that the first ATG fMet start site for bacterial, insect and mammalian expression was identical. In this case, the same signal sequence was used for all three organisms. The $Pro^{cat}$ developed here used the EF1a promoter for mammalian expression, the phoA promoter for E. coli expression, and the IL-2a signal peptide for secretion in both systems. Phage displaying the model scFv was produced from both promoter systems at equivalent levels (FIG. 25G). In addition, the IgG yield from the dual promoter systems in HEK-293 cells was equivalent to the yield using the EF1a promoter alone (FIGS. 25H-25J).

Thus, by combining together all of these elements, the pMINERVA system completely eliminated the labor-intensive subcloning and DNA sequence confirmation steps currently required to convert a scFv into a functional IgG antibody.

Discussion

Described in the present example is a vector system that enables high-throughput conversion of antibody fragments to full length immunoglobulin G (IgG) molecules that can be directly validated in standard immunoassays. The screening platform described in this example is desirably used with single-chain variable fragments (scFvs), but can also be used with any other polypeptide scaffolds known in the art, including, but not limited to, Fabs and yeast display libraries.

The pMINERVA system utilizes a phage integrase, phiC31, to induce site-specific recombination between a donor and acceptor plasmid in E. coli to generate a fusion of the antibody heavy chain variable domain ($V_H$) to the heavy chain constant domain ($C_H$) and to introduce regulatory elements upstream of the variable light chain gene ($V_L$). Recombinases such as Cre and FLP may also be used for genome engineering. As shown in the present example, however, phiC31 is preferred because it is greater than 90% efficient at inducing recombination between two plasmids in E. coli. Many additional known serine- and tyrosine-integrases known in the art (e.g., BxB1 and lambda) can also mediate unidirectional, site-specific recombination and may be similarly used in the present invention.

The phiC31 integrase has a 36 base pair (i.e., equivalent to 12 amino acids) recognition sequence. The pMINERVA system utilizes incorporation of these integrase attachment sites in the linker of the scFv, and subsequently, at the hinge junction between the heavy chain variable and constant domains and between the signal sequence and light chain variable domain. These 12 amino acid sequences did not interfere with phage production or IgG expression and function of the specific recombinant antibodies, as shown herein. In some instances, attP or attB mutations that alter the resulting linker peptide to a more flexible linker sequence may be used to support efficient integration. Additionally, splice sites flanking the integrase attachment sites may be incorporated into the vector to generate a seamless IgG. As shown herein, mammalian splicing can be used to excise the M13gpIII gene and fuse the light chain variable domain ($V_L$) to the light chain constant domain ($C_L$). Intron splicing has further been shown to enhance the expression of recombinant proteins in mammalian cells.

Two dual expression promoter systems are described herein that were effective for E. coli and mammalian expression. One system utilized mammalian splicing to excise bacterial expression elements, and the second system uses catenated promoters for mammalian, insect cell, and E. coli expression. The catenated promoter system required the same signal peptide to work in both E. coli and mammalian cells. As shown in the experiments described above, the IL-2 signal sequence was able to function as a secretion signal in bacteria. Other signal peptides that work in both mammalian and bacterial systems are known in the art and may be alternately used for expression. The human EF1a promoter was used to to build the dual function promoter systems described herein, but other promoters that enable high-level protein expression in mammalian cells (e.g., the CMV promoter) can be be used instead. The catenated promoter system further included the polyhedron promoter, such that insect cells could be used as an alternative to HEK-293 cells for high-throughput IgG production.

The current system was modeled on a human IgG1 antibody. However, additional pAcceptor plasmids can be constructed to extend the utility of the system. Acceptor vectors containing other human immunoglobulin isoforms (e.g., IgG2, IgG3, IgG4, and IgM) can be generated, as well as acceptor vectors containing the constant domains for mouse or rabbit antibodies. Different types of 3' fusions could also be generated, including, but not limited to, enzyme fusions, protein purification tags, labels, and fusion-tags that can direct proteins to the endosome. Further, both acceptor and donor plasmids may be constructed for conversion to and/or from other chimeric proteins known in the art (e.g., antibody fragments and chimeric antigen receptors).

Example 20: Dual Expression Promoter Systems

Figures 26A, 26B, 26C, 26D, 26E:
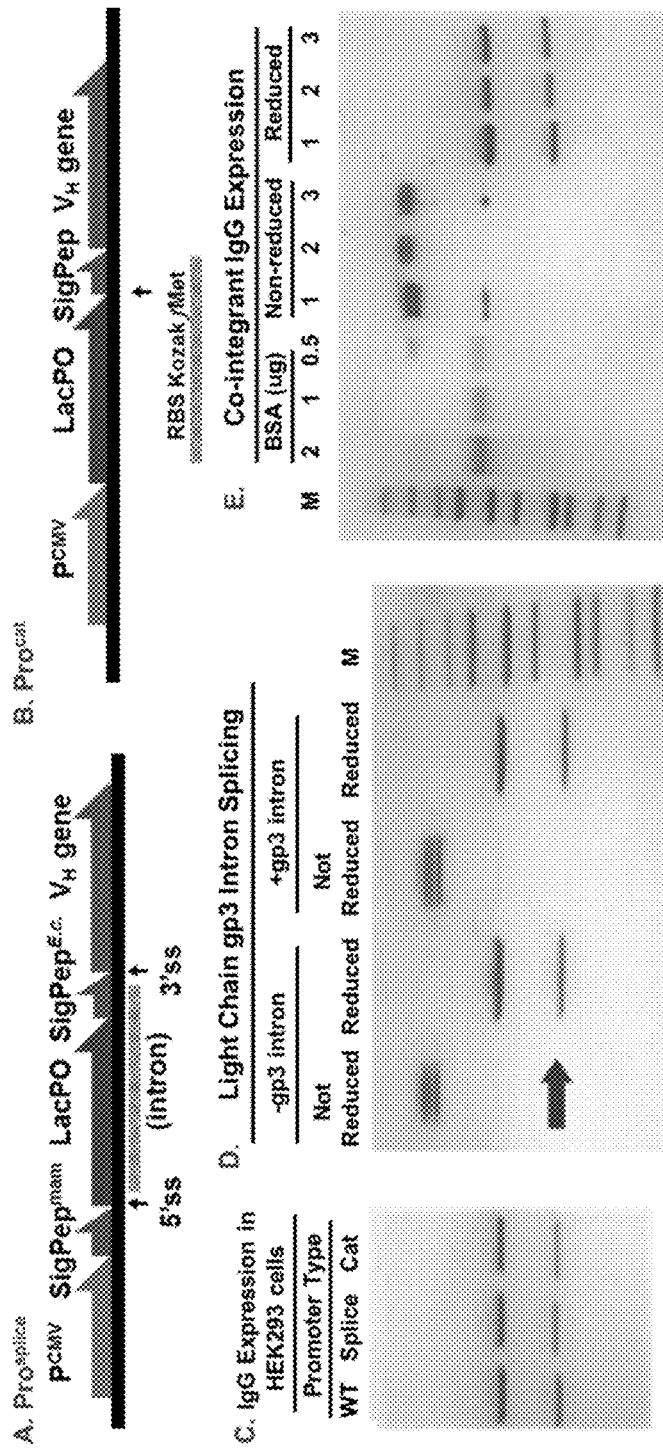
FIGS. 26A-26E are a series of diagrams showing expression and splicing in the pMINERVA system, including expression promoter systems and co-integrant expression yield. (A) Promoter type Pro$^{splice}$. In this dual function promoter, the LacPO and bacterial signal peptide (SigPep$^{E.c.}$) sequence are contained within the mammalian intron. The bacterial signal peptide sequence overlaps the 3' splice site (3'ss). In *E. coli*, transcription from the bacterial promoter within the mammalian intron results in the expression of the scFv in the bacterial periplasm fused to the M13gp3 protein in an amber-suppressing strain of *E. coli* (for example, TG1). In mammalian cells, intron splicing of the mRNA at the 5' (5'ss) and 3'ss removes the bacterial LacPO regulatory sequences located within the intron. Intron splicing generates the mammalian signal sequence. The intron nucleotide sequence was designed using promoter consensus sequences, signal sequence consensus sequences, and splice site consensus sequences. (B) Promoter type Pro$^{cat}$. In this catenated promoter system, the ATGs downstream of the mammalian CMV promoter (P$^{CMV}$) are removed from downstream polyhedron and lac promoter/operator (LacPO) controlling elements. The Kozak sequence and E. coli ribosomal binding site (RBS) are designed such that the first ATG fMet start site for either bacterial, insect, or mammalian expression is identical. In this case, the same signal sequence (SigPep) is used for all three organisms. (C) Expression of the wild type (WT), Pro$^{splice}$ and Pro$^{cat}$ promoters in HEK293 cell culture. IgG purification from HEK293 cells where the IgG gene was under the expression control of either an EF1A promoter, Pro$^{splice}$, or Pro$^{cat}$. (D) Light-chain gp3 splicing M13gp3 intron splicing in Pro$^{splice}$. A wild-type light chain protein was compared with a light chain protein incorporating a spliced M13gp3-splice gene. An ochre stop codon in pMINERVA placed 3' of the M13gp3 gene prevented full length light chain protein expression from non-spliced mRNAs. Arrow indicates the band corresponding to the light chain gene product. (E) Comparison of single-plasmid and co-integrant IgG yields from HEK293 cells. Estimated yields for co-integrants estimated by gel imaging (from SDS-PAGE): 1. pAX1984=19.4 ug/mL (wild-type IgG), 2. pAX3A-5=11.6 ug/mL (co-integrant), 3. pAX3B-5=13.5 ug/mL (co-integrant).

The scFv to IgG reformatting methods described herein may utilize a dual expression promoter system upstream of the affinity reagent. Two such dual expression promoter systems have been successfully tested to date: a promoter intron-splicing system ($Pro^{splice}$) and a catenated polyfunctional promoter system ($Pro^{cat}$) (FIGS. 26A-26B). In both systems, the scFv is expressed in E. coli from a lacOP operator/promoter. Expression in mammalian cell cultures has been successfully tested from the $Pro^{splice}$ and $Pro^{cat}$ promoters using either the CMV or EF1A promoter (FIGS. 26C-26E). The splicing and co-integration did not significant affect expression in HEK293 cells or functionality.

Example 21: Development of Additional pAcceptor Plasmids

Figure 27:
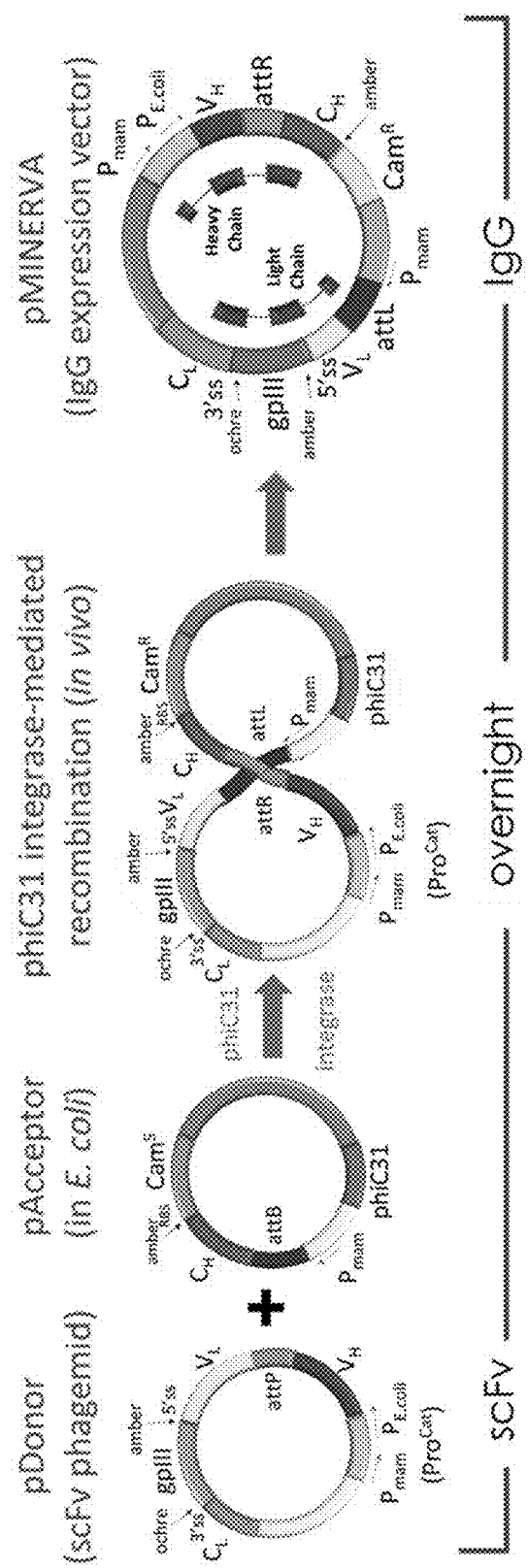
FIG. 27 is a diagram showing a pMINERVA scheme for in vivo overnight subcloning of an scFv into an IgG. All subcloning steps are performed by intron splicing and integrase recombination.

In this example, a set of pAcceptor plasmids was generated, e.g., for use in the pMINERVA system (e.g., as described herein). The version of the pMINERVA system in this example utilizes the phiC31 integrase to recombine a donor phagemid with a unique acceptor plasmid in bacteria to efficiently create an IgG expression vector, pMINERVA (FIG. 27). In mammalian cells, inherent cell splicing mechanisms may then remove the bacterial components of pMINERVA resulting in a functional IgG molecule. With a bifunctional, catenated promoter system (e.g., as described herein), a scFv can be expressed in E. coli as a fusion to the M13gpIII coat protein or as soluble protein prior to integration, and as a whole IgG molecule in mammalian cells post-integration.

Experimental Design and Results

Figure 28B:
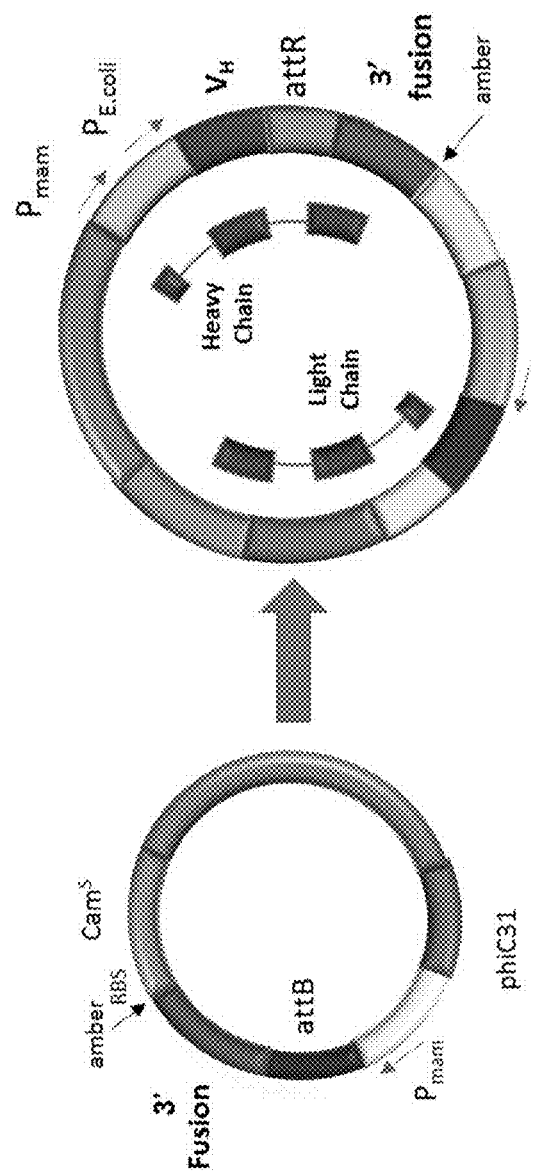

The pMINERVA system has a unique flexibility that allows for the construction of different 3' fusions to extend the utility of the system. The types of fusions may include, for example, different isotypes of IgG molecules, enzyme fusions, protein purification tags, CAR-Ts, and fusion-tags that can direct proteins to the endosomes. 3' fusion tags may be constructed, for example, using standard molecular biological methods. Non-limiting examples of 3' fusion constructs are shown in FIG. 28A. Testing of functionality may follow established protocols for each of the tag types. In one example, a pAcceptor vector encoding an scFv may be converted into a pMINERVA integrant vector encoding an IgG (FIG. 28B).

Figure 29:
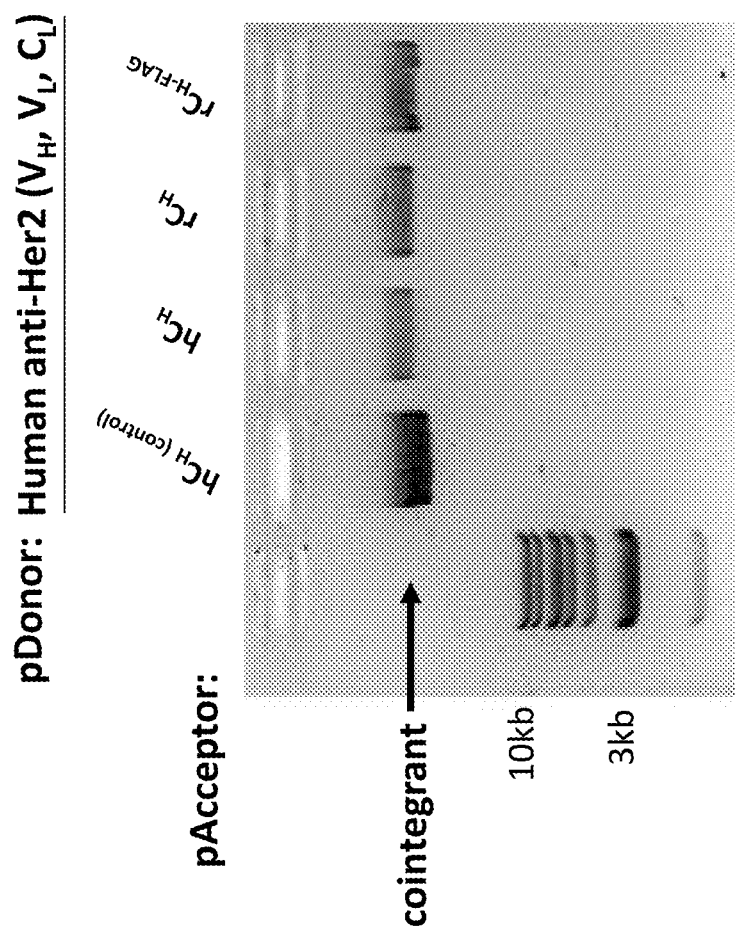
FIG. 29 is a diagram showing co-integration of each of a set of pAcceptor vectors with a pDonor vector encoding the $V_H$, $V_L$, and CL domains of a human anti-Her2 antibody. hc$_{H(control)}$=human IgG1 CH control; hC$_H$=human IgG1 C$_H$; rC$_H$=rabbit C$_H$; and rC$_{H\text{-}FLAG}$=rabbit CH with modified FLAG tag. Proper co-integration and sequence was confirmed for each of the resultant integrant vectors.

Testing of Additional pAcceptor Vectors. NEB5alpha F' strain E. coli cells containing pAcceptors with one of the human IgG1 constant domain ($hC_H$) pAcceptor, rabbit constant domain ($rC_H$), or rabbit constant domain with a C-terminal FLAG tag ($rC_H$-FLAG) were transduced with phage containing an anti-Her2 pDonor phagemid (with human $V_H$, $V_L$, and $C_L$ kappa domains). The phiC31 integrase expressed from the pAcceptor catalyzed recombination between the attP site on the phagemid and the attB site on the pAcceptor plasmid. After a 3-hour recovery period, the cells were plated on chloramphenicol-containing plates, which selected for co-integration. Plasmid DNA was extracted from chloramphenicol-resistant colonies and analyzed on a 1% agarose gel stained with SYBR safe. The integrant vector was approximately 17 kilobases in size. Proper co-integration of the vectors was confirmed (FIG. 29), with plasmids of the expected size generated. Vectors were also sequenced to confirm proper integration.

Figures 30A, 30B:
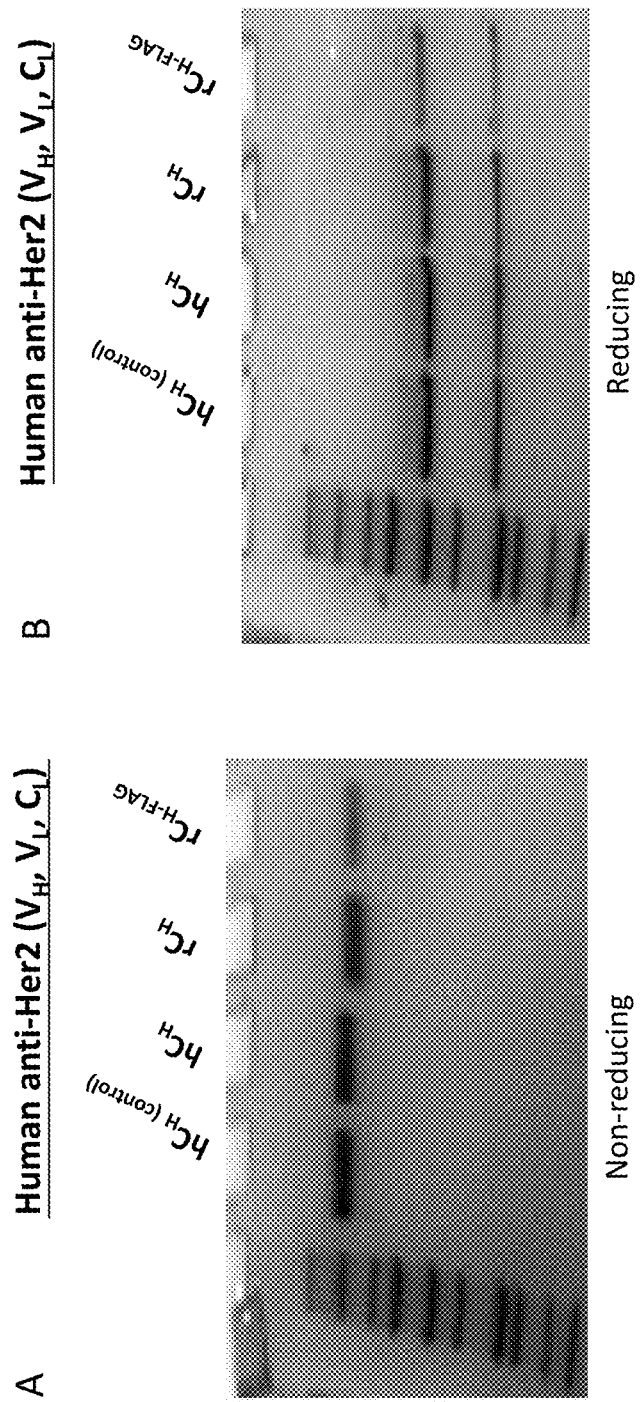
FIGS. 30A-30B are a series of diagrams showing expression of hybrid chimera IgGs under non-reducing (A) and reducing (B) conditions.

To determine if the integrant vectors were capable of producing the desired IgGs, HEK-293 Freestyle cells (Thermo Fisher) were transiently transfected with the integrant vectors, and IgG was purified from culture supernatants using Protein A resin. The purified antibodies were analyzed by SDS-PAGE under non-reducing (FIG. 30A) or reducing (FIG. 30B) conditions. Both the fully human antibodies and the human-rabbit hybrid chimeras were expressed.

Figures 31A, 31B, 31C:
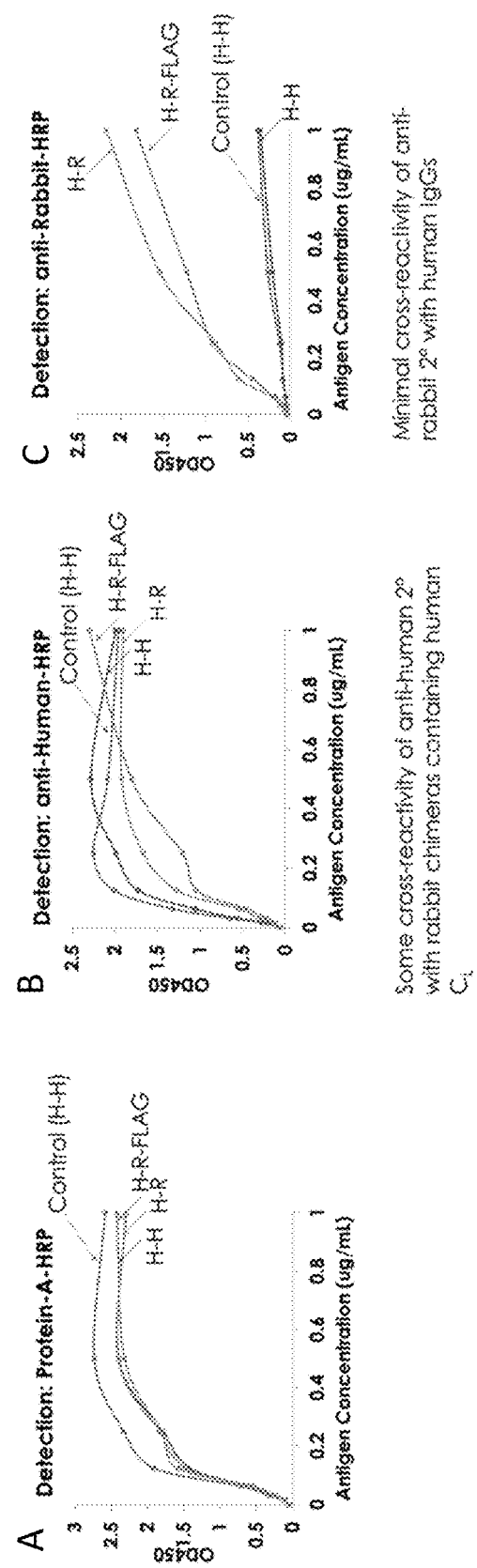
FIGS. 31A-31C are a series of graphs showing functional validation of human-human (H-H) and human-rabbit (H-R) hybrid chimeras using one of the following secondary antibodies for detection: protein A conjugated to horseradish peroxidase (HRP) (Protein-A-HRP) (FIG. 31A), anti-human polyclonal antibody conjugated to HRP (anti-human-HRP) (FIG. 31B), or anti-rabbit polyclonal antibody conjugated to HRP (anti-rabbit-HRP) (FIG. 31C).

The purified IgGs (at a concentration of 1 µg/ml) were analyzed by ELISA against titrating concentrations (0.01-1 µg/ml) of the target antigen, Her2 (FIG. 31). When protein A conjugated to HRP was used as the secondary antibody for detection of the IgGs, the fully-human anti-Her2 IgG1 antibody (H-H) showed comparable activity to the rabbit hybrid chimeras (H-R and H-R-FLAG; FIG. 31A). In a second experiment, HRP-conjugated, anti-human polyclonal antibody was used as the secondary antibody for detection of the IgGs. Since the variable domains and light chain of the IgG were derived from human, the rabbit chimeric antibodies showed some cross-reactivity with the anti-human secondary (FIG. 31B). Lastly, when a HRP-conjugated, anti-rabbit polyclonal antibody was used as the secondary antibody for detection, both rabbit chimeric antibodies showed good signal, and there was minimal cross-reactivity with the fully human IgGs (FIG. 31C).

The purified IgGs (at a concentration of 1 µg/ml) were also analyzed by ELISA against titrating concentrations (0.01-1 µg/ml) of the target antigen, Her2. A HRP-conjugated, anti-FLAG polyclonal antibody was used as the secondary for detection of the IgGs. Only the human-rabbit hybrid chimera with the C-terminal FLAG tag (H-R-FLAG) showed a signal in the ELISA, as expected (FIG. 32).

pAcceptor Variants

In one example, a pAcceptor plasmid may be constructed for a plurality of tag types (e.g., the first five tag types listed in FIG. 28A). It is contemplated that pAcceptor plasmids may be constructed separately for the Fc regions of, for example, mouse, rabbit, bovine, and the five primary classes of human immunoglobulins (IgG, IgM, IgA, IgD and IgE). Differences in heavy chain polypeptides may allow these immunoglobulins to function in different types of immune responses and at particular stages of the immune response. The polypeptide protein sequences responsible for these differences may generally be found in the Fc fragment. While there are five different types of heavy chains, there are two main types of light chains: kappa (κ) and lambda (λ). Different isotypes may display distinct structural and effector properties, such as, e.g., complement-dependent cytotoxicity (CDC) and antibody-dependent cell-mediated cytotoxicity (ADCC). These properties may be key features in selecting the backbone to use for a particular therapeutic antibody. For example, in humans, there are four subclasses of IgG: IgG1, IgG2, IgG3 and IgG4 (numbered in order of decreasing concentration in serum). Variance among different subclasses is generally less than the variance among different classes.

OTHER EMBODIMENTS

All publications, patent applications, and patents mentioned in this specification are herein incorporated by reference.

While the invention has been described in connection with the specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

What is claimed is:

1. A kit for converting a single-chain variable fragment (scFv) into a chimeric polypeptide comprising
   (a) a first vector including, in order from 5' to 3',
      a first mammalian expression control motif,
      a first E. coli expression control motif,
      a sequence encoding a heavy chain variable region (VH) of the scFv,
      a first site-specific recombination motif,
      a sequence encoding a light chain variable region (VL) of the scFv,
      a 5' mammalian splice site ($Mam_{5'ss}$),
      a fusion display protein sequence,
      a 3' mammalian splice site ($Mam_{3'ss}$), and
      a sequence encoding a light chain constant region (CL); and
   (b) a second vector including, in order from 5' to 3',
      a second mammalian expression control motif,
      a second site-specific recombination motif, and
      a sequence encoding a polypeptide.

2. The kit of claim 1, wherein said first vector is a phagemid vector.

3. The kit of claim 1, wherein said second vector is a phagemid vector.

4. The kit of claim 1, wherein said first vector is a phagemid vector and said second vector is not a phagemid vector.

5. The kit of claim 1, wherein said first vector further comprises:
   a second 5' mammalian splice site ($Mam_{5'ss}$) positioned between said first mammalian expression control motif and said first E. coli expression control motif, and
   a second 3' mammalian splice site ($Mam_{3'ss}$) positioned between said first E. coli expression control motif and said sequence encoding said VH of the scFv.

6. The kit of claim 5, wherein said first vector further comprises a leader sequence positioned between said second 3' mammalian splice site and said sequence encoding said VH of the scFv.

7. The kit of claim 1, wherein said first vector further comprises a leader sequence positioned between said first E. coli expression control motif and said sequence encoding said VH of the scFv.

8. The kit of claim 1, wherein said first vector further comprises:
   an additional 5' mammalian splice site ($Mam_{5'ss}$) positioned between said sequence encoding said VH of the scFv and said first site-specific recombination motif, and
   an additional 3' mammalian splice site ($Mam_{3'ss}$) positioned between said first site-specific recombination motif and said sequence encoding said VL of the scFv.

9. The kit of claim 1, wherein said second vector further comprises:
   a 5' mammalian splice site ($Mam_{5'ss}$) positioned between said second mammalian expression control motif and said second site-specific recombination motif, and
   a 3' mammalian splice site ($Mam_{3'ss}$) positioned between said second site-specific recombination motif and said sequence encoding said polypeptide.

10. The kit of claim 1, wherein said polypeptide comprises a heavy chain constant region.

11. The kit of claim 1, wherein said polypeptide comprises a fusion protein.

12. The kit of claim 1, wherein said polypeptide comprises a fusion protein comprising a tag.

13. The kit of claim 12, wherein said tag is a FLAG, HA, Myc, V5, His, GST, MBP, AviTag, or streptavidin tag.

14. The kit of claim 1, wherein said polypeptide comprises a fusion protein comprising a fluorescent protein.

15. The kit of claim 1, wherein said kit further comprises an additional vector comprising a polynucleotide encoding a recombinase enzyme capable of recombining said first site-specific recombination motif with said second site-specific recombination motif.

16. The kit of claim 1, wherein said kit further comprises a recombinase enzyme capable of recombining said first site-specific recombination motif with said second site-specific recombination motif.

17. The kit of claim 1, wherein said first vector or said second vector comprises a polynucleotide encoding a recombinase enzyme capable of recombining said first site-specific recombination motif with said second site-specific recombination motif.

* * * * *

SEQUENCE LISTING

<160> NUMBER OF SEQ ID NOS: 54

<210> SEQ ID NO 1
<211> LENGTH: 39
<212> TYPE: DNA
<213> ORGANISM: Artificial Sequence
<220> FEATURE:
<223> OTHER INFORMATION: Synthetic Construct

<400> SEQUENCE: 1
ccccaactgg ggtaaccttt gggctccccg ggcgcgtac                              39

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct

<400> SEQUENCE: 2

Pro Asn Trp Gly Asn Leu Trp Ala Pro Arg Ala Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Pro Thr Gly Val Thr Phe Gly Leu Pro Gly Arg Val
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic Construct

<400> SEQUENCE: 4

Val Arg Ala Arg Gly Ala Gln Arg Leu Pro Gln Leu Gly
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Construct

<400> SEQUENCE: 5

Tyr Ala Pro Gly Glu Pro Lys Gly Tyr Pro Ser Trp
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct

<400> SEQUENCE: 6

Thr Arg Pro Gly Ser Pro Lys Val Thr Pro Val Gly
1               5                   10

```
<210> SEQ ID NO 7
<211> LENGTH: 7
<212> TYPE: DNA
<213> ORGANISM: Artificial Sequence
<220> FEATURE:
<223> OTHER INFORMATION: Synthetic Construct

<400> SEQUENCE: 7 tttatac                                                                    7

<210> SEQ ID NO 8
<211> LENGTH: 7
<212> TYPE: DNA
<213> ORGANISM: Artificial Sequence
<220> FEATURE:
<223> OTHER INFORMATION: Synthetic Construct

<400> SEQUENCE: 8 aggtgaa                                                                    7

<210> SEQ ID NO 9
<211> LENGTH: 7
<212> TYPE: DNA
<213> ORGANISM: Artificial Sequence
<220> FEATURE:
<223> OTHER INFORMATION: Synthetic Construct

<400> SEQUENCE: 9 ttcgtaa                                                                    7

<210> SEQ ID NO 10
<211> LENGTH: 7
<212> TYPE: DNA
<213> ORGANISM: Artificial Sequence
<220> FEATURE:
<223> OTHER INFORMATION: Synthetic Construct

<400> SEQUENCE: 10 tttaaa                                                                     7

<210> SEQ ID NO 11
<211> LENGTH: 7
<212> TYPE: DNA
<213> ORGANISM: Artificial Sequence
<220> FEATURE:
<223> OTHER INFORMATION: Synthetic Construct

<400> SEQUENCE: 11 cttccaa                                                                    7

<210> SEQ ID NO 12
<211> LENGTH: 8
<212> TYPE: DNA
<213> ORGANISM: Artificial Sequence
<220> FEATURE:
<223> OTHER INFORMATION: Synthetic Construct

<400> SEQUENCE: 12 atgtatgc                                                                   8

<210> SEQ ID NO 13
<211> LENGTH: 8
<212> TYPE: DNA
<213> ORGANISM: Artificial Sequence
<220> FEATURE:
<223> OTHER INFORMATION: Synthetic Construct
```

```
<400> SEQUENCE: 13 tctagaaa                                                                 8

<210> SEQ ID NO 14
<211> LENGTH: 6
<212> TYPE: DNA
<213> ORGANISM: Artificial Sequence
<220> FEATURE:
<223> OTHER INFORMATION: Synthetic Construct

<400> SEQUENCE: 14 tgtaca                                                                   6

<210> SEQ ID NO 15
<211> LENGTH: 3
<212> TYPE: DNA
<213> ORGANISM: Artificial Sequence
<220> FEATURE:
<223> OTHER INFORMATION: Synthetic Construct

<400> SEQUENCE: 15 ttg                                                                      3

<210> SEQ ID NO 16
<211> LENGTH: 12
<212> TYPE: DNA
<213> ORGANISM: Artificial Sequence
<220> FEATURE:
<223> OTHER INFORMATION: Synthetic Construct

<400> SEQUENCE: 16
gaagcagtgg ta                                                           12

<210> SEQ ID NO 17
<211> LENGTH: 5
<212> TYPE: DNA
<213> ORGANISM: Artificial Sequence
<220> FEATURE:
<223> OTHER INFORMATION: Synthetic Construct

<400> SEQUENCE: 17 tcaat                                                                    5

<210> SEQ ID NO 18
<211> LENGTH: 10
<212> TYPE: DNA
<213> ORGANISM: Artificial Sequence
<220> FEATURE:
<223> OTHER INFORMATION: Synthetic Construct

<400> SEQUENCE: 18
tattataaat                                                              10

<210> SEQ ID NO 19
<211> LENGTH: 10
<212> TYPE: DNA
<213> ORGANISM: Artificial Sequence
<220> FEATURE:
<223> OTHER INFORMATION: Synthetic Construct

<400> SEQUENCE: 19
tattataaat                                                              10

<210> SEQ ID NO 20
```

<211> LENGTH: 2
<212> TYPE: DNA
<213> ORGANISM: Artificial Sequence
<220> FEATURE:
<223> OTHER INFORMATION: Synthetic Construct

<400> SEQUENCE: 20 ga                                                                    2

<210> SEQ ID NO 21
<211> LENGTH: 1314
<212> TYPE: DNA
<213> ORGANISM: Artificial Sequence
<220> FEATURE:
<223> OTHER INFORMATION: Synthetic Construct

<400> SEQUENCE: 21
gtcgaccgta cgcaggtaag tcaccatcac catcaccatt agactgttga aagttgttta      60
gcaaaacctc atacagaaaa ttcatttact aacgtctgga aagacgacaa aactttagat     120
cgttacgcta actatgaggg ctgtctgtgg aatgctacag gcgttgtggt ttgtactggt     180
gacgaaactc agtgttacgg tacatgggtt cctattgggc ttgctatccc tgaaaatgag     240
ggtggtggct ctgagggtgg cggttctgag ggtggcggtt ctgagggtgg cggtactaaa     300
cctcctgagt acggtgatac acctattccg ggctatactt atatcaaccc tctcgacggc     360
acttatccgc ctggtactga gcaaaacccc gctaatccta tccttctct tgaggagtct      420
cagcctctta atactttcat gtttcagaat aataggttcc gaaataggca gggtgcatta     480
actgtttata cgggcactgt tactcaaggc actgaccccg ttaaaactta ttaccagtac     540
actcctgtat catcaaaagc catgtatgac gcttactgga acgtaaatt cagagactgc      600
gctttccatt ctggctttaa tgaggatcca ttcgtttgtg aatatcaagg ccaatcgtct     660
gacctgcctc aacctcctgt caatgctggc ggcggctctg gtggtggttc tggtggcggc     720
tctgagggtg gcggctctga gggtggcggc tctgagggtg cggttctga gggtggcggc     780
tctgagggtg gcggttccgg tggcggctcc ggttccggtg attttgatta tgaaaaatg     840
gcaaacgcta ataaggggc tatgaccgaa aatgccgatg aaaacgcgct acagtctgac     900
gctaaaggca aacttgattc tgtcgctact gattacggtg ctgctatcga tggtttcatt     960
ggtgacgttt ccggccttgc taatggtaat ggtgctactg gtgattttgc tggctctaat    1020
tcccaaatgg ctcaagtcgg tgacggtgat aattcacctt aatgaataa tttccgtcaa    1080
tatttaccctt ctttgcctca gtcggttgaa tgtcgccctt atgtctttgg cgctggtaaa   1140
ccatatgaat tttctattga ttgtgacaaa ataaacttat tccgtggtgt ctttgcgttt   1200
ctttatatg ttgccaccctt tatgtatgta ttttcgacgt ttgctaacat actgcgtaat    1260
aaggagtctt aataactaat ctccttctcc tcctcccagg ccgtacgct cgag           1314

<210> SEQ ID NO 22
<211> LENGTH: 266
<212> TYPE: DNA
<213> ORGANISM: Artificial Sequence
<220> FEATURE:
<223> OTHER INFORMATION: Synthetic Construct

<400> SEQUENCE: 22
cctacttggc agtacatcta cgtattagtc atcgctatta ccatggtgat gcggttttgg     60
cagtacatca atgggcgtgg atagcggttt gactcacggg gatttccaag tctccacccc    120
attgacgtca atgggagttt gttttggcac caaaatcaac gggactttcc aaaatgtcgt    180

```
aacaactccg ccccattgac gcaaatgggc ggtaggcgtg tacggtggga ggtctatata    240
agcagactgg tttagtgaac cgtcag                                         266
```

<210> SEQ ID NO 23
<211> LENGTH: 14
<212> TYPE: PRT
<213> ORGANISM: Artificial Sequence
<220> FEATURE:
<223> OTHER INFORMATION: Synthetic Construct

<400> SEQUENCE: 23

```
Met Gly Trp Ser Cys Ile Leu Phe Leu Val Ala Thr Ala Thr
1               5                   10
```

<210> SEQ ID NO 24
<211> LENGTH: 42
<212> TYPE: DNA
<213> ORGANISM: Artificial Sequence
<220> FEATURE:
<223> OTHER INFORMATION: Synthetic Construct

<400> SEQUENCE: 24

```
atgggatgga gctgtatcct cttcttggta gcaacagtca ca                       42
```

<210> SEQ ID NO 25
<211> LENGTH: 205
<212> TYPE: DNA
<213> ORGANISM: Artificial Sequence
<220> FEATURE:
<223> OTHER INFORMATION: Synthetic Construct

<400> SEQUENCE: 25

```
ggtaaggggc tcacagtagc aggcttgagg tctggacata tatatgggtg acaagatctc    60
gcaacgcaat taatgtgagt tagctcactc attaggcacc ccaggcttta cactttatgc    120
ttccggctcg tatgttgtgt ggaattgtga gcggataaca atttctagaa ataattttgt    180
ttaactttaa gaaggagata tacat                                          205
```

<210> SEQ ID NO 26
<211> LENGTH: 15
<212> TYPE: PRT
<213> ORGANISM: Artificial Sequence
<220> FEATURE:
<223> OTHER INFORMATION: Synthetic Construct

<400> SEQUENCE: 26

```
Met Lys Tyr Leu Leu Pro Thr Ala Ala Ile Gly Leu Leu Leu Leu
1               5                   10                  15
```

<210> SEQ ID NO 27
<211> LENGTH: 45
<212> TYPE: DNA
<213> ORGANISM: Artificial Sequence
<220> FEATURE:
<223> OTHER INFORMATION: Synthetic Construct

<400> SEQUENCE: 27

```
atgaaatacc tgctgccgac cgctgcgatc ggtctccttc tcctc                    45
```

<210> SEQ ID NO 28
<211> LENGTH: 12
<212> TYPE: PRT
<213> ORGANISM: Artificial Sequence
<220> FEATURE:

```
<223> OTHER INFORMATION: Synthetic Construct

<400> SEQUENCE: 28

Leu Leu Thr Gly Val His Ala Gln Val Thr Leu Arg
1               5                   10

<210> SEQ ID NO 29
<211> LENGTH: 36
<212> TYPE: DNA
<213> ORGANISM: Artificial Sequence
<220> FEATURE:
<223> OTHER INFORMATION: Synthetic Construct

<400> SEQUENCE: 29
ctcctcacag gtgtccacgc acaggttacc ctgaga                              36

<210> SEQ ID NO 30
<211> LENGTH: 287
<212> TYPE: DNA
<213> ORGANISM: Artificial Sequence
<220> FEATURE:
<223> OTHER INFORMATION: Synthetic Construct

<400> SEQUENCE: 30
tgtgggcgga caataaagtc ttaaactgaa caaactagat attcttggag ataattaaat    60
tgataaccat ctcgcaaata aataagtatt ttactgtttt cgtaacagtt ttgtaataaa   120
aaaacctata aatattccgg attattcata ccgtccacca tcgggcgcgg atcgtcgact   180
tgacaattaa tcatcggtcg tataatttgt ggaagtcgac taatacgact cactatcggg   240
atctagaaat atctgagctc gtctgcaatt aggaggaggc caccatg                 287

<210> SEQ ID NO 31
<211> LENGTH: 14
<212> TYPE: PRT
<213> ORGANISM: Artificial Sequence
<220> FEATURE:
<223> OTHER INFORMATION: Synthetic Construct

<400> SEQUENCE: 31

Met Pro Thr Gly Val Thr Phe Glu Phe Ser Ser Trp Gly Gly
1               5                   10

<210> SEQ ID NO 32
<211> LENGTH: 89
<212> TYPE: DNA
<213> ORGANISM: Artificial Sequence
<220> FEATURE:
<223> OTHER INFORMATION: Synthetic Construct

<400> SEQUENCE: 32
tcatcggtcg tataatttgt ggaaggagga ggccaccatg ccccaactgg ggtaaccttt    60
gagttctcta gttgggggga taataataa                                     89

<210> SEQ ID NO 33
<211> LENGTH: 51
<212> TYPE: DNA
<213> ORGANISM: Artificial Sequence
<220> FEATURE:
<223> OTHER INFORMATION: Synthetic Construct
<220> FEATURE:
<221> NAME/KEY: n
<222> LOCATION: (43)..(43)
<223> OTHER INFORMATION: n is c or t
<220> FEATURE:
<221> NAME/KEY: misc_feature
```

```
<222> LOCATION: (43)..(43)
<223> OTHER INFORMATION: n is a, c, g, or t

<400> SEQUENCE: 33
ggtgccaggg cgtgcccttg ggctccccgg gcgcgtactg aantatacaa a          51

<210> SEQ ID NO 34
<211> LENGTH: 17
<212> TYPE: PRT
<213> ORGANISM: Artificial Sequence
<220> FEATURE:
<223> OTHER INFORMATION: Synthetic Construct

<400> SEQUENCE: 34

Val Pro Gly Arg Ala Leu Gly Leu Pro Gly Arg Val Thr Asn Tyr Thr
1               5                   10                  15
Lys

<210> SEQ ID NO 35
<211> LENGTH: 18
<212> TYPE: PRT
<213> ORGANISM: Artificial Sequence
<220> FEATURE:
<223> OTHER INFORMATION: Synthetic Construct

<400> SEQUENCE: 35

Met Pro Thr Gly Val Thr Phe Gly Leu Pro Gly Arg Val Thr Asn Tyr
1               5                   10                  15
Thr Lys

<210> SEQ ID NO 36
<211> LENGTH: 93
<212> TYPE: DNA
<213> ORGANISM: Artificial Sequence
<220> FEATURE:
<223> OTHER INFORMATION: Synthetic Construct
<220> FEATURE:
<221> NAME/KEY: n
<222> LOCATION: (84)..(84)
<223> OTHER INFORMATION: n is a, t, g, or c
<220> FEATURE:
<221> NAME/KEY: misc_feature
<222> LOCATION: (84)..(84)
<223> OTHER INFORMATION: n is a, c, g, or t

<400> SEQUENCE: 36
tcatcggtcg tataatttgt ggaaggagga ggccaccatg ccccaactgg ggtaaccttt   60
gggctccccg gcgcgtact gaantataca aaa                                93

<210> SEQ ID NO 37
<211> LENGTH: 441
<212> TYPE: DNA
<213> ORGANISM: Artificial Sequence
<220> FEATURE:
<223> OTHER INFORMATION: Synthetic Construct

<400> SEQUENCE: 37
ttttacggtt cctggccttt tgctggcctt ttgctcacat gtggggtgcc agggcgtgcc   60
cttgggctcc ccgggcgcgt aaggaagcta aaatggagaa aaaaatcact ggatatacca  120
ccgttgatat atcccaatgg catcgtaaag aacatttga ggcatttcag tcagttgctc   180
aatgtaacct ataaccagac cgttcagctg gatattacgg ccttttttaaa gaccgtaaag  240 aaaaataagc acaagtttta tccggccttt attcacattc ttgcccgcct gatgaaggct  300
```

```
catccggaat tccgtatggc aatgaaagac ggtgagctgg tgatatggga tagtggtcac    360
ccttgttaca ccgttttcca tgagcaaact gaaacgtttt catcgctctg gagtgaatac    420
cacgacgatt tccggcagtt t                                              441
```

<210> SEQ ID NO 38
<211> LENGTH: 135
<212> TYPE: PRT
<213> ORGANISM: Artificial Sequence
<220> FEATURE:
<223> OTHER INFORMATION: Synthetic Construct

<400> SEQUENCE: 38

```
Leu Phe Thr Val Pro Gly Leu Leu Ala Phe Cys Ser His Val Gly
1               5                   10                  15

Cys Gly Gly Val Pro Leu Gly Ser Pro Gly Ala Gly Ser Asn Gly Glu
                20                  25                  30

Lys Asn His Trp Leu Tyr His Arg Tyr Ile Pro Met Ala Ser Arg Thr
            35                  40                  45

Phe Gly Ile Ser Val Ser Cys Ser Met Tyr Leu Pro Asp Arg Ser Ala
        50                  55                  60

Gly Tyr Tyr Gly Leu Phe Lys Asp Arg Lys Glu Lys Ala Gln Val Leu
65                  70                  75                  80

Ser Gly Leu Tyr Ser His Ser Cys Pro Pro Asp Glu Cys Ser Ser Gly
                85                  90                  95

Ile Pro Tyr Gly Asn Glu Arg Arg Ala Gly Asp Met Gly Cys Ser Pro
            100                 105                 110

Leu Leu His Arg Phe Pro Ala Asn Asn Val Phe Ile Ala Leu Glu Ile
        115                 120                 125

Pro Arg Arg Phe Pro Ala Val
        130                 135
```

<210> SEQ ID NO 39
<211> LENGTH: 147
<212> TYPE: PRT
<213> ORGANISM: Artificial Sequence
<220> FEATURE:
<223> OTHER INFORMATION: Synthetic Construct

<400> SEQUENCE: 39

```
Phe Leu Arg Phe Leu Ala Phe Cys Trp Pro Phe Ala His Met Trp Gly
1               5                   10                  15

Ala Arg Ala Cys Pro Trp Ala Pro Arg Ala Arg Lys Glu Ala Lys Met
                20                  25                  30

Glu Lys Lys Ile Thr Gly Tyr Thr Thr Val Asp Ile Ser Gln Trp His
            35                  40                  45

Arg Lys Glu His Phe Glu Ala Phe Gln Ser Val Ala Gln Cys Thr Tyr
        50                  55                  60

Asn Gln Thr Val Gln Leu Asp Ile Thr Ala Phe Leu Lys Thr Val Lys
65                  70                  75                  80

Lys Asn Lys His Lys Phe Tyr Pro Ala Phe Ile His Ile Leu Ala Arg
                85                  90                  95

Leu Met Asn Ala His Pro Glu Phe Arg Met Ala Met Lys Asp Gly Glu
            100                 105                 110

Leu Val Leu Trp Asp Ser Val His Pro Cys Tyr Thr Val Phe His Glu
        115                 120                 125

Gln Thr Glu Thr Phe Ser Ser Leu Trp Ser Glu Tyr His Asp Asp Phe
        130                 135                 140
```

Arg Gln Phe
145

<210> SEQ ID NO 40
<211> LENGTH: 140
<212> TYPE: PRT
<213> ORGANISM: Artificial Sequence
<220> FEATURE:
<223> OTHER INFORMATION: Synthetic Construct

<400> SEQUENCE: 40

Phe Tyr Gly Ser Trp Pro Phe Ala Gly Leu Leu Thr Cys Gly Val
1               5                   10                  15

Pro Gly Arg Ala Leu Gly Leu Pro Gly Arg Val Arg Lys Leu Lys Trp
                20                  25                  30

Arg Lys Lys Ser Leu Asp Ile Pro Pro Leu Ile Tyr Pro Asn Gly Ile
            35                  40                  45

Val Lys Asn Ile Leu Arg His Phe Ser Gln Leu Leu Asn Val Pro Ile
    50                  55                  60

Thr Arg Pro Phe Ser Trp Ile Leu Arg Pro Phe Arg Pro Arg Lys Ile
65                  70                  75                  80

Ser Thr Ser Phe Ile Arg Pro Leu Phe Thr Phe Leu Pro Ala Met Leu
                85                  90                  95

Ile Arg Asn Ser Val Trp Gln Lys Thr Val Ser Trp Tyr Gly Ile Val
            100                 105                 110

Phe Thr Leu Val Thr Pro Phe Ser Met Ser Lys Leu Lys Arg Phe His
        115                 120                 125

Arg Ser Gly Val Asn Thr Thr Thr Ile Ser Gly Ser
    130                 135                 140

<210> SEQ ID NO 41
<211> LENGTH: 661
<212> TYPE: DNA
<213> ORGANISM: Artificial Sequence
<220> FEATURE:
<223> OTHER INFORMATION: Synthetic Construct

<400> SEQUENCE: 41
aaaatgagac gttgatcggc acgtaagagg ttccaacttt caccataatg aaataagatc      60
actaccgggc gtatttttg agttatcgag attttcagga gctagcggcc cgccccaact     120
ggggtaacct ttgagttctc tcagttgggg atgacccagg gtgttgttac cggtgttgat     180
acctatgccg gtgcatatga tcgtcagagc cctgaacgtg aaatagcag cgcagcaagt     240 ccggcaaccc agcgtagcgc aaatgaacat aaagcagccg atctgcagcg tgaagttgaa     300
cgtgatggtg gtcgttttcg ttttgttggt cattttagcg aagcaccggg tacaagcgca     360
tttggcaccg cagaacgtcc ggaatttgaa cgtattctga tgaatgtcg tgcaggtcgt     420 ctgaacatga ttattgttta tgatgtgagc cgttttagcc gtctgaaagt tatggatgca     480
attccgattg ttagcgaact gctggcactg gtgttaccca ttgttagcac ccaagaaggt     540 gttttcgtc agggtaatgt tatggatctg attcatctga ttatgcgtct ggatgcaagc     600
cataaagaaa gcagcctgaa aagcgcaaaa atcctggata ccaaaaacct gcagcgcgaa     660
c                                                                     661

<210> SEQ ID NO 42
<211> LENGTH: 205
<212> TYPE: PRT

<213> ORGANISM: Artificial Sequence
<220> FEATURE:
<223> OTHER INFORMATION: Synthetic Construct

<400> SEQUENCE: 42

```
Lys Met Arg Arg Ser Ala Arg Lys Arg Phe Gln Leu Ser Pro Asn Lys
1               5                   10                  15

Leu Thr Thr Gly Arg Ile Phe Val Ile Glu Ile Phe Arg Ser Arg Pro
            20                  25                  30

Pro Gln Leu Gly Pro Leu Ser Ser Leu Ser Trp Gly Pro Arg Val Leu
            35                  40                  45

Leu Pro Val Leu Ile Pro Met Pro Val His Met Ile Val Arg Ala Val
50                  55                  60

Asn Val Lys Leu Ala Ala Gln Gln Val Arg Gln Pro Ser Val Ala Gln
65                  70                  75                  80

Met Lys Ile Lys Gln Pro Ile Cys Ser Val Lys Leu Asn Val Met Val
                85                  90                  95

Val Val Phe Val Leu Leu Val Ile Leu Ala Lys His Val Gln Ala
            100                 105                 110

His Leu Ala Pro Gln Asn Val Arg Asn Leu Asn Val Phe Met Asn Val
            115                 120                 125

Val Gln Val Val Thr Leu Leu Phe Met Met Ala Val Leu Ala Val Lys
130                 135                 140

Leu Trp Met Gly Phe Arg Leu Leu Ala Asn Cys Trp His Trp Val Leu
145                 150                 155                 160

Pro Leu Leu Ala Pro Lys Lys Val Phe Phe Val Arg Val Met Leu Trp
                165                 170                 175

Ile Phe Ile Leu Cys Val Trp Met Gln Ala Ile Lys Lys Ala Ala Lys
            180                 185                 190

Ala Gln Lys Ser Trp Ile Pro Lys Thr Cys Ser Ala Asn
            195                 200                 205
```

<210> SEQ ID NO 43
<211> LENGTH: 197
<212> TYPE: PRT
<213> ORGANISM: Artificial Sequence
<220> FEATURE:
<223> OTHER INFORMATION: Synthetic Construct

<400> SEQUENCE: 43

```
Lys Asp Val Asp Arg His Val Arg Gly Ser Asn Phe His His Asn Glu
1               5                   10                  15

Ile Arg Ser Leu Pro Gly Val Phe Phe Glu Leu Ser Arg Phe Ser Gly
            20                  25                  30

Ala Ser Gly Arg Pro Asn Trp Gly Asn Leu Val Leu Ser Val Gly Asp
            35                  40                  45

Asp Pro Gly Cys Cys Tyr Arg Cys Tyr Leu Cys Arg Cys Ile Ser Ser
50                  55                  60

Glu Pro Thr Lys Gln Arg Ser Lys Ser Gly Asn Pro Ala Arg Lys Arg
65                  70                  75                  80

Ser Ser Arg Ser Ala Ala Ser Thr Trp Trp Ser Phe Ser Phe Cys Trp
                85                  90                  95

Ser Phe Arg Ser Thr Gly Tyr Lys Arg Ile Trp His Arg Arg Thr Ser
            100                 105                 110

Gly Ile Thr Tyr Ser Glu Met Ser Cys Arg Ser Ser Glu His Asp Tyr
            115                 120                 125
```

Cys Leu Cys Glu Pro Phe Pro Ser Glu Ser Tyr Gly Cys Asn Ser Asp
    130                 135                 140

Cys Arg Thr Ala Gly Thr Gly Cys Tyr His Cys His Pro Arg Arg Cys
145                 150                 155                 160

Phe Ser Ser Gly Cys Tyr Gly Ser Asp Ser Ser Asp Tyr Ala Ser Gly
                165                 170                 175

Cys Lys Pro Arg Lys Gln Pro Glu Lys Arg Lys Asn Pro Gly Tyr Gln
                180                 185                 190

Lys Pro Ala Ala Arg
        195

<210> SEQ ID NO 44
<211> LENGTH: 217
<212> TYPE: PRT
<213> ORGANISM: Artificial Sequence
<220> FEATURE:
<223> OTHER INFORMATION: Synthetic Construct

<400> SEQUENCE: 44

Asn Glu Thr Leu Ile Gly Thr Glu Val Pro Thr Phe Thr Ile Met Lys
1               5                   10                  15

Asp His Tyr Arg Ala Tyr Phe Leu Ser Tyr Arg Asp Phe Gln Glu Leu
                20                  25                  30

Ala Ala Ala Pro Thr Gly Val Thr Phe Glu Phe Ser Gln Leu Gly Met
            35                  40                  45

Thr Gln Gly Val Val Thr Gly Val Asp Thr Tyr Ala Gly Ala Tyr Asp
    50                  55                  60

Arg Gln Ser Arg Glu Arg Glu Asn Ser Ser Ala Ala Ser Pro Ala Thr
65                  70                  75                  80

Gln Arg Ser Ala His Glu Asp Lys Ala Ala Asp Leu Gln Arg Glu Val
                85                  90                  95

Glu Arg Asp Gly Gly Arg Phe Arg Phe Val Gly His Phe Ser Glu Ala
                100                 105                 110

Pro Gly Thr Ser Ala Phe Gly Thr Ala Glu Arg Pro Glu Phe Glu Arg
            115                 120                 125

Ile Leu Asn Glu Cys Arg Ala Gly Arg Leu Asn Met Ile Ile Val Tyr
    130                 135                 140

Asp Val Ser Arg Phe Ser Arg Leu Lys Val Met Asp Ala Ile Pro Ile
145                 150                 155                 160

Val Ser Glu Leu Leu Ala Leu Gly Val Thr Ile Val Ser Thr Gln Glu
                165                 170                 175

Gly Val Phe Arg Gln Gly Asn Val Met Asp Leu Ile His Leu Ile Met
                180                 185                 190

Arg Leu Asp Ala Ser His Lys Glu Ser Ser Leu Lys Ser Ala Lys Ile
                195                 200                 205

Leu Asp Thr Lys Asn Leu Gln Arg Glu
    210                 215

<210> SEQ ID NO 45
<211> LENGTH: 540
<212> TYPE: DNA
<213> ORGANISM: Artificial Sequence
<220> FEATURE:
<223> OTHER INFORMATION: Synthetic Construct

<400> SEQUENCE: 45
aaaatgagac gttgatcggc acgtaagagg ttccaacttt caccataatg aaataagatc    60

```
actaccgggc gtattttttg agttatcgag attttcagga gctagcggcc gccccaactg    120
gggtaacctt tgggctcccc gggcgcgtaa ggaagctaaa atggagaaaa aaatcactgg    180
atataccacc gttgatatat cccaatggca tcgtaaagaa cattttgagg catttcagtc    240
agttgctcaa tgtacctata accagaccgt tcagctggat attacggcct ttttaaagac    300
cgtaaagaaa aataagcaca agttttatcc ggcctttatt cacattcttg cccgcctgat    360
gaatgctcat ccggaattcc gtatggcaat gaaagacggt gagctggtga tatgggatag    420
tgttcaccct tgttacaccg ttttccatga gcaaactgaa acgttttcat cgctctggag    480
tgaataccac gacgatttcc ggcagtttct acacatatat tcgcaagatg tggcgtgtta    540
```

<210> SEQ ID NO 46
<211> LENGTH: 162
<212> TYPE: PRT
<213> ORGANISM: Artificial Sequence
<220> FEATURE:
<223> OTHER INFORMATION: Synthetic Construct

<400> SEQUENCE: 46

Lys Met Arg Arg Ser Ala Arg Lys Arg Phe Gln Leu Ser Pro Asn Lys
1               5                   10                  15

Ile Thr Thr Gly Arg Ile Phe Val Ile Glu Ile Phe Arg Ser Arg Pro
            20                  25                  30

Pro Gln Leu Gly Pro Leu Gly Ser Pro Gly Ala Gly Ser Asn Gly Glu
        35                  40                  45

Lys Asn His Trp Ile Tyr His Arg Tyr Ile Pro Met Ala Ser Arg Thr
    50                  55                  60

Phe Gly Ile Ser Val Ser Cys Ser Met Tyr Leu Pro Asp Arg Ser Ala
65                  70                  75                  80

Gly Tyr Tyr Gly Leu Phe Lys Asp Arg Lys Glu Lys Ala Gln Val Leu
                85                  90                  95

Ser Gly Leu Tyr Ser His Ser Cys Pro Pro Asp Glu Cys Ser Ser Gly
            100                 105                 110

Ile Pro Tyr Gly Asn Glu Arg Arg Ala Gly Asp Met Gly Cys Ser Pro
        115                 120                 125

Leu Leu His Arg Phe Pro Ala Asn Asn Val Phe Ile Ala Leu Glu Ile
    130                 135                 140

Pro Arg Arg Phe Pro Ala Val Ser Thr His Ile Phe Ala Arg Cys Gly
145                 150                 155                 160

Val Leu

<210> SEQ ID NO 47
<211> LENGTH: 178
<212> TYPE: PRT
<213> ORGANISM: Artificial Sequence
<220> FEATURE:
<223> OTHER INFORMATION: Synthetic Construct

<400> SEQUENCE: 47

Lys Asp Val Asp Arg His Val Arg Gly Ser Asn Phe His His Asn Glu
1               5                   10                  15

Ile Arg Ser Leu Pro Gly Val Phe Phe Glu Leu Ser Arg Phe Ser Gly
            20                  25                  30

Ala Ser Gly Arg Pro Asn Trp Gly Asn Leu Trp Ala Pro Arg Ala Arg
        35                  40                  45

Lys Glu Ala Lys Met Glu Lys Lys Ile Thr Gly Tyr Thr Thr Val Asp
    50                  55                  60

-continued

Ile Ser Gln Trp His Arg Lys Glu His Phe Glu Ala Phe Gly Ser Val
65                  70                  75                  80

Ala Gln Cys Thr Tyr Asn Gln Thr Val Gln Leu Asp Ile Thr Ala Phe
                85                  90                  95

Leu Lys Thr Val Lys Lys Asn Lys His Lys Phe Tyr Pro Ala Phe Ile
            100                 105                 110

His Ile Leu Ala Arg Leu Met Asn Ala His Pro Glu Phe Arg Met Ala
        115                 120                 125

Met Lys Asp Gly Glu Leu Val Ile Trp Asp Ser Val His Pro Cys Tyr
    130                 135                 140

Thr Val Phe His Glu Gln Thr Glu Thr Phe Ser Ser Leu Trp Ser Glu
145                 150                 155                 160

Tyr His Asp Asp Phe Arg Gln Phe Leu His Ile Tyr Ser Gln Asp Val
                165                 170                 175

Ala Cys

<210> SEQ ID NO 48
<211> LENGTH: 171
<212> TYPE: PRT
<213> ORGANISM: Artificial Sequence
<220> FEATURE:
<223> OTHER INFORMATION: Synthetic Construct

<400> SEQUENCE: 48

Asn Glu Thr Leu Ile Gly Thr Glu Val Pro Thr Phe Thr Ile Met Lys
1               5                   10                  15

Asp His Tyr Arg Ala Tyr Phe Leu Ser Tyr Arg Asp Phe Gln Glu Leu
            20                  25                  30

Ala Ala Ala Pro Thr Gly Val Thr Phe Gly Leu Pro Gly Arg Val Arg
        35                  40                  45

Lys Leu Lys Trp Arg Lys Lys Ser Leu Asp Ile Pro Pro Leu Ile Tyr
    50                  55                  60

Pro Asn Gly Ile Val Lys Asn Ile Leu Arg His Phe Ser Gln Leu Leu
65                  70                  75                  80

Asn Val Pro Ile Thr Arg Pro Phe Ser Trp Ile Leu Arg Pro Phe Arg
                85                  90                  95

Pro Arg Lys Ile Ser Thr Ser Phe Ile Arg Pro Leu Phe Thr Phe Leu
            100                 105                 110

Pro Ala Met Leu Ile Arg Asn Ser Val Trp Gln Lys Thr Val Ser Trp
        115                 120                 125

Tyr Gly Ile Val Phe Thr Leu Val Thr Pro Phe Ser Met Ser Lys Leu
    130                 135                 140

Lys Arg Phe His Arg Ser Gly Val Asn Thr Thr Thr Ile Ser Gly Ser
145                 150                 155                 160

Phe Tyr Thr Tyr Ile Arg Lys Met Trp Arg Val
                165                 170

<210> SEQ ID NO 49
<211> LENGTH: 99
<212> TYPE: DNA
<213> ORGANISM: Artificial Sequence
<220> FEATURE:
<223> OTHER INFORMATION: Synthetic Construct

<400> SEQUENCE: 49
tggggtcagg gcaccctggt taccgttagc agtgccccaa ctggggtaac ctttgagttc    60

```
tctcagttgg gggacatcca gatgacccag agcccgagc                            99
```

<210> SEQ ID NO 50
<211> LENGTH: 33
<212> TYPE: PRT
<213> ORGANISM: Artificial Sequence
<220> FEATURE:
<223> OTHER INFORMATION: Synthetic Construct

<400> SEQUENCE: 50

```
Trp Gly Gln Gly Thr Leu Val Thr Val Ser Ser Ala Pro Thr Gly Val
1               5                   10                  15

Thr Phe Glu Phe Ser Gln Leu Gly Asp Ile Gln Met Thr Gln Ser Pro
            20                  25                  30

Ser
```

<210> SEQ ID NO 51
<211> LENGTH: 78
<212> TYPE: DNA
<213> ORGANISM: Artificial Sequence
<220> FEATURE:
<223> OTHER INFORMATION: Synthetic Construct

<400> SEQUENCE: 51

```
attgcactaa gtcttgcact tgtcacgaat tcggggtgc cagggcgtgc ccttgggctc    60
cccgggcgcg tagctagc                                                  78
```

<210> SEQ ID NO 52
<211> LENGTH: 26
<212> TYPE: PRT
<213> ORGANISM: Artificial Sequence
<220> FEATURE:
<223> OTHER INFORMATION: Synthetic Construct

<400> SEQUENCE: 52

```
Ile Ala Leu Ser Leu Ala Leu Val Thr Asn Ser Gly Val Pro Gly Arg
1               5                   10                  15

Ala Leu Gly Leu Pro Gly Arg Val Ala Ser
            20                  25
```

<210> SEQ ID NO 53
<211> LENGTH: 78
<212> TYPE: DNA
<213> ORGANISM: Artificial Sequence
<220> FEATURE:
<223> OTHER INFORMATION: Synthetic Construct

<400> SEQUENCE: 53

```
tggggtcagg gcaccctggt taccgttagc agtgccccaa ctggggtaac ctttgggctc    60
cccgggcgcg tagctagc                                                  78
```

<210> SEQ ID NO 54
<211> LENGTH: 26
<212> TYPE: PRT
<213> ORGANISM: Artificial Sequence
<220> FEATURE:
<223> OTHER INFORMATION: Synthetic Construct

```
<400> SEQUENCE: 54

Trp Gly Gln Gly Thr Leu Val Thr Val Ser Ser Ala Pro Gly Val
1               5                   10                  15

Thr Phe Gly Leu Pro Gly Arg Val Ala Ser
                20                  25
```